(12) United States Patent
Finke et al.

(10) Patent No.: US 7,271,266 B2
(45) Date of Patent: Sep. 18, 2007

(54) SUBSTITUTED 2,3-DIPHENYL PYRIDINES

(75) Inventors: Paul E. Finke, Milltown, NJ (US); Laura C. Meurer, Scotch Plains, NJ (US); John S. Debenham, Scotch Plains, NJ (US); Richard B. Toupence, South Plainfield, NJ (US); Thomas F. Walsh, Watchung, NJ (US)

(73) Assignee: Merck & Co., Inc., Rahway, NJ (US)

( * ) Notice: Subject to any disclaimer, the term of this patent is extended or adjusted under 35 U.S.C. 154(b) by 397 days.

(21) Appl. No.: 10/508,043

(22) PCT Filed: Mar. 24, 2003

(86) PCT No.: PCT/US03/09005

§ 371 (c)(1),
(2), (4) Date: Sep. 17, 2004

(87) PCT Pub. No.: WO03/082191

PCT Pub. Date: Oct. 9, 2003

(65) Prior Publication Data

US 2005/0182103 A1  Aug. 18, 2005

Related U.S. Application Data

(60) Provisional application No. 60/368,334, filed on Mar. 28, 2002.

(51) Int. Cl.
C07D 211/82  (2006.01)
C07D 211/60  (2006.01)
(52) U.S. Cl. .................................. 546/336; 546/228.1
(58) Field of Classification Search ................ 546/336, 546/228.1
See application file for complete search history.

(56) References Cited

U.S. PATENT DOCUMENTS

| | | |
|---|---|---|
| 4,006,149 A | 2/1977 | Bonnemann et al. |
| 4,011,328 A | 3/1977 | Pinhas et al. |
| 4,169,951 A | 10/1979 | Beschke et al. |
| 4,533,666 A | 8/1985 | Matsumoto et al. |
| 4,973,587 A | 11/1990 | Ward et al. |
| 5,013,837 A | 5/1991 | Ward et al. |
| 5,077,142 A | 12/1991 | Sakun et al. |
| 5,081,122 A | 1/1992 | Ward |
| 5,112,820 A | 5/1992 | Ward |
| 5,217,982 A | 6/1993 | Fink et al. |
| 5,248,687 A | 9/1993 | Hayase et al. |
| 5,292,734 A | 3/1994 | Levin et al. |
| 5,380,700 A | 1/1995 | Miyazaki et al. |
| 5,492,915 A | 2/1996 | Dereu et al. |
| 5,593,994 A | 1/1997 | Batt et al. |
| 5,624,941 A | 4/1997 | Barth et al. |
| 5,672,609 A | 9/1997 | Bryant et al. |
| 5,686,470 A | 11/1997 | Weier et al. |
| 5,700,816 A | 12/1997 | Isakson et al. |
| 5,750,708 A | 5/1998 | Bryant et al. |
| 5,861,419 A | 1/1999 | Dube et al. |
| 5,916,905 A | 6/1999 | Weier et al. |
| 5,932,586 A | 8/1999 | Batt et al. |
| 6,001,843 A | 12/1999 | Dube et al. |
| 6,028,084 A | 2/2000 | Barth et al. |
| 6,127,386 A | 10/2000 | Lin et al. |
| 6,344,474 B1 | 2/2002 | Maruani et al. |

FOREIGN PATENT DOCUMENTS

| | | |
|---|---|---|
| EP | 0308020 | 3/1989 |
| EP | 444533 | 9/1991 |
| EP | 0363818 | 4/1994 |
| EP | 0359547 | 1/1996 |
| EP | 658546 | 5/2001 |
| EP | 1328269 | 5/2004 |
| EP | 1078920 | 7/2004 |
| GB | 1395110 | * 9/1973 |
| GB | 1401038 | 7/1995 |
| GB | 2323841 | 10/1998 |
| JP | 05-331164 | 12/1993 |

(Continued)

OTHER PUBLICATIONS

Konno et al. Yakugaku Zasshi (1993), 113(1), 40-52; CAPLUS Accession No. 1993:234009)).*

(Continued)

Primary Examiner—D. Margaret Seaman
Assistant Examiner—Nizal S. Chandrakumar
(74) Attorney, Agent, or Firm—Beerbel R. Brown; Catherine D. Fitch

(57) ABSTRACT

Novel compounds of the structural formula (I) are antagonists and/or inverse agonists of the Cannabinoid-1 (CB1) receptor and are useful in the treatment, prevention and suppression of diseases mediated by the CB1 receptor. The compounds of the present invention are useful as centrally acting drugs in the treatment of psychosis, memory deficits, cognitive disorders, migraine, neuropathy, neuro-inflammatory disorders including multiple sclerosis and Guillain-Barre syndrome and the inflammatory sequelae of viral encephalitis, cerebral vascular accidents, and head trauma, anxiety disorders, stress, epilepsy, Parkinson s disease, movement disorders, and schizophrenia. The compounds are also useful for the treatment of substance abuse disorders, the treatment of obesity or eating disorders, as well as the treatment of asthma, constipation, chronic intestinal pseudo-obstruction, and cirrhosis of the liver.

8 Claims, No Drawings

FOREIGN PATENT DOCUMENTS

| | | |
|---|---|---|
| JP | 6-16638 A | 1/1994 |
| JP | 07-247214 | 9/1995 |
| JP | 2001-247548 A | 9/2001 |
| WO | WO 92/01675 | 2/1992 |
| WO | WO 92/02513 | 2/1992 |
| WO | WO 92/20642 | 11/1992 |
| WO | WO 96/24584 | 8/1996 |
| WO | WO 96/41625 | 12/1996 |
| WO | WO 97/04778 | 2/1997 |
| WO | WO 97/29079 | 8/1997 |
| WO | WO 98/03484 | 1/1998 |
| WO | WO 98/31227 | 7/1998 |
| WO | WO 98/37061 | 8/1998 |
| WO | WO 98/41519 | 9/1998 |
| WO | WO 99/02499 | 1/1999 |
| WO | WO 99/59635 | 11/1999 |
| WO | WO 00/10967 | 3/2000 |
| WO | WO 00/10968 | 3/2000 |
| WO | WO 00/37107 | 6/2000 |
| WO | WO 00/38786 | 7/2000 |
| WO | WO 01/36387 | 5/2001 |
| WO | WO 01/58450 | 8/2001 |
| WO | WO 01/85092 | 11/2001 |
| WO | WO 02/055502 | 7/2002 |
| WO | WO 02/076945 | 10/2002 |
| WO | WO2002096516 * | 12/2002 |
| WO | WO 03/007887 | 1/2003 |
| WO | WO 03/051850 | 6/2003 |
| WO | WO 03/063781 | 8/2003 |
| WO | WO 03/075660 | 9/2003 |
| WO | WO 03/082256 | 10/2003 |
| WO | WO 03/084930 | 10/2003 |
| WO | WO 03/084943 | 10/2003 |
| WO | WO 03/086394 | 10/2003 |
| WO | WO 2004/012671 | 2/2004 |
| WO | WO 2004/029026 | 4/2004 |
| WO | WO 2004/029027 | 4/2004 |
| WO | WO 2004/029204 | 4/2004 |
| WO | WO 2004/111039 | 12/2004 |
| WO | WO 2005/000817 | 1/2005 |
| WO | WO 2005/016286 | 2/2005 |

OTHER PUBLICATIONS

Barth, Exp. Opin. Ther. Patents, vol. 8 (1998), pp. 301-313, "Cannabinoid receptor agonists and antagonists".

Xiang et al., Ann. Rep. Med. Chem., A. Doherty, ed., Academic Press, NY (1999), vol. 34, pp. 199-208, "Chapter 20. Pharmacology of cannabinoid receptor agonists and antagonists".

Goya et al., Exp. Opin. Ther. Patents, vol. 10 (2000), pp. 1529-1538, "Recent advances in cannabinoid receptor agonists and antagonists".

Piomelli et al., Trends in Pharm. Sci., vol. 21 (2000), pp. 218-224, "The endocannabinoid system as a target for therapeutic drugs".

Sano et al., Chem. Pharm. Bull., vol. 38 (1990), pp. 3283-3295, "Dioxopyrorolines. XLIX. Synthesis of azatropolones via photocycloaddition of 5-aryl-4-ethoxycarbonyl-1H-pyrrole-2,3-diones to acetylenes and ethylenes".

Van Aken et al., Tetra. Letters, vol. 33 (1992), pp. 2713-2716, "Functionalization in positino 3 of 3,5-dichloro-2H-1,4-oxazin-2-ones".

Brown et al., Tetra. Letters, vol. 33 (1992), pp. 3787-3790 "Retro-Diels-Alder fragmentation of 2,5,6-triphenyl-13,4-didehydropyridine generated by flash vacuum pyrolysis at 900 degree C".

Troschuetz et al., Arch. Pharm., vol. 327 (1994), pp. 33-40, "Synthesis of substituted 2-aminonicotinonitriles".

Kagabu et al., J. Chem. Soc., vol. 6 (1994), pp. 739-751, "Thermal rearrangement of N-arylmethyl- and N-alkyl-2,2-dihalogenocyclopropyl imines".

Hitzler et al., Synthesis, vol. 5 (1994), vol. 5, pp. 509-515, "On the reaction of 1,3-dichloro-2-azoniaallene salts with olefins and diphenylacetylene".

Nehl, Chem. Ber., vol. 127 (1994), pp. 2535-2537, "(.eta.3-Allyl)(.eta.5-pentamethylcyclopentadienyl)cobalt- a selective catalyst for the pyridine synthesis".

Tanaka et al., Chem. Pharm. Bull., vol. 42 (1994), pp. 1828-1834, "Studies on anti-platelet agents."

Palacios et al., Tetra. Letters, vol. 37 (1996), pp. 4577-4580, "A one-pot synthesis of of polysubstituted pyridines from metalated alkylphosphonates, nitriles and .alpha., .beta.-unsaturated ketones . . . ".

Paparin et al., J. Heterocycl. Chem., vol. 47 (2000), pp. 411-418, "Synthesis of 2,5-bisarylpyridines by [4 +2] cycloaddition of 2,4-bisaryl-2-aza-1,3-butadienes with electron-poor dienophiles . . . ".

Marcoux et al., Organic Letters, vol. 2 (2000), pp. 2339-2341, "Annulation of keones with vinamidinium hexafluorophosphate salts: An efficient preparation of trisubstituted pyridines".

Palacios et al., Tetrahedron, vol. 56 (2000), pp. 6319-6330, "Synthesis and reactivity of imines derived from bisphosphonates and 3-phosphorylated 2-aza-1,3-dienes".

Palacios et al., Eur. J. Org. Chem., vol. 11 (2001), pp. 2115-2122, "Cycloaddition reactions of neutral 2-azadienes with enamines—regiospecific synthesis of highly substituted dihydropyridines and pyridines".

Yamamoto et al., Chem. Pharm. Bull., vol. 33 (1985), pp. 975-981, "1,3-Oxazines and related compounds".

Gruseck et al., Tetradron Letters, vol. 28 (1987), pp. 6027-6030, "The remarkable reactivity of 2-alkylideneimidazolidines in inverse Diels-Alder reactions".

Tsuda et al., Heterocycles, vol. 12 (1979), pp. 1423-1426, "Establishment of the structures of azatropolones and their rearrangement products by X-ray analysis".

Van Aken et al., Tetrahedron, vol. 50 (1994), pp. 5211-5224, "The synthesis of 3-functionalized 5-chloro-6-methyl2H-1,4-oxazin-2-ones and of pyridines from cycloaddition-elimination . . . ".

Konno et al., Yakugaku Zasshi, vol. 113 (1993), pp. 40-52, "Studies on as-triazine derivatives."

* cited by examiner

SUBSTITUTED 2,3-DIPHENYL PYRIDINES

CROSS-REFERENCE TO RELATED APPLICATIONS

This application is a U.S. National Phase application under 35 U.S.C. §371 of PCT Application No. PCT/US03/09005, filed Mar. 24, 2003, which claims priority under 35 U.S.C. §119 from U.S. Provisional Application No. 60/368,334, filed Mar. 28, 2002.

BACKGROUND OF THE INVENTION

Marijuana (*Cannabis sativa L.*) and its derivatives have been used for centuries for medicinal and recreational purposes. A major active ingredient in marijuana and hashish has been determined to be $\Delta^9$-tetrahydrocannabinol ($\Delta^9$-THC). Detailed research has revealed that the biological action of $\Delta^9$-THC and other members of the cannabinoid family occurs through two G-protein coupled receptors termed CB1 and CB2. The CB1 receptor is primarily found in the central and peripheral nervous systems and to a lesser extent in several peripheral organs. The CB2 receptor is found primarily in lymphoid tissues and cells. Three endogenous ligands for the cannabinoid receptors derived from arachidonic acid have been identified (anandamide, 2-arachidonoyl glycerol, and 2-arachidonyl glycerol ether). Each is an agonist with activities similar to $\Delta^9$-THC, including sedation, hypothermia, intestinal immobility, antinociception, analgesia, catalepsy, anti-emesis, and appetite stimulation.

The genes for the respective cannabinoid receptors have each been disrupted in mice. The CB1$^{-/-}$ receptor knockout mice appeared normal and fertile. They were resistant to the effects of $\Delta^9$-THC and demonstrated a strong reduction in the reinforcing properties of morphine and the severity of withdrawal syndrome. They also demonstrated reduced motor activity and hypoalgesia. The CB2$^{-/-}$ receptor knockout mice were also healthy and fertile. They were not resistant to the central nervous system mediated effects of administered $\Delta^9$-THC. There were some effects on immune cell activation, reinforcing the role for the CB2 receptor in immune system functions.

Excessive exposure to $\Delta^9$-THC can lead to overeating, psychosis, hypothermia, memory loss, and sedation. Specific synthetic ligands for the cannabinoid receptors have been developed and have aided in the characterization of the cannabinoid receptors: CP55,940 (J. Pharmacol. Exp. Ther. 1988, 247, 1046-1051); WIN55212-2 (J. Pharmacol. Exp. Ther. 1993, 264, 1352-1363); SR141716A (FEBS Lett. 1994, 350, 240-244; Life Sci. 1995, 56, 1941-1947); and SR144528 (J. Pharmacol. Exp. Ther. 1999, 288, 582-589). The pharmacology and therapeutic potential for cannabinoid receptor ligands has been reviewed (Exp. Opin. Ther. Patents 1998, 8, 301-313; Ann. Rep. Med. Chem., A. Doherty, Ed.; Academic Press, NY 1999, Vol. 34, 199-208; Exp. Opin. Ther. Patents 2000, 10, 1529-1538; Trends in Pharma. Sci. 2000, 21, 218-224). There is at least one CB1 modulator characterized as an inverse agonist or an antagonist, N-(1-piperidinyl)-5-(4-chlorophenyl)-1-(2,4-dichlorophenyl)-4-methylpyrazole-3-carboxamide (SR141716A), in clinical trials for treatment of eating disorders at this time. There still remains a need for potent low molecular weight CB1 modulators that have pharmacokinetic and pharmacodynamic properties suitable for use as human pharmaceuticals.

Treatment of asthma with CB1 receptor modulators (such as CB1 inverse agonists) is supported by the finding that presynaptic cannabinoid CB1 receptors mediate the inhibition of noradrenaline release (in the guinea pig lung) (Europ. J. of Pharmacology, 2001, 431 (2), 237-244).

Treatment of cirrhosis of the liver with CB1 receptor modulators is supported by the finding that a CB1 receptor modulator will reverse the low blood pressure observed in rats with carbon tetrachloride-induced liver cirrhosis and will lower the elevated mesenteric blood flow and portal vein pressure (Nature Medicine, 2001, 7 (7), 827-832).

U.S. Pat. Nos. 5,624,941 and 6,028,084, PCT Application Nos. WO98/43636, WO98/43635, and WO 02/076945, and EPO Application No. EP-658546 disclose substituted pyrazoles having activity against the cannabinoid receptors.

PCT Application Nos. WO98/31227 and WO98/41519 also disclose substituted pyrazoles having activity against the cannabinoid receptors.

PCT Application Nos. WO98/37061, WO00/10967, and WO00/10968 disclose diaryl ether sulfonamides having activity against the cannabinoid receptors.

PCT Application Nos. WO97/29079 and WO99/02499 disclose alkoxy-isoindolones and alkoxyquinolones as having activity against the cannabinoid receptors.

U.S. Pat. No. 5,532,237 discloses N-benzoyl-indole derivatives having activity against the cannabinoid receptors.

U.S. Pat. Nos. 4,973,587, 5,013,837, 5,081,122, and 5,112,820, 5,292,736 disclose aminoalkylindole derivatives as having activity against the cannabinoid receptors.

PCT publication WO 01/58869 discloses pyrazoles, pyrroles and imidazole cannabinoid receptor modulators useful for treating respiratory and non-respiratory leukocyte activation-associated disorders.

PCT publications WO 01/64632, 01/64633, and 01/64634 assigned to Aventis are directed to azetidine derivatives as cannabinoid antagonists.

WO 92/01675 and U.S. Pat. No. 5,492,915 disclose leukotriene B4 antagonists of structural formula:

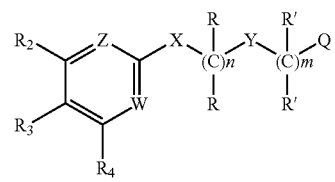

and in particular discloses ethyl 6-[(5,6-diphenyl-2-pyridyl)oxy]hexanoate, methyl 6-[(5,6-diphenyl-2-pyridyl)oxy]-2,2-dimethylhexanoate, ethyl 8-[(5,6-diphenyl-2-pyridyl)oxy]octanoate, 6-[(5,6-diphenyl-2-pyridy)oxy]hexanoic acid, 6-[(5,6-diphenyl-2-pyridyl)oxy]-2,2-dimethylhexanoic acid, and sodium 8-[(5,6-diphenyl-2-pyridyl)oxy]octanoate.

WO 92/02513 discloses heterocyclic compounds of structural formula:

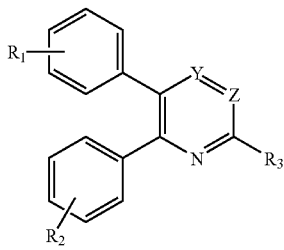

wherein R1 and R2 are each lower alkoxy, useful as antithromotic agents inhibiting cyclooxygenase, thrombin, phosphodiesterase and the like; and in particular, 6-ethyoxycarbonyl-2,3-bis(4-methoxyphenyl)pyridine, 6-acetylaminomethyl-2,3-bis-(4-methoxypheynl)pyridine, 6-(pyridine-4-yl)-2,3-bis(4-methoxyphenyl)pyridine, 2,3-bis(4-methoxyphenyl)-6-(N,N-dimethylaminomethyl)-pyridine, 2,3-bis(4-methoxyphenyl)-6-[(4-methyl-piperazin-1-yl)carbonyl]pyridine dihydrochloride, 2,3-bis(4-methoxyphenyl)-6-[[2-(N,N-dimethylamiono)-ethyl]carbamoyl]pyridine dihydorochloride, 2,3-bis(4-methoxyphenyl)-6-[(4-benzylpiperazin-1-yl)-carbamoyl]pyridine, 6-hydroxymethyl-2,3-bis(4-methoxyphenyl)pyridine, 2,3-bis(4-methoxyphenyl)-6-pyridinecarbaldehyde, 3-[2,3-bis(4-methoxyphenyl)pyridin-6-yl]-(E)-propenoic acid, 3-[2,3-bis(4-methoxyphenyl)pyridine-6-yl]propanoic acid, 6-aminomethyl-2,3-bis(4-methoxyphenyl)pyridine dihydrochloride, 2,3-bis(4-methoxyphenyl)-6-[(3-oxo-2,3,4,5-tetrahdyropyridazin-6-yl)-carbonylaminomethyl]pyridine, 2,3-bis(4-methoxyphenyl)-6-[2-[(3-oxo-2,3,4,5-tetrazhdyropyridazin-6-zy)carbonylamino]ethyl]pyridine, 6-(3-isopropylureidomethyl)-2,3-bis(4-methoxypenyl)-pyridine, 6-(2-aminoethyl)-2,3-bis(4-methoxyphenyl)pyridine, and 2,3-bis(4-methoxyphenyl-6-(N,N-dimethylaminomethyl)-pyridine dihydrochloride.

WO 96/24584 discloses for the treatment of inflammation 2,3-substituted pyridines of structural formula:

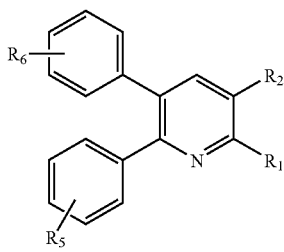

provided one of R5 and R6 is substituted with alkylsulfonyl, aminosulfonyl, or haloalkylsulfonyl. WO 00/38786, WO 00/38730, WO 00/38716. WO 00/37107, U.S. Pat. No. 5,916,905, U.S. Pat. No. 5,686,470, WO 98/47509; WO 98/16227, WO 96/41645, WO 96/41625, U.S. Pat. No. 5,700,816, WO 96/41626, U.S. Pat. No. 5,686,470, describe similar compounds as COX-2 inhibitors. WO 99/59635, U.S. Pat. No. 5,861,419, U.S. Pat. No. 6,001,843, WO 98/03484, to Merck & Co., Inc. or Merck Frosst Canada Inc. also disclose 2,3-diphenyl substituted pyridine COX-2 inhibitors, having alkylsulfonyl and aminosulfonyl subsituents on the 3-phenyl ring.

U.S. Pat. No. 4,011,328 and UK Patent 1,395,110 are directed to compounds of structural formula:

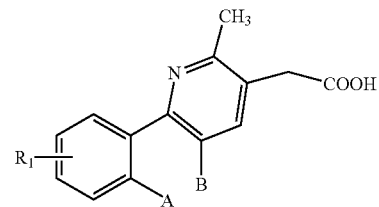

wherein R1 is hydrogen, halogen $C_{1-6}$ alkyl, $C_{1-6}$ alkoxy, and $C_{1-6}$ alkylthio, A taken separately is H and B is a monosubstitued or unsubstituted phenyl moiety substituted with hydrogen, halogen or C1-6 alkoxy, or A and B taken together form a radical —O—$CH_2$—. These compounds are reported to have analgesic and antiinflammatory properties.

U.S. Pat. No. 4,533,666 is directed to 1,2,6-triaryl pyridine derivatives useful in treating pain, fever, thrombosis, inflammation and arthritis of structural formula:

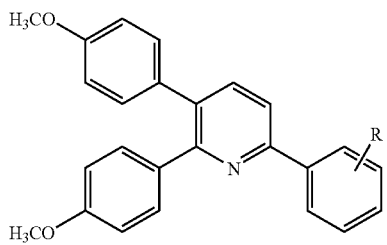

wherein R is hydrogen, trifluoromethyl, fluoro, chloro, bromo or iodo.

U.S. Pat. Nos. 5,593,994 and 5,932,586 are directed to prostaglandin synthase inhibitors of structural formula:

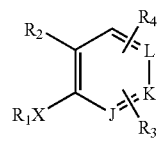

wherein J, K and L are independently $CR_3$, $CR_4$ or N; $R_2$ is p-methylsulfonyl or p-aminosulfonyl substituted phenyl, 3-pyridyl or 2-pyridyl; X is a single bond (i.e., is absent, or is various linkers; Z is O or S; $R_1$ is optionally substituted phenyl, optionally substituted 2-naphthyl, optionally substituted cycloalkyl, optionally substituted cycloalkenyl, or an optionally substituted heterocyclic ring system.

WO 97/04778 and U.S. Pat. Nos. 5,672,609 and 5,750,708 are directed compounds useful to the treatment of post menopausal symptoms such as osteoporosis, cardiovascular conditions including hyperlipidaemia and the like of structural formula:

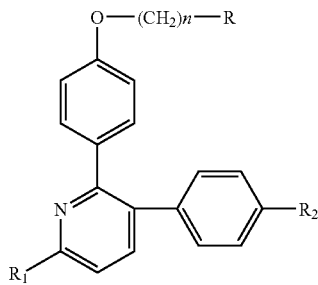

wherein n is 2 or 3,; R is dimethyl amino, diethylamino, 1-piperidinyl, 1-pyrrolidinyl, 4-morpholinyl, or 1-hexamethyleneimino; $R_1$ is hydrogen, loweralkyl, optionally substituted phenyl, or optionally substituted benzoyloxy; and $R_2$ is hydrogen, hydroxyl, loweralkoxy, benzyloxy, loweralkanoyloxy, optionally substituted benzoyloxy.

EP 0 308 020 is directed to 5,6-disubstitued 1-2-dihydro-2-oxo-3-pyridine carboxylic acids of structural formula:

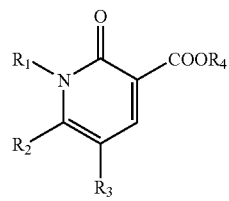

and their use for treating bacterial infections.

U.S. Pat. No. 6,127,386 is directed to 3-pyridloxymethyl heterocyclic ether compounds that are ligands at neuronal nicotinic cholinergic channel receptors of structural formula:

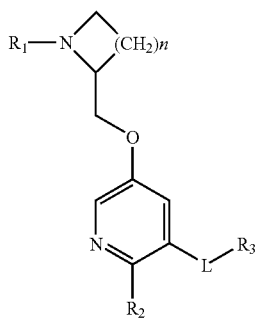

wherein n is 1, 2, or 3; $R_2$ is hydrogen, lower alkyl, fluorine, chlorine, ethenyl or phenyl; L is a linking group which is present or absent, and $R_3$ is selected from hydrogen, alkyl, alkenyl, haloalkyl, hydroxyalkyl, alkoxy, amino, alkylamino, azacyclo, dialkylamino, phenyl, naphthyl, biphenyl, and heterocycles, optionally substituted.

U.S. Pat. No. 5,077,142 is directed to an electroluminescent device comprising a cathod and one or a plurality of organic compound layers sandwiched therebetween which organic compound layers comprise an organic compound which included phenyl-substituted pyridine compounds.

U.S. Pat. No. 4,169,951 is directed to a process for making pyridine compounds substituted in the 2-and 3-positions by aromatic or heteroaromatic groups, including 2,3-diphenyl-6-methyl pyridine, U.S. Pat. No. 4,006,149 is directed to processes for catalytic production of pyridines from alkynes and nitriles.

UK Patent 1,401,038 discloses the use of 2,4,6-triphenyl pyridine, pentaphenylpyridine, 2,3,5,6-tetraphenyl pyridine, 2-methyl-5-ethyl pyridine, 2,6-dichloropyridine and mixtures of methyl pyridines as chlorination catalysts.

The compounds of the present invention are modulators of the Cannabinoid-1 (CB1) receptor and are useful in the treatment, prevention and suppression of diseases mediated by the Cannabinoid-1 (CB1) receptor. In particular, compounds of the present invention are antagonists or inverse agonists of the CB1 receptor. The invention is concerned with the use of these compounds to modulate the Cannabinoid-1 (CB1) receptor. As such, compounds of the present invention are useful as centrally acting drugs in the treatment of psychosis, memory deficits, cognitive disorders, migraine, neuropathy, neuro-inflammatory disorders including multiple sclerosis and Guillain-Barre syndrome and the inflammatory sequelae of viral encephalitis, cerebral vascular accidents, and head trauma, anxiety disorders, stress, epilepsy, Parkinson's disease, movement disorders, and schizophrenia. The compounds are also useful for the treatment of substance abuse disorders, particularly to opiates, alcohol, marijuana, and nicotine. The compounds are also useful for the treatment of eating disorders by inhibiting excessive food intake and the resulting obesity and complications associated therewith including left ventricular hypertropy. The compounds are also useful for the treatment of constipation and chronic intestinal pseudo-obstruction, as well as for the treatment of asthma, and cirrhosis of the liver.

SUMMARY OF THE INVENTION

The present invention is concerned with novel 2,3-disubstituted pyridine derivatives of general Formula I:

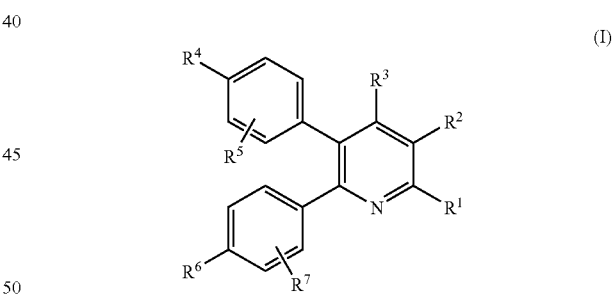

and pharmaceutically acceptable salts thereof which are antagonists and/or inverse agonists of the Cannabinoid-1 (CB1) receptor and are useful in the treatment, prevention and suppression of diseases mediated by the Cannabinoid-1 (CB1) receptor. The invention is concerned with the use of these novel compounds to selectively antagonize the Cannabinoid-1 (CB1) receptor. As such, compounds of the present invention are useful as centrally acting drugs in the treatment of psychosis, memory deficits, cognitive disorders, migraine, neuropathy, neuro-inflammatory disorders including multiple sclerosis and Guillain-Barre syndrome and the inflammatory sequelae of viral encephalitis, cerebral vascular accidents, and head trauma, anxiety disorders, stress, epilepsy, Parkinson's disease, movement disorders, and schizophrenia. The compounds are also useful for the treatment of substance abuse disorders, particularly to opiates, alcohol, marijuana, and nicotine, including smoking cessation. The compounds are also useful for the treatment of obesity or eating disorders associated with excessive food intake and complications associated therewith, including left ventricular hypertrophy. The compounds are also useful for the treatment of constipation and chronic intestinal pseudo-obstruction. The compounds are also useful for the treatment of cirrhosis of the liver. The compounds are also useful for the treatment of asthma.

The present invention is also concerned with treatment of these conditions, and the use of compounds of the present invention for manufacture of a medicament useful in treating these conditions. The present invention is also concerned with treatment of these conditions through a combination of compounds of formula I and other currently available pharmaceuticals.

The invention is also concerned with novel compounds of structural formula I.

The invention is also concerned with pharmaceutical formulations comprising one of the compounds as an active ingredient.

The invention is further concerned with processes for preparing the compounds of this invention.

DETAILED DESCRIPTION OF THE INVENTION

The compounds used in the methods of the present invention are represented by the compound of structural formula I:

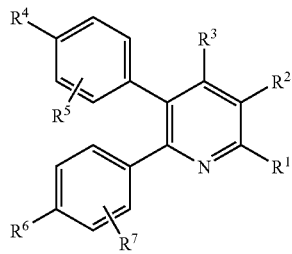

(I)

or a pharmaceutically acceptable salt thereof.

In one embodiment of the present invention, $R^1$ is selected from:
(1) hydrogen,
(2) halogen,
(3) $C_{1-4}$alkyl,
(4) cycloheteroalkyl,
(5) cycloheteroalkyl-$C_{1-4}$alkyl,
(6) heteroaryl,
(7) aryl-$C_{1-4}$alkyl,
(8) heteroaryl-$C_{1-4}$alkyl;
(9) —$OR^d$,
(10) —$SR^d$,
(11) —O—$(CR^fR^g)_n$—$NR^dR^e$,
(12) —O—$(CR^fR^g)_n$—NH—C(O)—$R^d$,
(13) —O—$(CR^fR^g)_n$—NH—S(O)$_p$$R^d$,
(14) —O—$(CR^fR^g)_n$—NH—C(O)—$NR^dR^e$,
(15) —O—$(CR^fR^g)_n$—C(O)—$NR^dR^e$,
(16) —$NR^dR^e$,
(17) —C(O)$R^d$,
(18) —$CO_2R^d$,
(19) —CN,
(20) —C(O)$NR^dR^e$,
(21) —$NR^eC(O)R^d$,
(22) —$NR^eC(O)OR^d$,
(23) —$NR^eC(O)NR^dR^e$, wherein the alkyl groups are optionally substituted with one to four substituents independently selected from $R^a$, and cycloheteroalkyl, aryl and heteroaryl are optionally substituted with one to four substituents independently selected from $R^b$;

In one class of this embodiment, $R^1$ is selected from:
(1) hydrogen,
(2) halogen,
(3) $C_{1-4}$alkyl,
(4) cycloheteroalkyl,
(5) cycloheteroalkyl-$C_{1-4}$alkyl,
(6) heteroaryl,
(7) aryl-$C_{1-4}$alkyl,
(8) heteroaryl-$C_{1-4}$alkyl;
(9) —$OR^d$,
(10) —$SR^d$,
(11) —O—$(CR^fR^g)_n$—$NR^dR^e$,
(12) —O—$(CR^fR^g)_n$—NH—C(O)—$R^d$,
(13) —O—$(CR^fR^g)_n$—NH—S(O)$_p$$R^d$,
(14) —O—$(CR^fR^g)_n$—NH—C(O)—$NR^dR^e$,
(15) —O—$(CR^fR^g)_n$—C(O)—$NR^dR^e$,
(16) —$NR^dR^e$,
(17) —$CO_2H$,
(18) —C(O)$NR^dR^e$,
(19) —$NR^eC(O)R^d$,
(20) —$NR^eC(O)OR^d$,
(21) —$NR^eC(O)NR^dR^e$, wherein the alkyl groups are optionally substituted with one to four substituents independently selected from $R^a$, and cycloheteroalkyl, aryl and heteroaryl are optionally substituted with one to four substituents independently selected from $R^b$.

In one subclass of this embodiment, $R^1$ is selected from:
(1) hydrogen,
(2) halogen,
(3) $C_{1-4}$alkyl,
(4) cycloheteroalkyl,
(5) heteroaryl,
(6) aryl-$C_{1-4}$alkyl,
(7) heteroaryl-$C_{1-4}$alkyl;
(8) —$OR^d$,
(9) —$SR^d$,
(10) —O—$(CH_2)_n$—$NR^dR^e$,
(11) —O—$(CH_2)_n$—NH—C(O)—$R^d$,
(12) —O—$(CH_2)_n$—NH—S(O)$_p$$R^d$,
(13) —O—$(CH_2)_n$—NH—C(O)—$NR^dR^e$,
(14) —O—$(CH_2)_n$—C(O)—$NR^dR^e$,
(15) —$NR^dR^e$, wherein $R^e$ is hydrogen,
(16) —$CO_2H$,
(17) —C(O)$NR^dR^e$,
(18) —NHC(O)$R^d$,
(19) —NHC(O)$OR^d$,
(20) —NHC(O)$NR^dR^e$, wherein the alkyl groups are optionally substituted with one to three substituents independently selected from $R^a$, and cycloheteroalkyl, aryl and heteroaryl are optionally substituted with one to three substituents independently selected from $R^b$.

In another class of this embodiment of the invention, $R^1$ is selected from:

(1) hydrogen,
(2) chloro,
(3) cycloheteroalkyl, selected from piperidyl, piperazinyl, pyrtolidinyl, morpholinyl, dihydroisoindolyl, pyranyl, tetrahydrofuranyl, and perhydroazepinyl,
(4) heteroaryl, selected from pyridinyl, oxazolidinyl, benzotriazolyl, imidazolyl, triazolyl, benzimidazolyl,
(5) benzyl,
(6) —$OR^d$,
(7) —$SR^d$,
(8) —O—$(CH_2)_2$—$NR^dR^e$,
(9) —O—$(CH_2)_2$—NH—C(O)—$R^d$,
(10) —O—$(CH_2)_2$—NH—$S(O)_pR^d$,
(11) —O—$(CH_2)_2$—NH—C(O)—$NR^dR^e$,
(12) —O—$(CH_2)_n$—C(O)—$NR^dR^e$,
(13) —$NR^dR^e$, wherein $R^e$ is hydrogen,
(14) —$CO_2H$,
(15) —$C(O)NR^dR^e$, wherein the cycloheteroalkyl, aryl and heteroaryl are optionally substituted with one to three substituents independently selected from $R^b$.

In another embodiment of the present invention, $R^2$ is selected from:
(1) hydrogen,
(2) cyano,
(3) —$C(O)OR^d$,
(4) —$C(O)NR^dR^e$,
(5) halogen,
(6) nitro,
(7) trifluoromethyl, and
(8) $C(O)NH$—$NR^dR^e$;

provided that R1 and R2 are not both hydrogen;

In one class of this embodiment, $R^2$ is selected from:
(1) hydrogen,
(2) cyano,
(3) —$C(O)OR^d$,
(4) —$C(O)NR^dR^e$,
(5) halogen,
(6) nitro, and
(7) $C(O)NH$—$NR^dR^e$;

provided that $R^1$ and $R^2$ are not both hydrogen.

In one subclass of this class, $R^2$ is selected from:
(1) hydrogen,
(2) cyano,
(3) —C(O)OH,
(4) —$C(O)OCH_3$,
(5) —$C(O)NR^dR^e$,
(6) halogen,
(7) nitro, and
(8) $C(O)NH$—$NR^dR^e$, wherein $R^e$ is hydrogen;

provided that $R^1$ and $R^2$ are not both hydrogen.

In one embodiment of the present invention, $R^3$ is selected from:
(1) hydrogen,
(2) $C_{1-3}$alkyl,
(3) cycloalkyl, and
(4) trifluoromethyl, wherein alkyl, and cycloalkyl are optionally substituted with one to four substituents independently selected from $R^a$.

In one class of this embodiment of the present invention, $R^3$ is selected from:
(1) hydrogen,
(2) $C_{1-3}$alkyl,
(3) cyclopropyl,
(4) trifluoromethyl, wherein alkyl and cyclopropyl are optionally substituted with a substituent independently selected from $R^a$.

In one subclass of this class, $R^3$ is selected from:
(1) hydrogen, and
(2) methyl.

In yet another subclass of this class, $R^3$ is hydrogen.

In one embodiment of the present invention, $R^4$, is selected from:
(1) hydrogen,
(2) halogen,
(3) amino,
(4) carboxy,
(5) $C_{1-4}$alkyl,
(6) $C_{1-4}$alkoxy,
(7) aryl,
(8) aryl $C_{1-4}$alkyl,
(9) hydroxy,
(10) trifluoromethyl,
(11) —$OC(O)C_{1-4}$alkyl, and
(12) —$OC(O)NR^dR^e$, In one class of this embodiment, $R^4$ is selected from:
(1) hydrogen,
(2) halogen,
(3) amino,
(4) carboxy,
(5) methyl,
(6) methoxy, and
(7) trifluoromethyl.

In one subclass of this class, $R^4$ is selected from:
(1) hydrogen,
(2) halogen, and
(3) methyl.

In another subclass of this class, $R^4$ is selected from:
(1) hydrogen,
(2) chloro
(3) fluoro, and
(4) methyl.

In one embodiment of the present invention, $R^5$ is selected from:
(1) hydrogen,
(2) halogen,
(3) amino,
(4) carboxy,
(5) $C_{1-4}$alkyl,
(6) $C_{1-4}$alkoxy,
(7) aryl,
(8) aryl $C_{1-4}$alkyl,
(9) hydroxy,
(10) trifluoromethyl,
(11) —$OC(O)C_{1-4}$alkyl, and
(12) —$OC(O)NR^dR^e$.

In one class of this embodiment, $R^5$ is selected from:
(1) hydrogen,
(2) halogen,
(3) amino,
(4) carboxy,
(5) methyl,
(6) methoxy, and
(7) trifluoromethyl.

In one subclass of this class, $R^5$ is selected from:
(1) hydrogen,
(2) halogen, and
(3) methyl.

In another subclass of this class, $R^5$ is hydrogen.

In another embodiment of the present invention, $R^6$ is selected from:
(1) hydrogen,
(2) halogen,
(3) amino,
(4) carboxy,
(5) $C_{1-4}$alkyl,
(6) $C_{1-4}$alkoxy,
(7) aryl,
(8) aryl $C_{1-4}$alkyl,
(9) hydroxy,
(10) trifluoromethyl,
(11) —OC(O)$C_{1-4}$alkyl, and
(12) —OC(O)NR$^d$R$^e$, provided that when $R^7$ is hydrogen, $R^6$ is not hydrogen.

In one class of this embodiment, $R^6$ is selected from:
(1) hydrogen,
(2) halogen,
(3) amino,
(4) carboxy,
(5) $C_{1-4}$alkyl,
(6) $C_{1-4}$alkoxy,
(7) aryl,
(8) benzyl,
(9) hydroxy,
(10) trifluoromethyl,
(11) —OC(O)$C_{1-4}$alkyl, and
(12) —OC(O)NR$^d$R$^e$, provided that when $R^7$ is hydrogen, $R^6$ is not hydrogen.

In one subclass of this class, $R^6$ is selected from:
(1) hydrogen,
(2) halogen,
(3) amino,
(4) carboxy,
(5) methyl,
(6) methoxy, and
(7) trifluoromethyl;

provided that when $R^7$ is hydrogen, $R^6$ is not hydrogen.

In another subclass of the present invention, $R^6$ is selected from:
(1) hydrogen, and
(2) halogen, provided that when $R^7$ is hydrogen, $R^6$ is not hydrogen.

In yet another subclass of the present invention, $R^6$ is selected from:
(1) hydrogen, and
(2) chloro, provided that when $R^7$ is hydrogen, $R^6$ is not hydrogen.

In another embodiment of the present invention, $R^7$ is selected from:
(1) hydrogen,
(2) halogen,
(3) amino,
(4) carboxy,
(5) $C_{1-4}$alkyl,
(6) $C_{1-4}$alkoxy,
(7) aryl,
(8) aryl $C_{1-4}$alkyl,
(9) hydroxy,
(10) trifluoromethyl,
(11) —OC(O)$C_{1-4}$alkyl, and
(12) —OC(O)NR$^d$R$^e$, provided that when $R^6$ is hydrogen, $R^7$ is not hydrogen.

In one class of this embodiment, $R^7$ is selected from:
(1) hydrogen,
(2) halogen,
(3) amino,
(4) carboxy,
(5) $C_{1-4}$alkyl,
(6) $C_{1-4}$alkoxy,
(7) aryl,
(8) benzyl,
(9) hydroxy,
(10) trifluoromethyl,
(11) —OC(O)$C_{1-4}$alkyl, and
(12) —OC(O)NR$^d$R$^e$, provided that when $R^6$ is hydrogen, $R^7$ is not hydrogen.

In one subclass of this class, $R^7$ is selected from:
(1) hydrogen,
(2) halogen,
(3) amino,
(4) carboxy,
(5) methyl,
(6) methoxy, and
(7) trifluoromethyl;

provided that when $R^6$ is hydrogen, $R^7$ is not hydrogen.

In another subclass of this class, $R^7$ is selected from:
(1) hydrogen, and
(2) halogen;

provided that when $R^6$ is hydrogen, $R^7$ is not hydrogen.

In yet another subclass of this class, $R^7$ is selected from:
(1) hydrogen, and
(2) chloro;

provided that when $R^6$ is hydrogen, $R^7$ is not hydrogen.

In one embodiment of the present invention, each $R^a$ is independently selected from:
(1) —OR$^d$,
(2) —NR$^e$S(O)$_m$R$^d$,
(3) —NO$_2$,
(4) halogen,
(5) —S(O)$_m$R$^d$,
(6) —SR$^d$,
(7) —S(O)$_2$OR$^d$,
(8) —S(O)$_m$NR$^d$R$^e$,
(9) —NR$^d$R$^e$,
(10) —O(CR$^f$R$^g$)$_n$NR$^d$R$^e$,
(11) —C(O)R$^d$,
(12) —CO$_2$R$^d$,
(13) —CO$_2$(CR$^f$R$^g$)$_n$CONR$^d$R$^e$,
(14) —OC(O)R$^d$,
(15) —CN,
(16) —C(O)NR$^d$R$^e$,
(17) —NR$^e$C(O)R$^d$,
(18) —OC(O)NR$^d$R$^e$,
(19) —NR$^e$C(O)OR$^d$,
(20) —NR$^e$C(O)NR$^d$R$^e$,
(21) —CR$^d$(N—OR$^d$),
(22) CF$_3$,
(23) —OCF$_3$, and
(24) $C_{3-8}$cycloalkyl.

In one class of this embodiment, each $R^a$ is independently selected from:
(1) —OR$^d$,
(2) —NR$^e$S(O)$_m$R$^d$,
(3) —NO$_2$,
(4) halogen,
(5) —S(O)$_m$R$^d$,
(6) —SR$^d$, (7) —S(O)$_2$OR$^d$,
(8) —S(O)$_m$NR$^d$R$^e$,
(9) —NR$^d$R$^e$,
(10) —O(CR$^f$R$^g$)$_n$NR$^d$R$^e$,
(11) —C(O)R$^d$,
(12) —CO$_2$R$^d$,
(13) —CO$_2$(CR$^f$R$^g$)$_n$CONR$^d$R$^e$,
(14) —OC(O)R$^d$,
(15) —CN,
(16) —C(O)NR$^d$R$^e$,
(17) —NR$^e$C(O)R$^d$,
(18) —OC(O)NR$^d$R$^e$,
(19) —NR$^e$C(O)OR$^d$,
(20) —NR$^e$C(O)NR$^d$R$^e$,
(21) —CR$^e$(N—OR$^d$),
(22) —CF$_3$,
(23) —OCF$_3$, and
(24) C$_{3-8}$cycloalkyl.

In one subclass of this embodiment, each R$^a$ is independently selected from:
(1) OR$^d$,
(2) —NHS(O)$_2$R$^d$,
(3) —NO$_2$,
(4) halogen,
(5) —S(O)$_2$R$^d$,
(6) —SR$^d$,
(7) —S(O)$_2$OR$^d$,
(8) —S(O)$_2$NH$_2$,
(9) —NHR$^d$,
(10) —O(CH$_2$)$_n$NHR$^d$,
(11) —C(O)R$^d$,
(12) —CO$_2$R$^d$,
(13) —CO$_2$(CH$_2$)$_n$CONHR$^d$,
(14) —OC(O)R$^d$,
(15) —CN,
(16) —C(O)NHR$^d$,
(17) —NHC(O)R$^d$,
(18) —OC(O)NHR$^d$,
(19) —NHC(O)OR$^d$,
(20) —NHC(O)NHR$^d$,
(21) —CH(N—OR$^d$),
(22) —CF$_3$,
(23) —OCF$_3$, and
(24) C$_{3-8}$cycloalkyl.

In one embodiment of the present invention, each R$^b$ is independently selected from:
(1) R$^a$,
(2) C$_{1-4}$ alkyl,
(3) C$_{2-4}$ alkenyl,
(4) C$_{2-4}$ alkynyl,
(5) aryl, and
(6) aryl-C$_{1-4}$ alkyl;

wherein alkyl, alkenyl, alkynyl, and aryl are optionally substituted with one to four substituents selected from a group independently selected from R$^c$.

In one class of this embodiment, each R$^b$ is independently selected from:
(1) R$^a$,
(2) C$_{1-4}$ alkyl,
(3) aryl, and
(4) aryl-C$_{1-4}$ alkyl;

wherein alkyl and aryl are optionally substituted with one to four substituents selected from a group independently selected from R$^c$.

In one subclass of this class, alkyl and aryl are optionally substituted with one to three substituents selected from a group independently selected from R$^c$.

In another subclass of this class, each R$^b$ is independently selected from:
(1) halogen,
(2) —CF$_3$,
(3) cyclopropyl, and
(4) methyl.

In one embodiment of the present invention, each R$^c$ is independently selected from:
(1) halogen,
(2) amino,
(3) carboxy,
(4) C$_{1-4}$alkyl,
(5) C$_{1-4}$alkoxy,
(6) aryl,
(7) aryl C$_{1-4}$alkyl,
(8) hydroxy,
(9) CF$_3$,
(10) —OC(O)C$_{1-4}$alkyl, and
(11) —OC(O)NR$^d$R$^e$.

In one class of this embodiment, each R$^c$ is independently selected from:
(1) halogen,
(2) amino,
(3) carboxy,
(4) methyl,
(5) methoxy,
(6) phenyl,
(7) benzyl,
(8) hydroxy,
(9) CF$_3$,
(10) —OC(O)C$_{1-4}$alkyl, and
(11) —OC(O)NHR$^d$.

In one embodiment of the present invention, each R$^d$ is independently selected from:
(1) hydrogen;
(2) C$_{1-10}$alkyl, unsubstituted or substituted with one to three substituents selected from R$^h$;
(3) C$_{2-10}$alkenyl;
(4) C$_{2-10}$alkynyl;
(5) cycloalkyl, unsubstituted or substituted with one to three substituents selected from R$^h$;
(6) cycloalkyl-C$_{1-4}$alkyl;
(7) cycloheteroalkyl, unsubstituted or substituted with one to three substituents selected from R$^h$;
(8) cycloheteroalkyl-C$_{1-4}$ alkyl, unsubstituted or substituted with an R$^h$ substitutent;
(9) aryl, unsubstituted or substituted with one to three substituents selected from R$^h$;
(10) heteroaryl, unsubstituted or substituted with one to three substituents selected from R$^h$;
(11) aryl-C$_{1-4}$alkyl, unsubstituted or substituted with one to three substituents selected from R$^h$; and
(12) heteroaryl-C$_{1-4}$alkyl, unsubstituted or substituted with one to three substituents selected from R$^h$; or R$^d$ together with R$^e$ and with the atom(s) to which they are attached form a heterocyclic ring of 4 to 7 members containing 0-2 additional heteroatoms independently selected from oxygen, sulfur and N—R$^h$, unsubstituted or substituted with one or two oxo groups.

In one class of this embodiment, R$^d$ is selected from:
(1) hydrogen;
(2) C$_{1-10}$alkyl, unsubstituted or substituted with one to three substituents selected from R$^h$;

(3) $C_{2-4}$ alkenyl;
(4) cycloalkyl, unsubstituted or substituted with one to three substituents selected from $R^h$;
(5) cycloalkyl-$C_{1-4}$alkyl;
(6) cycloheteroalkyl, unsubstituted or substituted with one to three substituents selected from $R^h$;
(7) cycloheteroalkyl-$C_{1-4}$ alkyl, unsubstituted or substituted with an Rh substituent;
(8) aryl, unsubstituted or substituted with one to three substituents selected from $R^h$;
(9) heteroaryl, unsubstituted or substituted with one to three substituents selected from $R^h$;
(10) aryl-$C_{1-4}$alkyl, unsubstituted or substituted with one to three substituents selected from $R^h$; and
(11) heteroaryl-$C_{1-4}$alkyl, unsubstituted or substituted with one to three substituents selected from $R^h$;

$R^d$ together with $R^e$ and with the atom(s) to which they are attached form a heterocyclic ring of 4 to 7 members containing 0 to 2 additional heteroatoms independently selected from oxygen, sulfur and N—$R^h$, unsubstituted or substituted with one or two oxo groups.

In one subclass of this class, $R^d$ is selected from:
(1) hydrogen;
(2) $C_{1-10}$alkyl;
(3) $C_{2-4}$ alkenyl;
(4) cycloalkyl;
(5) cycloalkyl-$C_{1-4}$alkyl;
(6) cycloheteroalkyl, unsubstituted or substituted with one to three substituents selected from $R^h$;
(7) cycloheteroalkyl-$C_{1-4}$ alkyl, unsubstituted or substitute with a Rh substituent;
(8) aryl, unsubstituted or substituted with one to three substituents selected from $R^h$;
(9) heteroaryl, unsubstituted or substituted with one to three substituents selected from $R^h$;
(10) aryl-$C_{1-4}$alkyl, unsubstituted or substituted with one to two substituents selected from $R^h$; and
(11) heteroaryl-$C_{1-4}$alkyl, unsubstituted or substituted with one to three substituents selected from $R^h$;

$R^d$ together with $R^e$ and with the atom(s) to which they are attached form a heterocyclic ring of 4 to 7 members containing 0 to 2 additional heteroatoms independently selected from oxygen, sulfur and N—$R^h$, unsubstituted or substituted with one or two oxo groups.

In another class of the present embodiment, In one class of this embodiment, $R^d$ is selected from:
(1) hydrogen;
(2) $C_{1-10}$alkyl, unsubstituted or substituted with one to three substituents selected from $R^h$;
(3) $C_{2-4}$ alkenyl;
(4) cycloalkyl, unsubstituted or substituted with one to three substituents selected from $R^h$;
(5) cycloalkyl-$C_{1-4}$alkyl;
(6) cycloheteroalkyl, unsubstituted or substituted with one to three substituents selected from $R^h$;
(7) cycloheteroalkyl-$C_{1-4}$ alkyl, unsubstituted or substituted with an Rh substituent;
(8) aryl, unsubstituted or substituted with one to three substituents selected from $R^h$;
(9) heteroaryl, unsubstituted or substituted with one to three substituents selected from $R^h$;
(10) aryl-$C_{1-4}$alkyl, unsubstituted or substituted with one to three substituents selected from $R^h$; and
(11) heteroaryl-$C_{1-4}$alkyl, unsubstituted or substituted with one to three substituents selected from $R^h$;

$R^d$ together with $R^e$ and with the atom(s) to which they are attached form a heterocyclic ring of 4 to 7 members containing 0 to 1 additional heteroatoms independently selected from oxygen, sulfur and N—$R^h$, unsubstituted or substituted with one or two oxo groups.

In one embodiment of the present invention, each $R^e$ is independently selected from:
(1) hydrogen;
(2) $C_{1-10}$alkyl, unsubstituted or substituted with one to three substituents selected from $R^h$;
(3) $C_{2-10}$alkenyl;
(4) $C_{2-10}$alkynyl;
(5) cycloalkyl, unsubstituted or substituted with one to three substituents selected from $R^h$;
(6) cycloalkyl-$C_{1-4}$alkyl;
(7) cycloheteroalkyl, unsubstituted or substituted with one to three substituents selected from $R^h$;
(8) cycloheteroalkyl-$C_{1-4}$ alkyl, unsubstituted or substituted with an $R^h$ substitutent;
(9) aryl, unsubstituted or substituted with one to three substituents selected from $R^h$;
(10) heteroaryl, unsubstituted or substituted with one to three substituents selected from $R^h$;
(11) aryl-$C_{1-4}$alkyl, unsubstituted or substituted with one to three substituents selected from $R^h$; and
(12) heteroaryl-$C_{1-4}$alkyl, unsubstituted or substituted with one to three substituents selected from $R^h$; or $R^e$ together with $R^d$ and with the atom(s) to which they are attached form a heterocyclic ring of 4 to 7 members containing 0-2 additional heteroatoms independently selected from oxygen, sulfur and N—$R^h$, unsubstituted or substituted with one or two oxo groups.

In one class of this embodiment, $R^e$ is selected from:
(1) hydrogen;
(2) $C_{1-10}$alkyl, unsubstituted or substituted with one to three substituents selected from $R^h$;
(3) $C_{2-4}$ alkenyl;
(4) cycloalkyl, unsubstituted or substituted with one to three substituents selected from $R^h$;
(5) cycloalkyl-$C_{1-4}$alkyl;
(6) cycloheteroalkyl, unsubstituted or substituted with one to three substituents selected from $R^h$;
(7) cycloheteroalkyl-$C_{1-4}$ alkyl, unsubstituted or substituted with an Rh substituent;
(8) aryl, unsubstituted or substituted with one to three substituents selected from $R^h$;
(9) heteroaryl, unsubstituted or substituted with one to three substituents selected from $R^h$;
(10) aryl-$C_{1-4}$alkyl, unsubstituted or substituted with one to three substituents selected from $R^h$; and
(11) heteroaryl-$C_{1-4}$alkyl, unsubstituted or substituted with one to three substituents selected from $R^h$;

$R^e$ together with $R^d$ and with the atom(s) to which they are attached form a heterocyclic ring of 4 to 7 members containing 0 to 2 additional heteroatoms independently selected from oxygen, sulfur and N—$R^h$, unsubstituted or substituted with one or two oxo groups.

In one subclass of this class, $R^e$ is selected from:
(1) hydrogen;
(2) $C_{1-10}$alkyl;
(3) $C_{2-4}$alkenyl;
(4) cycloalkyl;
(5) cycloalkyl-$C_{1-4}$alkyl;
(6) cycloheteroalkyl, unsubstituted or substituted with one to three substituents selected from $R^h$;

(7) cycloheteroalkyl-$C_{1-4}$ alkyl, unsubstituted or substitute with a Rh substituent;
(8) aryl, unsubstituted or substituted with one to three substituents selected from $R^h$;
(9) heteroaryl, unsubstituted or substituted with one to three substituents selected from $R^h$;
(10) aryl-$C_{1-4}$alkyl, unsubstituted or substituted with one to two substituents selected from $R^h$; and
(11) heteroaryl-$C_{1-4}$alkyl, unsubstituted or substituted with one to three substituents selected from $R^h$;

$R^e$ together with $R^d$ and with the atom(s) to which they are attached form a heterocyclic ring of 4 to 7 members containing 0 to 2 additional heteroatoms independently selected from oxygen, sulfur and N—$R^h$, unsubstituted or substituted with one or two oxo groups.

In one subclass of this class, $R^e$ is hydrogen.

In another class of the present embodiment, $R^e$ is selected from:
(1) hydrogen;
(2) $C_{1-10}$alkyl, unsubstituted or substituted with one to three substituents selected from $R^h$;
(3) $C_{2-4}$ alkenyl;
(4) cycloalkyl, unsubstituted or substituted with one to three substituents selected from $R^h$;
(5) cycloalkyl-$C_{1-4}$alkyl;
(6) cycloheteroalkyl, unsubstituted or substituted with one to three substituents selected from $R^h$;
(7) cycloheteroalkyl-$C_{1-4}$ alkyl, unsubstituted or substituted with an Rh substituent;
(8) aryl, unsubstituted or substituted with one to three substituents selected from $R^h$;
(9) heteroaryl, unsubstituted or substituted with one to three substituents selected from $R^h$;
(10) aryl-$C_{1-4}$alkyl, unsubstituted or substituted with one to three substituents selected from $R^h$; and
(11) heteroaryl-$C_{1-4}$alkyl, unsubstituted or substituted with one to three substituents selected from $R^h$;

$R^e$ together with $R^d$ and with the atom(s) to which they are attached form a heterocyclic ring of 4 to 7 members containing 0 to 1 additional heteroatoms independently selected from oxygen, sulfur and N—$R^h$, unsubstituted or substituted with one or two oxo groups.

In one subclass of this class, $R^e$ is hydrogen.

In one embodiment of the present invention, $R^f$ and $R^g$ are independently selected from:
(1) hydrogen, and
(2) $C_{1-4}$alkyl.

In one class of this embodiment, $R^f$ and $R^g$ are independently selected from:
(1) hydrogen, and
(2) methyl.

In one embodiment of the present invention, each $R^h$ is independently selected from:
(1) halogen,
(2) amino,
(3) hydroxycarbonyl,
(4) $C_{1-4}$alkyl,
(5) $C_{1-4}$alkoxy,
(6) aryl,
(7) aryl $C_{1-4}$alkyl,
(8) hydroxy,
(9) —$CF_3$,
(10) —OC(O)$C_{1-4}$alkyl,
(11) aryloxy,
(12) $C_{1-4}$alkyloxycarbonyl-, and
(13) —C(O)—NH—$C_{1-4}$alkyl.

In one class of this embodiment, each $R^h$ is independently selected from:
(1) halogen,
(2) amino,
(3) hydroxycarbonyl,
(4) methyl,
(5) methoxy-,
(6) phenyl,
(7) benzyl,
(8) hydroxy,
(9) trifluoromethyl,
(10) methylcarbonyloxy-,
(11) $C_{1-4}$alkyloxycarbonyl-, and
(12) —C(O)—NH—$C_{1-4}$alkyl;

Particular novel compounds of structural formula I which may be employed in the methods, uses and compositions of the present invention, include:
(1) methyl 2-(benzyloxy)-6-(4-chlorophenyl)-5-(phenyl)pyridine-3-carboxylate;
(2) methyl 2-(allyloxy)-6-(4-chlorophenyl)-5-(phenyl)pyridine-3-carboxylate;
(3) 2-(benzyloxy)-6-(4-chlorophenyl)-5-(phenyl)pyridine-3-nitrile;
(4) 2-(methoxy)-6-(4-chlorophenyl)-5-(phenyl)pyridine-3-nitrile; methyl 2-(methoxy)-6-(4-chlorophenyl)-5-(phenyl)pyridine-3-carboxylate;
(6) methyl 2-(methoxy)-6-(4-chlorophenyl)-5-(phenyl)pyridine-3-carboxylate;
(7) N-(piperidin-1-yl)-2-(methoxy)-6-(4-chlorophenyl)-5-(phenyl)pyridine-3-carboxamide;
(8) 2-(methoxy)-6-(4-chlorophenyl)-5-(phenyl)-3-(piperidin-1-ylcarbonyl)pyridine;
(9) N-(morpholin-4-yl)-2-(methoxy)-6-(4-chlorophenyl)-5-(phenyl)pyridine-3-carboxamide;
(10) N-(t-butyl)-2-(methoxy)-6-(4-chlorophenyl)-5-(phenyl)pyridine-3-carboxamide;
(11) N-(cyclopentyl)-2-(methoxy)-6-(4-chlorophenyl)-5-(phenyl)pyridine-3-carboxamide;
(12) N-(phenyl)-2-(methoxy)-6-(4-chlorophenyl)-5-(phenyl)pyridine-3-carboxamide;
(13) N-(cyclohexyl)-2-(benzyloxy)-6-(4-chlorophenyl)-5-(phenyl)pyridine-3-carboxamide;
(14) N-benzyl-2-(benzyloxy)-6-(4-chlorophenyl)-5-(phenyl)pyridine-3-carboxamide;
(15) N-(n-pentyl)2-(benzyloxy)-6-(4-chlorophenyl)-5-(phenyl)pyridine-3-carboxamide;
(16) N-(t-butyl)-2-(benzyloxy)-6-(4-chlorophenyl)-5-(phenyl)pyridine-3-carboxamide;
(17) N-(piperidin-1-yl)-2-(benzyloxy)-6-(4-chlorophenyl)-5-(phenyl)pyridine-3-carboxamide;
(18) N,N-dimethyl-2-(benzyloxy)-6-(4-chlorophenyl)-5-(phenyl)pyridine-3-carboxamide;
(19) N-methyl-2-(benzyloxy)-6-(4-chlorophenyl)-5-(phenyl)pyridine-3-carboxamide;
(20) 2-(benzyloxy)-6-(2,4-dichlorophenyl)-5-(4-chlorophenyl)pyridine-3-nitrile;
(21) 2-(4-fluorobenzyloxy)-6-(2,4-dichlorophenyl)-5-(4-chlorophenyl)pyridine-3-nitrile;
(22) 2-(2,4-difluorobenzyloxy)-6-(2,4-dichlorophenyl)-5-(4-chlorophenyl)pyridine-3-nitrile;
(23) 2-(3,4-difluorobenzyloxy)-6-(2,4-dichlorophenyl)-5-(4-chlorophenyl)pyridine-3-nitrile;
(24) 2-(3,5-difluorobenzyloxy)-6-(2,4-dichlorophenyl)-5-(4-chlorophenyl)pyridine-3-nitrile;
(25) 2-(4-trifluoromethylbenzyloxy)-6-(2,4-dichlorophenyl)-5-(4-chlorophenyl)pyridine-3-nitrile;

(26) 5-(4-chlorophenyl)-6-(2,4-dichlorophenyl)-2-[2-(1,3-dioxo-1,3-dihydro-2H-isoindol-2-yl)ethoxy]nicotinonitrile;
(27) 2-(2-aminoethoxy)-5-(4-chlorophenyl)-6-(2,4-dichlorophenyl)nicotinonitrile;
(28) N-(2-{[5-(4-chlorophenyl)-3-cyano-6-(2,4-dichlorophenyl)pyridin-2-yl]oxy}ethyl)benzamide;
(29) N-(2-{[5-(4-chlorophenyl)-3-cyano-6-(2,4-dichlorophenyl)pyridin-2-yl]oxy}ethyl)4-fluorobenzamide;
(30) N-(2-{[5-(4-chlorophenyl)-3-cyano-6-(2,4-dichlorophenyl)pyridin-2-yl]oxy}ethyl)cyclopentanecarboxamide;
(31) N-(2-{[5-(4-chlorophenyl)-3-cyano-6-(2,4-dichlorophenyl)pyridin-2-yl]oxy}ethyl)cyclobutanecarboxamide;
(32) N-(2-{[5-(4-chlorophenyl)-3-cyano-6-(2,4-dichlorophenyl)pyridin-2-yl]oxy}ethyl)cyclopropanecarboxamide;
(33) 2-chloro-5-(4-chlorophenyl)-6-(2,4-dichlorophenyl)-N-piperidin-1-ylnicotinamide;
(34) N-(n-hexyl)-2-(chloro)-6-(2,4-dichlorophenyl)-5-(4-chlorophenyl)pyridine-3-carboxamide;
(35) N-(n-propyl)-2-(chloro)-6-(2,4-dichlorophenyl)-5-(4-chlorophenyl)pyridine-3—
(36) N-N-(dimethyl)-2-(chloro)-6-(2,4-dichlorophenyl)-5-(4-chlorophenyl)pyridine-3-carboxamide;
(37) 2-chloro-5-(4-chlorophenyl)-6-(2,4-dichlorophenyl)nicotinonitrile;
(38) 2-[(3-chlorobenzyl)oxy]-5-(4-chlorophenyl)-6-(2,4-dichlorophenyl)nicotinonitrile;
(39) 5-(4-chlorophenyl)-2-(cyclohexyloxy)-6-(2,4-dichlorophenyl)nicotinonitrile;
(40) 5-(4-chlorophenyl)-2-[(5-chloropyridin-3-yl)oxy]-6-(2,4-dichlorophenyl)-nicotinonitrile;
(41) 5-(4-chlorophenyl)-2-(3,5-dichlorophenoxy)-6-(2,4-dichlorophenyl) nicotinonitrile;
(42) 5-(4-chlorophenyl)-6-(2,4-dichlorophenyl)-2-(pyridin-3-yloxy)nicotinonitrile;
(43) 5-(4-chlorophenyl)-6-(2,4-dichlorophenyl)-2-(4-methoxyphenoxy) nicotinonitrile;
(44) 2-(3-chlorophenoxy)-5-(4-chlorophenyl)-6-(2,4-dichlorophenyl)nicotinonitrile;
(45) 2-(4-chlorophenoxy)-5-(4-chlorophenyl)-6-(2,4-dichlorophenyl)nicotinonitrile;
(46) 5-(4-chlorophenyl)-6-(2,4-dichlorophenyl)-2-(4-fluorophenoxy)nicotinonitrile;
(47) 5-(4-chlorophenyl)-6-(2,4-dichlorophenyl)-2-(3-fluorophenoxy)nicotinonitrile;
(48) 5-(4-chlorophenyl)-6-(2,4-dichlorophenyl)-2-(3,4-difluorophenoxy) nicotinonitrile;
(49) 5-(4-chlorophenyl)-6-(2,4-dichlorophenyl)-2-[1-(4-fluorophenyl)ethoxy]-nicotinonitrile;
(50) 5-(4-chlorophenyl)-6-(2,4-dichlorophenyl)-2-[(4-fluorophenyl)thio]nicotinonitrile;
(51) 5-(4-chlorophenyl)-6-(2,4-dichlorophenyl)-2-(3,4-difluorobenzyl) nicotinonitrile;
(52) methyl 2-(benzyloxy)-6-(2,4-dichlorophenyl)-5-(4-chlorophenyl)pyridine-3-carboxylate;
(53) N-(piperidin-1-yl)-2-(benzyloxy)-6-(2,4-dichlorophenyl)-5-(4-chlorophenyl)pyridine-3-carboxamide;
(54) 2-(benzyloxy)-6-(2,4-dichlorophenyl)-5-(4-chlorophenyl)-3-(piperidinocarbonyl)pyridine;
(55) N-(n-pentyl)-2-(benzyloxy)-6-(2,4-dichlorophenyl)-5-(4-chlorophenyl) pyridine-3-carboxamide;
(56) N-(n-propyl)-2-(benzyloxy)-6-(2,4-dichlorophenyl)-5-(4-chlorophenyl) pyridine-3-carboxamide;
(57) N-(methyl)-2-(benzyloxy)-6-(2,4-dichlorophenyl)-5-(4-chlorophenyl)pyridine-3-carboxamide;
(58) N-N-(dimethyl)-2-(benzyloxy)-6-(2,4-dichlorophenyl)-5-(4-chlorophenyl) pyridine-3-carboxamide;
(59) N-(ethyl)-2-(benzyloxy)-6-(2,4-dichlorophenyl)-5-(4-chlorophenyl)pyridine-3-carboxamide;
(60) N-(n-butyl)-2-(benzyloxy)-6-(2,4-dichlorophenyl)-5-(4-chlorophenyl)pyridine-3-carboxamide;
(61) N-(cyclopentyl)-2-(benzyloxy)-6-(2,4-dichlorophenyl)-5-(4-chlorophenyl) pyridine-3-carboxamide;
(62) 2-(benzyloxy)-6-(2,4-dichlorophenyl)-5-(4-chlorophenyl)pyridine-3-carboxamide;
(63) methyl 6-(2,4-dichlorophenyl)-5-(4-chlorophenyl)pyridine-3-carboxylate;
(64) N-(piperidin-1-yl)-6-(2,4-dichlorophenyl)-5-(4-chlorophenyl)pyridine-3-carboxamide;
(65) 6-(2,4-dichlorophenyl)-5-(4-chlorophenyl)-3-(piperidinocarbonyl)pyridine;
(66) N-(cyclohexyl)-6-(2,4-dichlorophenyl)-5-(4-chlorophenyl)pyridine-3-carboxamide;
(67) N-(n-hexyl)-6-(2,4-dichlorophenyl)-5-(4-chlorophenyl)pyridine-3-carboxamide;
(68) methyl 2-(n-butoxy)-6-(2,4-dichlorophenyl)-5-(4-chlorophenyl)pyridine-3-carboxylate;
(69) methyl 2-(n-pentoxy)-6-(2,4-dichlorophenyl)-5-(4-chlorophenyl)pyridine-3-carboxylate;
(70) methyl 2-(cyclopropylmethoxy)-6-(2,4-dichlorophenyl)-5-(4-chlorophenyl) pyridine-3-carboxylate;
(71) methyl 2-(cyclohexylmethoxy)-6-(2,4-dichlorophenyl)-5-(4-chlorophenyl) pyridine-3-carboxylate;
(72) methyl 2-(2-ethoxyethoxy)-6-(2,4-dichlorophenyl)-5-(4-chlorophenyl) pyridine-3-carboxylate;
(73) N-methyl-2-(cyclohexylmethoxy)-6-(2,4-dichlorophenyl)-5-(4-chlorophenyl)pyridine-3-carboxamide;
(74) N-(n-propyl)-2-(cyclohexylmethoxy)-6-(2,4-dichlorophenyl)-5-(4-chlorophenyl)pyridine-3-carboxamide;
(75) 2-(n-butoxy)-6-(2,4-dichlorophenyl)-5-(4-chlorophenyl)pyridine-3-carboxamide;
(76) N-methyl-2-(n-butoxy)-6-(2,4-dichlorophenyl)-5-(4-chlorophenyl)pyridine-3-carboxamide;
(77) N-(n-propyl)-2-(n-butoxy)-6-(2,4-dichlorophenyl)-5-(4-chlorophenyl)pyridine-3-carboxamide;
(78) N-cyclopentyl-2-(n-butoxy)-6-(2,4-dichlorophenyl)-5-(4-chlorophenyl) pyridine-3-carboxamide;
(79) methyl 2-(3,4-difluorobenzyloxy)-6-(2,4-dichlorophenyl)-5-(4-chlorophenyl)pyridine-3-carboxylate;
(80) 5-(4-chlorophenyl)-6-(2,4-dichlorophenyl)-2-[(3,4-difluorobenzyl)oxy]nicotinic acid;
(81) 5-(4-chlorophenyl)-6-(2,4-dichlorophenyl)-2-[(3,4-difluorobenzyl)oxy]-N-methylnicotinamide;
(82) N-(ethyl)-2-(3,4-difluorobenzyloxy)-6-(2,4-dichlorophenyl)-5-(4-chlorophenyl)pyridine-3-carboxamide;
(83) N-(n-propyl)-2-(3,4-difluorobenzyloxy)-6-(2,4-dichlorophenyl)-5-(4-chlorophenyl)pyridine-3-carboxamide;
(84) N-(2-fluoroethyl)-2-(3,4-difluorobenzyloxy)-6-(2,4-dichlorophenyl)-5-(4-chlorophenyl)pyridine-3-carboxamide;
(85) N-(i-propyl)-2-(3,4-difluorobenzyloxy)-6-(2,4-dichlorophenyl)-5-(4-chlorophenyl)pyridine-3-carboxamide;
(86) methyl 2-chloro-5-(4-chlorophenyl)-6-(2,4-dichlorophenyl)nicotinate;
(87) methyl 5-(4-chlorophenyl)-6-(2,4-dichlorophenyl)-2-(3,4-difluorophenoxy)nicotinate;
(88) methyl 5-(4-chlorophenyl)-2-[(5-chloropyridin-3-yl)oxy]-6-(2,4-dichlorophenyl)nicotinate;
(89) 5-(4-chlorophenyl)-6-(2,4-dichlorophenyl)-2-(3,4-difluorophenoxy)nicotinic acid;

(90) 5-(4-chlorophenyl)-6-(2,4-dichlorophenyl)-2-(3,4-difluorophenoxy)-N-ethylnicotinamide;
(91) 5-(4-chlorophenyl)-6-(2,4-dichlorophenyl)-2-(3,4-difluorophenoxy)-N-methylnicotinamide;
(92) 5-(4-chlorophenyl)-6-(2,4-dichlorophenyl)-2-(3,4-difluorophenoxy)-N',N'-dimethylnicotinohydrazide;
(93) 5-(4-chlorophenyl)-6-(2,4-dichlorophenyl)-2-(3,4-difluorophenoxy)-N-pyrrolidin-1-ylnicotinamide;
(94) 5-(4-chlorophenyl)-N-cyclohexyl-6-(2,4-dichlorophenyl)-2-(3,4-difluorophenoxy)nicotinamide;
(95) 5-(4-chlorophenyl)-6-(2,4-dichlorophenyl)-2-(3,4-difluorophenoxy) nicotinamide;
(96) 5-(4-chlorophenyl)-6-(2,4-dichlorophenyl)-2-(3,4-difluorophenoxy)-N-isopropylnicotinamide;
(97) 3-(4-chlorophenyl)-2-(2,4-dichlorophenyl)-6-[(3,4-difluorobenzyl)oxy]pyridine;
(98) methyl 6-(2,4-dichlorophenyl)-5-(4-chlorophenyl)pyridine-2-carboxylate;
(99) N-(cyclohexyl)-6-(2,4-dichlorophenyl)-5-(4-chlorophenyl)pyridine-2-carboxamide;
(100) N-(piperidin-1-yl)-6-(2,4-dichlorophenyl)-5-(4-chlorophenyl)pyridine-2-carboxamide;
(101) 6-(2,4-dichlorophenyl)-5-(4-chlorophenyl)-2-(piperidinyl-1-carbonyl)pyridine;
(102) N-(n-hexyl)-6-(2,4-dichlorophenyl)-5-(4-chlorophenyl)pyridine-2-carboxamide;
(103) N-(cyclopentyl)-6-(2,4-dichlorophenyl)-5-(4-chlorophenyl)pyridine-2-carboxamide;
(104) N-(cycloheptyl)-6-(2,4-dichlorophenyl)-5-(4-chlorophenyl)pyridine-2-carboxamide;
(105) N-(heptyl)-6-(2,4-dichlorophenyl)-5-(4-chlorophenyl) pyxidine-2-carboxamide;
(106) N-(benzyl)-6-(2,4-dichlorophenyl)-5-(4-chlorophenyl)pyridine-2-carboxamide;
(107) N-(phenyl)-6-(2,4-dichlorophenyl)-5-(4-chlorophenyl)pyridine-2-carboxamide; methyl 6-(2,4-dichlorophenyl)-2-[(3,4-difluorobenzyl)oxy]-5-(4-fluorophenyl)nicotinate;
(109) 6-(2,4-dichlorophenyl)-2-[(3,4-difluorobenzyl)oxy]-5-(4-fluorophenyl) nicotinic acid;
(110) 6-(2,4-dichlorophenyl)-2-[(3,4-difluorobenzyl)oxy]-5-(4-fluorophenyl)-N-methylnicotinamide;
(111) 2-[(3-chlorobenzyl)oxy]-6-(2,4-dichlorophenyl)-5-(4-fluorophenyl) nicotinonitrile;
(112) 6-(2,4-dichlorophenyl)-2-[(3,4-difluorobenzyl)oxy]-5-(4-fluorophenyl) nicotinonitrile;
(113) 6-(2,4-dichlorophenyl)-5-(4-fluorophenyl)-2-(pyridin-3-ylmethoxy) nicotinonitrile;
(114) 2-[(4-chlorobenzyl)oxy]-6-(2,4-dichlorophenyl)-5-(4-fluorophenyl) nicotinonitrile;
(115) 2-[(6-chloropyridin-3-yl)methoxy]-6-(2,4-dichlorophenyi)-5-(4-fluorophenyl) nicotinonitrile;
(116) methyl 2-chloro-6-(2,4-dichlorophenyl)-5-(4-fluorophenyl)nicotinate;
(117) methyl 6-(2,4-dichlorophenyl)-2-(3,4-difluorophenoxy)-5-(4-fluorophenyl) nicotinate;
(118) 2-chloro-6-(2,4-dichlorophenyl)-5-(4-methylphenyl) nicotinonitrile;
(119) 6-(2,4-dichlorophenyl)-5-(4-methylphenyl)-2-(1-(4-fluorophenyl)ethoxy)nicotinonitrile;
(120) 6-(2,4-dichlorophenyl)-2-[2-(diethylamino)ethoxy]-5-(4-methylphenyl) nicotinonitrile;
(121) 6-(2,4-dichlorophenyl)-2-(3,4-difluorophenoxy)-5-(4-methylphenyl) nicotinonitrile;
(122) 2-(cyclohexylmethoxy)-6-(2,4-dichlorophenyl)-5-(4-methylphenyl) nicotinonitrile;
(123) 2-butoxy-6-(2,4-dichlorophenyl)-5-(4-methylphenyl) nicotinonitrile;
(124) 6-(2,4-dichlorophenyl)-2-[(3,4-difluorobenzyl)oxy]-5-(4-methylphenyl)-nicotinonitrile;
(125) methyl 4-({[3-cyano-6-(2,4-dichlorophenyl)-5-(4-methylphenyl)pyridin-2-yl]oxy}methyl)benzoate;
(126) 4-({[3-cyano-6-(2,4-dichlorophenyl)-5-(4-methylphenyl)pyridin-2-yl]oxy}methyl)benzoic acid;
(127) 4-({[3-cyano-6-(2,4-dichlorophenyl)-5-(4-methylphenyl)pyridin-2-yl]oxy}methyl)-N-methylbenzamide;
(128) 6-(2,4-dichlorophenyl)-5-(4-methylphenyl)-2-piperidin-1-ylnicotinonitrile;
(129) 2-(cyclohexylamino)-6-(2,4-dichlorophenyl)-5-(4-methylphenyl) nicotinonitrile;
(130) 6-(2,4-dichlorophenyl)-5-(4-methylphenyl)-2-(4-methylpiperazin-1-yl) nicotinonitrile;
(131) 6-(2,4-dichlorophenyl)-2-[(3,4-difluorobenzyl)amino]-5-(4-methylphenyl)-nicotinonitrile
(132) 6-(2,4-dichlorophenyl)-5-(4-methylphenyl)-2-pyrrolidin-1-ylnicotinonitrile;
(133) 6-(2-chlorophenyl)-5-(4-chlorophenyl)-2-[(3,4-difluorobenzyl)oxy]nicotinonitrile;
(134) 6-(2-chlorophenyl)-5-(4-chlorophenyl)-2-[(3,4-difluorobenzyl)oxy]nicotinamide;
(135) 2-chloro-6-(2-chlorophenyl)-5-(4-chlorophenyl)nicotinonitrile;
(136) 6-(2-chlorophenyl)-5-(4-chlorophenyl)-2-[(5-chloropyridin-3-yl)oxy]nicotinonitrile;
(137) 6-(2-chlorophenyl)-5-(4-chlorophenyl)-2-(3,4-difluorophenoxy)nicotinonitrile;
(138) 6-(2-chlorophenyl)-5-(4-chlorophenyl)-2-[2-(1,3-dioxo-1,3-dihydro-2H-isoindol-2-yl)ethoxy]nicotinonitrile;
(139) 2-(2-aminoethoxy)-6-(2-chlorophenyl)-5-(4-chlorophenyl)nicotinonitrile;
(140) N-(2-{[6-(2-chlorophenyl)-5-(4-chlorophenyl)-3-cyanopyridin-2-yl]oxy}ethyl)benzenesulfonamide;
(141) N-(2-{[6-(2-chlorophenyl)-5-(4-chlorophenyl)-3-cyanopyridin-2-yl]oxy}ethyl)acetamide;
(142) N-(2-{[6-(2-chlorophenyl)-5-(4-chlorophenyl)-3-cyanopyridin-2-yl]oxy}ethyl)cyclopropanecarboxamide
(143) N-(2-{[6-(2-chlorophenyl)-5-(4-chlorophenyl)-3-cyanopyridin-2-yl]oxy}ethyl)benzamide;
(144) N-(2-{[6-(2-chlorophenyl)-5-(4-chlorophenyl)-3-cyanopyridin-2-yl]oxy}ethyl)methanesulfonamide;
(145) N'-(2-{[6-(2-chlorophenyl)-5-(4-chlorophenyl)-3-cyanopyridin-2-yl]oxy}ethyl)-N,N-dimethylurea;
(146) N-(2-{[6-(2-chlorophenyl)-5-(4-chlorophenyl)-3-cyanopyridin-2-yl]oxy}ethyl)morpholine-4-carboxamide;

and pharmaceutically acceptable salts thereof.

One embodiment of the compounds of the present invention include compounds of structural formula II:

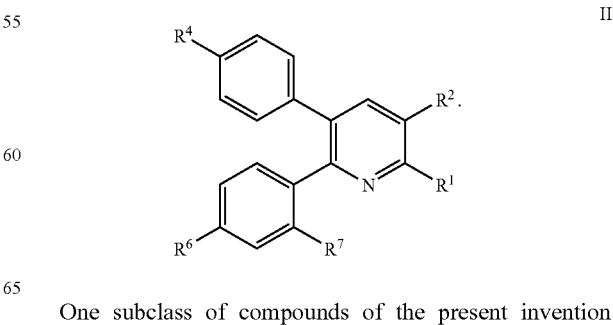

II

One subclass of compounds of the present invention includes compounds wherein $R^3$ is hydrogen, $R^4$ is chloro, R⁵ is hydrogen, R⁶ is chloro, and R⁷ is 2-chloro. Particular compounds of this subclass include:

(1) 2-(benzyloxy)-5-(4-chlorophenyl)-6-(2,4-dichlorophenyl)nicotinonitrile,
(2) 2-chloro-5-(4-chlorophenyl)-6-(2,4-dichlorophenyl)-N-hexylnicotinamide,
(3) 2-chloro-5-(4-chlorophenyl)-6-(2,4-dichlorophenyl)-N-propylnicotinamide,
(4) 2-(benzyloxy)-5-(4-chlorophenyl)-6-(2,4-dichlorophenyl)-N-methyinicotinamide,
(5) 2-(benzyloxy)-5-(4-chlorophenyl)-6-(2,4-dichlorophenyl)-N,N-dimethylnicotinamide,
(6) 2-(benzyloxy)-5-(4-chlorophenyl)-6-(2,4-dichlorophenyl)-N-propyinicotinamide,
(7) 2-(benzyloxy)-5-(4-chlorophenyl)-6-(2,4-dichlorophenyl)-N-pentylnicotinamide,
(8) 2-(benzyloxy)-5-(4-chlorophenyl)-6-(2,4-dichlorophenyl)-N-piperidin-1-ylnicotinamide,
(9) 2-(benzyloxy)-5-(4-chlorophenyl)-6-(2,4-dichlorophenyl)nicotinamide,
(10) methyl 2-(benzyloxy)-5-(4-chlorophenyl)-6-(2,4-dichlorophenyl)nicotinate,
(11) 5-(4-chlorophenyl)-6-(2,4-dichlorophenyl)-N-hexylnicotinamide,
(12) 5-(4-chlorophenyl)-6-(2,4-dichlorophenyl)-2-[(4-fluorobenzyl)oxy]nicotinonitrile,
(13) 5-(4-chlorophenyl)-6-(2,4-dichlorophenyl)-2-[(2,4-difluorobenzyl)oxy]nicotinonitrile,
(14) 5-(4-chlorophenyl)-6-(2,4-dichlorophenyl)-2-[(3,4-difluorobenzyl)oxy]nicotinonitrile,
(15) 5-(4-chlorophenyl)-6-(2,4-dichlorophenyl)-2-{[4-trifluoromethyl)benzyl]oxy}nicotinonitrile,
(16) 5-(4-chlorophenyl)-6-(2,4-dichlorophenyl)-2-[(3,5-difluorobenzyl)oxy]nicotinonitrile,
(17) methyl 5-(4-chlorophenyl)-2-(cyclobexylmethoxy)-6-(2,4-dichlorophenyl) nicotinate,
(18) methyl 5-(4-chlorophenyl)-2-(cyclopropylmethoxy)-6-(2,4-dichlorophenyl) nicotinate,
(19) methyl 5-(4-chlorophenyl)-6-(2,4-dichlorophenyl)-2-(pentyloxy)nicotinate,
(20) 2-(benzyloxy)-5-(4-chlorophenyl)-6-(2,4-dichlorophenyl)-N-ethyl nicotinamide,
(21) 2-(benzyloxy)-N-butyl-5-(4-chlorophenyl)-6-(2,4-dichlorophenyl) nicotinamide,
(22) 2-(benzyloxy)-5-(4-chlorophenyl)-N-cyclopentyl-6-(2,4-dichiorophenyl) nicotinamide,
(23) methyl 5-(4-chlorophenyl)-6-(2,4-dichlorophenyl)-2-(2-ethoxyethoxy) nicotinate,
(24) 5-(4-chlorophenyl)-2-(cyclohexylmethoxy)-6-(2,4-dichlorophenyl)-N-methylnicotinamide,
(25) 2-butoxy-5-(4-chlorophenyl)-6-(2,4-dichlorophenyl) nicotinamide,
(26) 2-butoxy-5-(4-chlorophenyl)-6-(2,4-dichlorophenyl)-N-methylnicotinamide,
(27) 2-butoxy-5-(4-chlorophenyl)-6-(2,4-dichlorophenyl)-N-propylnicotinamide,
(28) 2-butoxy-5-(4-chlorophenyl)-N-cyclopentyl-6-(2,4-dichlorophenyl) nicotinamide,
(29) 5-(4-chlorophenyl)-6-(2,4-dichlorophenyl)-2-[(3,4-difluorobenzyl)oxy]-N-ethylnicotinamide,
(30) 5-(4-chlorophenyl)-6-(2,4-dichlorophenyl)-2-[(3,4-difluorobenzyl)oxy]-N-propylnicotinamide
(31) 5-(4-chlorophenyl)-N-cyclohexyl-6-(2,4-dichlorophenyl)pyridine-2-carboxamide,
(32) 5-(4-chlorophenyl)-6-(2,4-dichlorophenyl)-2-[(3,4-difluorobenzyl)oxy]-N-methylnicotinamide,
(33) 5-(4-chlorophenyl)-6-(2,4-dichlorophenyl)-2-[(3,4-difluorobenzyl)oxy]-N-(2-fluoroethyl)nicotinamide,
(34) 5-(4-chlorophenyl)-6-(2,4-dichlorophenyl)-2-[(3,4-difluorobenzyl)oxy]-N-isopropylnicotinamide,
(35) methyl 5-(4-chlorophenyl)-6-(2,4-dichlorophenyl)-2-[(3,4-difluorobenzyl)oxy]nicotinate,
(36) 5-(4-chlorophenyl)-6-(2,4-dichlorophenyl)-N-piperidin-1-ylpyridine-2-carboxamide,
(37) 5-(4-chlorophenyl)-6-(2,4-dichlorophenyl)-N-hexylpyridine-2-carboxamide,
(38) 5-(4-chlorophenyl)-N-cyclopentyl-6-(2,4-dichlorophenyl)pyridine-2-carboxamide,
(39) 5-(4-chlorophenyl)-N-cycloheptyl-6-(2,4-dichlorophenyl)pyridine-2-carboxamide,
(40) 5-(4-chlorophenyl)-6-(2,4-dichlorophenyl)-N-(1-propylbutyl)pyridine-2-carboxamide,
(41) N-benzyl-5-(4-chlorophenyl)-6-(2,4-dichlorophenyl)pyridine-2-carboxamide,
(42) 5,6-bis(2,4-dichlorophenyl)-2-[(3,4-difluorobenzyl)oxy]nicotinonitrile,
(43) 6-(2,4-dichlorophenyl)-5-(3,4-dichlorophenyl)-2-[(3,4-difluorobenzyl)oxy]nicotinonitrile,
(44) 5-(4-chlorophenyl)-6-(2,4-dichlorophenyl)-2-[1-(4-fluorophenyl)ethoxy]nicotinonitrile,
(45) 5-(4-chlorophenyl)-6-(2,4-dichlorophenyl)-2-(3,4-difluorophenoxy) nicotinonitrile,
(46) 2-(1,3-benzodioxol-5-ylmethoxy)-5-(4-chlorophenyl)-6-(2,4-dichlorophenyl) nicotinonitrile,
(47) 5-(4-chlorophenyl)-6-(2,4-dichlorophenyl)-2-(2-methoxyethoxy) nicotinonitrile,
(48) 5-(4-chlorophenyl)-6-(2,4-dichlorophenyl)-2-(3-fluorophenoxy)nicotinonitrile,
(49) 5-(4-chlorophenyl)-2-(cyclohexyloxy)-6-(2,4-dichlorophenyl)nicotinonitrile,
(50) 2-(4-chlorophenoxy)-5-(4-chlorophenyl)-6-(2,4-dichlorophenyl)nicotinonitrile,
(51) 2-(3-chlorophenoxy)-5-(4-chlorophenyl)-6-(2,4-dichlorophenyl)nicotinonitrile,
(52) 5-(4-chlorophenyl)-6-(2,4-dichlorophenyl)-2-(4-methoxyphenoxy) nicotinonitrile,
(53) 5-(4-chlorophenyl)-6-(2,4-dichlorophenyl)-2-(pyridin-3-yloxy)nicotinonitrile,
(54) 2-[(3-chlorobenzyl)oxy]-5-(4-chlorophenyl)-6-(2,4-dichlorophenyl) nicotinonitrile,
(55) 3-(4-chlorophenyl)-2-(2,4-dichlorophenyl)-6-[(3,4-difluorobenzyl)oxy]pyridine,
(56) 5-(4-chlorophenyl)-2-[(5-chloropyridin-3-yl)oxy]-6-(2,4-dichlorophenyl) nicotinonitrile,
(57) methyl 5-(4-chlorophenyl)-6-(2,4-dichlorophenyl)-2-(3,4-difluorophenoxy) nicotinate,
(58) 5-(4-chlorophenyl)-6-(2,4-dichlorophenyl)-2-(3,4-difluorophenoxy)-N-methyl nicotinamide,
(59) 5-(4-chlorophenyl)-N-cyclohexyl-6-(2,4-dichlorophenyl)-2-(3,4-difluorophenoxy)nicotinamide,
(60) 5-(4-chlorophenyl)-6-(2,4-dichlorophenyl)-2-(3,4-difluorophenoxy)-N-pyrrolidin-1-ylnicotinamide,
(61) 5-(4-chlorophenyl)-6-(2,4-dichlorophenyl)-2-(3,4-difluorophenoxy)-N',N'-dimethylnicotinohydrazide,
(62) 5-(4-chlorophenyl)-6-(2,4-dichlorophenyl)-2-(3,4-difluorophenoxy)-N-ethylnicotinamide,
(63) 5-(4-chlorophenyl)-6-(2,4-dichlorophenyl)-2-(3,4-difluorophenoxy)-N-isopropylnicotinamide,
(64) methyl 5-(4-chlorophenyl)-2-[(5-chloropyridin-3-yl)oxy]-6-(2,4-dichlorophenyl)nicotinate,
(65) 5-(4-chlorophenyl)-6-(2,4-dichlorophenyl)-2-(3,4-difluorophenoxy)nicotinamide,

(66) N-(2-{[5-(4-chlorophenyl)-3-cyano-6-(2,4-dichlorophenyl)pyridin-2-yl]oxy}ethyl)cyclopropanecarboxamide,
(67) N-(2-{[5-(4-chlorophenyl)-3-cyano-6-(2,4-dichlorophenyl)pyridin-2-yl]oxy}ethyl)cyclobutanecarboxamide,
(68) N-(2-{[5-(4-chlorophenyl)-3-cyano-6-(2,4-dichlorophenyl)pyridin-2-yl]oxy}ethyl)cyclopentanecarboxamide,,
(69) N-(2-{[5-(4-chlorophenyl)-3-cyano-6-(2,4-dichlorophenyl)pyridin-2-yl]oxy}ethyl)benzamide,
(70) N-(2-{[5-(4-chlorophenyl)-3-cyano-6-(2,4-dichlorophenyl)pyridin-2-yl]oxy}ethyl)4-fluorobenzamide,
(71) 5-(4-chlorophenyl)-6-(2,4-dichlorophenyl)-2-(pyridin-2-yloxy)nicotinonitrile,
(72) 5-(4-chlorophenyl)-3-cyano-N-cyclohexyl-6-(2,4-dichlorophenyl)pyridine-2-carboxamide,
(73) 5-(4-chlorophenyl)-6-(2,4-dichlorophenyl)-2-(3,5-difluorophenoxy) nicotinonitrile,
(74) 5-(4-chlorophenyl)-6-(2,4-dichlorophenyl)-2-(1H-imidazol-1-yl)nicotinonitrile,
(75) [5-(4-chlorophenyl)-6-(2,4-dichlorophenyl)-2-(3,4-difluorophenoxy)pyridin-3-yl]methanol,
(76) 5-(4-chlorophenyl)-6-(2,4-dichlorophenyl)-2-(2-methyl-1H-imidazol-1-yl)nicotinonitrile,
(77) 5-(4-chlorophenyl)-3-cyano-N-cyclopentyl-6-(2,4-dichlorophenyl)pyridine-2-carboxamide,
(78) 5-(4-chlorophenyl)-6-(2,4-dichlorophenyl)-2-(4,4-dimethyl-2-oxo-1,3-oxazolidin-3-yl)nicotinonitrile,
(79) 5-(4-chlorophenyl)-6-(2,4-dichlorophenyl)-2-(tetrahydro-2H-pyran-2-ylmethoxy)nicotinonitrile,
(80) 5-(4-chlorophenyl)-6-(2,4-dichlorophenyl)-2-isopropoxynicotinonitrile,
(81) 5-(4-chlorophenyl)-6-(2,4-dichlorophenyl)-2-ethoxynicotinonitrile,
(82) N-[5-(4-chlorophenyl)-3-cyano-6-(2,4-dichlorophenyl)pyridin-2-yl]benzamide,
(83) N-benzoyl-N-[5-(4-chlorophenyl)-3-cyano-6-(2,4-dichlorophenyl)pyridin-2-yl]benzamide,
(84) 5-(4-chlorophenyl)-6-(2,4-dichlorophenyl)-2-(tetrahydrofuran-3-yloxy) nicotinonitrile,
(85) 5-(4-chlorophenyl)-6-(2,4-dichlorophenyl)-2-(tetrahydrofuran-3-ylmethoxy) nicotinonitrile,
(86) 2-(1H-1,2,3-benzotriazol-1-yl)-5-(4-chlorophenyl)-6-(2,4-dichlorophenyl) nicotinonitrile,
(87) N-[5-(4-chlorophenyl)-3-cyano-6-(2,4-dichlorophenyl)pyridin-2-yl]-3,4-difluorobenzamide,
(88) 5-(4-chlorophenyl)-6-(2,4-dichlorophenyl)-2-(piperidin-1-yloxy) nicotinonitrile,
(89) N-[5-(4-chlorophenyl)-3-cyano-6-(2,4-dichlorophenyl)pyridin-2-yl]-2,2-dimethylpropanamide,
(90) methyl 2-(3-chlorophenoxy)-5-(4-chlorophenyl)-6-(2,4-dichlorophenyl) nicotinate,
(91) 2-(3-chlorophenoxy)-5-(4-chlorophenyl)-6-(2,4-dichlorophenyl)-N',N'-dimethylnicotinohydrazide,
(92) 5-(4-chlorophenyl)-6-(2,4-dichlorophenyl)-2-(1H-1,2,3-triazol-1-yl)nicotinonitrile,
(93) 5-(4-chlorophenyl)-6-(2,4-dichlorophenyl)-2-[(3,4-difluorobenzyl)oxy]-N',N'-dimethylnicotinohydrazide,
(94) methyl 2-butoxy-5-(4-chlorophenyl)-6-(2,4-dichlorophenyl)nicotinate,
(95) 5-(4-chlorophenyl)-2-(cyclohexylmethoxy)-6-(2,4-dichlorophenyl)-N-propylnicotinamide,
(96) 5-(4-chlorophenyl)-6-(2,4-dichlorophenyl)-2-(4-fluorophenoxy)nicotinonitrile,
(97) 5-(4-chlorophenyl)-2-(3,5-dichlorophenoxy)-6-(2,4-dichlorophenyl) nicotinonitrile,
(98) 5-(4-chlorophenyl)-6-(2,4-dichlorophenyl)-2-(3,4-difluorobenzyl) nicotinonitrile,
(99) 5-(4-chlorophenyl)-6-(2,4-dichlorophenyl)-2-(3,4-difluorophenoxy) nicotinamide,
(100) 5'-(4-chlorophenyl)-6'-(2,4-dichlorophenyl)-2-oxo-2H-1,2'-bipyridine-3'-carbonitrile,
(101) 5-(4-chlorophenyl)-6-(2,4-dichlorophenyl)-2-(isopropylamino)nicotinonitrile, and pharmacuetically acceptable salts thereof.

"Alkyl", as well as other groups having the prefix "alk", such as alkoxy, alkanoyl, means carbon chains which may be linear or branched or combinations thereof. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means mono- or bicyclic or bridged saturated carbocyclic rings, each having from 3 to 10 carbon atoms. The term also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, decahydronaphthyl, indanyl, and the like.

"Aryl" means mono- or bicyclic aromatic rings containing only carbon atoms. The term also includes aryl group fused to a monocyclic cycloalkyl or monocyclic cycloheteroalkyl group in which the point of attachment is on the aromatic portion. Examples of aryl include phenyl, naphthyl, indanyl, indenyl, tetrahydronaphthyl, 2,3-dihydrobenzofuranyl, dihydrobenzopyranyl, 1,4-benzodioxanyl, and the like. A preferred aryl substituent is phenyl.

"Heteroaryl" means a mono- or bicyclic aromatic ring containing at least one heteroatom selected from N, O and S, with each ring containing 5 to 6 atoms. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, benzothiazolyl, furo(2,3-b)pyridyl, quinolyl, indolyl, isoquinolyl, oxazolidinyl, and the like. The heteroaryl ring may be substituted on one or more carbon atoms. In one embodiment of the present invention, heteroaryl is pyridinyl, benzimidazolyl, imidazolyl, oxazolidinyl, triazolyl, and benzotriazolyl.

"Cycloheteroalkyl" means mono- or bicyclic or bridged saturated rings containing at least one heteroatom selected from N, S and O, each of said ring having from 3 to 10 atoms in which the point of attachment may be carbon or nitrogen. The term also includes monocyclic heterocycle fused to an aryl or heteroaryl group in which the point of attachment is on the non-aromatic portion. Examples of "cycloheteroalkyl" include pyrrolidinyl, piperidinyl, piperazinyl, imidazolidinyl, pyranyl, tetrahydrofuranyl, 2,3-dihydrofuro(2,3-b)pyridyl, benzoxazinyl, tetrahydrohydroquinolinyl, morpholinyl, dioxanyl, oxanyl, tetrahydroisoquinolinyl, dihydroindolyl, dihydroisoindolyl, and the like. The term also includes partially unsaturated monocyclic rings that are not aromatic, such as 2- or 4-pyridones attached through the nitrogen or N-substituted-(1H, 3H)-pyrimidine-2,4-diones (N-substituted uracils). The cycloheteroalkyl ring may be substituted on the ring carbons and/or the ring nitrogens. In one embodiment of the present invention, cycloheteroalkyl is pyrrolidinyl, piperidinyl, piperazinyl, morpholinyl, dihydroisoindolyl, pyranyl, perhydroazepinyl, and tetrahydrofuranyl.

"Halogen" includes fluorine, chlorine, bromine and iodine.

When any variable (e.g., $R^1$, $R^d$, etc.) occurs more than one time in any constituent or in formula I, its definition on each occurrence is independent of its definition at every other occurrence. Also, combinations of substituents and/or variables are permissible only if such combinations result in stable compounds.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to

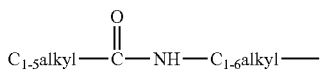

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Compounds of Formula I may contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers. The individual tautomers as well as mixture thereof are encompassed with compounds of Formula I.

Compounds of the Formula I may be separated into diastereoisomeric pairs of enantiomers by, for example, fractional crystallization from a suitable solvent, for example MeOH or ethyl acetate or a mixture thereof. The pair of enantiomers thus obtained may be separated into individual stereoisomers by conventional means, for example by the use of an optically active amine as a resolving agent or on a chiral HPLC column.

Alternatively, any enantiomer of a compound of the general Formula I may be obtained by stereospecific synthesis using optically pure starting materials or reagents of known configuration.

Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylamninoethanol, 2-dimethylaminoethanol, ethanolarnine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. The term "pharmaceutically acceptable salt" further includes all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations.

It will be understood that, as used herein, references to the compounds of Formula I are meant to also include the pharmaceutically acceptable salts.

Compounds of the present invention are modulators of the CB1 receptor. In particular, the compounds of structural formula I are antagonists or inverse agonists of the CB1 receptor.

An "agonist" is a compound (hormone, neurotransmitter or synthetic compound) which binds to a receptor, and, in turn, produces a response such as contraction, relaxation, secretion, change in enzyme activity, etc. similar to that elicited by the physiologically relevant agonist ligand(s) for that receptor. An "antagonist" is a compound which attenuates the effect of an agonist. An "inverse agonist" is a compound which acts on a receptor but produces the opposite effect produced by the agonist of the particular receptor.

Compounds of this invention are modulators of the CB1 receptor and as such are useful as centrally acting drugs in the treatment of psychosis, memory deficits, cognitive disorders, migraine, neuropathy, neuro-inflammatory disorders including multiple sclerosis and Guillain-Barre syndrome and the inflammatory sequelae of viral encephalitis, cerebral vascular accidents, and head trauma, anxiety disorders, stress, epilepsy, Parkinson's disease, movement disorders, and schizophrenia. The compounds are also useful for the treatment of substance abuse disorders, particularly to opiates, alcohol, marijuana, and nicotine. The compounds are also useful for the treatment of obesity or eating disorders associated with excessive food intake and complications associated therewith including left ventricular hypertrophy. The compounds are also useful for the treatment of constipation and chronic intestinal pseudo-obstruction. The compounds are also useful for the treatment of cirrhosis of the liver. The compounds are also useful for the treatment of asthma.

The terms "administration of" and or "administering a" compound should be understood to mean providing a compound of the invention or a prodrug of a compound of the invention to the individual in need of treatment.

The administration of the compound of structural formula I in order to practice the present methods of therapy is carried out by administering an effective amount of the compound of structural formula I to the patient in need of such treatment or prophylaxis. The need for a prophylactic administration according to the methods of the present invention is determined via the use of well known risk factors. The effective amount of an individual compound is determined, in the final analysis, by the physician in charge of the case, but depends on factors such as the exact disease to be treated, the severity of the disease and other diseases or conditions from which the patient suffers, the chosen route of administration other drugs and treatments which the patient may concomitantly require, and other factors in the physician's judgment.

The utilities of the present compounds in these diseases or disorders may be demonstrated in animal disease models that have been reported in the literature. The following are examples of such animal disease models: a) suppression of food intake and resultant weight loss in rats (Life Sciences 1998, 63, 113-117); b) reduction of sweet food intake in marmosets (Behavioural Pharm. 1998, 9, 179-181); c) reduction of sucrose and ethanol intake in mice (Psychopharm. 1997, 132, 104-106); d) increased motor activity and place conditioning in rats (Psychopharm. 1998, 135, 324-332; Psychopharmacol 2000, 151: 25-30); e) spontaneous locomotor activity in mice (J. Pharm. Exp. Ther. 1996, 277, 586-594); f) reduction in opiate self-administration in mice (Sci. 1999, 283, 401-404); g) bronchial hyperresponsiveness in sheep and guinea pigs as models for the various phases of asthma (for example, see W. M. Abraham et al., "$\alpha_4$-Integrins mediate antigen-induced late bronchial responses and prolonged airway hyperresponsiveness in sheep." J. Clin. Invest. 93, 776 (1993) and A. A. Y. Milne and P. P. Piper, "Role of VLA-4 integrin in leucocyte recruitment and bronchial hyperresponsiveness in the gunea-pig." Eur. J. Pharmacol., 282; 243 (1995)); h) mediation of the vasodilated state in advanced liver cirrhosis induced by carbon tetrachloride (Nature Medicine, 2001, 7 (7), 827-832); i) amitriptyline-induced constipation in cynomolgus monkeys is beneficial for the evaluation of laxatives (Biol. Pharm. Bulletin (Japan), 2000, 23(5), 657-9); j) neuropathology of paediatric chronic intestinal pseudo-obstruction and animal models related to the neuropathology of paediatric chronic intestinal pseudo-obstruction (Journal of Pathology (England), 2001, 194 (3), 277-88).

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

For use where a composition for intravenous administration is employed, a suitable dosage range is from about 0.001 mg to about 100 mg (preferably from 0.01 mg to about 50 mg, more preferably 0.1 mg to 10 mg) of a compound of Formula I per kg of body weight per day.

In the case where an oral composition is employed, a suitable dosage range is, e.g. from about 0.01 mg to about 1000 mg of a compound of Formula I per day, preferably from about 0.1 mg to about 10 mg per day. For oral administration, the compositions are preferably provided in the form of tablets containing from 0.01 to 1,000 mg, preferably 0.01, 0.05, 0.1, 0.5, 1, 2.5, 5, 10, 15, 20, 25, 30, 40, 50, 100, 250, 500, 750 or 1000 milligrams of the active ingredient for the symptomatic adjustment of the dosage to the patient to be treated.

For the treatment of diseases of the eye, ophthalmic preparations for ocular administration comprising 0.001-1% by weight solutions or suspensions of the compounds of Formula I in an acceptable ophthalmic formulation may be used.

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

Any suitable route of administration may be employed for providing a mammal, especially a human, with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. By "pharmaceutically acceptable" it is meant the carrier, diluent or excipient must be compatible with the other ingredients of the formulation and not deleterious to the recipient thereof. In particular, the term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulizers. The compounds may also be delivered as powders which may be formulated and the powder composition may be inhaled with the aid of an insufflation powder inhaler device. The preferred delivery systems for inhalation are metered dose inhalation (MDI) aerosol, which may be formulated as a suspension or solution of a compound of Formula I in suitable propellants, such as fluorocarbons or hydrocarbons and dry powder inhalation (DPI) aerosol, which may be formulated as a dry powder of a compound of Formula I with or without additional excipients.

Suitable topical formulations of a compound of formula I include transdermal devices, aerosols, creams, solutions, ointments, gels, lotions, dusting powders, and the like. The topical pharmaceutical compositions containing the compounds of the present invention ordinarily include about 0.005% to 5% by weight of the active compound in admixture with a pharmaceutically acceptable vehicle. Transdermal skin patches useful for administering the compounds of the present invention include those well known to those of ordinary skill in that art. To be administered in the form of a transdermal delivery system, the dosage administration will, of course be continuous rather than intermittent throughout the dosage regimen.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules (including timed release and sustained release formulations), pills, cachets, powders, granules or tablets each containing a predetermined amount of the active ingredient, as a powder or granules or as a solution or a suspension in an aqueous liquid, a non-aqueous liquid, an oil-in-water emulsion or a water-in-oil liquid emulsion, including elixirs, tinctures, solutions, suspensions, syrups and emulsions. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from 0.01 to 1,000 mg, particularly 0.01, 0.05, 0.1, 0.5, 1, 2.5, 3, 5, 6, 10, 15, 25, 50, 75, 100, 125, 150, 175, 180, 200, 225, 500, 750 and 1,000 milligrams of the active ingredient for the symptomatic adjustment of the dosage to the patient to be treated. and each cachet or capsule contains from about 0.01 to 1,000 mg, particularly 0.01, 0.05, 0.1, 0.5, 1.0, 2.5, 3, 5, 6, 10, 15, 25, 50, 75, 100, 125, 150, 175, 180, 200, 225, 500, 750 and 1,000 milligrams of the active ingredient for the symptomatic adjustment of the dosage to the patient to be treated.

Additional suitable means of administration of the compounds of the present invention include injection, intravenous bolus or infusion, intraperitoneal, subcutaneous, intramuscular and topical, with or without occlusion.

Exemplifying the invention is a pharmaceutical composition comprising any of the compounds described above and a pharmaceutically acceptable carrier. Also exemplifying the invention is a pharmaceutical composition made by combining any of the compounds described above and a pharmaceutically acceptable carrier. An illustration of the invention is a process for making a pharmaceutical composition comprising combining any of the compounds described above and a pharmaceutically acceptable carrier.

The dose may be administered in a single daily dose or the total daily dosage may be administered in divided doses of two, three or four times daily. Furthermore, based on the properties of the individual compound selected for administration, the dose may be administered less frequently, e.g., weekly, twice weekly, monthly, etc. The unit dosage will, of course, be correspondingly larger for the less frequent administration.

When administered via intranasal routes, transdermal routes, by rectal or vaginal suppositories, or through a continual intravenous solution, the dosage administration will, of course, be continuous rather than intermittent throughout the dosage regimen.

The following are examples of representative pharmaceutical dosage forms for the compounds of Formula I:

| Injectable Suspension (I.M.) | mg/mL |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 mL | |

| Tablet | mg/tablet |
|---|---|
| Compound of Formula I | 25 |
| Microcrystalline Cellulose | 415 |
| Povidone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

| Aerosol | Per canister |
|---|---|
| Compound of Formula I | 24 mg |
| Lecithin, NF Liq. Conc. | 1.2 mg |
| Trichlorofluoromethane, NF | 4.025 g |
| Dichlorodifluoromethane, NF | 12.15 g |

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I include, but are not limited to: antipsychotic agents, cognition enhancing agents, anti-migraine agents, anti-asthmatic agents, antiinflammatory agents, anxiolytics, anti-Parkinson's agents, anti-epileptics, anorectic agents, serotonin reuptake inhibitors, and other anti-obesity agents, which may be administered separately or in the same pharmaceutical compositions.

The present invention also provides a method for the treatment or prevention of a CB1 receptor modulator mediated disease, which method comprises administration to a patient in need of such treatment or at risk of developing a CB1 receptor modulator mediated disease of an amount of a CB1 receptor modulator and an amount of one or more active ingredients, such that together they give effective relief.

In a further aspect of the present invention, there is provided a pharmaceutical composition comprising a CB1 receptor modulator and one or more active ingredients, together with at least one pharmaceutically acceptable carrier or excipient.

Thus, according to a further aspect of the present invention there is provided the use of a CB1 receptor modulator and one or more active ingredients for the manufacture of a medicament for the treatment or prevention of a CB1 receptor modulator mediated disease. In a further or alternative aspect of the present invention, there is therefore provided a product comprising a CB1 receptor modulator and one or more active ingredients as a combined preparation for simultaneous, separate or sequential use in the treatment or prevention of CB1 receptor modulator mediated disease. Such a combined preparation may be, for example, in the form of a twin pack.

It will be appreciated that for the treatment or prevention of eating disorders, including obesity, bulimia nervosa and compulsive eating disorders, a compound of the present invention may be used in conjunction with other anorectic agents.

The present invention also provides a method for the treatment or prevention of eating disorders, which method comprises administration to a patient in need of such treatment an amount of a compound of the present invention and an amount of an anorectic agent, such that together they give effective relief.

Suitable anoretic agents of use in combination with a compound of the present invention include, but are not limited to, aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof.

A particularly suitable class of anorectic agent are the halogenated amphetamine derivatives, including chlorphentermine, cloforex, clortermine, dexfenfluramine, fenfluramine, picilorex and sibutramine; and pharmaceutically acceptable salts thereof Particularly preferred halogenated amphetamine derivatives of use in combination with a compound of the present invention include: fenfluramine and dexfenfluramine, and pharmaceutically acceptable salts thereof.

It will be appreciated that for the treatment or prevention of obesity, the compounds of the present invention may also be used in combination with a selective serotonin reuptake inhibitor (SSRI).

The present invention also provides a method for the treatment or prevention of obesity, which method comprises administration to a patient in need of such treatment an amount of a compound of the present invention and an amount of an SSRI, such that together they give effective relief.

Suitable selective serotonin reuptake inhibitors of use in combination with a compound of the present invention include: fluoxetine, fluvoxamine, paroxetine, sertraline, and imipramine and pharmaceutically acceptable salts thereof.

It will be appreciated that for the treatment or prevention of obesity, the compounds of the present invention may also be used in combination with an opioid antagonist.

The present invention also provides a method for the treatment or prevention of obesity, which method comprises administration to a patient in need of such treatment an amount of a compound of the present invention and an amount of an opioid antagonist, such that together they give effective relief.

Suitable opioid antagonists of use in combination with a compound of the present invention include: naltrexone, 3-methoxynaltrexone, naloxone and nalmefene, and pharmaceutically acceptable salts thereof.

It will be appreciated that for the treatment or prevention of obesity, the compounds of the present invention may also be used in combination with another anti-obesity agent.

The present invention also provides a method for the treatment or prevention of obesity, which method comprises administration to a patient in need of such treatment an amount of a compound of the present invention and an amount of another anti-obesity agent, such that together they give effective relief.

Suitable anti-obesity agents of use in combination with a compound of the present invention, include, but are not limited to: 1) growth hormone secretagogues, such as those disclosed and specifically described in U.S. Pat. No. 5,536,716; 2) growth hormone secretagogue receptor agonists/antagonists, such as NN703, hexarelin, MK-0677, SM-130686, CP-424,391, L-692,429 and L-163,255, and such as those disclosed in U.S. Pat. No. 6,358,951, U.S. Patent Application Nos. 2002/049196 and 2002/022637, and PCT Application Nos. WO 01/56592 and WO 02/32888; 3) melanocortin agonists, such as Melanotan II or those described in WO 99/64002 and WO 00/74679; 4) Mc4r (melanocortin 4 receptor) agonists, such as CHIR86036 (Chiron), ME-10142, and ME-10145 (Melacure), and those disclosed in PCT Application Nos. WO 01/991752, WO 01/74844, WO 02/12166, WO 02/11715, and WO 02/12178; 5) β-3 agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, SR 59119A, and such as those disclosed in U.S. patent application Ser. No. 5,705,515, and U.S. Pat. No. 5,451,677 and PCT Patent Publications WO94/18161, WO95/29159, WO97/46556, WO98/04526 and WO98/32753, WO 01/74782, and WO 02/32897; 6) 5HT-2 agonists; 7) 5HT2C (serotonin receptor 2C) agonists, such as BVT933, DPCA37215, WAY161503, R-1065, and those disclosed in U.S. Pat. No. 3,914,250, and PCT Application Nos. WO 02/36596, WO 02/48124, WO 02/10169, WO 01/66548, WO 02/44152, WO 02/51844, WO 02/40456, and WO 02/40457; 8) orexin antagonists, such as SB-334867-A, and those disclosed in PCT Patent Application Nos. WO 01/96302, WO 01/68609, WO 02/51232, WO 02/51838 and WO 02/090355; 9) melanin concentrating hormone antagonists; 10) melanin-concentrating hormone 1 receptor (MCH1R) antagonists, such as T-226296 (Takeda), and those disclosed in PCT Patent Application Nos. WO 01/82925, WO 01/87834, WO 02/06245, WO 02/04433, WO 02/51809 and WO 02/083134, and Japanese Patent Application No. JP 13226269; 11) melanin-concentrating hormone 2 receptor (MCH2R) agonist/antagonists; 12) galanin antagonists; 13) CCK agonists; 14) CCK-A (cholecystokinin-A) agonists, such as AR-R 15849, GI 181771, JMV-180, A-71378, A-71623 and SR146131, and those described in U.S. Pat. No. 5,739,106; 15) GLP-1 agonists; 16) corticotropin-releasing hormone agonists; 17) NPY 5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104, and those disclosed in U.S. Pat. Nos. 6,140,354, 6,191,160, 6,313,298, 6,337,332, 6,329,395, 6,326,375, 6,335,345, and 6,340,683, European Patent Nos. EP-01010691, and EP-01044970, and PCT Patent Publication Nos. WO 97/19682, WO 97/20820, WO 97/20821, WO 97/20822, WO 97/20823, WO 98/27063, WO 00/64880, WO 00/68197, WO 00/69849, WO 01/09120, WO 01/14376, WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/22592, WO 0248152, and WO 02/49648; 18) NPY 1 antagonists, such as BIBP3226, J-115814, BIBO 3304, LY-357897, CP-671906, GI-264879A, and those disclosed in U.S. Pat. No. 6,001,836, and PCT Patent Publication Nos. WO 96/14307, WO 01/23387, WO 99/51600, WO 01/85690, WO 01/85098, WO 01/85173, and WO 01/89528; 19) histamine receptor-3 (H3) modulators; 20) histamine receptor-3 (H3) antagonists/inverse agonists, such as hioperamide, 3-(1H-imidazol-4-yl)propyl N-(4-pentenyl) carbamate, clobenpropit, iodophenpropit, imoproxifan, GT2394 (Gliatech), and those described and disclosed in PCT Application No. WO 02/15905, and O-[3-(1H-imidazol-4-yl)propanol]-carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm.(Weinheim) 334: 45-52 (2001)), substituted N-phenylcarbamates (Reidemeister, S. et al., Pharmazie, 55:83-6 (2000)), and proxifan derivatives (Sasse, A. et al., J. Med. Chem.. 43:3335-43 (2000)); 21) β-hydroxy steroid dehydrogenase-1 inhibitors (β-HSD-1); 22) PDE (phosphodiesterase) inhibitors, such as theophylline, pentoxifylline, zaprinast, sildenafil, amrinone, milrinone, cilostamide, rolipram, and cilomilast; 23) phosphodiesterase-3B (PDE3B) inhibitors; 24) NE (norepinephrine) transport inhibitors, such as GW 320659, despiramine, talsupram, and nomifensine; 25) non-selective serotonin/norepinephrine transport inhibitors, such as sibutramine or fenfluramine; 26) ghrelin antagonists, such as those disclosed in PCT Application Nos. WO 01/87335, and WO 02/08250; 27) leptin, including recombinant human leptin (PEG-OB, Hoffman La Roche) and recombinant methionyl human leptin (Amgen); 28) leptin derivatives, such as those disclosed in U.S. Pat. Nos. 5,552,524, 5,552,523, 5,552,522, 5,521,283, and PCT International Publication Nos. WO 96/23513, WO 96/23514, WO 96/23515, WO 96/23516, WO 96/23517, WO 96/23518, WO 96/23519, and WO 96/23520; 29) BRS3 (bombesin receptor subtype 3) agonists; 30) CNTF (Ciliary neurotrophic factors), such as GI-181771 (Glaxo-SmithKline), SR146131 (Sanofi Synthelabo), butabindide, PD170,292, and PD 149164 (Pfizer); 31) CNTF derivatives, such as axokine (Regeneron), and those disclosed in PCT Application Nos. WO 94/09134, WO 98/22128, and WO 99/43813; 32) monoamine reuptake inhibitors, such as those disclosed in PCT Application Nos. WO 01/27068, and WO 01/62341; 33) UCP-1 (uncoupling protein-1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), retinoic acid, and those disclosed in PCT Patent Application No. WO 99/00123; 34) thyroid hormone β agonists, such as KB-2611 (KaroBioBMS), and those disclosed in PCT Application No. WO 02/15845, and Japanese Patent Application No. JP 2000256190; 35) FAS (fatty acid synthase) inhibitors, such as Cerulenin and C75; 36) DGAT1 (diacylglycerol acyltransferase 1) inhibitors; 37) DGAT2 (diacylglycerol acyltransferase 2) inhibitors; 38) ACC2 (acetyl-CoA carboxylase-2) inhibitors; 39) glucocorticoid antagonists; 40) acylestrogens, such as oleoyl-estrone, disclosed in del Mar-Grasa, M. et al., Obesity Research, 9:202-9 (2001); 41) lipase inhibitors, such as orlistat (Xenical®), Triton WR1339, RHC80267, lipstatin, tetrahydrolipstatin, teasaponin, diethylumbelliferyl phosphate, and those disclosed in PCT Application No. WO 01/77094; 42) fatty acid transporter inhibitors; 43) dicarboxylate transporter inhibitors; 44) glucose transporter inhibitors; 45) phosphate transporter inhibitors; 46) serotonin reuptake inhibitors, such as those disclosed in U.S. patent application Ser. No. 6,365,633, and PCT Patent Application Nos. WO 01/27060, and WO 01/162341; 47) Metformin (Glucophage®); and/or 48) Topiramate (Topimax®).

Specific NPY5 antagonists of use in combination with a compound of the present invention are selected from the group consisting of:

(1) 3-oxo-N-(5-phenyl-2-pyrazinyl)-spiro[isobenzofuran-1(3H),4'-piperidine]-1'-carboxamide,
(2) 3-oxo-N-(7-trifluoromethylpyrido[3,2-b]pyridin-2-yl) spiro-[isobenzofuran-1(3H),4'-piperidine]-1'-carboxamide,
(3) N-[5-(3-fluorophenyl)-2-pyrimidinyl]-3-oxospiro-[isobenzofuran-1(3H),4'-piperidine]-1'-carboxamide,
(4) trans-3'-oxo-N-(5-phenyl-2-pyrimidinyl)spiro[cyclohexane-1,1'(3'H)-isobenzofuran]4-carboxamide,
(5) trans-3'-oxo-N-[1-(3-quinolyl)4-imidazolyl]spiro[cyclohexane-1,1'(3'H)-isobenzofuran]4-carboxamide,
(6) trans-3-oxo-N-(5-phenyl-2-pyrazinyl)spiro[4-azaisobenzofuran-1(3 Hz, 1'-cyclohexane]4'-carboxamide,
(7) trans-N-[5-(3-fluorophenyl)-2-pyrimidinyl]-3-oxospiro[5-azaisobenzofuran-1(3H), 1-cyclohexane]4'-carboxamide,
(8) trans-N-[5-(2-fluorophenyl)-2-pyrimidinyl]-3-oxospiro[5-azaisobenzofuran-1(3H), 1-cyclohexane]4'-carboxamide,
(9) trans-N-[1-(3,5-difluorophenyl)4-imidazolyl]-3-oxospiro[7-azaisobenzofuran-1(3H), 1'-cyclohexane]4'-carboxamide,
(10) trans-3-oxo-N-(1-phenyl-4-pyrazolyl)spiro[4-azaisobenzofuran-1(3H),1'-cyclohexane]-4'-carboxamide,
(11) trans-N-[1-(2-fluorophenyl)-3-pyrazolyl]-3-oxospiro [6-azaisobenzofuran-1(3H), 1'-cyclohexane]4'-carboxamide,
(12) trans-3-oxo-N-(1-phenyl-3-pyrazolyl)spiro[6-azaisobenzofuran-1(3H), 1-cyclohexane]-4'-carboxamide,
(13) trans-3-oxo-N-(2-phenyl-1,2,3-triazol-4-yl)spiro[6-azaisobenzofuran-1(3H),1'-cyclohexane]-4'-carboxamide, and pharmaceutically acceptable salts and esters thereof.

It will be appreciated that for the treatment or prevention of obesity, the compounds of the present invention may also be used in combination with are inhibitors of the enzyme 11β-HSD1. Generally, glucocorticoid concentrations are modulated by tissue-specific 11β-hydroxysteroid dehydrogenase enzymes. The 11β-hydroxysteroid dehydrogenase type 1 enzyme (11β-HSD1) is a low affinity enzyme that generally uses NADP+ as a cofactor rather than NAD+ (Agarwal et al., 1989). In vitro studies have shown that 11β-HSD1 is capable of acting as both a reductase and a dehydrogenase. However, 11β-HSD1 in vivo generally acts as a reductase, converting 11-ketoglucocorticoids, such as cortisone, to 11β-hydroxyglucocorticoids such as cortisol. Excessive levels of cortisol have been associated with obesity, perhaps due to increased hepatic gluconeogenesis. Thus, the administration of an effective amount of an 11β-HSD1 inhibitor in combination with a CB1 antagonist of the present invention may be useful in the treatment or control of obesity. Particular inhibitors of 11β-HSD1 useful in combination with the compounds of the present invention include: 3-(1-adamantyl)-4-ethyl-5-(ethylthio)-4H-1,2,4-triazole, 3-(1-adamantyl)-5-(3,4,5-trimethoxyphenyl)-4-methyl-4H-1,2,4-triazole, and 3-adamantanyl-4,5,6,7,8,9,10, 11,12,3a-decahydro-1,2,4-triazolo[4,3-a][11]annulene.

"Obesity" is a condition in which there is an excess of body fat. The operational definition of obesity is based on the Body Mass Index (BMI), which is calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BMI) greater than or equal to 30 $kg/m^2$ or a subject with at least one co-morbidity with a BMI greater than or equal to 27 $kg/m^2$. A "subject at risk for obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity that requires weight reduction or that would be improved by weight reduction, has a BMI greater than or equal to 25 $kg/m^2$. In Asian countries, including Japan, an "obese subject" refers to a subject with at least one obesity-induced or obesity-related co-morbidity that requires weight reduction or that would be improved by weight reduction, with a BMI greater than or equal to 25 $kg/m^2$. In Asian countries, a "subject at risk of obesity" is a subject with a BMI of greater than 23 $kg/m^2$ to less than 25 $kg/m^2$.

As used herein, the term "obesity" is meant to encompass all of the above definitions of obesity.

Obesity-induced or obesity-related co-morbidities include, but are not limited to, diabetes, non-insulin dependent diabetes mellitus—type 2, impaired glucose tolerance, impaired fasting glucose, insulin resistance syndrome, dyslipidemia, hypertension, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

"Treatment" (of obesity and obesity-related disorders) refers to the administration of the compounds of the present invention to reduce or maintain the body weight of an obese subject. One outcome of treatment may be reducing the body weight of an obese subject relative to that subject's body weight immediately before the administration of the compounds of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

"Prevention" (of obesity and obesity-related disorders) refers to the administration of the compounds of the present invention to reduce or maintain the body weight of a subject at risk of obesity. One outcome of prevention may be reducing the body weight of a subject at risk of obesity relative to that subject's body weight immediately before the administration of the compounds of the present invention. Another outcome of prevention may be preventing body-weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

The obesity-related disorders herein are associated with, caused by, or result from obesity. Examples of obesity-related disorders include overeating and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovarian disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. Further examples of obesity-related disorders are metabolic syndrome, also known as syndrome X, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. The compounds of the present invention are also useful for reducing the risk of secondary outcomes of obesity, such as reducing the risk of left ventricular hypertrophy.

The term "diabetes," as used herein, includes both insulin-dependent diabetes mellitus (i.e., IDDM, also known as type I diabetes) and non-insulin-dependent diabetes mellitus (i.e., NIDDM, also known as Type II diabetes. Type I diabetes, or insulin-dependent diabetes, is the result of an absolute deficiency of insulin, the hormone which regulates glucose utilization. Type II diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type II diabetics are also obese. The compounds of the present invention are useful for treating both Type I and Type II diabetes. The compounds are especially effective for treating Type II diabetes. The compounds of the present invention are also useful for treating and/or preventing gestational diabetes mellitus.

It will be appreciated that for the treatment or prevention of migraine, a compound of the present invention may be used in conjunction with other anti-migraine agents, such as ergotamines or 5-HT$_1$ agonists, especially sumatriptan, naratriptan, zolmatriptan or rizatriptan.

It will be appreciated that for the treatment of depression or anxiety, a compound of the present invention may be used in conjunction with other anti-depressant or anti-anxiety agents.

Suitable classes of anti-depressant agents include norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, $\alpha$-adrenoreceptor antagonists, neurokinin-1 receptor antagonists and atypical anti-depressants.

Suitable norepinephrine reuptake inhibitors include tertiary amine tricyclics and secondary amine tricyclics. Suitable examples of tertiary amine tricyclics include: amitriptyline, clomipramine, doxepin, imipramine and trimipramine, and pharmaceutically acceptable salts thereof. Suitable examples of secondary amine tricyclics include: amoxapine, desipramine, maprotiline, nortriptyline and protriptyline, and pharmaceutically acceptable salts thereof.

Suitable selective serotonin reuptake inhibitors include: fluoxetine, fluvoxamine, paroxetine, sertraline, and imipramine and pharmaceutically acceptable salts thereof.

Suitable monoamine oxidase inhibitors include: isocarboxazid, phenelzine, tranylcypromine and selegiline, and pharmaceutically acceptable salts thereof.

Suitable reversible inhibitors of monoamine oxidase include: moclobemide, and pharmaceutically acceptable salts thereof.

Suitable serotonin and noradrenaline reuptake inhibitors of use in the present invention include: venlafaxine, and pharmaceutically acceptable salts thereof.

Suitable CRF antagonists include those compounds described in International Patent Specification Nos. WO 94/13643, WO 94/13644, WO 94/13661, WO 94/13676 and WO 94/13677.

Suitable neurokinin-1 receptor antagonists may be peptidal or non-peptidal in nature, however, the use of a non-peptidal neurokinin-1 receptor antagonist is preferred. In a preferred embodiment, the neurokinin-1 receptor antagonist is a CNS-penetrant neurokinin-1 receptor antagonist. In addition, for convenience the use of an orally active neurokinin-1 receptor antagonist is preferred. To facilitate dosing, it is also preferred that the neurokinin-1 receptor antagonist is a long acting neurokinin-1 receptor antagonist. An especially preferred class of neurokinin-1 receptor antagonists of use in the present invention are those compounds which are orally active and long acting.

Neurokinin-1 receptor antagonists of use in the present invention are fully described, for example, in U.S. Pat. Nos. 5,162,339, 5,232,929, 5,242,930, 5,373,003, 5,387,595, 5,459,270, 5,494,926, 5,496,833, 5,637,699; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942, 97/21702, 97/49710, 98/24438-98/24441, 98/24442-98/24445, 02/16343, and 02/16344; and in British Patent Publication Nos. 2 266 529, 2 268 931, 2 269 170, 2 269 590, 2 271 774, 2 292 144, 2 293 168, 2 293 169, and 2 302 689.

Specific neurokinin-1 receptor antagonists of use in the present invention include:

(±)-(2R3R,2S3S)-N-{[2-cyclopropoxy-5-(trifluoromethoxy)-phenyl]methyl}-2-phenylpiperidin-3-amine;

2-(S)-(3,5-bis(trifluoromethyl)benzyloxy)-3(S)-(4-fluorophenyl)-4-(3-(5-oxo-1H,4H-1,2,4-triazolo)methyl)morpholine;

2-(R)-(1-(R)-(3,5-bis(trifluoromethyl)phenyl)ethoxy)4-(3-(5-oxo-1H,4H-1,2,4-triazolo)methyl)-3-(S)-phenyl-morpholine;

2-(S)-(3,5-bis(trifluoromethyl)benzyloxy)-4-(3-(5-oxo-1H,4H-1,2,4-triazolo)methyl)-3-(S)-phenyl-morpholine;

2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine;

2-(R)-(1-(R)-(3,5-bis(trifluoromethyl)phenyl)ethoxy)-4-(5-(N,N-dimethylamino)methyl-1,2,3-triazol-4-yl)methyl-3-(S)-phenylmorpholine;

2-(R)-(1-(R)-(3,5-bis(trifluoromethyl)phenyl)ethoxy)-4-(5-(N,N-dimethylamino)methyl-1,2,3-triazol-4-yl)methyl-3-(S)-(4-fluorophenyl)morpholine;

(3S,5R,6S)-3-[2-cyclopropoxy-5-(trifluoromethoxy)phenyl]-6-phenyl-1-oxa-7-aza-spiro[4.5]decane;

(3R,5R,6S)-3-[2-cyclopropoxy-5-(trifluoromethoxy)phenyl]-6-phenyl-1-oxa-7-aza-spiro[4.5]decane;

2-(R)-(1-(S)-(3,5-bis(trifluoromethyl)phenyl)-2-hydroxyethoxy)-3-(S)-(4-fluorophenyl)-4-(1,2,4-triazol-3-yl)methylmorpholine;

2-(R)-(1-(R)-(3,5-bis(trifluoromethyl)phenyl)ethoxy)-3-(S)-(4-fluorophenyl)-4-(3-(4-monophosphoryl-5-oxo-1H-1,2,4-triazolo)methyl)morpholine;

2-(R)-(1-(R)-(3,5-bis(trifluoromethyl)phenyl)ethoxy)-3-(S)-(4-fluorophenyl)-4-(3-(1-monophosphoryl-5-oxo-1H-1,2,4-triazolo)methyl)morpholine;

2-(R)-(1-(R)-(3,5-bis(trifluoromethyl)phenyl)ethoxy)-3-(S)-(4-fluorophenyl)-4-(3-(2-monophosphoryl-5-oxo-1H-1,2,4-triazolo)methyl)morpholine;

2-(R)-(1-(R)-(3,5-bis(trifluoromethyl)phenyl)ethoxy)-3-(S)-(4-fluorophenyl)-4-(3-(5-oxyphosphoryl-1H-1,2,4-triazolo)methyl)morpholine;

2-(S)-(1-(R)-(3,5-bis(trifluoromethyl)phenyl)ethoxy)-3-(S)-(4-fluorophenyl)-4-(3-(1-monophosphoryl-5-oxo-4H-1,2,4-triazolo)methyl)morpholine;

2-(R)-(1-(R)-(3,5-bis(trifluoromethyl)phenyl)ethoxy)-4-(4-N,N-dimethylaminobut-2-yn-yl)-3-(S)-(4-fluorophenyl) morpholine;

or a pharmaceutically acceptable salt thereof.

Suitable atypical anti-depressants include: bupropion, lithium, nefazodone, trazodone and viloxazine, and pharmaceutically acceptable salts thereof.

Suitable classes of anti-anxiety agents include benzodiazepines and 5-HT$_{1A}$ agonists or antagonists, especially 5-HT$_{1A}$ partial agonists, and corticotropin releasing factor (CRF) antagonists.

Suitable benzodiazepines include: alprazolam, chlordiazepoxide, clonazepam, chlorazepate, diazepam, halazepam, lorazepam, oxazepam and prazepam, and pharmaceutically acceptable salts thereof.

Suitable 5-HT$_{1A}$ receptor agonists or antagonists include, in particular, the 5-HT$_{1A}$ receptor partial agonists buspirone, flesinoxan, gepirone and ipsapirone, and pharmaceutically acceptable salts thereof.

Suitable corticotropin releasing factor (CRF) antagonists include those previously discussed herein.

As used herein, the term "substance abuse disorders" includes substance dependence or abuse with or without physiological dependence. The substances associated with these disorders are: alcohol, amphetamines (or amphetamine-like substances), caffeine, cannabis, cocaine, hallucinogens, inhalants, marijuana, nicotine, opioids, phencyclidine (or phencyclidine-like compounds), sedative-hypnotics or benzodiazepines, and other (or unknown) substances and combinations of all of the above.

In particular, the term "substance abuse disorders" includes drug withdrawal disorders such as alcohol withdrawal with or without perceptual disturbances; alcohol withdrawal delirium; amphetamine withdrawal; cocaine withdrawal; nicotine withdrawal; opioid withdrawal; sedative, hypnotic or anxiolytic withdrawal with or without perceptual disturbances; sedative, hypnotic or anxiolytic withdrawal delirium; and withdrawal symptoms due to other substances. It will be appreciated that reference to treatment of nicotine withdrawal includes the treatment of symptoms associated with smoking cessation.

Other "substance abuse disorders" include substance-induced anxiety disorder with onset during withdrawal; substance-induced mood disorder with onset during withdrawal; and substance-induced sleep disorder with onset during withdrawal.

It will be appreciated that a combination of a conventional antipsychotic drug with a CB1 receptor modulator may provide an enhanced effect in the treatment of mania. Such a combination would be expected to provide for a rapid onset of action to treat a manic episode thereby enabling prescription on an "as needed basis". Furthermore, such a combination may enable a lower dose of the antispychotic agent to be used without compromising the efficacy of the antipsychotic agent, thereby minimizing the risk of adverse side-effects. A yet further advantage of such a combination is that, due to the action of the CB1 receptor modulator, adverse side-effects caused by the antipsychotic agent such as acute dystonias, dyskinesias, akathesia and tremor may be reduced or prevented.

Thus, according to a further aspect of the present invention there is provided the use of a CB1 receptor modulator and an antipsychotic agent for the manufacture of a medicament for the treatment or prevention of mania.

The present invention also provides a method for the treatment or prevention of mania, which method comprises administration to a patient in need of such treatment or at risk of developing mania of an amount of a CB1 receptor modulator and an amount of an antipsychotic agent, such that together they give effective relief.

In a further aspect of the present invention, there is provided a pharmaceutical composition comprising a CB1 receptor modulator and an antipsychotic agent, together with at least one pharmaceutically acceptable carrier or excipient.

It will be appreciated that the CB1 receptor modulator and the antipsychotic agent may be present as a combined preparation for simultaneous, separate or sequential use for the treatment or prevention of mania. Such combined preparations may be, for example, in the form of a twin pack.

In a further or alternative aspect of the present invention, there is therefore provided a product comprising a CB1 receptor modulator and an antipsychotic agent as a combined preparation for simultaneous, separate or sequential use in the treatment or prevention of mania.

It will be appreciated that when using a combination of the present invention, the CB1 receptor modulator and the antipsychotic agent may be in the same pharmaceutically acceptable carrier and therefore administered simultaneously. They may be in separate pharmaceutical carriers such as conventional oral dosage forms which are taken simultaneously. The term "combination" also refers to the case where the compounds are provided in separate dosage forms and are administered sequentially. Therefore, by way of example, the antipsychotic agent may be administered as a tablet and then, within a reasonable period of time, the CB1 receptor modulator may be administered either as an oral dosage form such as a tablet or a fast-dissolving oral dosage form. By a "fast-dissolving oral formulation" is meant, an oral delivery form which when placed on the tongue of a patient, dissolves within about 10 seconds.

Included within the scope of the present invention is the use of CB1 receptor modulators in combination with an antipsychotic agent in the treatment or prevention of hypomania.

It will be appreciated that a combination of a conventional antipsychotic drug with a CB1 receptor modulator may provide an enhanced effect in the treatment of schizophrenic disorders. Such a combination would be expected to provide for a rapid onset of action to treat schizophrenic symptoms thereby enabling prescription on an "as needed basis". Furthermore, such a combination may enable a lower dose of the CNS agent to be used without compromising the efficacy of the antipsychotic agent, thereby minimizing the risk of adverse side-effects. A yet further advantage of such a combination is that, due to the action of the CB1 receptor modulator, adverse side-effects caused by the antipsychotic agent such as acute dystonias, dyskinesias, akathesia and tremor may be reduced or prevented.

As used herein, the term "schizophrenic disorders" includes paranoid, disorganized, catatonic, undifferentiated and residual schizophrenia; schizophreniform disorder; schizoaffective disorder; delusional disorder; brief psychotic disorder; shared psychotic disorder; substance-induced psychotic disorder; and psychotic disorder not otherwise specified.

Other conditions commonly associated with schizophrenic disorders include self-injurious behavior (e.g. Lesch-Nyhan syndrome) and suicidal gestures.

Suitable antipsychotic agents of use in combination with a CB1 receptor modulator include the phenothiazine, thioxanthene, heterocyclic dibenzazepine, butyrophenone, diphenylbutylpiperidine and indolone classes of antipsychotic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. Suitable examples of dibenzazepines include clozapine and olanzapine. An example of a butyrophenone is haloperidol. An example of a diphenylbutylpiperidine is pimozide. An example of an indolone is molindolone. Other antipsychotic agents include loxapine, sulpiride and risperidone. It will be appreciated that the antipsychotic agents when used in combination with a CB1 receptor modulator may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, olanzapine, haloperidol, pimozide and risperidone are commonly used in a non-salt form.

Other classes of antipsychotic agent of use in combination with a CB1 receptor modulator include dopamine receptor antagonists, especially D2, D3 and D4 dopamine receptor antagonists, and muscarinic m1 receptor agonists. An example of a D3 dopamine receptor antagonist is the compound PNU-99194A. An example of a D4 dopamine receptor antagonist is PNU-101387. An example of a muscarinic m1 receptor agonist is xanomeline.

Another class of antipsychotic agent of use in combination with a CB1 receptor modulator is the 5-$HT_{2A}$ receptor antagonists, examples of which include MDL100907 and fananserin. Also of use in combination with a CB1 receptor modulator are the serotonin dopamine antagonists (SDAs) which are believed to combine 5-$HT_{2A}$ and dopamine receptor antagonist activity, examples of which include olanzapine and ziperasidone.

Still further, NK-1 receptor antagonists may be favorably employed with the CB1 receptor modulators of the present invention. Preferred NK-1 receptor antagonists for use in the present invention are selected from the classes of compounds described in European Patent Specification No. 0 577 394, and International Patent Specification Nos. 95/08549, 95/18124, 95/23798, 96/05181, and 98/49710 (Application No. PCT/GB97/01630). The preparation of such compounds is fully described in the aforementioned publications.

Particularly preferred NK-1 receptor antagonists of use in the present invention include: (3S,5R,6S)-3-[2-cyclopropoxy-5-(trifluoromethoxy)phenyl]-6-phenyl-1-oxa-7-aza-spiro[4.5]decane;

(3R,5R,6S)-3-[2-cyclopropoxy-5-(trifluoromethoxy)phenyl]-6-phenyl-1-oxa-7-aza-spiro[4.5]decane;

(±)-(2R3R,2S3S)-N-{[2-cyclopropoxy-5-(trifluoromethoxy)phenyl]methyl}-2-phenylp iperidin-3-amine;

2-(S)-(3,5-bis(trifluoromethyl)benzyloxy)-3(S)-(4-fluorophenyl)-4-(3-(5-oxo-1H,4H-1,2,4-triazolo)methyl)morpholine;

2-(R)-(1-(R)-(3,5-bis(trifluoromethyl)phenyl)ethoxy)-4-(3-(5-oxo-1H,4H-1,2,4-triazolo)methyl)-3-(S)-phenyl-morpholine;

2-(S)-(3,5-bis(trifluoromethyl)benzyloxy)-4-(3-(5-oxo-1H,4H-1,2,4-triazolo)methyl)-3-(S)-phenyl-morpholine;

2-(R)-(1-(R)-(3,5-bis(trfluoromethyl)phenyl)ethoxy)-3-(S)-(4-fluorophenyl)-4-(3-(5-oxo-1H,4H-1,2,4-triazolo)methyl)morpholine;

2-(R)-(1-(R)-(3,5-bis(trifluoromethyl)phenyl)ethoxy)-4-(5-(N,N-dimethylamino)methyl-1,2,3-triazol4-yl)methyl-3-(S)-phenylmorpholine;

2-(R)-(1-(R)-(3,5-bis(trifluoromethyl)phenyl)ethoxy)-4-(5-(N,N-dimethylamino)methyl-1,2,3-triazol-4-yl)methyl-3-(S)-(4-fluorophenyl)morpholine;

2-(R)-(1-(R)-(3,5-bis(trifluoromethyl)phenyl)ethoxy)-3-(S)-(4-fluorophenyl)-4-(3-(4-monophosphoryl-5-oxo-1H-1,2,4-triazolo)methyl)morpholine;

2-(R)-(1-(R)-(3,5-bis(trifluoromethyl)phenyl)ethoxy)-3-(S)-(4-fluorophenyl)-4-(3-(1-monophosphoryl-5-oxo-1H-1,2,4-triazolo)methyl)morpholine;

2-(R)-(1-(R)-(3,5-bis(trifluoromethyl)phenyl)ethoxy)-3-(S)-(4-fluorophenyl)-4-(3-(2-monophosphoryl-5-oxo-1H-1,2,4-triazolo)methyl)morpholine;

2-(R)-(1-(R)-(3,5-bis(trifluoromethyl)phenyl)ethoxy)-3-(S)-(4-fluorophenyl)-4-(3-(5-oxyphosphoryl-1H-1,2,4-triazolo)methyl)morpholine;

2-(S)-(1-(R)-(3,5-bis(trifluoromethyl)phenyl)ethoxy)-3-(S)-(4-fluorophenyl)-4-(3-(1-monophosphoryl-5-oxo-4H-1,2,4-triazolo)methyl)morpholine;

2-(R)-(1-(R)-(3,5-bis(trifluoromethyl)phenyl)ethoxy)-4-(4-N,N-dimethylaminobut-2-yn-yl)-3-(S)-(4-fluorophenyl)morpholine;

2-(R)-(1-(S)-(3,5-bis(trifluoromethyl)phenyl)-2-hydroxyethoxy)-3-(S)-(4-fluorophenyl)-4-(1,2,4-triazol-3-yl)methylmorpholine;

or a pharraceutically acceptable salt thereof.

It will be appreciated that a combination of a conventional anti-asthmatic drug with a CB1 receptor modulator may provide an enhanced effect in the treatment of asthma.

Thus, according to a further aspect of the present invention there is provided the use of a CB1 receptor modulator and an anti-asthmatic agent for the manufacture of a medicament for the treatment or prevention of asthma.

The present invention also provides a method for the treatment or prevention of asthma, which method comprises administration to a patient in need of such treatment an amount of a compound of the present invention and an amount of an anti-asthmatic agent, such that together they give effective relief.

Suitable anti-asthmatic agents of use in combination with a compound of the present invention include, but are not limited to: (a) VLA-4 antagonists such as natalizumab and the compounds described in U.S. Pat. No. 5,510,332, WO97/03094, WO97/02289, WO96/40781, WO96/22966, WO96/20216, WO96/01644, WO96/06108, WO95/15973 and WO96/31206; (b) steroids and corticosteroids such as beclomethasone, methylprednisolone, betamethasone, prednisone, dexamethasone, and hydrocortisone; (c) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, desloratadine, cetirizine, fexofenadine, descarboethoxyloratadine, and the like; (d) non-steroidal anti-asthmatics including β2-agonists (such as terbutaline, metaproterenol, fenoterol, isoetharine, albuterol, bitolterol, salmeterol, epinephrine, and pirbuterol), theophylline, cromolyn sodium, atropine, ipratropium bromide, leukotriene antagonists (such as zafirlukast, montelukast, pranlukast, iralukast, pobilukast, and SKB-106,203), and leukotriene biosynthesis inhibitors (such as zileuton and BAY-1005); (e) anti-cholinergic agents including muscarinic antagonists (such as ipratropium bromide and atropine); and (f) antagonists of the chemokine receptors, especially CCR-3; and pharmaceutically acceptable salts thereof.

It will be appreciated that a combination of a conventional anti-constipation drug with a CB1 receptor modulator may provide an enhanced effect in the treatment of constipation.

Thus, according to a further aspect of the present invention there is provided the use of a CB1 receptor modulator and an anti-constipation agent for the manufacture of a medicament for the treatment or prevention of constipation.

The present invention also provides a method for the treatment or prevention of constipation, which method comprises administration to a patient in need of such treatment an amount of a compound of the present invention and an amount of an anti-constipation agent, such that together they give effective relief.

It will be appreciated that a combination of a conventional anti-constipation drug with a CB1 receptor modulator may provide an enhanced effect in the treatment of chronic intestinal pseudo-obstruction.

Thus, according to a further aspect of the present invention there is provided the use of a CB1 receptor modulator and an anti-constipation agent for the manufacture of a medicament for the treatment or prevention of chronic intestinal pseudo-obstruction.

The present invention also provides a method for the treatment or prevention of chronic intestinal pseudo-obstruction, which method comprises administration to a patient in need of such treatment an amount of a compound of the present invention and an amount of an anti-constipation agent, such that together they give effective relief.

Suitable anti-constipation agents of use in combination with a compound of the present invention include, but are not limited to, osmotic agents, laxatives and detergent laxatives (or wetting agents), bulking agents, and stimulants; and pharmaceutically acceptable salts thereof.

A particularly suitable class of osmotic agents include, but are not limited to sorbitol, lactulose, polyethylene glycol, magnesium, phosphate,and sulfate; and pharmaceutically acceptable salts thereof.

A particularly suitable class of laxatives and detergent laxatives, include, but are not limited to, magnesium, and docusate sodium; and pharmaceutically acceptable salts thereof.

A particularly suitable class of bulking agents include, but are not limited to, psyllium, methylcellulose, and calcium polycarbophil; and pharmaceutically acceptable salts thereof.

A particularly suitable class of stimulants include, but are not limited to, anthroquinones, and phenolphthalein; and pharmaceutically acceptable salts thereof.

It will be appreciated that a combination of a conventional anti-cirrhosis drug with a CB1 receptor modulator may provide an enhanced effect in the treatment of cirrhosis of the liver.

Thus, according to a further aspect of the present invention there is provided the use of a CB1 receptor modulator and an anti-cirrhosis agent for the manufacture of a medicament for the treatment or prevention of cirrhosis of the liver.

The present invention also provides a method for the treatment or prevention of cirrhosis of the liver, which method comprises administration to a patient in need of such treatment an amount of a compound of the present invention and an anti-cirrhosis agent, such that together they give effective relief.

Suitable anti-cirrhosis agents of use in combination with a compound of the present invention include, but are not limited to, corticosteroids, penicillamine, colchicine, interferon-γ, 2-oxoglutarate analogs, prostaglandin analogs, and other anti-inflammatory drugs and antimetabolites such as azathioprine, methotrexate, leflunamide, indomethacin, naproxen, and 6-mercaptopurine; and pharmaceutically acceptable salts thereof.

The method of treatment of this invention comprises a method of modulating the CB1 receptor and treating CB1 receptor mediated diseases by administering to a patient in need of such treatment a non-toxic therapeutically effective amount of a compound of this invention that selectively antagonizes the CB1 receptor in preference to the other CB or G-protein coupled receptors.

The term "therapeutically effective amount" means the amount the compound of structural formula I that will elicit the biological or medical response of a tissue, system, animal or human that is being sought by the researcher, veterinarian, medical doctor or other clinician, which includes alleviation of the symptoms of the disorder being treated. The novel methods of treatment of this invention are for disorders known to those skilled in the art. The term "mammal" includes humans.

The weight ratio of the compound of the Formula I to the second active ingredient may be varied and will depend upon the effective dose of each ingredient. Generally, an effective dose of each will be used. Thus, for example, when a compound of the Formula I is combined with a β-3 agonist the weight ratio of the compound of the Formula I to the β-3 agonist will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

Abbreviations used in the following Schemes and Examples:

| | |
|---|---|
| aq.: | aqueous |
| brine: | saturated sodium chloride solution |
| cat.: | catalytic |
| DIPEA: | N,N-diisopropylethylamine |
| DMF: | dimethylformamide |
| DMSO: | dimethylsulfoxide |
| EDC: | 1-ethyl-3-(3-dimethylaminopropyl)-carbodiimide hydrochloride |
| FC: | flash chromatography |

-continued

| | |
|---|---|
| g: | gram |
| h: | hours |
| HPLC: | high pressure liquid chromatography |
| HPLC/MS: | high pressure liquid chromatography/mass spectrum |
| $H_2SO_4$ | sulfuric acid |
| in vacuo: | rotoevaporation |
| Me: | methyl |
| MeOH: | methanol |
| mg: | milligram |
| MHz: | megahertz |
| min: | minutes |
| mL: | milliliter |
| mmol: | millimole |
| MPLC: | medium pressure liquid chromatography |
| MS or ms: | mass spectrum |
| μL: | microliter |
| Ph: | phenyl |
| $POCl_3$: | phosphoryl trichloride |
| PyBOP: | (benzotriazol-1-yloxy)tripyrrolidinophosphonium hexafluorophosphate |
| $R_t$: | retention time |
| rt: | room temperature |
| TEA: | triethylamine |
| TFA: | trifluoroacetic acid |
| THF: | tetrahydrofuran |
| TLC: | thin layer chromatography |

Compounds of the present invention may be prepared by procedures illustrated in the accompanying schemes.

Reaction Schemes 1-5 illustrate the methods employed in the synthesis of the compounds of the present invention of structural formula I. All substituents are as defined above unless indicated otherwise. A variety of synthetic methods known in the literature of organic synthesis are available for the preparation of the novel compounds of general formula I.

Scheme 1 illustrates a synthetic method for the preparation of compounds of general formula I when it is desired that the 2-position substituent on the pyridine ring bear a substituted oxygen substituent. An aryl benzyl ketone of general formula 3 is the starting point for the synthesis. Arylbenzyl ketones of general formula 3 may be available commercially or they can be synthesized using one of several methods known in organic synthesis. For example, reaction a nitrile of general formula 2 with a benzyl Grignard reagent derived from a benzyl halide of general formula 1 followed by acidic hydrolysis of the intermediate imine, affords an arylbenzyl ketone of general formula 3. The arylbenzyl ketone of general formula 3 is then converted to a vinylogous amide of general formula 5 by reaction with an amide acetal of general formula 4. The condensation reaction can be conducted using the amide acetal as the reaction solvent or a suitable polar aprotic solvent such as DMF may be used. The reaction is conducted at elevated temperature, typically between room temperature and 150° C. for periods of 1-8 hours. Condensation of the resulting vinylogous amide 5 with a substituted amide of general formula 6 then affords a 2-pyridone of general formula 7. This later reaction is facilitated when the substituent $R^2$ is chosen to be an electron-withdrawing group such an ester, nitrile, nitro, sulphonyl or the like. The reaction is usually conducted in a polar aprotic solvent such as DMF in the presence of a strong base such as sodium or potassium hydride or a sodium or potassium alkoxide. The resulting 2-pyridone 7 is then O-alkylated with an alkylating agent 8 to afford a substituted pyridine of general formula 9. This latter reaction product is generally attended by the N-alkylated 2-pyridinone (10) which is separated from the desired derivative 9 by chromatographic methods or fractional recrystallization.

Reaction conditions which favor the formation of the O-alkylated product 9 over the N-alkylated product 10 are known in the art of organic synthesis. For instance when the alkylation reaction of the 2-pyridinone 7 with the alkylating agent 8 is conducted with bases such as cesium carbonate in a solvent like DMF, or with silver carbonate in aprotic solvents like toluene or DMF a product mixture is produced wherein the desired isomer 9 predominates.

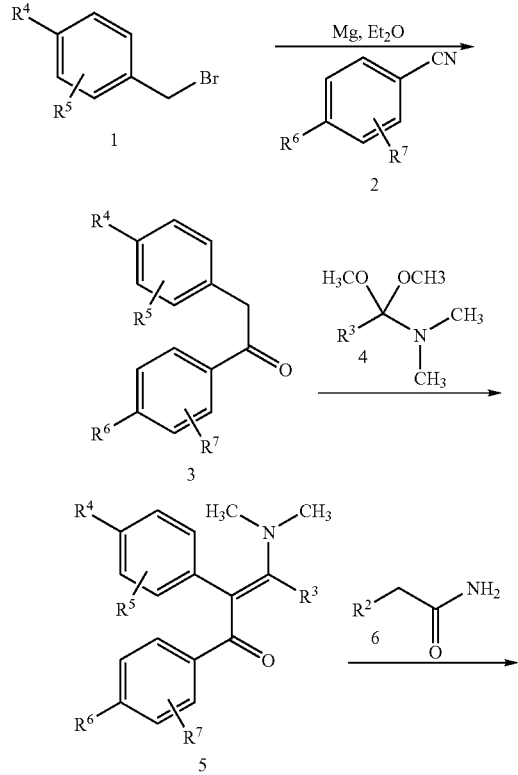

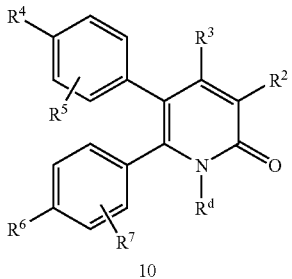

Scheme 2-4 illustrate further examples for the conversion of 2-pyridones of general formula 7 to the novel compounds of general formula I. In these examples the generalized 2-pyridone 7 is first converted to substituted 2-chloropyridine of general formula 11. This chlorination reaction can be accomplished using several chlorination reagents. For instance, treatment of 7 with oxalyl chloride at elevated temperatures in an inert solvent such as methylene chloride at an elevated temperature produces the 2-chloropyridine 11. This chlorination is typically conducted at temperatures between room temperature and the reflux temperature of the solvent being used for periods of 1-24 h. Alternatively, heating the 2-pyridone 7 with phosphorus oxychloride in the absence of a solvent at a temperature between room temperature and 105° C. also affords the 2-chloropyridine of general formula 11. In some instances it is desirable to conduct the chlorination reaction described here with a 2-pyridone of general formula 7 which bears a carboxylic acid substituent. For instance when the compound of general formula 7 has $R^2$=$CO_2H$, then a 2-chloropyridine of general formula 11 where $R^2$=COCl is produced. Compounds of general formula 11 bearing a carboxylic acid chloride at the 3-position are useful intermediates for the preparation of additional novel compounds of general formula I.

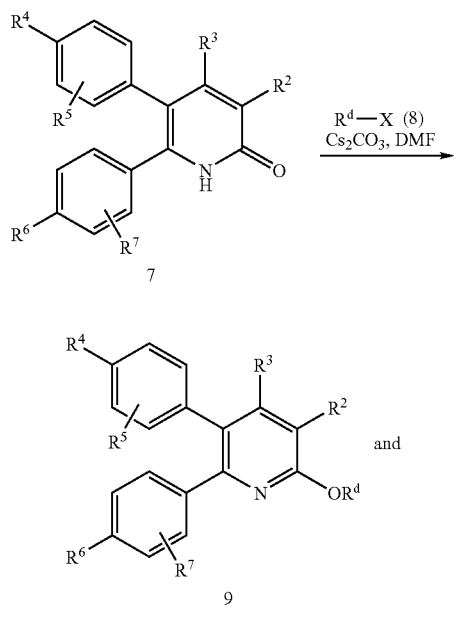

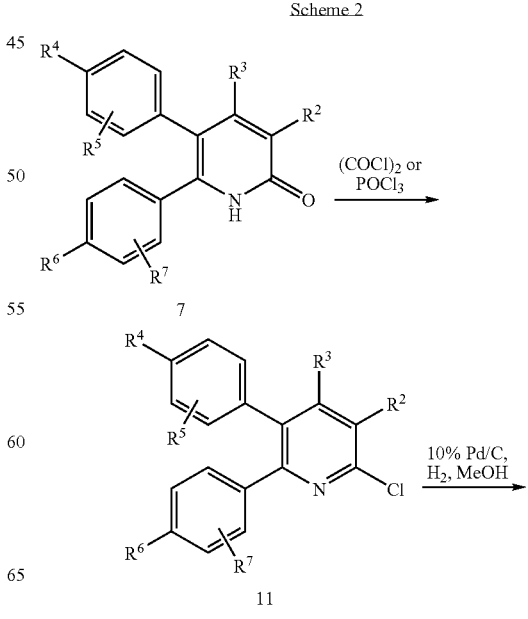

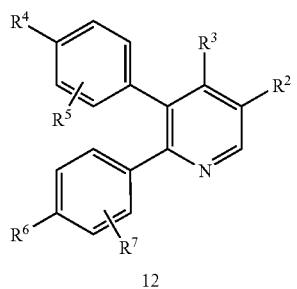

12

When it is desirable to prepare a compound of general formula I wherein the $R^1$ substituent is a hydrogen atom (12), it can be readily accomplished by reduction of the 2-chloro substituent in a compound of general formula 11 as shown at the bottom of Scheme 2. Thus, catalytic hydrogenation of compounds of general formula 11 using a 10% Pd/C catalyst under an atmosphere of hydrogen in a solvent such as methanol or ethanol affords a pyridine derivative of general formula 12.

The 2-chloropyridine derivatives of general formula 11 are useful intermediates for the incorporation of additional substituents at the pyridine 2-position which are within the scope of this invention. For instance, 2-chloropyridines of general formula 11 can be reacted with nucleophilic agents such as alkoxides, amines, thiolates and the like in a nucleophilic aromatic substitution process as shown in Scheme 3. When the nucleophilic agent employed is an alcohol or phenol of general formula 13, the reaction is conducted in the presence of a suitable base such as potassium or cesium carbonate in a solvent like toluene, at elevated temperature and the product (9) is one of the preferred compounds of general formula I wherein $R^1$=$OR^d$. This reaction sequence provides an alternative route to the compounds of general formula 9 shown in Scheme 1 which does not lead to a product mixture containing the N-alkylated 2-pyridone of general formula 10 shown above. Similarly, when a 2-chloropyridine derivative of general formula 11 is reacted with an excess of a primary or secondary amine of general formula 14 at elevated temperature, in a suitable solvent such as toluene, the substituted 2-aminopyridine of general formula 15 is produced. Additionally, when a 2-chloropyridine derivative of general formula 11 is reacted with a thiol derivative of general formula 16 in the presence of a suitable base such as potassium or cesium carbonate and in a solvent such as toluene, then a substituted 2-thiopyridine derivative of general formula 17 is produced.

Scheme 3

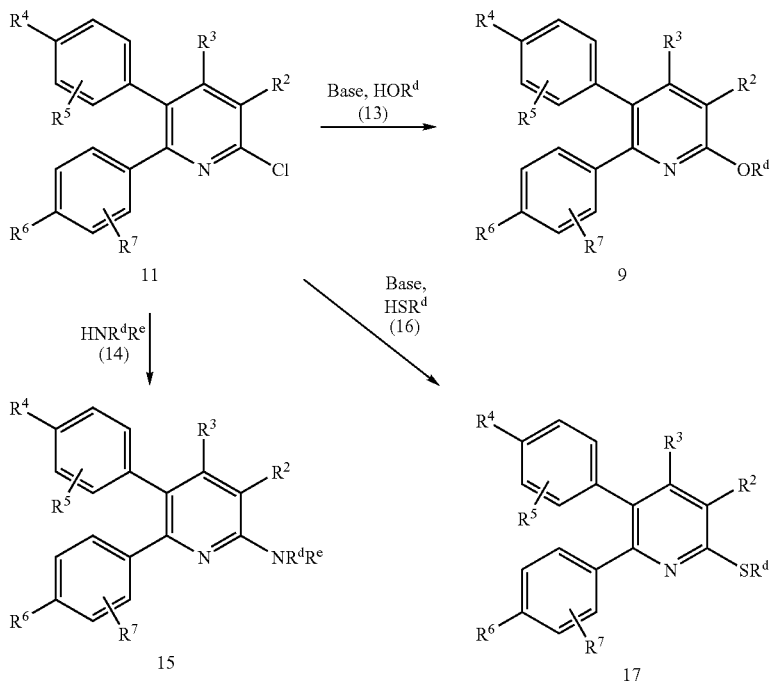

Compound of general formula I wherein the $R^2$ substituent is a hydrogen atom (12), may be produced from a 2-pyridone of general formula 7 using the methods illustrated in Scheme 4. A 2-pyridone of general formula 7 wherein the $R^2$ group is a cyano or ester group is first obtained using the methods described in Scheme 1 above and is then converted to a carboxylic acid of general formula 18. If the $R^2$ substituent in the compound of general formula 7 is a cyano group, then the hydrolysis step is typically performed under strongly acidic conditions. For instance, reaction of a compound of general formula 7 ($R^2$=CN) with 50% aqueous sulfuric acid effects hydrolysis of the nitrite and affords a carboxylic acid of general formula 18. The reaction is conducted at elevated temperatures, typically between 100-150° C. for periods of 5-24 h. Alternatively when a 2-pyridone of general formula 7 wherein the $R^2$ group is an ester is chosen as the starting material, the hydrolysis is typically conducted under basic conditions. In this case, reaction of a compound of general formula 7 ($R^2$=$CO_2R$) with several equivalents of aqueous sodium or potassium hydroxide in a solvent like methanol effects hydrolysis of the ester to afford a carboxylic acid of general formula 18. The basic hydrolysis of the ester 7 is typically conducted at temperatures between room temperature and the reflux temperature of the solvent being used. A carboxylic acid of general formula 18 may then be decarboxylated to afford a 2-pyridone (19) of general formula 7 wherein the $R^2$ group is a hydrogen atom using one of the various methods for decarboxylation of carboxylic acids that are known in organic synthesis. In Scheme 4 a carboxylic acid of general formula 18 is decarboxylated to afford the 2-pyridone of general formula 19 by heating in quinoline at 235° C. The 2-pyridones of general formula 19 are then converted to the title compounds of this invention of general formula I ($R^2$=H) using the methods described in Schemes 1-3 above.

Scheme 4

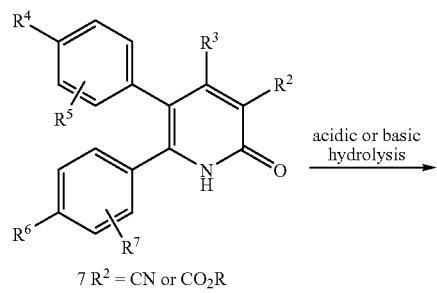

7 $R^2$ = CN or $CO_2R$

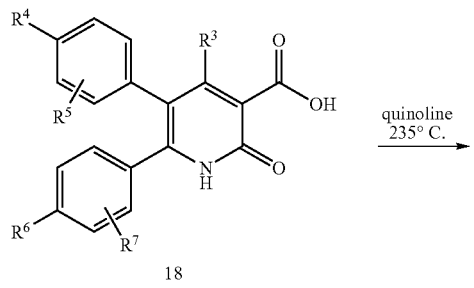

18

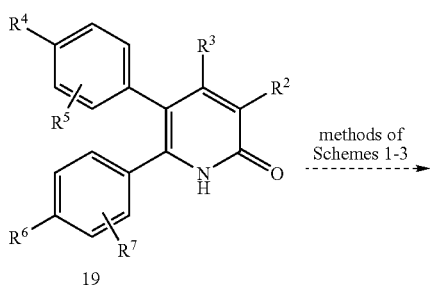

19

-continued

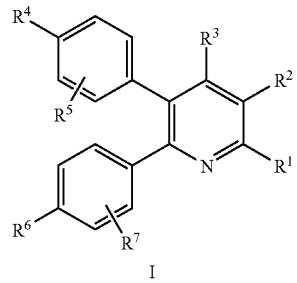

I

Scheme 5 illustrates a method for the synthesis of title compounds of general formula I wherein the $R^1$ substituent is an carboxylic ester or similar functional group that can in turn be prepared from an ester. In this synthetic method, a cinnamaldehyde of general formula 22 is used as the starting material. If the cinnamaldehyde derivative of general formula 22 with the desired substitution pattern is not readily available, it may be prepared in two step from the cinnamic acid of general formula 20 as shown. In this case the cinnamic acid of general formula 20 is converted to a mixed anhydride with a reagent such as ethyl chloroformate in a solvent like THF. The intermediate mixed anhydride is then reduced with sodium borohydride which affords a cinnamyl alcohol of general formula 21. The cinnamyl alcohol of general formula 21 is then oxidized to the cinnamaldehyde of general formula 22 using one of the methods for the oxidation of alcohols known in organic synthesis. For example reaction of the cinnamyl alcohol of general formula 21 with DMSO and oxalyl chloride using the Swern modification of the Moffatt reaction affords the cinnamaldehyde 22. The aldehyde 22 is condensed with methyl azidoacetate under basic conditions to afford the azidodiene 23. Reaction of the azide 23 with triphenylphosphine affords the intermediate 2-aza-$1\lambda^5$-phosphahexa-1,3,5-triene 24 which condenses with an benzaldehyde of general formula 25 to yield the methyl 5,6-diarylpyridine-2-carboxylate 26 after endocyclic ring closure and air oxidation of an intermediate dihydropyridine.

Scheme 5

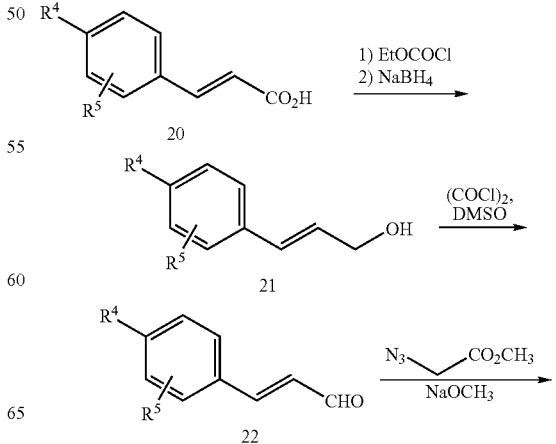

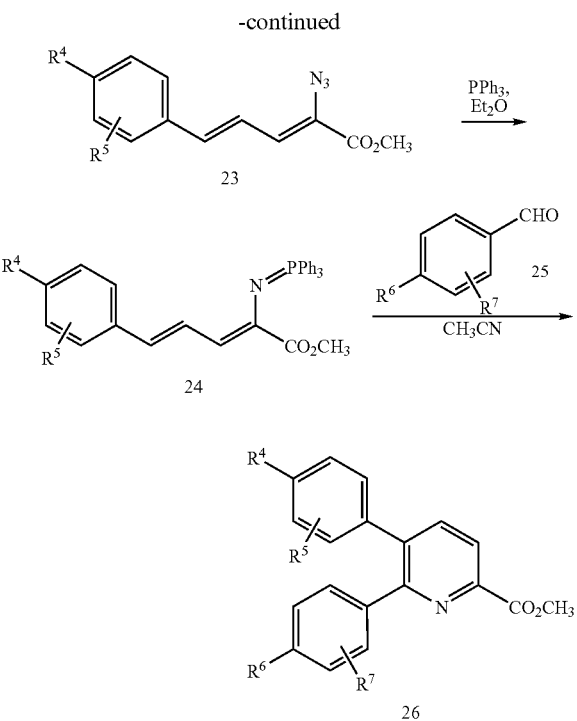

In order to illustrate the invention, the following examples are included. These examples do not limit the invention. They are only meant to suggest a method of reducing the invention to practice. Those skilled in the art may find other methods of practicing the invention which are readily apparent to them. However, those methods are also deemed to be within the scope of this invention.

General Procedures

The HPLC/MS analyses were performed using a Micromass ZMD mass spectrometer coupled to an Agilent 1100 Series HPLC utilizing a YMC ODS-A 4.6×50 mm column eluting at 2.5 mL/min with a solvent gradient of 10 to 95% B:A over 4.5 min, then 0.5 min at 95% B: solvent A=0.06% TFA in water; solvent B=0.05% TFA in acetonitrile.

Proton NMR spectra were obtained with a 400 MHz Varian Spectrometer in $CDCl_3$ or $CD_3OD$ and chemical shifts are reported as δ using the deuterium of the solvent as standard and coupling constants are reported in hertz.

EXAMPLE 1

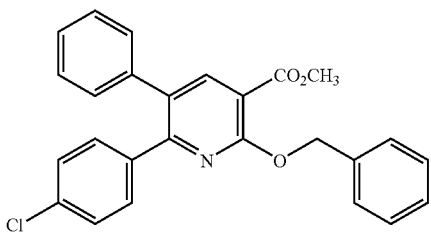

Methyl 2-(benzyloxy)-6-(4-chlorophenyl)-5-(phenyl)pyridine-3-carboxylate

Step A: 3-Dimethylamino-1-(4-chlorophenyl)-2-(phenyl)prop-2-en-1-one

A solution of benzyl 4-chlorophenyl ketone (10.0 g, 43.3 mmol) and dimethylformamide dimethylacetal (23 mL, 173 mmol) in DMF (125 mL) was heated at 75° C. for 20 h. The volatiles were removed in vacuo to provide 3-dimethylamino-1-(4-chlorophenyl)-2-(phenyl)prop-2-en-1-one (43.3 mmol assumed) which was used directly in the next step. $^1$HNMR ($CDCl_3$): δ 2.76 (s, 6H), 7.15 (m, 2H), 7.16-7.3 (m, 5H), 7.36 (m, 2H), 7.41 (s, 1H).

Step B: 6-(4-Chlorophenyl)-5-(phenyl)-2-oxo-1,2-dihydropyridine-3-nitrile

A solution of 3-dimethylamino-1-(4-chlorophenyl)-2-(phenyl)prop-2-en-1-one (43.3 mmol assumed) from Step A, cyanoacetamide (4.0 g, 47.6 mmol), and methanol (3.9 mL, 95 mmol) in DMF (100 mL) was added dropwise to a suspension of sodium hydride (60% in mineral oil) (4.3 g, 108 mmol) in DMF (50 mL) at rt. After the slow addition was complete, the reaction was heated to 95° C. for 2 h. Most of the DMF was then removed in vacuo before the reaction was diluted with aqueous 18% citric acid solution. The mixture was extracted twice with methylene chloride and the organic layers were washed with a portion of brine. The combined organic layers were dried over anhydrous sodium sulfate and concentrated in vacuo. The solid residue was triturated with ether, filtered, and air dried to afford 6-(4-chlorophenyl)-5-(phenyl)-2-oxo-1,2-dihydropyridine-3-nitrile. HPLC/MS: 307 (M+1); $R_t$=3.0 min;
$^1$HNMR ($CDCl_3$): δ 7.07 (2 d, J=5.8 and 7.5 Hz, 2H), 7.27 (br d, J=8.5 Hz, 2H), 7.32 (m, 3H), 7.36 (br d, J=8.5 Hz, 2H), 8.00 (s, 1H).

Step C: 6-(4-Chlorophenyl)-5-(phenyl)-2-oxo-1,2-dihydropyridine-3-carboxylic acid A suspension of 6-(4-chlorophenyl)-5-(phenyl)-2-oxo-1,2-dihydropyridine-3-nitrile (5.0 g, 16.2 mmol) from Step B in 50% sulfuric acid (80 mL) was heated at 140° C. for 20 h. The reaction was then cooled, diluted with water and extracted twice with methylene chloride. The organic layers were washed with a portion of brine and the combined organic layers were dried over anhydrous sodium sulfate and concentrated in vacuo to give the title compound as a yellow solid. HPLC/MS indicated a small amount of unreacted starting nitrile. HPLC/MS: 326 (M+1); $R_t$=2.99 min;
$^1$HNMR ($CDCl_3$): δ 7.12 (2 d, J=5.3 and 7.6 Hz, 2H), 7.27 (br d, J=8.6 Hz, 2H), 7.3 (m, 3H), 7.39 (br d, J=8.6 Hz, 2H), 8.70 (s, 1H).

Step D: Methyl 6-(4-chlorophenyl)-5-(phenyl)-2-oxo-1,2-dihydropyridine-3-carboxylate Into a suspension of 6-(4-chlorophenyl)-5-(phenyl)-2-oxo-1,2-dihydropyridine-3-carboxylic acid (5.0 g, 15.3 mmol) from Step C in methanol (400 mL) was bubbled HCl gas until the resulting solution was saturated. The mixture was stirred at rt for 20 h, then heated at 60° C. for 8 h, and again at rt for 16 h. The reaction was concentrated in vacuo, made basic with saturated sodium carbonate solution, and extracted twice with methylene chloride. The organic layers were washed with a portion of brine and the combined organic layers were dried over anhydrous sodium sulfate and concentrated in vacuo to give the crude product. The crude product was purified by flash column chromatography on silica gel eluted with 100% methylene chloride, then a gradient of 1 to 4% methanol in methylene chloride to afford the desired title compound. HPLC/MS: 340 (M+1); $R_t$=3.0 min;

¹HNMR (CDCl₃): δ 3.990 (s, 3H), 7.14 (2 d, J=5.8 and 7.4 Hz, 2H), 7.26 (br d, J=8.6 Hz, 2H), 7.3 (m, 3H), 7.34 (br d, J=8.6 Hz, 2H), 8.31 (s, 1H).

Further elution afforded a small amount of 6-(4-chlorophenyl)-5-(phenyl)-2-oxo-1,2-dihydropyridine-3-carboxamide as a by-product from the partial hydrolysis of the residual nitrile in Step C. HPLC/MS: 325 (M+1); R_f=2.6 min;

¹HNMR (CDCl₃): δ 5.85 (br d, 1H), 7.11 (m, 2H), 7.26-7.34 (m, 5H), 7.34 (d, J=8.4 Hz, 2H), 8.70 (s, 1H), 9.15 (m, 1H).

Step E: Methyl 2-(benzyloxy)-6-(4-chlorophenyl)-5-(phenyl)pyridine-3-carboxylate To a solution of methyl 6-(4-chlorophenyl)-5-(phenyl)-2-oxo-1,2-dihydropyridine-3-carboxylate (500 mg, 1.47 mmol) from Step D in DMF (6 mL) was added benzyl bromide (0.22 mL, 1.91 mmol) and then cesium carbonate (622 mg, 1.91 mmol). The reaction was stirred at 55° C. for 4 h and was then diluted with water and extracted twice with methylene chloride. The organic layers were washed with a portion of brine and the combined organic layers were dried over anhydrous sodium sulfate and concentrated in vacuo to give a 4:1 mixture of the crude products. The products were separated by flash column chromatography on silica gel eluted with a gradient of 5 to 10% ethyl acetate in hexanes to first yield the desired higher Rf O-alkylation title product. HPLC/MS: 430 (M+1); R_f=4.9 min;

¹HNMR (CDCl₃): δ 3.955 (s, 3H), 5.643 (s, 2H), 7.17 (m, 2H), 7.24 (d, J=8.5 Hz, 2H), 7.28-7.36 (m, 6H), 7.41 (br t, J=7.6 Hz, 2H), 7.57 (br d, J=7.2 Hz, 2H), 8.256 (s, 1H).

Further elution with 30 to 50% ethyl acetate in hexanes afforded the lower Rf N-alkylation by-product, methyl 1-benzyl-6-(4-chlorophenyl)-5-(phenyl)-2-oxo-1,2-dihdropyridine-3-carboxylate. HPLC/MS: 430 (M+1); R_f=3.80 min;

¹HNMR (CDCl₃): δ 3.968 (s, 3H), 5.22 (br s, 2H), 6.84 (br d, J=8.0 Hz, 2 H), 6.91 (m, 2H), 6.94 (2 d, J=6.1 and 7.3 Hz, 2H), 7.16 (m, 5H), 7.22 (m, 3H), 8.306 (S, 1H).

EXAMPLE 2

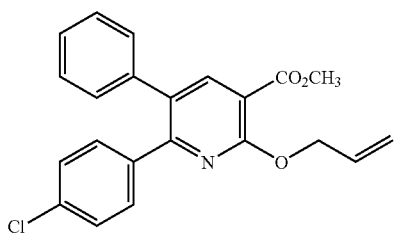

Methyl 2-(allyloxy)-6-(4-chlorophenyl)-5-(phenyl)pyridine-3-carboxylate

Using essentially the same procedure as in Example 1, Step E, but substituting allyl bromide for benzyl bromide, methyl 6-(4-chlorophenyl)-5-(phenyl)-2-oxo-1,2-dihydropyridine-3-carboxylate (500 mg, 1.47 mmol) from Example 1, Step D afforded the desired higher Rf O-alkylation title compound after purification by flash column chromatography on silica gel (eluted with a gradient of 5 to 10% ethyl acetate in hexanes). HPLC/MS: 380 (M+1); R_f=4.7 min. ¹HNMR (CDCl₃): δ 3.954 (s, 3H), 5.09 (br d, J=5 Hz, 2H), 5.32 (dd, J=1.5 and 10.5 Hz, 1H), 5.45 (br dd, J=1.6 and 18 Hz, 1H), 6.13-6.23 (m, 1H), 7.16-7.21 (m, 2H), 7.22 (d, J=8.6 Hz, 2H), 7.30-7.36 (m, 3H), 7.37 (d, J=8.6 Hz, 2H), 8.246 (s, 1H).

EXAMPLE 3

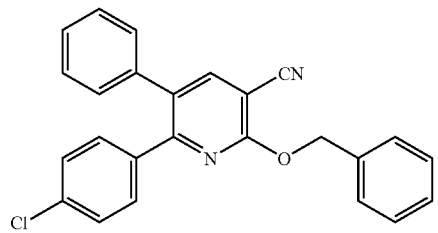

2-(Benzyloxy)-6-(4-chlorophenyl)-5-(phenyl)pyridine-3-nitrile

To a solution of 6-(4-chlorophenyl)-5-(phenyl)-2-oxo-1,2-dihydropyridine-3-nitrile (200 mg, 0.65 mmol) from Example 1, Step B in DMF (3 mL) was added benzyl bromide (0.10 mL, 0.85 mmol) and then cesium carbonate (276 mg, 0.85 mmol). The reaction was stirred at 55° C. for 3 h and was then diluted with water and extracted twice with methylene chloride. The organic layers were washed with a portion of brine and the combined organic layers were dried over anhydrous sodium sulfate and concentrated in vacuo. The products were separated by preparative TLC (30% ethyl acetate in hexanes) to give the desired higher Rf O-alkylation title product.

HPLC/MS: 397 (M+1); R_f=4.8 min. ¹HNMR (CDCl₃): δ 5.614 (s, 2H), 7.13 (m, 2H), 7.24 (br d, J=8.6 Hz, 2H), 7.27-7.40 (m, 6H), 7.43 (br t, J=7.6 Hz, 2H), 7.54 (br d, J=7.2 Hz, 2H), 7.922 (s, 1H).

The lower Rf band gave the N-alkylation by-product, methyl 1-benzyl-6-(4-chlorophenyl)-5-(phenyl)-2-oxo-1,2-dihydropyridine-3-nitrile.

HPLC/MS: 397 (M+1); R_f=3.9 min

EXAMPLE 4

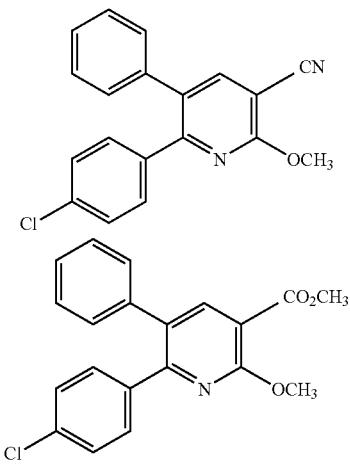

2-(Methoxy)-6-(4-chlorophenyl)-5-(phenyl)pyridine-3-nitrile (A) and methyl 2-(methoxy)-6-(4-chlorophenyl)-5-(phenyl)pyridine-3-carboxylate (B)

To a solution of 6-(4-chlorophenyl)-5-(phenyl)-2-oxo-1,2-dihydropyridine-3-carboxylic acid (50 mg, 0.15 mmol) from Example 1, Step C (containing a trace of the 3-nitrile starting material) in methylene chloride (3 mL) and methanol (1 mL) was added 2M trimethylsilyldiazomethane in hexanes until the yellow color persisted. The volatiles were removed under a stream of nitrogen and the residue was separated by preparative TLC on silica gel (eluted with 30% ethyl acetate in hexanes) to obtain 2-(methoxy)-6-(4-chlorophenyl)-5-(phenyl)pyridine-3-nitrile (A) and methyl 2-(methoxy)-6-(4-chlorophenyl)-5-(phenyl)pyridine-3-carboxylate (B) as minor products (along with some of the N-alkylation by-products). The main product was the expected methyl 6-(4-chlorophenyl)-5-(phenyl)-2-oxo-1,2-dihydropyridine-3-carboxylate (same product as obtained in Example 1, Step D).

2-(Methoxy)-6-(4-chlorophenyl)-5-(phenyl)pyridine-3-nitrile (A):

HPLC/MS: 321 (M+1); $R_t$=4.3 min. $^1$HNMR (CDCl$_3$): δ 4.158 (s, 31), 7.14 (m, 2H), 7.24 (d, J=8.5 Hz, 2H), 7.34 (m, 3H), 7.36 (br d, J=8.5 Hz, 2H), 7.913 (s, 1H).

Methyl 2-(methoxy)-6-(4-chlorophenyl)-5-(phenyl)pyridine-3-carboxylate (B):

HPLC/MS: 354 (M+1); $R_t$=4.3 min. $^1$HNMR (CDCl$_3$): δ 3.944 (s, 3H), 4.153 (s, 3H), 6.84 (br d, J=8.1 Hz, 2H), 6.95 (br t, J=8.1 Hz, 1H), 7.18 (m, 2H), 7.21-7.30 (m, 2H), 7.39 (br d, J=8.4 Hz, 2H), 8.238 (s, 1H).

EXAMPLE 5

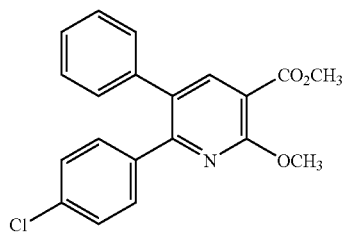

Methyl 2-(methoxy)-6-(4-chlorophenyl)-5-(phenyl)pyridine-3-carboxylate

Using essentially the same procedure as in Example 1, Step E, but substituting methyl iodide for benzyl bromide, methyl 6-(4-chlorophenyl)-5-(phenyl)-2-oxo-1,2-dihydropyridine-3-carboxylate (500 mg, 1.47 mmol) from Example 1, Step D was converted into methyl 2-(methoxy)-6-(4-chlorophenyl)-5-(phenyl)pyridine-3-carboxylate. The final product was purified by flash column chromatography on silica gel (eluted with 10% ethyl acetate in hexanes) to afford the title compound as the faster eluting product. HPLC/MS: 354 (M+1); $R_t$=4.3 min. $^1$HNMR (CDCl$_3$): δ 3.944 (s, 3H), 4.153 (s, 3H), 6.84 (br d, J=8.1 Hz, 2H), 6.95 (br t, J=8.1 Hz, 1H), 7.18 (m, 2H), 7.21-7.30 (m, 2H), 7.39 (br d, J=8.4 Hz, 2H), 8.238 (s, 1H).

EXAMPLE 6

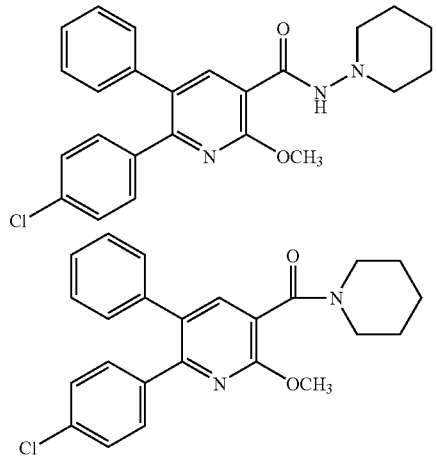

N-(Piperidin-1-yl)-2-(methoxy)-6-(4-chlorophenyl)-5-(phenyl)pyridine-3-carboxamide and 2-(methoxy)-6-(4-chlorophenyl)-5-(phenyl)-3-(piperidin-1-ylcarbonyl)pyridine.

Step A: 2-(Methoxy)-6-(4-chlorophenyl)-5-(phenyl)pyridine-3-carboxylic acid

To a solution of methyl 2-(methoxy)-6-(4-chlorophenyl)-5-(phenyl)pyridine-3-carboxylate (150 mg, 0.42 mmol) from Example 5 in methanol (5 mL) was added 5N sodium hydroxide (0.42 mL, 2.1 mmol). The reaction was stirred at rt for 72 h and was then diluted with water and acidified with 2N hydrochloric acid. The mixture was extracted twice with methylene chloride. The organic layers were washed with a portion of brine and the combined organic layers were dried over anhydrous sodium sulfate and concentrated in vacuo to give the crude title product as a white solid.

Step B: 2-(Methoxy)-6-(4-chlorophenyl)-5-(phenyl)pyridine-3-carbonyl chloride.

To a suspension of 2-(methoxy)-6-(4-chlorophenyl)-5-(phenyl)pyridine-3-carboxylic acid (126 mg, 0.37 mmol) from Step A and a drop of DMF (cat.) in methylene chloride (5 mL) was added oxalyl chloride (0.16 mL, 1.85 mmol). The reaction was stirred at rt for 2 h and was then evaporated to dryness in vacuo. The crude acid chloride was used directly in the subsequent amide formations.

Step C: N-(Piperidin-1-yl)-2-(methoxy)-6-(4-chlorophenyl)-5-(phenyl)pyridine-3-carboxamide and 2-(methoxy)-6-(4-chlorophenyl)-5-(phenyl)-3-(piperidin-1-ylcarbonyl)pyridine.

A solution of 2-(methoxy)-6-(4-chlorophenyl)-5-(phenyl)pyridine-3-carbonyl chloride (0.08 mmol) from Step B in methylene chloride (1 mL) was added to a solution of 1-aminopiperidine (containing a few percent of piperidine as an impurity) (0.017 mL, 0.16 mmol) and TEA (0.022 mL, 0.16 mmol) in methylene chloride (0.5 mL). The reaction was stirred at rt for 20 h and was then diluted with brine and extracted twice with methylene chloride. The combined organic layers were dried over anhydrous sodium sulfate and concentrated in vacuo to give a mixture of the crude products. These were separated by preparative TLC (5% methanol in methylene chloride) to give N-(piperidin-1-yl)-2-(methoxy)-6-(4-chlorophenyl)-5-(phenyl)pyridine-3-carboxamide as the lower eluting product. HPLC/MS: 422 (M+1); $R_t$=3.8 min;

$^1$HNMR (CDCl$_3$): δ 1.55 (br m, 2H), 1.85 (br m, 4H), 3.05 (br m, 4H), 4.214 (s, 3H), 7.18 (m, 2H), 7.23 (d, J=8.5 Hz, 2H), 7.28-7.34 (m, 3H), 7.37 (br d, J=8.5 Hz, 2H), 8.533 (s, 1H), 8.75 (br s, 1H).

The higher Rf band afforded the piperidine amide by-product 2-(methoxy)-6-(4-chlorophenyl)-5-(phenyl)-3-(piperidin-1-ylcarbonyl)pyridine.

HPLC/MS: 407 (M+1); $R_t$=4.2 min

In the following Examples 7-10, the procedure described in Example 6, Step C was repeated but substituting the appropriate amine in place of 1-aminopiperidine to afford the following amides:

EXAMPLE 7

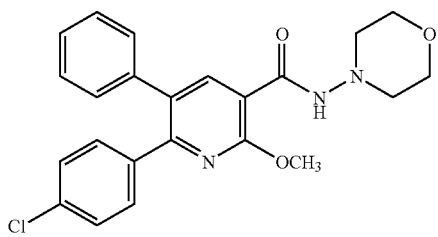

N-(Morpholin-4-yl)-2-(methoxy)-6-(4-chlorophenyl)-5-(phenyl)pyridine-3-carboxamide HPLC/MS: 424 (M+1); $R_t$=3.6 min

EXAMPLE 8

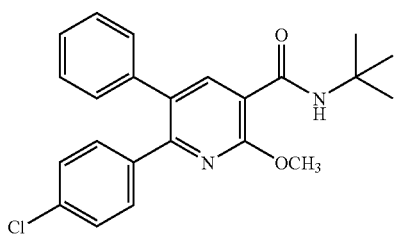

N-(t-Butyl)-2-(methoxy)-6-(4-chlorophenyl)-5-(phenyl)pyridine-3-carboxamide

HPLC/MS: 395 (M+1); $R_t$=4.72 min

EXAMPLE 9

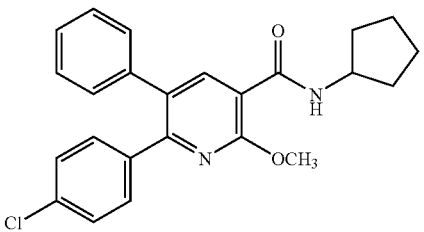

N-(Cyclopentyl)-2-(methoxy)-6-(4-chlorophenyl)-5-(phenyl)pyridine-3-carboxamide

HPLC/MS: 407 (M+1); $R_t$=4.7 min

EXAMPLE 10

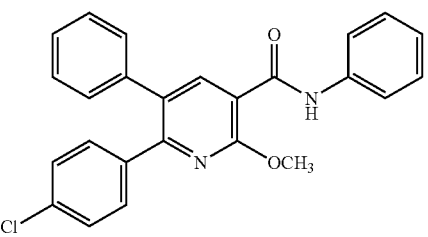

N-(Phenyl)-2-(methoxy)-6-(4-chlorophenyl)-5-(phenyl)pyridine-3-carboxamide

HPLC/MS: 415(M+1); $R_t$=4.77 min

EXAMPLE 11

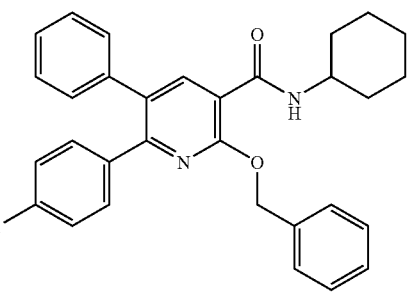

N-(Cyclohexyl)-2-(benzyloxy)-6-(4-chlorophenyl)-5-(phenyl)pyridine-3-carboxamide Using essentially the same three step procedure described in Example 6, Steps A-C, but substituting methyl 2-(benzy loxy)-6-(4-chlorophenyl)-5-(phenyl)pyridine-3-carboxylate from Example 1, Step E for methyl 2-(methoxy)-6-(4-chlorophenyl)-5-(phenyl)pyridine-3-carboxylate in Step A and substituting cyclohexylamine for 1-aminopiperidine in Step C, N-(cyclohexyl)-2-(benzyloxy)-6-(4-chlorophenyl)-5-(phenyl)pyridine-3-carboxamide was prepared. HPLC/MS: 497 (M+1); $R_t$=5.28 min In the following Examples 12-18, the procedure described in Example 6, Step C was repeated but substituting 2-(benzyloxy)-6-(4-chlorophenyl)-5-(phenyl)pyridine-3-carbonyl chloride from Example 11, Step B for 2-(methoxy)-6-(4-chlorophenyl)-5-(phenyl)pyridine-3-carbonyl chloride and using the appropriate amines to afford the following amides:

EXAMPLE 12

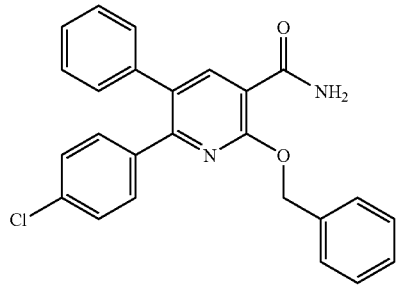

2-(Benzyloxy)-6-(4-chlorophenyl)-5-(phenyl)pyridine-3-carboxamide

HPLC/MS: 415 (M+1); $R_t$=4.29 min

EXAMPLE 13

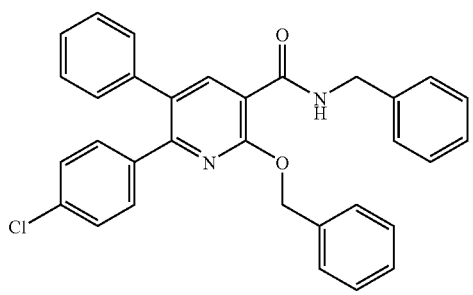

N-Benzyl-2-(benzyloxy)-6-(4-chlorophenyl)-5-(phenyl)pyridine-3-carboxamide

HPLC/MS: 505 (M+1); $R_t$=4.96 min

EXAMPLE 14

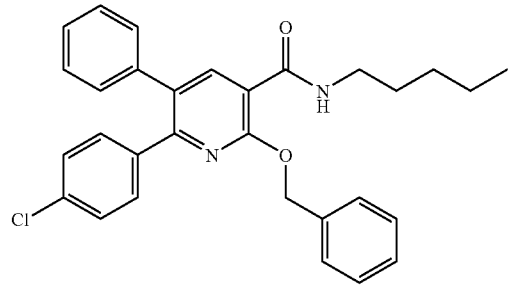

N-(n-Pentyl)-2-(benzyloxy)-6-(4-chlorophenyl)-5-(phenyl)pyridine-3-carboxamide

HPLC/MS: 485 (M+1); $R_t$=5.2 min

EXAMPLE 15

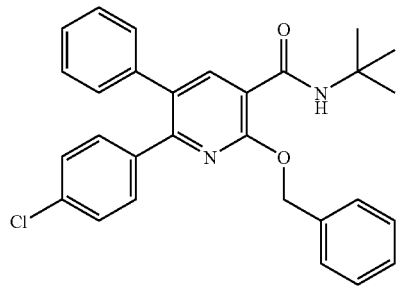

N-(t-Butyl)-2-(benzyloxy)-6-(4-chlorophenyl)-5-(phenyl)pyridine-3-carboxamide

HPLC/MS: 471 (M+1); $R_t$=5.15 min

EXAMPLE 16

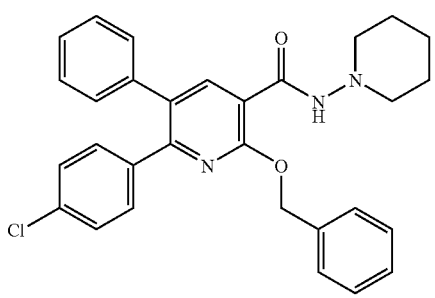

N-(Piperidin-1-yl)-2-(benzyloxy)-6-(4-chlorophenyl)-5-(phenyl)pyridine-3-carboxamide HPLC/MS: 498 (M+1); $R_t$=4.3 min

EXAMPLE 17

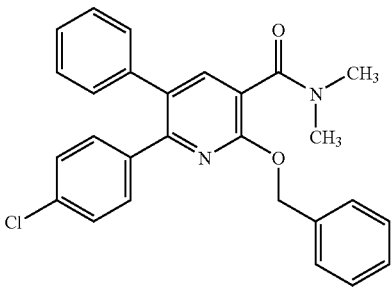

N,N-Dimethyl-2-(benzyloxy)-6-(4-chlorophenyl)-5-(phenyl)pyridine-3-carboxamide

HPLC/MS: 443 (M+1); $R_t$=4.32 min

EXAMPLE 18

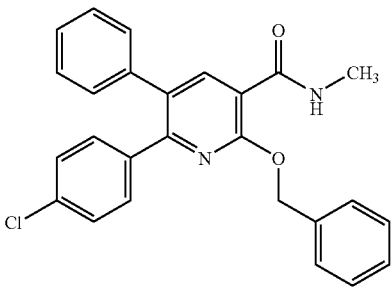

N-Methyl-2-(benzyloxy)-6-(4-chlorophenyl)-5-(phenyl)pyridine-3-carboxamide

HPLC/MS: 430 (M+1); $R_t$=4.88 min

EXAMPLE 19

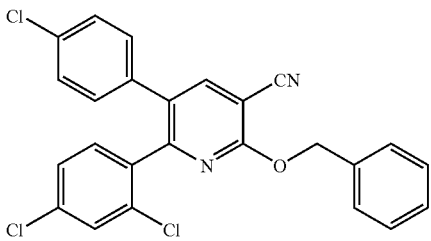

2-(Benzyloxy)-6-(2,4-dichrorophenyl)-5-(4-chlorophenyl)pyridine-3-nitrile

Step A: 3-Dimethylamino-1-(2,4-dichlorophenyl)-2-(4-chlorophenyl)prop-2-en-1-one.

A solution of 4-chlorobenzyl 2,4-dichlorophenyl ketone (4.5 g, 14.4 mmol) and dimethylformamide dimethylacetal (7.7 mL, 58 mmol) in DMF (60 mL) was heated at 75° C. for 20 h. The volatiles were removed in vacuo to provide the crude 3-dimethylamino-1-(2,4-dichlorophenyl)-2-(4-chlorophenyl)prop-2-en-1-one (14.4 mmol assumed) which was used directly in the next step. HPLC/MS: 354 (M+1), 356 (M+3); $R_t$=3.47 min Step B: 6-(2,4-Dichlorophenyl)-5-(4-chlorophenyl)-2-oxo-1,2-dihydropyridine-3-nitrile.

A solution of 3-dimethylamino-1-(2,4-dichlorophenyl)-2-(4-chlorophenyl)prop-2-en-1-one (14.4 mmol assumed) from Step A, cyanoacetamide (1.33 g, 15.8 mmol), and methanol (1.3 mL, 32 mmol) in DMF (35 mL) was added dropwise to a suspension of sodium hydride (60% in mineral oil) (1.45 g, 36 mmol) in DMF (16 mL) at rt. After the slow addition was complete, the reaction was heated to 95° C. for 2.5 h. Most of the DMF was then removed in vacuo before the reaction was diluted with aqueous 18% citric acid solution. The mixture was extracted twice with methylene chloride and the organic layers were washed with a portion of brine. The combined organic layers were dried over anhydrous sodium sulfate and concentrated in vacuo. The solid residue was triturated with ether, filtered, and air dried to afford 6-(2,4-dichlorophenyl)-5-(4-chlorophenyl)-2-oxo-1,2-dihydropyridine-3-nitrile. HPLC/MS: 375 (M+1), 377 (M+3); $R_t$=3.47 min; $^1$HNMR (CDCl$_3$): δ 6.96 (br d, J=8.4 Hz, 2H), 7.14 (d, J=8.2 Hz, 1H), 7.25 (br d, J=8.4 Hz, 2H), 7.31 (dd, J=1.9 and 8.2 Hz, 1H), 7.50 (d, J=2.0 Hz, 1H), 7.996 (s, 1H).

Step C: 2-(Benzyloxy)-6-(2,4-dichlorophenyl)-5-(4-chlorophenyl)pyridine-3-nitrile.

To a solution of 6-(2,4-dichlorophenyl)-5-(4-chlorophenyl)-2-oxo-1,2-dihydropyridine-3-nitrile (460 mg, 1.22 mmol) from Step B in DMF (7 mL) was added benzyl bromide (0.19 mL, 1.58 mmol) and then cesium carbonate (517 mg, 1.58 mmol). The reaction was stirred at 55° C. for 1.5 h and was then diluted with water and extracted twice with ethyl acetate. The organic layers were washed with a portion of brine and the combined organic layers were dried over anhydrous sodium sulfate and concentrated in vacuo to give a mixture of the desired 2-(benzyloxy)-6-(2,4-dichlorophenyl)-5-(4-chlorophenyl)pyridine-3-nitrile and the corresponding N-alkylation 2-pyridone by-product. The products were separated by flash column chromatography on silica gel eluted with a gradient of 5 to 10% ethyl acetate in hexanes to afford the faster eluting O-alkylation title product. HPLC/MS: 465 (M+1), 467 (M+3); $R_t$=5.07 min; $^1$HNMR (CDCl$_3$): δ 5.547 (s, 2H), 7.00 (br d, J=8.6 Hz, 2H), 7.11 (d, J=8.4 Hz, 1H), 7.22-7.27 (m, 3H), 7.34-7.44 (m, 4H), 7.50 (br d, J=6.5 Hz, 2H), 7.958 (s, 1H).

Further elution with 30 to 50% ethyl acetate in hexanes afforded the lower Rf N-alkylation by-product, 1-benzyl-6-(2,4-dichlorophenyl)-5-(4-chlorophenyl)-2-oxo-1,2-dihdropyridine-3-nitrile. HPLC/MS: 465 (M+1), 467 (M+3); $R_t$=4.27 min; $^1$HNMR (CDCl$_3$): δ 4.58 and 5.76 (Abq, J=15 Hz, 2H), 6.56 (d, J=8.4Hz, 1H), 6.82 (m, 2H), 6.91 (dt, J=1.7 and 8.4 Hz, 2H), 6.99 (dd, J=2.0 and 8.4 Hz, 1H), 7.17 (dt, J=1.7 and 8.4 Hz, 2H), 7.18-7.5 (m, 3H), 7.40 (d, J=2.0 Hz, 1H), 7.882 (s, 1H).

In the following Examples 20-24, the procedure described in Example 19, Step C was repeated but substituting the appropriately substituted benzyl halide for benzyl bromide in the reaction with 6-(2,4-dichlorophenyl)-5-(4-chlorophenyl)-2-oxo-1,2-dihydropyridine-3-nitrile to afford the following compounds:

EXAMPLE 20

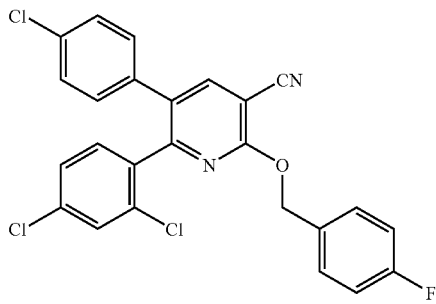

2-(4-Fluorobenzyloxy)-6-(2,4-dichlorophenyl)-5-(4-chlorophenyl)pyridine-3-nitrile HPLC/MS: 485 (M+1), 487 (M+3); $R_t$=5.01 min

EXAMPLE 21

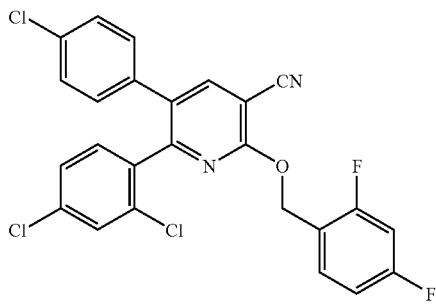

2-(2,4-Difluorobenzyloxy)-6-(2,4-dichlorophenyl)-5-(4-chlorophenyl)pyridine-3-nitrile HPLC/MS: 501 (M+1), 503 (M+3); $R_t$=5.07 min

EXAMPLE 22

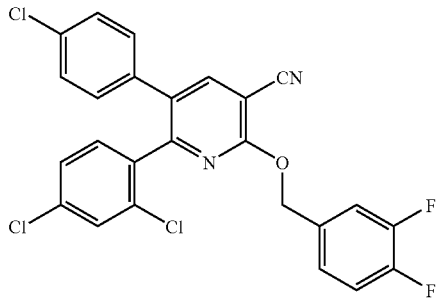

2-(3,4-Difluorobenzyloxy)-6-(2,4-dichlorophenyl)-5-(4-chlorophenyl)pyridine-3-nitrile HPLC/MS: 501 (M+1), 503 (M+3); $R_t$=5.01 min; $^1$HNMR (CDCl$_3$): δ 5.480 (s, 2H), 7.00 (br d, J=8.4 Hz, 2H), 7.085 (d, J=8.2 Hz, 1H), 7.15-7.37 (m, 6H), 7.36 (d, J=1.9 Hz, 1H), 7.976 (s, 1H).

EXAMPLE 23

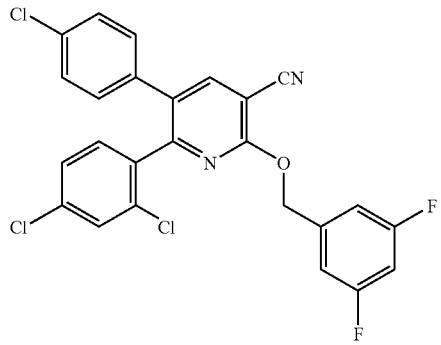

2-(3,5-Difluorobenzyloxy)-6-(2,4-dichlorophenyl)-5-(4-chlorophenyl)pyridine-3-nitrile HPLC/MS: 501 (M+1), 503 (M+3); $R_t$=5.04 min

EXAMPLE 24

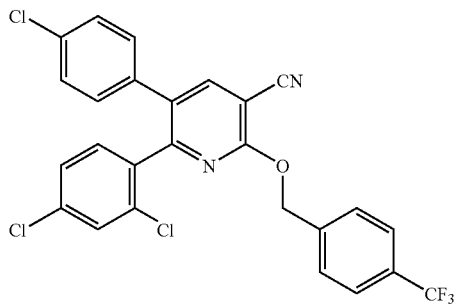

2-(4-Trifluoromethylbenzyloxy)-6-(2,4-dichlorophenyl)-5-(4-chlorophenyl)pyridine-3-nitrile HPLC/MS: 533 (M+1), 535 (M+3); $R_t$=5.12 min

EXAMPLE 25

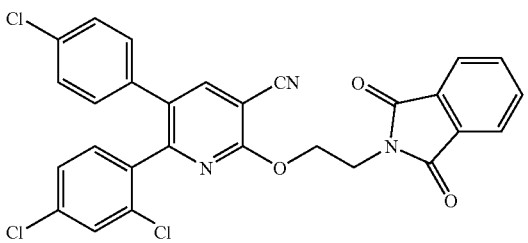

5-(4-Chlorophenyl)-6-(2,4-dichlorophenyl)-2-[2-(1,3-dioxo-1,3-dihydro-2H-isoindol-2-yl)ethoxy]nicotinonitrile To the product of Step B Example 19 (600 mg, 1.597 mmol) was added N-(2-bromoethyl)-phthalimide (690 mg, 2.715 mmol), $K_2CO_3$ (331 mg, 2.396 mmol) and DMF (8 mL). The mixture was heated to 70° C. for 20 hours. The mixture was filtered, concentrated and passed through a short plug of silica gel eluting with 33% ethyl acetate/hexane. The partially purified material was carried on without further purification. MS (electrospray) m/e 547.8 MH$^+$ (retention time=4.4 min LC/MS).

EXAMPLE 26

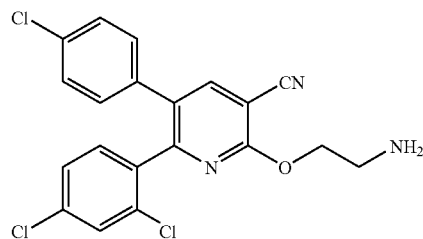

2-(2-Aminoethoxy)-5-(4-chlorophenyl)-6-(2,4-dichlorophenyl)nicotinonitrile

To the product of Example 25 (971 mg) was added acetonitrile (14 mL) and ethanol (5 mL). The mixture was heated to 80° C. to dissolve the material before adding hydrazine hydrate (0.60 mL, 12.24 mmol). After 2.3 hours the mixture was filtered through Celite®545 diatomaceous earth and then concentrated. The residue was purified by flash chromatography (silica gel) eluting with 2% triethylamine/4% methanol/94% dichloromethane affording the product. MS (electrospray) m/e 418.0 MH$^+$ (retention time=3.0 min LC/MS).

EXAMPLE 27

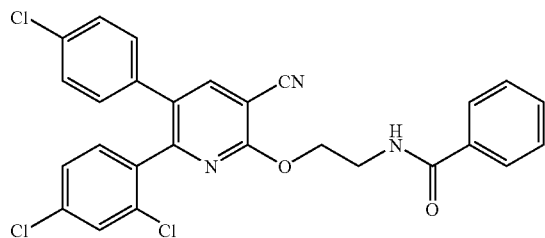

N-(2-{[5-(4-Chlorophenyl)-3-cyano-6-(2,4-dichlorophenyl)pyridin-2-yl]oxy}ethyl)benzamide To the product of Example 26 (55.0 mg, 0.1314 mmol) in dichloromethane (2.05 mL) was added triethylamine (54.9 μL, 0.3941 mmol) and benzoyl chloride (30.5 μL, 0.2628 mmol). After 15 hours the reaction volume was reduced to about 1.2 mL before it was purified by preparative thin layer chromatography (20 cm×20 cm, 1000 μm, silica gel) eluting with 10% ethyl acetate/dichloromethane affording the product. MS (electrospray) m/e 523.9 MH$^+$ (retention time=4.3 min LC/MS).

In the following Examples 28-31, the procedure described in Example 27 was repeated but substituting the appropriate acid chloride for benzoyl chloride in the reaction with 2-(2-aminoethoxy)-5-(4-chlorophenyl)-6-(2,4-dichlorophenyl)-nicotinonitrile from Example 26 to afford the following compounds:

EXAMPLE 28

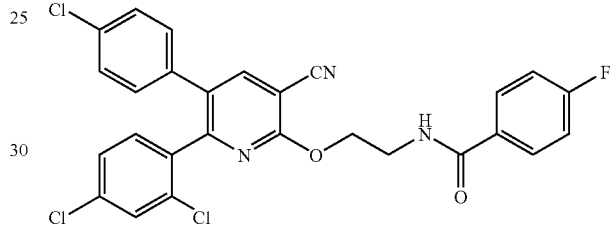

N-(2-{[5-(4-Chlorophenyl)-3-cyano-6-(2,4-dichlorophenyl)pyridin-2-yl]oxy}ethyl)-4-fluorobenzamide MS (electrospray) m/e 541.9 MH$^+$ (retention time=4.3 min LC/MS).

EXAMPLE 29

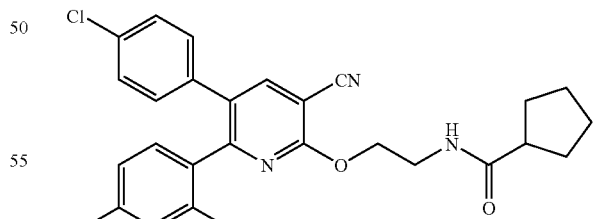

N-(2-{[5-(4-Chlorophenyl)-3-cyano-6-(2,4-dichlorophenyl)pyridin-2-yl]oxy}ethyl)cyclopentanecarboxamide MS (electrospray) m/e 513.9 MH$^+$ (retention time=4.3 min LC/MS).

EXAMPLE 30

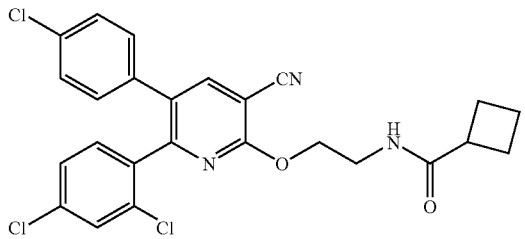

N-(2-{[5-(4-Chlorophenyl)-3-cyano-6-(2,4-dichlorophenyl)pyridin-2-yl]oxy}ethyl)cyclobutanecarboxamide MS (electrospray) m/e 501.9 MH$^+$ (retention time=4.2 min LC/MS).

EXAMPLE 31

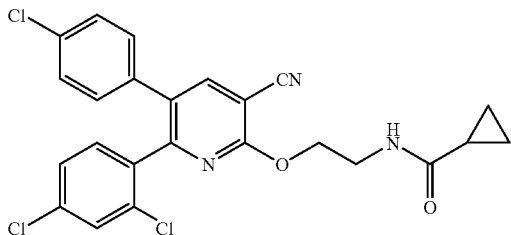

N-(2-{[5-(4-Chlorophenyl)-3-cyano-6-(2,4-dichlorophenyl)pyridin-2-yl]oxy}ethyl)cyclopropanecarboxamide MS (electrospray) m/e 486.1 MH$^+$ (retention time=4.1 min LC/MS).

EXAMPLE 32

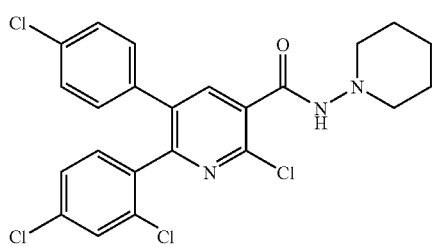

2-Chloro-5-(4-chlorophenyl)-6-(2,4-dichlorophenyl)-N-piperidin-1-ylnicotinamide

Step A: 5-(4-Chlorophenyl)-6-(2,4-dichlorophenyl)-2-oxo-1,2-dihydropyridine-3-carboxylic acid Method A:

A suspension of 2-(benzyloxy)-6-(2,4-dichlorophenyl)-5-(4-chlorophenyl)pyridine-3-nitrile (326 mg, 0.70 mmol) from Example 19, Step C in 50% sulfuric acid (5 mL) was heated at 140° C. for 20 h. The reaction was diluted with water and extracted three times with methylene chloride. The organic layers were washed with a portion of brine and the combined organic layers were dried over anhydrous sodium sulfate and concentrated in vacuo to give crude 6-(2,4-dichlorophenyl)-5-(4-chlorophenyl)-2-oxo-1,2-dihydropyridine-3-arboxylic acid as a white solid. HPLC/MS: 394 (M+1), 396 (M+3); R$_t$=3.44 min; $^1$HNMR (CDCl$_3$): δ 7.65 (dt, J=1.7 and 8.6 Hz, 2H), 7.18 (d, J=8.4 Hz, 1H), 7.26 (dt, J=1.7 and 8.6 Hz, 2H), 7.35 (dd, J=2.0 and 8.2 Hz, 1H), 7.55 ( J=2.0 Hz, 1H), 8.707 (s, 1H).

Method B:

A suspension of 6-(2,4-dichlorophenyl)-5-(4-chlorophenyl)-2-oxo-1,2-dihydropyridine-3-nitrile (3.58 g, 8.73 mmol) from Example 19, Step B in 50% sulfuric acid (60 mL) was heated at 140° C. for 24 h. The reaction was then cooled, diluted with water and extracted twice with methylene chloride. The organic layers were washed with a portion of brine and the combined organic layers were dried over anhydrous sodium sulfate and concentrated in vacuo to give crude 6-(2,4-dichlorophenyl)-5-(4-chlorophenyl)-2-oxo-1,2-dihydropyridine-3-carboxylic acid as a yellow solid. HPLC/MS: 394 (M+1), 396 (M+3); R$_t$=3.44 min Step B: 2-(Chloro)-6-(2,4-dichlorophenyl)-5-(4-chlorophenyl)pyridine-3-carbonyl chloride To a suspension of 6-(2,4-dichlorophenyl)-5-(4-chlorophenyl)-2-oxo-1,2-dihydropyridine-3-carboxylic acid (200 mg, 0.41 mmol) from Step A in methylene chloride was added a drop of DMF (cat.) and oxalyl chloride (0.18 mL, 2.0 mmol). The reaction was stirred at rt for 1 h and then evaporated to dryness. The acid chloride was dissolved in methylene chloride and used directly in the subsequent amide formation.

Step C: 2-Chloro-5-(4-chlorophenyl)-6-(2,4-dichlorophenyl)-N-piperidin-1-ylnicotinamide To a portion of the methylene chloride (1 mL) solution of 2-(chloro)-6-(2,4-dichlorophenyl)-5-(4-chlorophenyl)pyridine-3-carbonyl chloride (0.068 mmol) from Step B was added a solution of 1-aminopiperidine (0.010 mL, 0.088 mmol) and TEA (0.014 mL, 0.10 mmol) in methylene chloride (1 mL). The reaction was stirred at rt for 16 h and was then evaporated. The residue was purified by preparative TLC (40% ethyl acetate in hexanes) to yield N-(piperidin-1-yl)-2-(chloro)-6-(2,4-dichlorophenyl)-5-(4-chlorophenyl)pyridine-3-carboxamide. HPLC/MS: 494 (M+1), 496 (M+3); R$_t$=3.97 min In the following Examples 33-35, the procedure described in Example 32, Step C was repeated but substituting the appropriate amine for 1-aminopiperidine in the reaction with 2-chloro-6-(2,4-dichlorophenyl)-5-(4-chlorophenyl)pyridine-3-carbonyl chloride from Example 32, Step B to afford the following compounds:

EXAMPLE 33

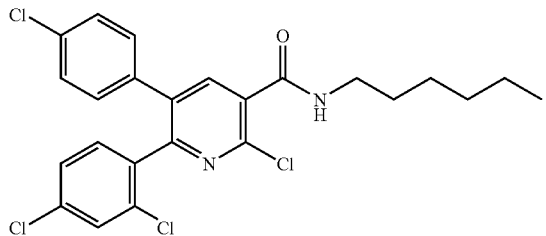

N-(n-Hexyl)-2-(chloro)-6-(2,4-dichlorolphenyl)-5-(4-chlorophenyl)pyridine-3-carboxamide HPLC/MS: 495 (M+1), 497 (M+3); $R_t$=4.61 min

EXAMPLE 34

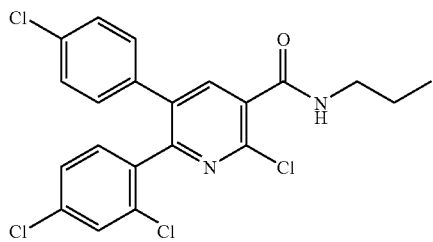

N-(n-Propyl)-2-(chloro)-6-(2,4-dichlorolphenyl)-5-(4-chlorophenyl)pyridine-3-carboxamide HPLC/MS: 453 (M+1), 455 (M+3); $R_t$=4.13 min; $^1$HNMR (CDCl$_3$): δ 1.063 (t, J=7.4 Hz, 3H), 1.72 (hex, J=7.4 Hz, 2H), 3.52 (q, J=7.1 Hz, 2H), 7.07 (br d, J=8.0 Hz, 2H), 7.23-7.30 (m, 4H), 7.35 (d, J=1.7 Hz, 1H), 8.210 (s, 1H).

EXAMPLE 35

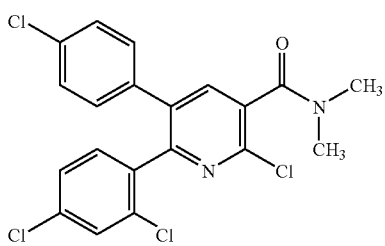

N-N-(Dimethyl)-2-(chloro)-6-(2,4-dichlorophenyl)-5-(4-chlorophenyl)pyridine-3-carboxamide HPLC/MS: 439 (M+1), 441 (M+3); $R_t$=4.00 min; $^1$HNMR (CDCl$_3$): δ 3.049 (s, 3H), 3.211 (s, 3H), 7.06 (br d, J=8.0 Hz, 2H), 7.23-7.30 (m, 4H), 7.35 (br d, 1H), 7.740 (s, 1H).

EXAMPLE 36

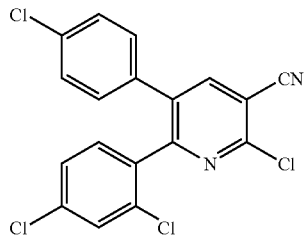

2-Chloro-5-(4-chlorophenyl)-6-(2,4-dichlorophenyl)nicotinonitrile

To a dried round bottom flask fitted with a condenser was added the product of Step B in Example 19 (2.0 g; 5.33 mmol) and excess phosphorous oxychloride (6 mL). The reaction mixture was heated to reflux for 16 hours. The reaction mixture was allowed to cool to room temperature, and the volatiles were removed in vacuo. The reaction mixture was then dissolved in methylene chloride and washed with saturated NaHCO$_3$ solution (2×), water, brine, dried (Na$_2$SO$_4$), filtered, and concentrated in vacuo. Purification was done by MPLC (silica gel; 0-10% ethyl acetate:hexane) to afford the desired product: m/e=395 (M+3) $R_t$=4.4 min on LCMS.

EXAMPLE 37

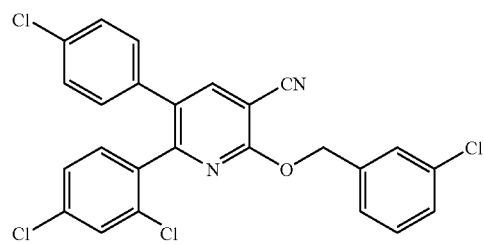

2-[(3-Chlorobenzyl)oxy]-5-(4-chlorolphenyl)-6-(2,4-dichlorophenyl)nicotinonitrile To a dried round bottom flask was added toluene (1 mL), the product of Example 36 (0.050 g; 0.127 mmol); 3-chlorobenzyl alcohol (0.080 mL; 0.670 mmol), and cesium carbonate (0.218 g; 0.670 mmol). The reaction mixture was heated at 100° C. and stirred for 16 hours. The reaction mixture was allowed to cool to room temperature and was then partitioned between ethyl acetate and 2N aq. NaOH solution. The organic portion was separated and washed with more 2N aq. NaOH solution (2×), brine, dried (Na$_2$SO$_4$), filtered, and concentrated in vacuo. Purification was done by MPLC (silica gel; 0-10% ethyl acetate:hexane) to afford the desired product: m/e=501 (M+2); $R_t$=5.08 min on LCMS.

In the following Examples 37-48, the procedure described in Example 37 was repeated but substituting the appropriate alcohol or phenol for 3-chlorobenzyl alcohol in the reaction with 2-chloro-5-(4-chlorophenyl)-6-(2,4-dichlorophenyl)nicotinonitrile from Example 36 to afford the following compounds:

EXAMPLE 38

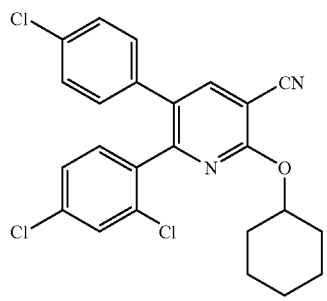

5-(4-Chlorophenyl)-2-(cyclohexyloxy)-6-(2,4-dichlorophenyl)nicotinonitrile

HPLC/MS: m/e=374 (M-cyclohexyl); $R_t$=5.25 min.

EXAMPLE 39

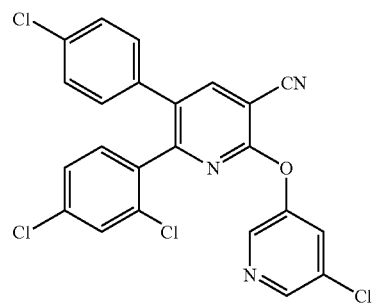

5-(4-Chlorophenyl)-2-[(5-chloropyridin-3-yl)oxy]-6-(2,4-dichlorophenyl)-nicotinonitrile HPLC/MS: m/e=488 (M+3); $R_t$=4.56 min.

EXAMPLE 40

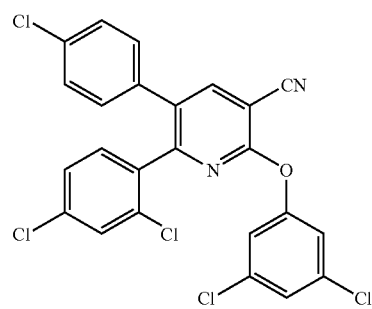

5-(4-Chlorophenyl)-2-(3,5-dichlorophenoxy)-6-(2,4-dichlorophenyl)nicotinonitrile HPLC/MS: m/e=521 (M+3); $R_t$=5.13 min.

EXAMPLE 41

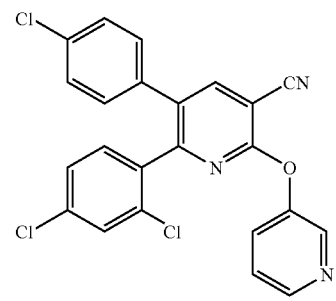

5-(4-Chlorophenyl)-6-(2,4-dichlorophenyl)-2-(pyridin-3-yloxy)nicotinonitrile

HPLC/MS: m/e=454 (M+3); $R_t$=3.74 min.

EXAMPLE 42

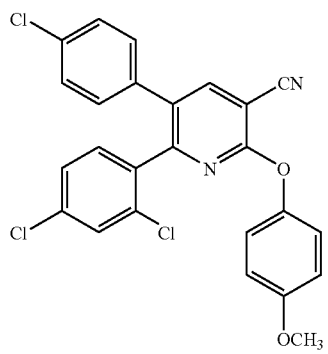

5-(4-Chlorophenyl)-6-(2,4-dichlorophenyl)-2-(4-methoxyphenoxy)nicotinonitrile

HPLC/MS: m/e=483 (M+3); $R_t$=4.62 min.

EXAMPLE 43

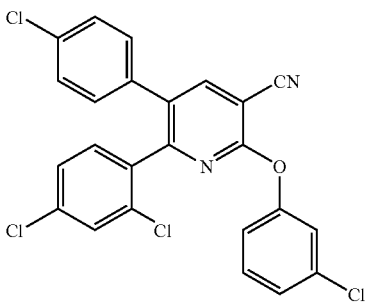

2-(3-Chlorophenoxy)-5-(4-chlorophenyl)-6-(2,4-dichlorophenyl)nicotinonitrile

HPLC/MS: m/e=487 (M+3); $R_t$=4.85 min.

EXAMPLE 44

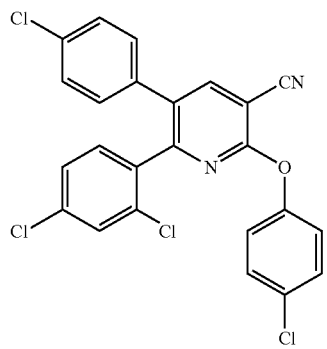

2-(4-Chlorophenoxy)-5-(4-chlorophenyl)-6-(2,4-dichlorophenyl)nicotinonitrile

HPLC/MS: m/e=487 (M+3); $R_t$=4.90 min.

EXAMPLE 45

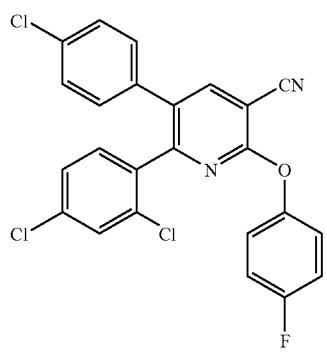

5-(4-Chlorophenyl)-6-(2,4-dichlorophenyl)-2-(4-fluorophenoxy)nicotinonitrile

HPLC/MS: m/e=469 (M+1); $R_t$=4.70 min.

EXAMPLE 46

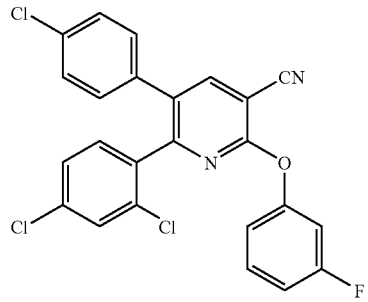

5-(4-Chlorophenyl)-6-(2,4-dichlorophenyl)-2-(3-fluorophenoxy)nicotinonitrile

HPLC/MS: m/e=471 (M+3); $R_t$=4.60 min.

EXAMPLE 47

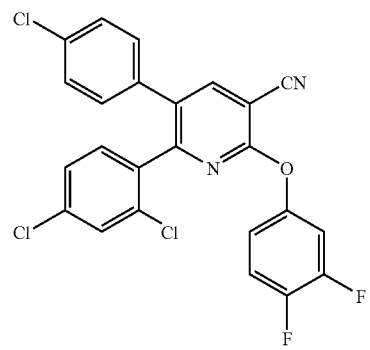

5-(4-Chlorophenyl)-6-(2,4-dichlorophenyl)-2-(3,4-difluorophenoxy)nicotinonitrile HPLC/MS: m/e=489 (M+3); $R_t$=4.70 min.

EXAMPLE 48

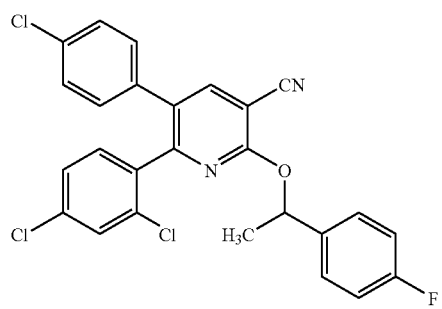

5-(4-Chlorophenyl)-6-(2,4-dichlorophenyl)-2-[1-(4-fluorophenyl)ethoxy]-nicotinonitrile HPLC/MS: m/e=377 (M-1-(4-flourophenyl)ethyl); $R_t$=5.00 min

EXAMPLE 49

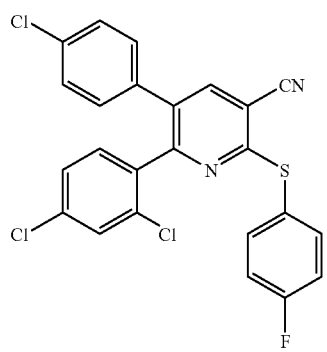

5-(4-Chlorophenyl)-6-(2,4-dichlorophenyl)-2-[(4-fluorophenyl)thio]nicotinonitrile An oven-dried round bottom flask was charged with 60.0 mg (0.152 mmol) of the product of Example 36 and Cs$_2$CO$_3$ (250.0 mg, 0.767 mmol), toluene (1.0 mL) and 4-fluorobenzene thiol (97.5 mg, 0.761 mmol) were added sequentially.

The reaction was heated to 100° C. for 23 hours and then allowed to cool to room temperature at which point the reaction was filtered and concentrated. The residue was purified by preparative thin layer chromatography (20 cm×20 cm, 1000 μm, silica gel) eluting with 10:90 EtOAc-hexane affording a white solid). MS (electrospray) m/e 487 MH+.

EXAMPLE 50

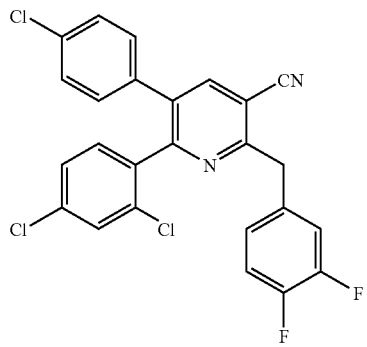

5-(4-Chlorophenyl)-6-(2,4-dichlorophenyl)-2-(3,4-difluorobenzyl)nicotinonitrile

To a dried round bottom flask was added THF (1 mL), the product of Example 36 (0.050 g; 0.127 mmol), 3,4-diflourobenzylzinc bromide (0.27 mL of a 0.5 M solution in THF; 0.134 mmol), and tetrakis(triphenylphosphine) palladium (0) (0.008 g; 5 mol %). The reaction was evacuated and purged with nitrogen several times and stirred at 50° C. for 16 hours. The reaction mixture was cooled to room temperature and diluted with ethyl acetate and washed with saturated aq. NaHCO₃ solution (3×), and brine. The organic portion was dried (Na₂SO₄), filtered, and concentrated in vacuo. Purification done by MPLC (silica gel; 0-10% ethyl acetate/hexane gradient) afforded the desired product: m/e=487 (M+3); $R_t$=4.8 min.

EXAMPLE 51

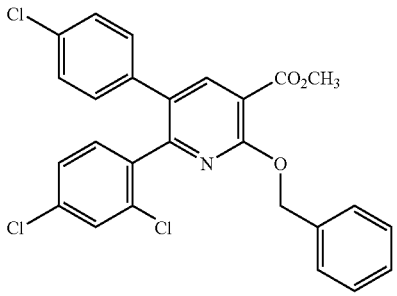

Methyl 2-(benzyloxy)-6-(2,4-dichlorophenyl)-5-(4-chlorophenyl)pyridine-3-carboxylate Step A: Methyl 6-(2,4-dichlorophenyl)-5-(4-chlorophenyl)-2-oxo-1,2-dihydropyridine-3-carboxylate Into a suspension of 6-(2,4-dichlorophenyl)-5-(4-chlorophenyl)-2-oxo-1,2-dihydropyridine-3-carboxylic acid (3.5 g, 8.7 mmol) from Example 32, Step A in methanol (350 mL) was bubbled HCl gas until the resulting solution was saturated. The mixture was stirred at rt for 72 h. The reaction was concentrated in vacuo, made basic with saturated sodium carbonate solution, and extracted twice with methylene chloride. The organic layers were washed with a portion of brine and the combined organic layers were dried over anhydrous sodium sulfate and concentrated in vacuo to give the crude methyl 6-(2,4-dichlorophenyl)-5-(4-chlorophenyl)-2-oxo-1,2-dihydropyridine-3-carboxylate (3.8 g) which was purified by flash column chromatography on silica gel eluted with 100% methylene chloride, then a gradient of 1 to 3% methanol in methylene chloride to give methyl 6-(2,4-dichlorophenyl)-5-(4-chlorophenyl)-2-oxo-1,2-dihydropyridine-3-carboxylate as an off-white solid.

HPLC/MS: 408 (M+1), 410 (M+3); $R_t$=3.47 min

Step B: Methyl 2-(benzyloxy)-6-(2,4-dichlorophenyl)-5-(4-chlorophenyl)pyridine-3-carboxylate.

To a solution of methyl 6-(2,4-dichlorophenyl)-5-(4-chlorophenyl)-2-oxo-1,2-dihydropyridine-3-carboxylate (700 mg, 1.7 mmol) from Step A in DMF (8 mL) was added benzyl bromide (0.26 mL, 2.2 mmol) and then cesium carbonate (720 mg, 2.2 mmol). The reaction was stirred at 55° C. for 4 h and was then diluted with water and extracted twice with methylene chloride. The organic layers were washed with a portion of brine and the combined organic layers were dried over anhydrous sodium sulfate and concentrated in vacuo to give a 1:1 mixture of methyl 2-(benzyloxy)-6-(2,4-dichlorophenyl)-5-(4-chlorophenyl)pyridine-3-carboxylate and the corresponding N-alkylated 2-oxo derivative. The products were separated by flash column chromatography on silica gel eluted with a gradient of 5 to 10% ethyl acetate in hexanes to afford first the faster eluting O-alkylation product, methyl 2-(benzyloxy)-6-(2,4-dichlorophenyl)-5-(4-chlorophenyl)pyridine-3-carboxylate.

HPLC/MS: 498 (M+1), 500 (M+3); $R_t$=5.1 min

EXAMPLE 52

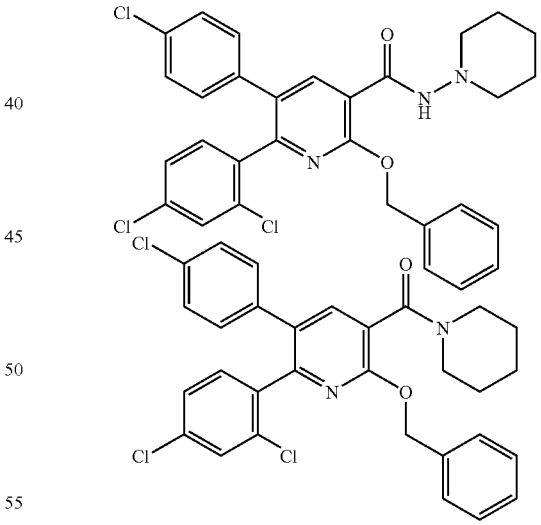

N-(Piperidin-1-yl)-2-(benzyloxy)-6-(2,4-dichlorophenyl)-5-(4-chlorophenyl)pyridine-3-carboxamide and 2-(benzyloxy)-6-(2,4-dichlorophenyl)-5-(4-chlorophenyl)-3-(piperidinocarbonyl)pyridine Step A: 2-(Benzyloxy)-6-(2,4-dichlorophenyl)-5-(4-chlorophenyl)pyridine-3-carboxylic acid To a solution of methyl 2-(benzyloxy)-6-(2,4-dichlorophenyl)-5-(4-chlorophenyl)pyridine-3-carboxylate (390 mg, 0.78 mmol) from Example 51, Step B in methanol (5 mL) was added 5N sodium hydroxide (0.31 mL, 1.56 mmol). The reaction was stirred at rt 20 h and then at 40° C. for 1 h. The reaction was diluted with water, acidified with 2N hydrochloric acid, and extracted twice with methylene chloride. The organic layers were washed with a portion of brine and the combined organic layers were dried over anhydrous sodium sulfate and concentrated in vacuo to give crude 2-(benzyloxy)-6-(2,4-dichlorophenyl)-5-(4-chlorophenyl)pyridine-3-carboxylic acid.

HPLC/MS: 486 (M+1), 488 (M+3); $R_t$=4.67 min

Step B: N-(Piperidin-1-yl)-2-(benzyloxy)-6-(2,4-dichlorophenyl)-5-(4-chlorophenyl)pyridine-3-carboxamide and 2-(benzyloxy)-6-(2,4-dichlorophenyl)-5-(4-chlorophenyl)-3-(piperidinocarbonyl)pyridine.

To a solution of 2-(benzyloxy)-6-(2,4-dichlorophenyl)-5-(4-chlorophenyl)pyridine-3-carboxylic acid (30 mg, 0.062 mmol) from Step A in methylene chloride (1 mL) was added 1-aminopiperidine (9.3 mg, 0.093 mmol), DIPEA (0.016 mL, 0.093 mmol) and PyBOP (17.4 mg, 0.093 mmol). The reaction was stirred at rt for 20 h and was then diluted with aq. saturated sodium carbonate and extracted twice with methylene chloride. The organic layers were washed with a portion of brine and the combined organic layers were dried over anhydrous sodium sulfate and concentrated in vacuo. The residue was purified by preparative TLC eluted with 50% ethyl acetate in hexanes to yield N-(piperidin-1-yl)-2-(benzyloxy)-6-(2,4-dichlorophenyl)-5-(4-chlorophenyl)pyridine-3-carboxamide as the slower eluting band. HPLC/MS: 566 (M+1), 568 (M+3); $R_t$=4.56 min; $^1$HNMR (CDCl$_3$): δ 1.2-1.9 (4 m, 6H), 2.7-3.1 (2 m, 4H), 7.07 (m, 2H), 7.20-7.38 (m, 10H), 7.668 and 8.074 (2 s, 1H).

The higher Rf band afforded 2-(benzyloxy)-6-(2,4-dichlorophenyl)-5-(4-chlorophenyl)-3-(piperidinocarbonyl)pyridine. HPLC/MS: 464 (M+1), 466 (M+3); $R_t$=5.25 min In the following Examples 53-59, the procedure described in Example 52, Step B was repeated but substituting the appropriate amine for 1-aminopiperidine in the reaction with 2-(benzyloxy)-6-(2,4-dichlorophenyl)-5-(4chlorophenyl) pyridine-3-carboxylic acid from Example 52, Step A to afford the following compounds:

EXAMPLE 53

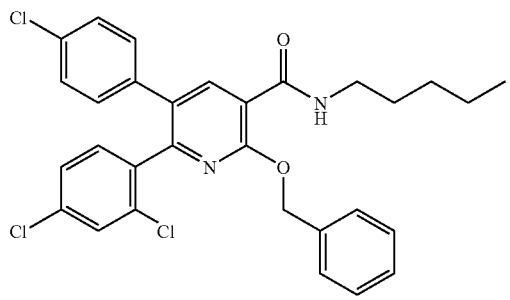

N-(n-Pentyl)-2-(benzyloxy)-6-(2,4-dichlorophenyl)-5-(4-chlorophenyl)pyridine-3-carboxamide HPLC/MS: 553 (M+1), 555 (M+3); $R_t$=5.47 min

EXAMPLE 54

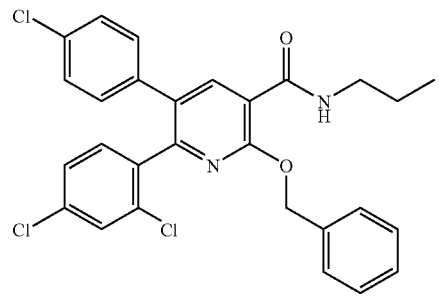

N-(n-Propyl)-2-(benzyloxy)-6-(2,4-dichlorophenyl)-5-(4-chlorophenyl)pyridine-3-carboxamide HPLC/MS: 525 (M+1), 527 (M+3); $R_t$=5.15 min

EXAMPLE 55

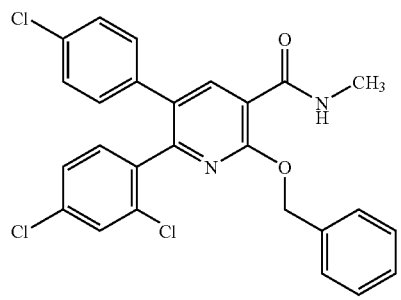

N-(Methyl)-2-(benzyloxy)-6-(2,4-dichlorophenyl)-5-(4-chlorophenyl)pyridine-3-carboxamide HPLC/MS: 497 (M+1), 499 (M+3); $R_t$=4.80 min

EXAMPLE 56

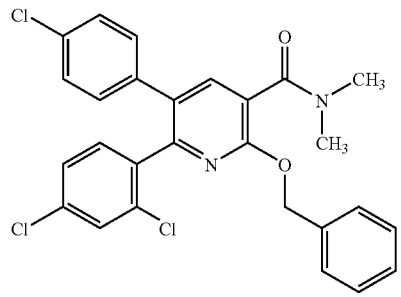

N-N-(Dimethyl)-2-(benzyloxy)-6-(2,4-dichlorophenyl)-5-(4-chlorophenyl)pyridine-3-carboxamide HPLC/MS: 511 (M+1), 513 (M+3); $R_t$=4.67 min

EXAMPLE 57

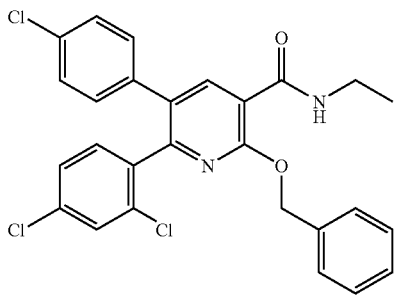

N-(Ethyl)-2-(benzyloxy)-6-(2,4-dichlorophenyl)-5-(4-chlorophenyl)pyridine-3-carboxamide HPLC/MS: 511 (M+1), 513 (M+3); $R_t$=4.99 min. ¹HNMR (CDCl₃): δ 1.134 (t, J=7.2 Hz, 3H), 3.47 (m, 2H), 5.553 (s, 2H), 7.07 (br d, J=8.6 Hz, 2H), 7.14 (d, J=8.4 Hz, 1H), 7.23 (m, 3H), 7.36-7.50 (m, 6H), 7.97 (br t, 1H), 8.620 (s, 1H).

EXAMPLE 58

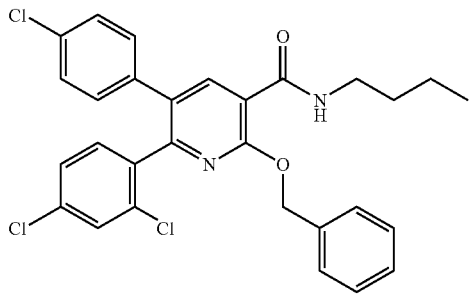

N-(n-Butyl)-2-(benzyloxy)-6-(2,4-dichlorophenyl)-5-(4-chlorophenyl)pyrdine-3-carboxamide HPLC/MS: 539 (M+1), 541 (M+3); $R_t$=5.31 min. ¹HNMR (CDCl₃): δ 0.863 (t, J=7.4 Hz, 3H), 1.24 (m, 2H), 1.46 (m, 2H), 3.43 (q, J=5.7 Hz, 2H), 5.538 (s, 2H), 7.07 (br d, J=8.6 Hz, 2H), 7.15 (d, J=8.4 Hz, 1H), 7.23 (m, 3H), 7.36-7.50 (m, 6H), 7.97 (br t, 1H), 8.623 (s, 1H).

EXAMPLE 59

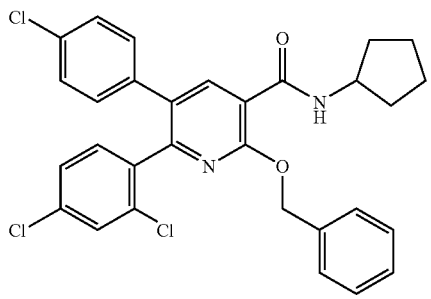

N-(Cyclopentyl)-2-(benzyloxy)-6-(2,4-dichlorophenyl)-5-(4-chlorophenyl)pyridine-3-carboxamide HPLC/MS: 551 (M+1), 553 (M+3); $R_t$=5.31 min

EXAMPLE 60

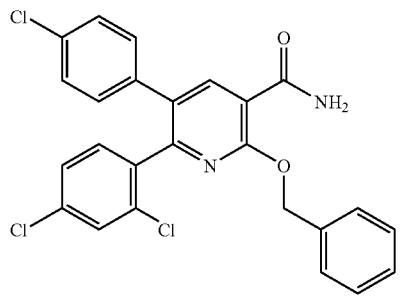

2-(Benzyloxy)-6-(2,4-dichlorophenyl)-5-(4-chlorophenyl)pyridine-3-carboxamide

Step A: 2-(benzyloxy)-6-(2,4-dichlorophenyl)-5-(4-chlorophenyl)-3-carbonyl chloride.

To a suspension of 2-(benzyloxy)-6-(2,4-dichlorophenyl)-5-(4-chlorophenyl)-3-carboxylic acid (50 mg, 0.10 mmol) from Example 52, Step A in methylene chloride (3 mL) was added a trace of DMF (cat.) and oxalyl chloride (0.045 mL, 0.51 mmol). The reaction was stirred at rt for 1 h and then evaporated to dryness. The acid chloride was dissolved in THF and used directly in the subsequent amide formation.

Step B: 2-(Benzyloxy)-6-(2,4-dichlorophenyl)-5-(4-chlorophenyl)pyridine-3-carboxamide.

To the solution of the above acid chloride (0.10 mmol) in THF (1 mL) was added an aq. solution of ammonium hydroxide (0.020 mL, 0.30 mmol). The reaction was stirred at rt for 1 h and was then diluted with water and extracted twice with methylene chloride. The organic layers were washed with a portion of brine and the combined organic layers were dried over anhydrous sodium sulfate and concentrated in vacuo. The residue was purified by preparative TLC eluted with 50% ethyl acetate in hexanes to afford 2-(benzyloxy)-6-(2,4-dichlorophenyl)-5-(4-chlorophenyl) pyridine-3-carboxamide. HPLC/MS: 483 (M+1), 485 (M+3); $R_t$=4.64 min

EXAMPLE 61

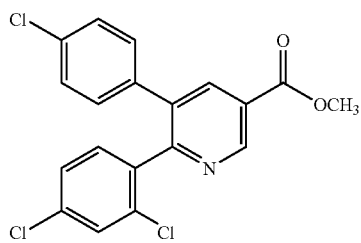

Methyl 6-(2,4-dichlorophenyl)-5-(4-chlorophenyl) pyridine-3-carboxylate

Step A: Methyl 2-chloro-6-(2,4-dichlorophenyl)-5-(4-chlorophenyl)pyridine-3-carboxylate.

To a solution of methyl 6-(2,4-dichlorophenyl)-5-(4-chlorophenyl)-2-oxo-1,2-dihydropyridine-3-carboxylate (0.90 g, 2.2 mmol) from Example 51, Step A in dichloromethane (5 mL) was added oxalyl chloride (1.0 mL, 11.4 mmol) and the reaction was heated at 50° C. for 24 h. The reaction was concentrated in vacuo and the residue was dissolved in methylene chloride and washed with aq. sodium bicarbonate. The organic layer was washed with a portion of brine, dried over sodium sulfate, and concentrated in vacuo. The residue was purified by flash column chromatography on silica gel eluted with 5 to 10% ethyl acetate in hexanes to yield methyl 2-chloro-6-(2,4-dichlorophenyl)-5-(4-chlorophenyl)pyridine-3-carboxylate.

HPLC/MS: 426 (M+1), 428 (M+3); $R_t$=4.56 min

Step B: Methyl 6-(2,4-dichlorophenyl)-5-(4-chlorophenyl)pyridine-3-carboxylate.

To a solution of methyl 2-chloro-6-(2,4-dichlorophenyl)-5-(4-chlorophenyl)pyridine-3-carboxylate (750 mg, 1.76 mmol) from Step A in methanol (10 mL) and ethyl acetate (10 mL) was added 10% Pd/C (100 mg). The suspension was stirred under an atmosphere of hydrogen (balloon pressure) for 45 min and was then filtered to remove the catalyst. HPLC/MS indicated a mixture of starting material, desired product, and minor amounts of several possible phenyl ring dechlorination products. The filtrate was evaporated and the residue was purified by flash column chromatography on silica gel eluted with 5 to 20% ethyl acetate in hexanes. The fractions containing the title compound were repurified by preparative TLC eluted with 15% ethyl acetate in hexanes to give pure methyl 6-(2,4-dichlorophenyl)-5-(4-chlorophenyl) pyridine-3-carboxylate. HPLC/MS: 392 (M+1), 394 (M+3); $R_t$=4.29 min. $^1$HNMR (CDCl$_3$): δ 4.024 (s, 3H), 7.11 (br d, J=8.6 Hz, 2H), 7.23-7.35 (m, 4H), 7.36 (d, J=2.0 Hz, 1H), 7.37 (d, J=1.9 Hz,, 1H), 9.286 (d, J=1.9 Hz, 1H).

EXAMPLE 62

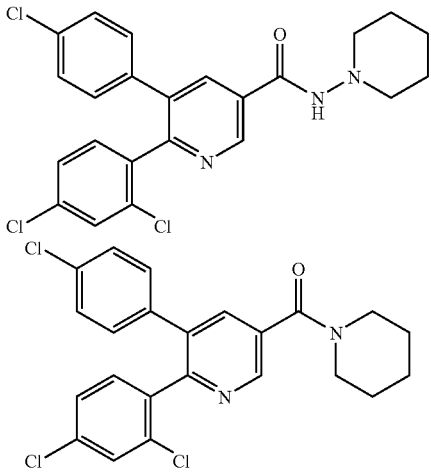

N-(Piperidin-1-yl)-6-(2,4-dichlorophenyl)-5-(4-chlorophenyl)pyridine-3-carboxamide and 6-(2,4-dichlorophenyl)-5-(4-chlorophenyl)-3-(piperidinocarbonyl) pyridine Step A: 6-(2,4-Dichlorophenyl)-5-(4-chlorophenyl)pyridine-3-carboxylic acid To a solution of methyl 6-(2,4-dichlorophenyl)-5-(4-chlorophenyl)pyridine-3-carboxylate (170 mg, 0.43 mmol) from Example 61, Step B in methanol (5 mL) was added 5N sodium hydroxide (0.20 mL, 1.0 mmol). The reaction was stirred at rt for 20 h and was then acidified with 2N hydrochloric acid and extracted twice with methylene chloride. The organic layer was washed with a portion of brine, dried over sodium sulfate, and concentrated in vacuo to give 6-(2,4-dichlorophenyl)-5-(4-chlorophenyl)pyridine-3-carboxylic acid as a white solid. HPLC/MS: 378 (M+1), 380 (M+3); $R_t$=3.65 min Step B: N-(Piperidin-1-yl)-6-(2,4-dichlorophenyl)-5-(4-chlorophenyl)pyridine-3-carboxamide and 6-(2,4-dichlorophenyl)-5-(4-chlorophenyl)-3-(piperidinocarbonyl)pyridine.

6-(2,4-Dichlorophenyl)-5-(4-chlorophenyl)pyridine-3-carboxylic acid (135 mg, 0.36 mmol) from Step A was converted to the acid chloride as in Step B of Example 32. To a portion of this (0.18 mmol) in methylene chloride (1.5 mL) was added a solution of 1-aminopiperidine (0.039 mL, 0.36 mmol) and DIPEA (0.050 mL, 0.36 mmol) in methylene chloride (1 mL). The reaction was stirred at rt for 1 h and was then diluted with aq. sodium bicarbonate and extracted twice with methylene chloride. The organic layer was washed with a portion of brine, dried over sodium sulfate, and concentrated in vacuo. The residue was purified by preparative TLC eluted with 30% ethyl acetate in hexanes to yield the slower eluting N-(piperidin-1-yl)-6-(2,4-dichlorophenyl)-5-(4-chlorophenyl)pyridine-3-carboxamide. HPLC/MS: 460 (M+1), 462 (M+3); $R_t$=3.33 min. $^1$HNMR (CDCl$_3$): δ 1.4-2.0 (3 m, 6H), 2.95 (m, 4H), 7.10 (br d, J=8.4 Hz, 2H), 7.21 (d, J=8.3 Hz, 1H), 7.23-7.35 (m, 4H), 7.36 (br s, 1H), 8.18 and 8.29 (2 br s, 1H), 8.98 and 9.26 (2 br s, 1H).

The higher Rf band afforded 6-(2,4-dichlorophenyl)-5-(4-chlorophenyl)-3-(piperidinocarbonyl)pyridine. HPLC/MS: 445 (M+1), 447 (M+3); $R_t$=4.05 min. $^1$HNMR (CDCl$_3$): δ 1.5-1.9 (2 m, 6H), 3.50 (m, 2H), 3.78 (m, 2H), 7.09 (br d, J=8.4 Hz, 2H), 7.2-7.35 (m, 5H), 7.36 (d, J=2 Hz, 1H), 7.83 (d, J=2.1 Hz, 1H), 8.73 (d, J=2.1 Hz, 1H).

In the following Examples 63-64, the procedure described in Example 62, Step B was repeated but substituting the appropriate amine for 1-aminopiperidine in the reaction with 6-(2,4-dichlorophenyl)-5-(4-chlorophenyl)pyridine-3-carboxylic acid from Example 62, Step A to afford the following compounds:

EXAMPLE 63

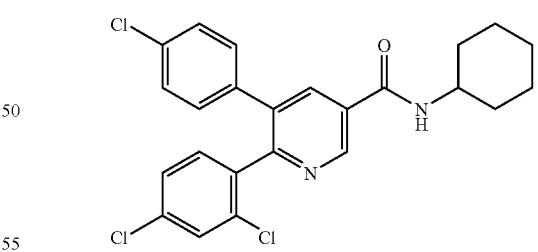

N-(Cyclohexyl)-6-(2,4-dichlorophenyl)-5-(4-chlorophenyl)pyridine-3-carboxamide

HPLC/MS: 459 (M+1), 461 (M+3); $R_t$=4.29 min. $^1$HNMR (CDCl$_3$): δ 1.2-1.4 (m, 3H), 1.4-1.55 (m, 2H), 1.65-1.75 (m, 1H), 1.75-1.85 (m, 2H), 2.05-2.15 (m, 2H), 4.05 (m, 1H), 6.07 (d, J=7.6 Hz, 1H), 7.09 (br d, J=8.4 Hz, 2H), 7.15 and 7.21 (2 d, J=8.2 Hz, 1H), 7.24-7.35 (m, 3H), 7.36 (br d, 1H), 8.12 and 8.16 (2 d, J=2.0 Hz, 1H), 8.99 and 9.01 (2 d, J=2.0 Hz, 1H).

EXAMPLE 64

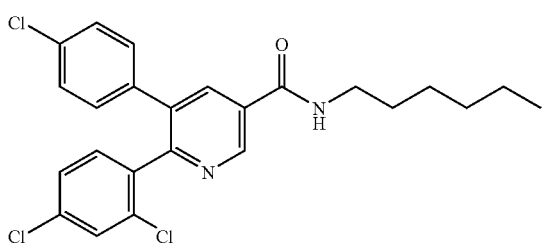

N-(n-Hexyl)-6-(2,4-dichlorophenyl)-5-(4-chlorophenyl)pyridine-3-carboxamide

HPLC/MS: 461 (M+1), 463 (M+3); $R_t$=4.53 min. $^1$HNMR (CDCl$_3$): δ 0.925 (t, J=7.0 Hz, 3H), 1.3-1.5 (2 m, 6H), 1.679 (p, J=7.4 Hz, 2H), 3.53 (q, J=7.3 Hz, 2H), 6.23 (br t, 1H), 7.11 (br d, J=8.6 Hz, 2H), 7.22 (d, J=8.2 Hz, 1H), 7.24-7.32 (m, 3H), 7.365 (d, J=2.0 Hz, 1H), 8.18 (d, J=2.1 Hz,, 1H), 8.998 (d, J=2.1 Hz, 1H).

In the following Examples 65-69, the procedure described in Example 51, Step B was repeated but substituting the appropriate haloalkane in the reaction with methyl 6-(2,4-dichlorophenyl)-5-(4-chlorophenyl)-2-oxo-1,2-dihydropyridine-3-carboxylate from Example 51, Step A to afford the following compounds:

EXAMPLE 65

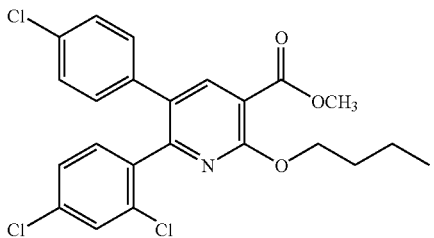

Methyl 2-(n-butoxy)-6-(2,4-dichlorophenyl)-5-(4-chlorophenyl)pyridine-3-carboxylate HPLC/MS: 464 (M+1), 466 (M+3); $R_t$=5.1 min. $^1$HNMR (CDCl$_3$): δ 0.992 (t, J=7.4 Hz, 3H), 1.53 (m, 2H), 1.83 (m, 2H), 3.950 (s, 3H), 4.459 (t, J=6.7 Hz, 2H), 7.04 (br d, J=8.4 Hz, 2H), 7.15 (d, J=8.2 Hz, 1H), 7.20 (m, 3H), 7.37 (d, J=1.9 Hz, 1H), 8.220 (s, 1H).

EXAMPLE 66

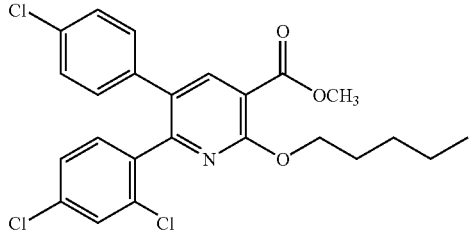

Methyl 2-(n-pentoxy)-6-(2,4-dichlorophenyl)-5-(4-chlorophenyl)pyridine-3-carboxylate HPLC/MS: 478 (M+1), 480 (M+3); $R_t$=5.36 mn. $^1$HNMR (CDCl$_3$): δ 0.939 (t, J=7.2 Hz, 3H), 1.35-1.52 (2 m, 4H), 1.844 (p, J=6.8 Hz, 2H), 3.952 (s, 3H), 4.448 (t, J=6.2 Hz, 2H), 7.04 (br d, J=8.4 Hz, 2H), 7.15 (d, J=8.3 Hz, 1H), 7.2-7.4 (m, 4H), 7.37 (d, J=1.9 Hz, 1H), 8.220 (s, 1H).

EXAMPLE 67

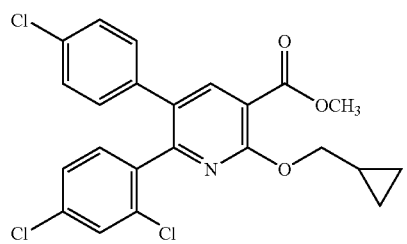

Methyl 2-(cyclopropylmethoxy)-6-(2,4-dichlorophenyl)-5-(4-chlorophenyl)pyridine-3-carboxylate HPLC/MS: 462 (M+1), 464 (M+3); $R_t$=5.04 min

EXAMPLE 68

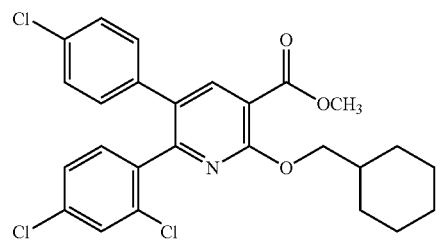

Methyl 2-(cyclohexylmethoxy)-6-(2,4-dichlorophenyl)-5-(4-chlorophenyl)pyridine-3-carboxylate HPLC/MS: 504 (M+1), 506 (M+3); $R_t$=4.69 min. $^1$HNMR (CDCl$_3$): δ 1.0-1.4 (2 m, 5H), 1.5-1.9 (m, 6H), 3.953 (s, 3H), 4.25 (d, J=6.3Hz, 1H), 7.03 (br d, J=8.4 Hz, 2H), 7.16 (d, J=8.3 Hz, 1H), 7.2-7.4 (m, 4H), 7.37 (d, J=2.0 Hz, 1H), 8.222 (s, 1H).

EXAMPLE 69

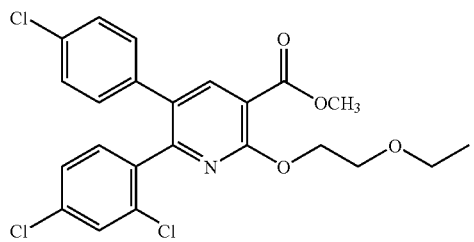

Methyl 2-(2-ethoxyethoxy)-6-(2,4-dichlorophenyl)-5-(4-chlorophenyl)pyridine-3-carboxylate HPLC/MS: 480 (M+1), 482 (M+3); $R_t$=4.69 min In the following Examples 70-71, the procedure described in Example 52, Steps A-B were repeated but substituting the appropriate amine in the reaction with methyl 2-(cyclohexylmethoxy)-6-(2,4-dichlorophenyl)-5-(4-chlorophenyl)pyridine-3-carboxylate from Example 68 to afford the following compounds:

EXAMPLE 70

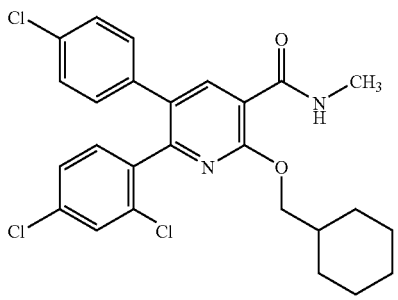

N-Methyl-2-(cyclohexylmethoxy)-6-(2,4-dichlorophenyl)-5-(4-chlorophenyl)pyridine-3-carboxamide HPLC/MS: 407 (100%, M+1−96 ($C_7H_{12}$), 409 (M+3−96 ($C_7H_{12}$), 503 (M+1), 505 (M+3); $R_t$=3.20 min

EXAMPLE 71

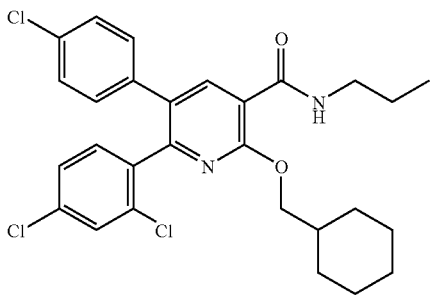

N-(n-Propyl)-2-(cyclohexylmethoxy)-6-(2,4-dichlorophenyl)-5-(4-chloroyhenyl)pyridine-3-carboxamide

EXAMPLE 72

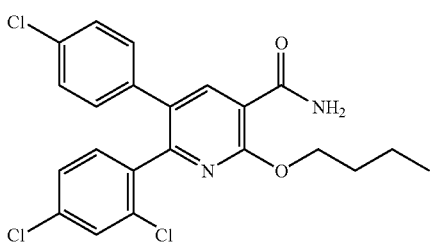

2-(n-Butoxy)-6-(2,4-dichlorophenyl)-5-(4-chlorophenyl)pyridine-3-carboxamide

Using essentially the same procedures as in Example 52, Steps A-B, but substituting methyl 2-(n-butoxy)-6-(2,4-dichlorophenyl)-5-(4-chlorophenyl)pyridine-3-carboxylate from Example 65 for 2-(benzyloxy)-6-(2,4-dichlorophenyl)-5-(4-chlorophenyl)-3-carboxylic acid, 2-(n-butoxy)-6-(2,4-dichlorophenyl)-5-(4-chlorophenyl)pyridine-3-carboxamide was prepared.

HPLC/MS: 449 (M+1), 451 (M+3); $R_t$=4.72 min

In the following Examples 73-75 the procedure described in Example 52, Steps A-B were repeated but substituting the appropriate amine in the reaction with methyl 2-(n-butoxy)-6-(2,4-dichlorophenyl)-5-(4-chlorophenyl)pyridine-3-carboxylate from Example 65 to afford the following compounds:

EXAMPLE 73

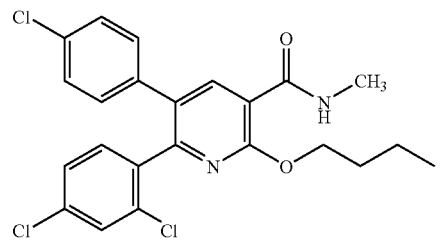

N-Methyl-2-(n-butoxy)-6-(2,4-dichlorophenyl)-5-(4-chlorophenyl)pyridine-3-carboxamide HPLC/MS: 463 (M+1), 465 (M+3); $R_t$=4.91 min

EXAMPLE 74

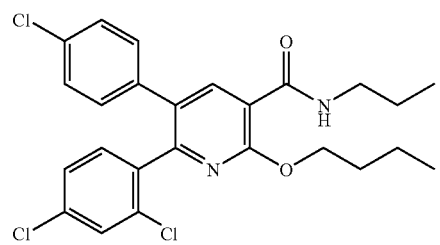

N-(n-Propyl)-2-(n-butoxy)-6-(2,4-dichlorophenyl)-5-(4-chlorophenyl)pyridine-3-carboxamide HPLC/MS: 491 (M+1), 493 (M+3); $R_t$=5.28 min

EXAMPLE 75

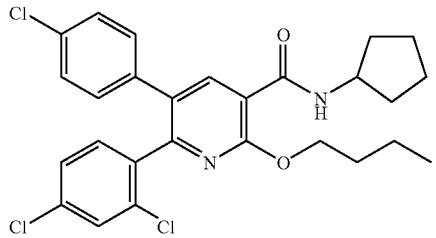

N-Cyclopentyl-2-(n-butoxy)-6-(2,4-dichlorophenyl)-5-(4-chlorophenyl)pyridine-3-carboxamide HPLC/MS: 5.17 (M+1), 5.19 (M+3); $R_t$=3.41 min (faster gradient)

EXAMPLE 76

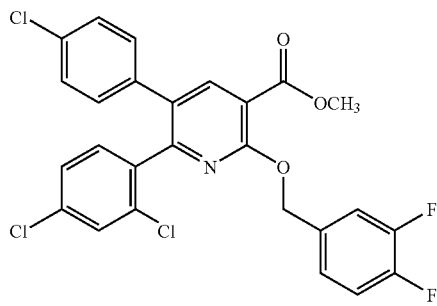

Methyl 2-(3,4-difluorobenzyloxy)-6-(2,4-dichlorophenyl)-5-(4-chlorophenyl)pyridine-3-carboxylate To a solution of methyl 6-(2,4-dichlorophenyl)-5-(4-chlorophenyl)-2-oxo-1,2-dihydropyridine-3-carboxylate (300 mg, 0.73 mmol) from Example 51, Step A in DMF (3 mL) was added 3,4-difluorobenzyl bromide (0.122 mL, 0.95 mmol) and then cesium carbonate (310 mg, 0.95 mmol). The reaction was stirred at 50° C. for 3 h and was then diluted with water and extracted three times with methylene chloride. The organic layers were washed with a portion of brine and the combined organic layers were dried over anhydrous sodium sulfate and concentrated in vacuo to give the crude products. The products were separated by preparative TLC (3×1 mm) eluted with 25% ethyl acetate in hexanes to yield faster eluting O-alkylation title product. HPLC/MS: 534 (M+1), 536 (M+3); $R_t$=5.17 min. $^1$HNMR (CDCl$_3$): δ 3.981 (s, 3H), 5.489 (s, 2H), 7.04 (br d, J=8.4 Hz, 2H), 7.11 (d, J=8.2 Hz, 1H), 7.2-7.6 (m, 3H), 7.38 (d, J=2.0 Hz, 1H), 8.285 (s, 1H).

EXAMPLE 77

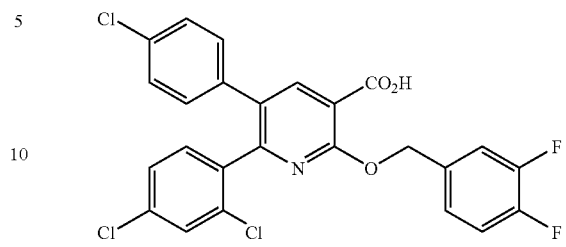

5-(4-Chlorophenyl)-6-(2,4-dichlorophenyl)-2-[(3,4-difluorobenzyl)oxy]nicotinic acid To a solution of methyl 2-(3,4-difluorobenzyloxy)-6-(2,4-dichlorophenyl)-5-(4-chlorophenyl)pyridine-3-carboxylate (150 mg, 0.28 mmol) from Example 76 in methanol (3 mL) was added 5N sodium hydroxide (0.170 mL, 0.84 mmol). The reaction was stirred at rt for 20 h and then at 40° C. for 2 h. The reaction was diluted with water, acidified with 2N hydrochloric acid, and extracted twice with methylene chloride. The organic layers were washed with a portion of brine and the combined organic layers were dried over anhydrous sodium sulfate and concentrated in vacuo to yield crude 2-(3,4-difluorobenzyloxy)-6-(2,4-dichlorophenyl)-5-(4-chlorophenyl)pyridine-3-carboxylic acid. HPLC/MS: 520 (M+1), 522 (M+3); $R_t$=4.61 min.

EXAMPLE 78

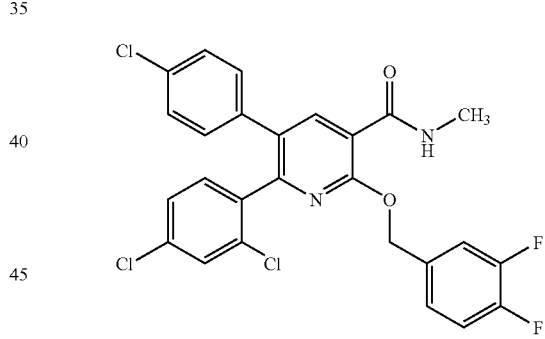

5-(4-Chlorophenyl)-6-(2,4-dichlorophenyl)-2-[(3,4-difluorobenzyl)oxy]-N-methylnicotinamide Step A: 5-(4-Chlorophenyl)-6-(2,4-dichlorophenyl)-2-[(3,4-difluoro-benzyl)oxy]nicotinoyl chloride To a solution of 2-(3,4-difluorobenzyloxy)-6-(2,4-dichlorophenyl)-5-(4-chlorophenyl)pyridine-3-carboxylic acid (120 mg, 0.20 mmol) from Example 77 in methylene chloride (3 mL) was added a drop of DMF (cat.) and oxalyl chloride (0.100 mL, 1.1 mmol). The reaction was stirred at rt for 1 h and was then evaporated to dryness. The acid chloride was dissolved in methylene chloride and used directly in the subsequent amide formation.

Step B: 5-(4-Chlorophenyl)-6-(2,4-dichlorophenyl)-2-[(3,4-difluoro-benzyl)oxy]-N-methylnicotinamide To a portion of the methylene chloride (1 mL) solution of 2-(3,4-difluorobenzyloxy)-6-(2,4-dichlorophenyl)-5-(4-chlorophenyl)pyridine-3-carbonyl chloride (0.044 mmol)

was added methylamine hydrochloride (6 mg, 0.088 mmol) and TEA (0.018 mL, 0.13 mmol). The reaction was stirred at rt for 16 h and was then evaporated. The residue was purified by preparative TLC eluted with 25% ethyl acetate in hexanes to yield N-(methyl)-2-(3,4-difluorobenzyloxy)-6-(2,4-dichlorophenyl)-5-(4-chlorophenyl)pyridine-3carboxamide. HPLC/MS: 533 (M+1), 535 (M+3); $R_t$=4.77 min In the following Examples 79-82 the procedure described in Step B of Example 78 was repeated but substituting the appropriate amine in the reaction with 2-(3,4-difluorobenzyloxy)-6-(2,4-dichlorophenyl)-5-(4-chlorophenyl)pyridine-3-carbonyl chloride from Step A of Example 78 to afford the following compounds:

EXAMPLE 79

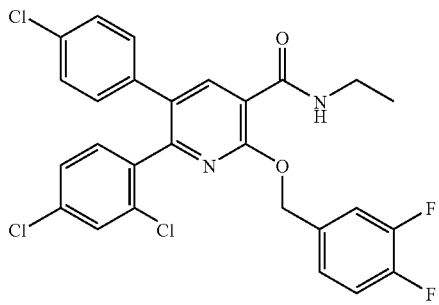

N-(Ethyl)-2-(3,4-difluorobenzyloxy)-6-(2,4-dichlorophenyl)-5-(4-chlorophenyl)pyridine-3-carboxamide HPLC/MS: 547 (M+1), 549 (M+3); $R_t$=4.88 min

EXAMPLE 80

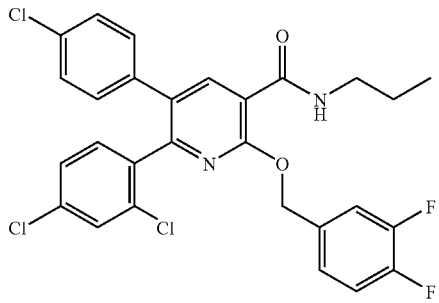

N-(n-Propyl)-2-(3,4-difluorobenzyloxy)-6-(2,4-dichlorophenyl)-5-(4-chlorophenyl)pyridine-3-carboxamide HPLC/MS: 561 (M+1), 563 (M+3); $R_t$=5.07 min.
$^1$HNMR (CDCl$_3$): δ 0.903 (t, J=7.5 Hz, 3H), 1.56 (hex, J=7.3 Hz, 2H), 3.43 (q, J=5.5 Hz, 2H), 5.504 (s, 2H), 7.06 (br d, J=8.4 Hz, 2H), 7.11 (d, J=8.3 Hz, 1H), 7.17-7.35 (m, 7H), 7.40 (d, J=2.0 Hz, 1H), 7.86 (br t, 1H), 8.620 (s, 1H).

EXAMPLE 81

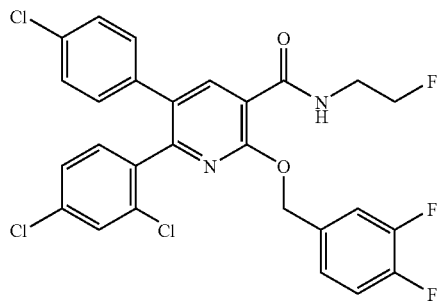

N-(2-Fluoroethyl)-2-(3,4-difluorobenzyloxy)-6-(2,4-dichlorophenyl)-5-(4-chlorophenyl)pyridine-3-carboxamide HPLC/MS: 565 (M+1), 567 (M+3); $R_t$=4.85 min

EXAMPLE 82

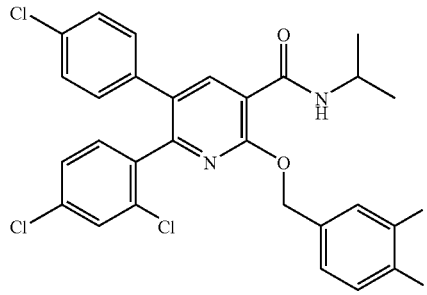

N-(i-Propyl)-2-(3,4-difluorobenzyloxy)-6-(2,4-dichlorophenyl)-5-(4-chlorophenyl)pyridine-3-carboxamide HPLC/MS: 561 (M+1), 563 (M+3); $R_t$=5.09 min

EXAMPLE 83

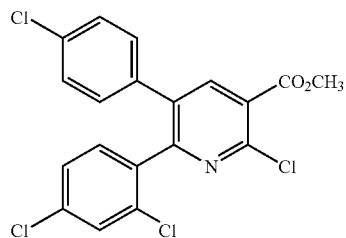

Methyl 2-chloro-5-(4-chlorophenyl)-6-(2,4-dichlorophenyl)nicotinate

To a dried round bottom flask fitted with a condenser was added methyl 6-(2,4-dichlorophenyl)-5-(4-chlorophenyl)-2- oxo-1,2-dihydropyridine-3-carboxylate from Step A of Example 51 (1.50 g; 3.67 mmol) and excess phosphorous oxychloride (4 mL). The reaction mixture was heated to reflux for 16 hours. The reaction mixture was allowed to cool to room temperature, and the volatiles were removed in vacuo. The residue was redissolved in methylene chloride and washed with saturated NaHCO$_3$ solution (2×), water, brine, dried (Na$_2$SO$_4$), filtered, and concentrated in vacuo. Purification was done by MPLC (silica gel; 0-10% ethyl acetate:hexane) to afford the desired product: m/e=428 (M+2) R$_t$=4.42 min on LCMS.

EXAMPLE 84

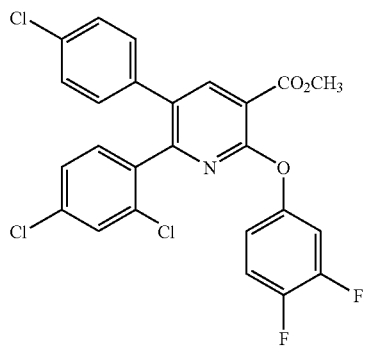

Methyl 5-(4-chlorophenyl)-6-(2,4-dichlorophenyl)-2-(3,4-difluorophenoxy)nicotinate To a dried round bottom flask was added toluene (10 mL), of Example 83 (0.600 g; 1.41 mmol); 3,4-difluorophenol (0.365 g; 2.82 mmnol), and cesium carbonate (0.915 g; 2.82 mmol). The reaction mixture was heated at 100° C. and stirred for 16 hours. The reaction mixture was allowed to cool to room temperature and was partitioned between ethyl acetate and 2N aq. NaOH solution. The organic portion was separated and washed with more 2N aq. NaOH solution (2×), brine, dried (Na$_2$SO$_4$), filtered, and concentrated in vacuo. Purification was done by MPLC (silica gel; 0-10% ethyl acetate:hexane) to afford the desired product: m/e=521 (M+1); R$_t$=4.82 min on LCMS.

EXAMPLE 85

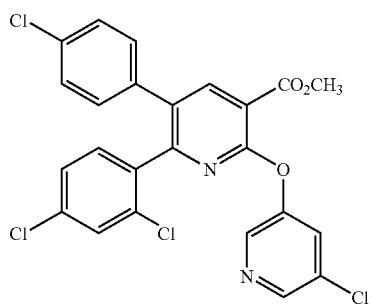

Methyl 5-(4-chlorophenyl)-2-[(5-chloropyridin-3-yl)oxy]-6-(2,4-dichlorophenyl)-nicotinate Using the procedure described in Example 84, methyl 6-(2,4-dichlorophenyl)-5-(4-chlorophenyl)-2-chloro-nicotinate Example 83 was reacted with 3-chloro-5-hydroxypyridine to afford the title compound: m/e=521 (M+3); R$_t$=4.65 min

EXAMPLE 86

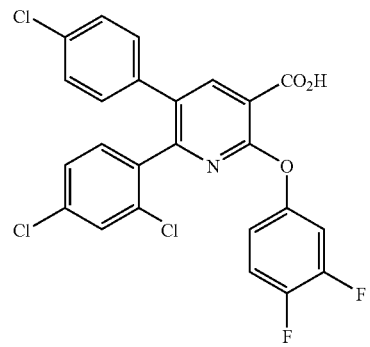

5-(4-Chlorophenyl)-6-(2,4-dichlorophenyl)-2-(3,4-difluorophenoxy)nicotinic acid

To a dried round bottom flask was added methanol (12 mL), the product of Example 84 (0.630 g; 1.21 mmol), and 3N aq. NaOH (2.42 mL, 7.26 mmol). The reaction mixture was heated at 50° C. and stirred for 2 hours. The reaction mixture was allowed to cool to room temperature. The methanol was removed in vacuo. The pH of the reaction mixture was adjusted with 2N aq. HCl solution to pH=5-6, and it was extracted with methylene chloride (5×). The combined extracts were dried (Na$_2$SO$_4$), filtered, and concentrated in vacuo to afford the desired product: m/e=508 (M+3); R$_t$=4.29 min on LCMS.

EXAMPLE 87

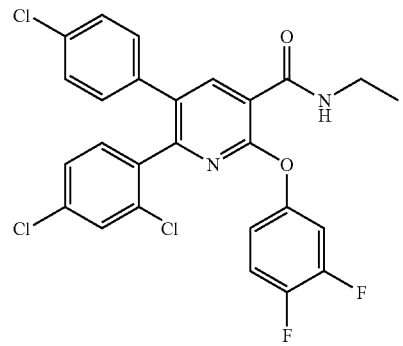

5-(4-Chlorophenyl)-6-(2,4-dichlorophenyl)-2-(3,4-difluorophenoxy)-N-ethylnicotinamide Step A: 5-(4-Chlorophenyl)-6-(2,4-dichlorophenyl)-2-(3,4-difluoro-phenoxy)nicotinoyl chloride To a dried round bottom flask was added methylene chloride (2 mL), the product of Example 86 (0.110 g; 0.217 mmol), oxalyl chloride (0.02 mL, 0.217 mmol), and DMF (1 drop; cat.). The reaction mixture was stirred for 1.5 hours at room temperature. Toluene (1 mL) was added to the reaction mixture and the volatiles were removed in vacuo.

Step B: 5-(4-Chlorophenyl)-6-(2,4-dichlorophenyl)-2-(3,4-difluorophenoxy)-N-ethylnicotinamide The crude acid chloride from Step A was dissolved in methylene chloride (1 mL) and treated with ethylamine hydrochloride (0.018 g; 0.217 mmol) and triethylamine (0.06 mL; 0.434 mmol) then stirred at room temperature for 1 h. The volatiles were removed in vacuo and purified by MPLC (silica gel; 0-50% ethyl acetate:hexane gradient) to afford the desired product: m/e=534 (M+2); $R_t$=4.57 min on LCMS.

In the following Examples 88-93 the procedure described in Step B of Example 87 was repeated but substituting the appropriate amine in the reaction with 5-(4-chlorophenyl)-6-(2,4-dichlorophenyl)-2-(3,4-difluoro-phenoxy)nicotinoyl chloride from Step A of Example 87 to afford the following compounds:

EXAMPLE 88

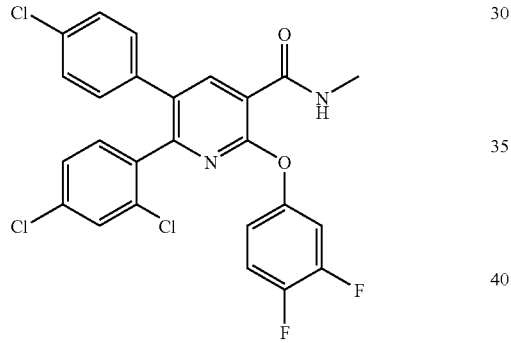

5-(4-Chlorophenyl)-6-(2,4-dichlorophenyl)-2-(3,4-difluorophenoxy)-N-methylnicotinamide HPLC-MS: m/e=521 (M+3); $R_t$=4.38 min.

EXAMPLE 89

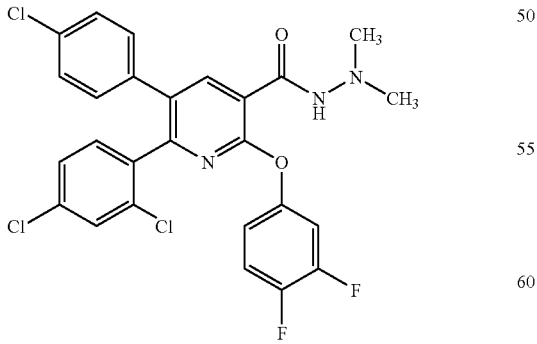

5-(4-Chlorophenyl)-6-(2,4-dichlorophenyl)-2-(3,4-difluorophenoxy)-N',N'-dimethylnicotinohydrazide HPLC-MS: m/e=548 (M+1); $R_t$=4.04 min.

EXAMPLE 90

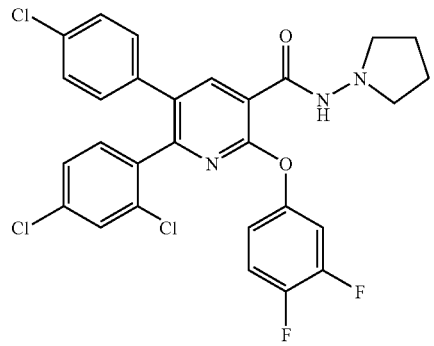

5-(4-Chlorophenyl)-6-(2,4-dichlorophenyl)-2-(3,4-difluorophenoxy)-N-pyrrolidin-1-ylnicotinamide HPLC-MS: m/e=574 (M+1); $R_t$=3.96 min.

EXAMPLE 91

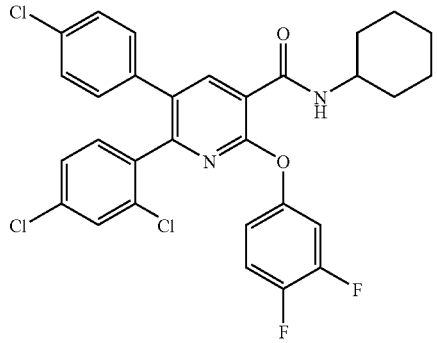

5-(4-Chlorophenyl)-N-cyclohexyl-6-(2,4-dichlorophenyl)-2-(3,4-difluorophenoxy)nicotinamide HPLC-MS: m/e=589 (M+3); $R_t$=5.05 min.

EXAMPLE 92

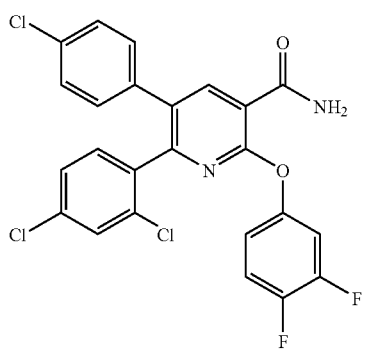

5-(4-Chlorophenyl)-6-(2,4-dichlorophenyl)-2-(3,4-difluorophenoxy)nicotinamide

HPLC-MS: m/e=507 (M+3); $R_t$=4.23 min.

EXAMPLE 93

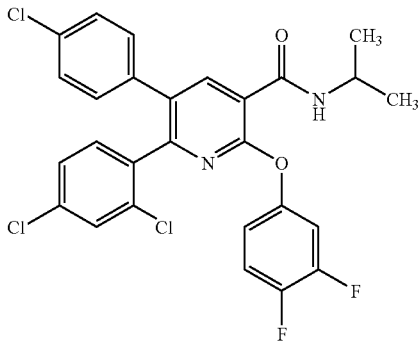

5-(4-Chlorophenyl)-6-(2,4-dichlorophenyl)-2-(3,4-difluorophenoxy)-N-isopropylnicotinamide HPLC-MS: m/e=549 (M+3); $R_t$=4.71 min.

EXAMPLE 94

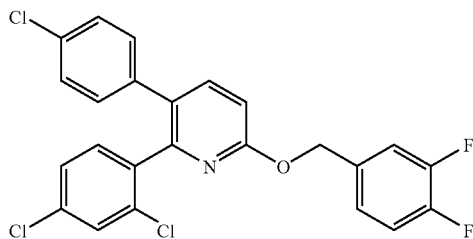

3-(4-Chlorophenyl)-2-(2,4-dichlorophenyl)-6-[(3,4-difluorobenzyl)oxy]pyridine

Step A: 5-(4-Chlorophenyl)-6-(2,4-dichlorophenyl)pyridin-2(1H)-one

An oven-dried round bottom flask equipped with a magnetic stir bar and a reflux condenser was charged with 0.365 g (0.93 mmol) of 5-(4-chlorophenyl)-6-(2,4-dichlorophenyl)-2-oxo-1,2-dihydropyridine-3-carboxylic acid from the product of Step A in Example 32 and 5 mL of freshly distilled quinoline. The reaction mixture was stirred and heated to 235° C. under a nitrogen atmosphere for 3 hours then cooled to room temperature. The reaction mixture was partitioned between excess EtOAc and 1N HCl, separated and the organic layer was extracted again twice with 1N HCl. The organic layer was washed with saturated brine, dried (MgSO₄), filtered and evaporated in vacuo. The residual amorphous solid was used directly in the next step without further purification.

Step B: 3-(4-Chlorophenyl)-2-(2,4-dichlorophenyl)-6-[(3,4-difluoro-benzyl)oxy]pyridine An oven-dried 10 mL round bottom flask equipped with a magnetic stir bar and a septum was charged with 0.298 g (0.85 mmol) of the product of Step A, 0.346 g (1.06 mmol) cesium carbonate, 5.0 mL anhydrous DMF and 0.194 g (0.94 mmol) 3,4-difluorobenzyl bromide. The reaction mixture was stirred at 50° C. for 4 h, then partitioned between EtOAc and water. The organic layer was washed with water, saturated brine, then dried (MgSO₄), filtered and evaporated. The residue was purified on a Biotage™ silica gel flash chromatography apparatus eluted with 20-50% EtOAc-hexane which afforded the title O-benzylated pyridine derivative (followed by the more polar N-benzylated pyridone byproduct.) HPLC/MS: 476 (M+1), 478 (M+3); $R_t$=5.09 min.

EXAMPLE 95

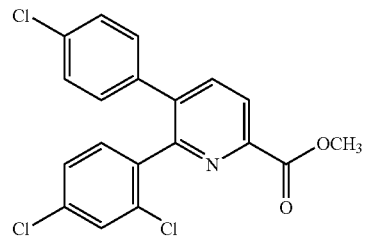

Methyl 6-(2,4-dichlorophenyl)-5-(4-chlorophenyl)pyridine-2-carboxylate

The title compound was prepared following the general procedures of J. Barluenga, M. Ferrero and F. Palacios, *J. Chem. Soc., Perkin Trans.* 1, 1990, 2193-2197 for the synthesis of ethyl 5,6-diphenylpyridine-2-carboxylate.

Step A: 4-Chlorocinnamyl alcohol

The title compound was prepared according to the general procedure described by K. Ishizumi et al. (*Chem. Pharm. Bull.*, 1968, 16, 492-497). A solution of ethyl chloroformate (5.2 mL, 55 mmol) in THF (15 mL) was added over 30 min to a solution of 4-chlorocinnamic acid (10 g, 55 mmol) and TEA (7.6 mL, 55 mmol) in THF (80 mL) while cooled to −5° C. The reaction was stirred for another 30 min at 0° C. and then sodium borohydride (4.2 gm, 110 mmol) was added. After 30 min., the reaction was slowly quenched with 2N hydrochloric acid and extracted twice with methylene chloride. The organic layers were washed with a portion of brine containing some aq. sodium bicarbonate, dried over sodium sulfate, and evaporated to give the title compound as a white solid. ¹HNMR (CDCl₃): δ 4.345 (dd, J=1.5 and 5.7 Hz, 2H), 6.36 (dt, J=5.7 and 15.8 Hz, 1H), 6.59 (br dt, J=1.5 and 15.8 Hz, 1H), 7.32 (Abq, 4H).

Step B: 4-Chlorocinnamaldehyde

A solution of oxalyl chloride (2.6 mL, 30 mmol) in methylene chloride was cooled to −70° C. in a dry ice/acetone bath and DMSO (4.2 mL, 60 mmol) was added slowly. After 10 minutes, a solution of 4-chlorocinnamyl alcohol (2.0 g, 12 mmol) from Step A in methylene chloride (12 mL) was added. The reaction was stirred at −70° C. for 80 min and then DIPEA (20 mL, 120 mmol) was added. After 5 min, the reaction was allowed to warm to rt over 2 h. The mixture was diluted with methylene chloride and washed with cold 2N hydrochloric acid (80 mL). The organic layer was washed with brine containing some aq. sodium bicarbonate, dried over sodium sulfate, and evaporated. The residue was purified by FC (0 to 10% ethyl acetate in hexanes) to give the title compound as a white solid. ¹HNMR (CDCl₃): δ 6.71 (dd, J=7.7 and 16.0 Hz, 1H), 7.450 (d, J=16 Hz, 1H), 7.43 and 7.52 (Abq, J=8.4 Hz, 4H), 9.72 (d, J=7.6 Hz, 1H).

Step C: Methyl 2-azido-5-(4-chlorophenyl)pent-1,3-dienoate

The title compound was prepared according to the general procedure described by J. P. Boukou-Poba (*Tetrahedron Letters*, 1979, 19, 1717-1720). To a 0.5M solution of sodium methoxide in methanol (122 mL, 61 mmol) at −10° C. was added a solution of 4-chlorocinnamaldehyde (1.7 g, 10.2 mmol) and ethyl azidoacetate (A. T. Moore and H. N. Rydon, *Organic Synthesis*, Collective Volume 5, 586-589) in methanol (20 mL). After 2 h, the reaction was diluted with cold water and diethyl ether. The layers were separated and the organic layer was washed with brine, dried over anhydrous sodium sulfate and concentrated without heating to 20 mL. The solution was used immediately in Step D.

Step D: 3-Methoxycarbonyl-6-(4-chlorophenyl)-1,1,1-triphenyl-2-aza-1λ$^5$-phosphahexa-1,3,5-triene The solution of methyl 2-azido-5-(4-chlorophenyl)pent-1,3-dienoate (10.2 mmol) in diethyl ether from Step C at 0° C. was added dropwise to a 0° C. solution of triphenylphosphene (2.67 g, 10.2 mmol) in diethyl ether (30 mL). The reaction was stirred at 0° C. for 30 min and then at rt for 16 h. The volatiles were then removed in vacuo and the residue was used directly in Step E.

Step E: Methyl 6-(2,4-dichlorophenyl)-5-(4-chlorophenyl)pyridine-2-carboxylate

The residue of 3-methoxycarbonyl-6-(4-chlorophenyl)-1,1,1-triphenyl-2-aza-1λ$^5$-phosphahexa-1,3,5-triene (10.2 mmol) from Step D was dissolved in acetonitrile (40 mL) and 2,4-dichlorobenzaldehyde (1.78 g, 10.2 mmol) was added. The reaction was heated to 60° C. under a condenser (left open to the air) for 20 h. HPLC/MS indicated a mixture of the desired title pyridine and dihydropyridine intermediate 394 (M+1), 396 (M+3), $R_t$=4.75 min). The reaction was heated a further 4 h and was then concentrated. The residue was purified by flash column chromatography on silica gel eluted with 0 to 20% ethyl acetate in hexanes to afford methyl 6-(2,4-dichlorophenyl)-5-(4-chlorophenyl)pyridine-2-carboxylate. HPLC/MS: 392 (M+1), 394 (M+3); $R_t$=4.16 min. $^1$HNMR (CDCl$_3$): δ 4.039 (s, 3H), 7.09 (br d, J=8.5 Hz, 2H), 7.26 (br d, J=8.4 Hz, 2H), 7.28 (d, J=2 Hz, 1H), 7.30 (dd, J=2.0 and 8.3 Hz, 1H), 7.34 (d, J=8.3 Hz, 1H), 7.90 (d, J=8 Hz, 1H), 8.26 (d, J=8.0 Hz, 1H).

EXAMPLE 96

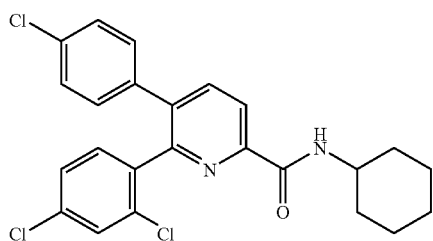

N-(Cyclohexyl)-6-(2,4-dichlorophenyl)-5-(4-chlorophenyl)pyridine-2-carboxamide

Step A: 6-(2,4-Dichlorophenyl)-5-(4-chlorophenyl)pyridine-2-carboxylic acid.

To a solution of methyl 6-(2,4-dichlorophenyl)-5-(4-chlorophenyl)pyridine-2-carboxylate (300 mg, 0.76 mmol) from Example 95, Step E in methanol (6 mL) was added 5N sodium hydroxide (0.300 mL, 1.5 mmol). The reaction was stirred at rt for 20 h and was then concentrated in vacuo. The residue was partitioned between methylene chloride and 2N hydrochloric acid. The organic layer was washed with brine, dried over sodium sulfate, and evaporated to give the crude title compound as a yellow foam. HPLC/MS: 378 (M+1), 380 (M+3); $R_t$=3.73 min Step B: N-(Cyclohexyl)-6-(2,4-dichlorophenyl)-5-(4-chlorophenyl)pyridine-2-carboxamide.

Using essentially the same procedure as Example 52, Step B, 6-(2,4-dichlorophenyl)-5-(4-chlorophenyl)pyridine-2-carboxylic acid (30 mg, 0.079 mmol) from Step A was converted to N-(cyclohexyl)-6-(2,4-dichlorophenyl)-5-(4-chlorophenyl)pyridine-2-carboxamide using PyBOP (37 mg, 0.198 mmol), DIPEA (0.034 mL, 0.198 mmol), and cyclohexylamine (0.021 mL, 0.2 mmol) in methylene chloride (1.0 mL). HPLC/MS: 459 (M+1), 461 (M+3); $R_t$=4.93 min. $^1$HNMR (CDCl$_3$): δ 1.16-1.38 (m, 3H), 1.38-1.52 (m, 2H), 1.62-1.71 (m, 1H), 1.72-1.82 (m, 2H), 1.98-2.06 (m, 2H), 3.99 (m, 1H), 7.08 (br d, J=8.5 Hz, 2H), 7.21 (d, J=8.2 Hz, 1H), 7.24-7.29 (m, 4H), 7.39 (d, J=1.9 Hz, 1H), 7.80 (br d, 1H), 7.90 (d, J=8 Hz, 1H), 8.31 (d, J=8.0 Hz, 1H).

In the following Examples 97-103, the procedures described in Example 32, Steps B-C or Example 52, Step B were repeated but substituting the appropriate amine in the reaction with 6-(2,4-dichlorophenyl)-5-(4chlorophenyl)pyridine-2-carboxylic acid from Example 96, Step A to afford the following compounds:

EXAMPLE 97

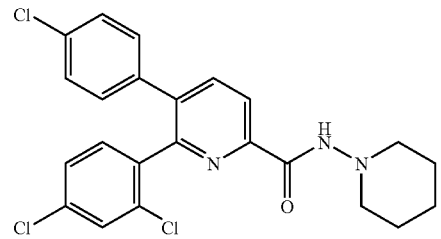

N-(Piperidin-1-yl)-6-(2,4-dichlorophenyl)-5-(4-chlorophenyl)pyridine-2-carboxamide HPLC/MS: 460 (M+1), 462 (M+3); $R_t$=3.95 min and 6-(2,4-Dichlorophenyl)-5-(4-chlorophenyl)-2-(piperidinyl-1-carbonyl)pyridine HPLC/MS: 445 (M+1), 447 (M+3); $R_t$=4.32 min

EXAMPLE 98

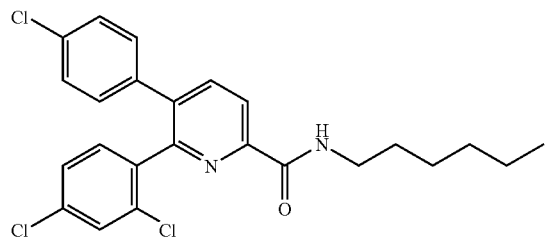

N-(n-Hexyl)-6-(2,4-dichlorophenyl)-5-(4-chlorophenyl)pyridine-2-carboxamide

HPLC/MS: 461 (M+1), 463 (M+3); $R_t$=5.07 min

EXAMPLE 99

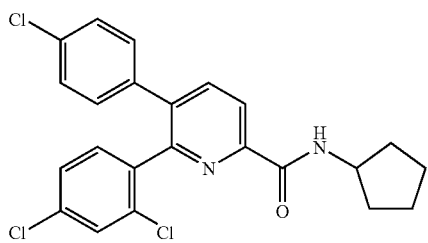

N-(Cyclopentyl)-6-(2,4-dichlorophenyl)-5-(4-chlorophenyl)pyridine-2-carboxamide

HPLC/MS: 445 (M+1), 447 (M+3); $R_t$=4.75 min

EXAMPLE 100

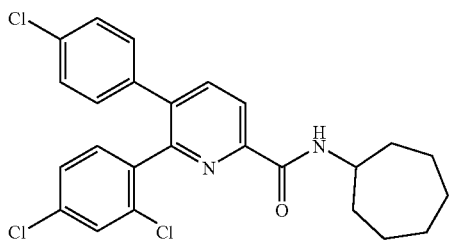

N-(Cycloheptyl)-6-(2,4-dichlorophenyl)-5-(4-chlorophenyl)pyridine-2-carboxamide

HPLC/MS: 473 (M+1), 475 (M+3); $R_t$=5.12 min

EXAMPLE 101

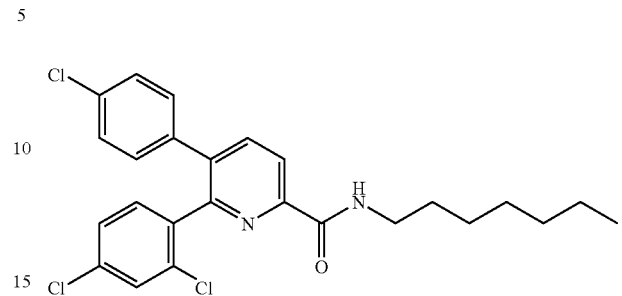

N-(Heptyl)-6-(2,4-dichlorophenyl)-5-(4-chlorophenyl)pyridine-2-carboxamide

HPLC/MS: 475 (M+1), 477 (M+3); $R_t$=5.20 min

EXAMPLE 102

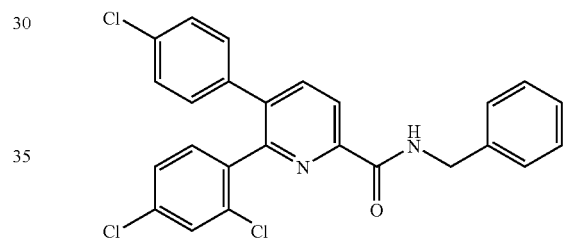

N-(Benzyl)-6-(2,4-dichlorophenyl)-5-(4-chlorophenyl)pyridine-2-carboxamide

HPLC/MS: 467 (M+1), 469 (M+3); $R_t$=4.61 min

EXAMPLE 103

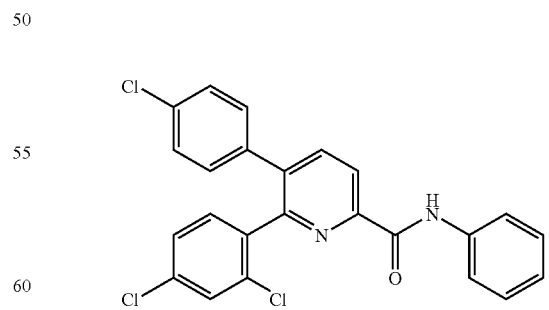

N-(Phenyl)-6-(2,4-dichlorophenyl)-5-(4-chlorophenyl)pyridine-2-carboxamide

HPLC/MS: 453 (M+1), 454 (M+3); $R_t$=4.83 min

EXAMPLE 104

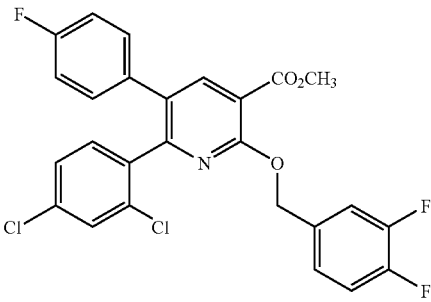

Methyl 6-(2,4-dichlorophenyl)-2-[(3,4-difluorobenzyl)oxy]-5-(4-fluorolphenyl)-nicotinate Step A: 1-(2,4-Dichlorophenyl)-2-(4-fluorophenyl)ethanone To an oven-dried three-neck round bottom flask fitted with a condenser and addition funnel flushed with $N_2$ was added magnesium (4.23 g; 174 mmol) and anhydrous ether (100 mL). A solution of 4-flourobenzyl bromide (8.69 mL; 69.7 mmol) in ether (50 mL) was added dropwise via the addition funnel at room temperature. After the addition, the reaction mixture was heated at 40° C. for 2 hours. The reaction mixture was allowed to cool to room temperature and was cannulated into another dried flask charged with a solution of 2,4-dichlorobenzonitrile (10.0 g; 58.0 mmol) in ether (150 mL) under an $N_2$ atmosphere. The resulting reaction mixture was stirred at 40° C. for 6 hours. The reaction was cooled to room temperature and quenched slowly with 2N aq. HCl, then partitioned between ethyl acetate and 2N aq. HCl. The organic portion was washed with 2N aq. HCl, water, brine, dried ($Na_2SO_4$), filtered, and concentrated in vacuo. The crude product was filtered through a silica gel plug (eluted with 20% ethyl acetate/hexane), and recrystallized from hexane to afford product: m/e=283 (M+1).

Step B: 1-(2.4-Dichlorophenyl)-3-(dimethylamino)-2-(4-fluorophenyl)prop-2-en-1-one To a solution of the ketone product from Step A (6.0 g; 21.3 mmol) in DMF (100 mL) in a dried round bottom flask was added N,N-dimethylformamide dimethyl acetal (11.3 mL; 85.1 mmol) under a $N_2$ atmosphere, and the reaction was stirred at 75° C. for 16 hours. Most of the volatiles were removed in vacuo to afford the crude product as a oil which was used in the next step without further purification.

Step C: 6-(2,4-Dichlorophenyl)-5-(4-fluorophenyl)-2-oxo-1,2-dihydropyridine-3-carbonitrile To an oven-dried round bottom flask was added 1.87 g of a 60% oil dispersion of NaH (46.8 mmol), DMF (50 mL), and methanol (1.89 mL; 46.8 mmol) under a $N_2$ atmosphere. To this suspension was added a solution of 2-cyanoacetamide (1.97 g; 23.4 mmol) in DMF (10 mL) via syringe followed by a solution of the crude product of Step B (21.3 mmol) in DMF (20 mL). The resulting reaction mixture was heated to 95° C. and stirred for 3 hours. The reaction was the quenched with saturated aqueous $NaHSO_4$ solution and extracted with methylene chloride (3×). The combined extracts were dried ($Na_2SO_4$), filtered, and concentrated in vacuo. Purification was done by trituration in ethanol. The precipitate was collected and washed with cold ethanol to afford the desired product: m/e=359 (M+1).

Step D: 6-(2,4-Dichlorophenyl)-5-(4-fluorophenyl)-2-oxo-1,2-dihydropyridine-3-carboxylic acid In a round bottom flask fitted with a condenser, a suspension of the product of Step C (3.98 g; 11.1 mmol) in 50% $H_2SO_4$ in water was heated at 140° C. for 36 hours. The reaction mixture was allowed to cool to room temperature and diluted with water and extracted with methylene chloride (5×). The combined extracts were washed with brine, dried ($Na_2SO_4$), filtered, and concentrated in vacuo. Azeotropic removal of moisture with toluene gave a yellow solid. NMR and LCMS indicated the crude product was clean and was used without further purification: m/e=378 (M+1).

Step E: Methyl 6-(2,4-dichlorophenyl)-5-(4-fluorophenyl)-2-oxo-1,2-dihydropyridine-3-carboxylate In a round bottom flask fitted with a condenser, a suspension of the product from Step D (2.89 g; 7.60 mmol) in methanol (60 mL) was treated with concentrated $H_2SO_4$ (0.5 mL; cat.) and heated to reflux overnight. The reaction mixture was allowed to cool to room temperature, and the volatiles were removed in vacuo. The reaction was quenched with saturated aq. $NaHCO_3$ solution and extracted with methylene chloride (5×). The combined extracts were washed with brine, dried ($Na_2SO_4$), filtered, and concentrated in vacuo. Trituration with methanol gave the desired product: m/e=392 (M+1).

Step F: Methyl 6-(2,4-dichlorophenyl)-2-[(3,4-difluorobenzyl)oxy]-5-(4-fluorophenyl)nicotinate To an oven-dried round bottom flask was added DMF (5 mL), the product of Step E (0.500 g; 1.27 mmol), $Cs_2CO_3$ (0.910 g; 2.79 mmol), and 3,4-difluorobenzyl bromide (0.162 mL; 1.27 mmol). The reaction was stirred at room temperature for 16 h. The reaction mixture was diluted with ethyl acetate and washed with saturated aq. $NaHCO_3$ solution (3×), and brine. The organic portion was dried ($Na_2SO_4$), filtered, and concentrated in vacuo. Purification done by MPLC (silica gel; 0-10% ethyl acetate/hexane gradient) afforded the desired product: m/e=518 (M+1).

EXAMPLE 105

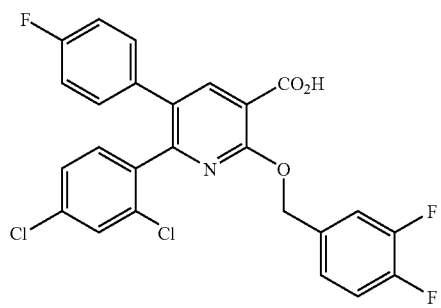

6-(2,4-Dichlorophenyl)-2-[(3,4-difluorobenzyl)oxy]-5-(4-fluorophenyl)nicotinic acid A solution of the product from Example 104 Step F (0.280 g; 0.541 mmol) in methanol (4 mL) and THF (1 mL) in a round bottom flask was treated with 3N aq. NaOH (1.08 mL; 3.24 mmol) and heated to 50° C. for 2 hours. The volatiles were removed in vacuo, and the reaction was quenched with saturated aq. $NaHSO_4$ solution and extracted with methylene chloride (5×). The combined extracts were dried (Na₂SO₄), filtered, and concentrated in vacuo to afford the crude product. NMR and LCMS indicated good purity and the crude product was used without further purification: m/e=504 (M+1).

EXAMPLE 106

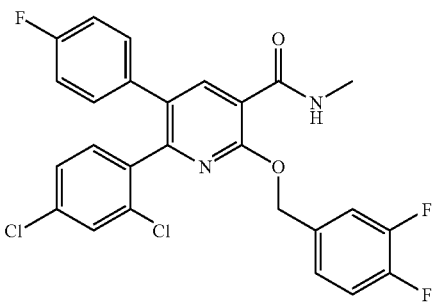

6-(2,4-Dichloropyhenyl)-2-[(3,4-difluorobenzyl)oxy]-5-(4-fluorophenyl)-N-methylnicotinamide To an oven-dried round bottom flask was added methylene chloride (0.5 mL), the product of Example 105 (0.050 g; 0.0992 mmol), methylamine hydrochloride (0.0073 g; 0.101 mmol), EDC (0.0286 g; 0.149 mmol), DMAP (0.0121 g; 0.0992 mmol), and N-methylmorpholine (0.04 mL; 0.397 mmol). The reaction mixture was stirred at room temperature overnight under a nitrogen atmosphere. The reaction mixture was partitioned between ethyl acetate and saturated aq. NaHCO₃ solution. The organic portion was separated and washed again with saturated aq. NaHCO₃ solution (2×), brine, dried (Na₂SO₄), filtered, and concentrated in vacuo. Purification by MPLC (silica gel; 0-30% ethyl acetate/hexane gradient) gave product: m/e=517 (M+1).

EXAMPLE 107

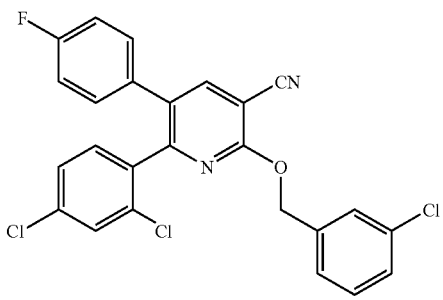

2-[(3-Chlorobenzyl)oxy]-6-(2,4-dichlorophenyl)-5-(4-fluorophenyl)nicotinonitrile To an oven-dried round bottom flask was added DMF (4 mL), the product of Step C in Example 104 (0.300 g; 0.838 mmol), Cs₂CO₃ (0.600 g; 1.84 mmol), and 3-chlorobenzyl bromide (0.110 mL; 0.838 mmol). The reaction was stirred at room temperature for 1 hour. The reaction mixture was diluted with ethyl acetate and washed with saturated aq. NaHCO₃ solution (3×), and brine. The organic portion was dried (Na₂SO₄), filtered, and concentrated in vacuo. Purification done by MPLC (silica gel; 0-10% ethyl acetate/hexane gradient) afforded the desired product: HPLC-MS: m/e=485 (M+3); R$_t$=4.9 min.

In the following Examples 108-111 the procedure described in Example 107 was repeated but substituting the appropriate benzyl bromide or chloride in the reaction with 6-(2,4-dichlorophenyl)-5-(4-fluorophenyl)-2-oxo-1,2-dihydropyridine-3-carbonitrile from Step C of Example 104 to afford the following compounds:

EXAMPLE 108

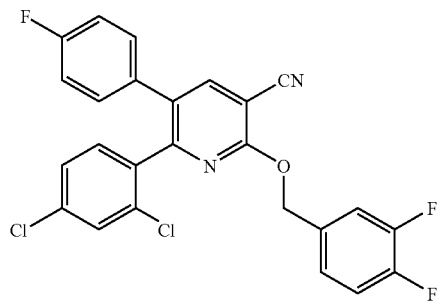

6-(2,4-Dichlorophenyl)-2-[(3,4-difluorobenzyl)oxy]-5-(4-fluorophenyl)nicotinonitrile HPLC/MS: 485 (M+1); R$_t$=4.8 min

EXAMPLE 109

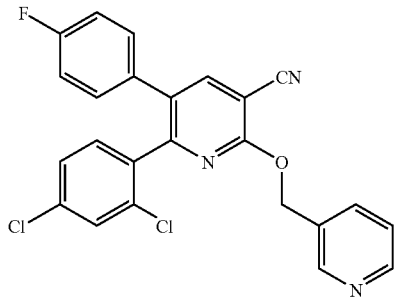

6-(2,4-Dichlorophenyl)-5-(4-fluorophenyl)-2-(pyridin-3-ylmethoxy)nicotinonitrile HPLC/MS: 450 (M+1); R$_t$=3.1 min

EXAMPLE 110

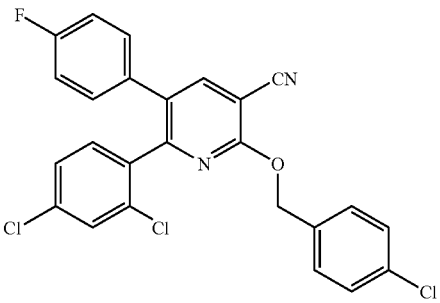

2-[(4-Chlorobenzyl)oxy]-6-(2,4-dichlorophenyl)-5-(4-fluorophenyl)nicotinonitrile HPLC/MS: 483 (M+1); $R_t$=4.9 min

EXAMPLE 111

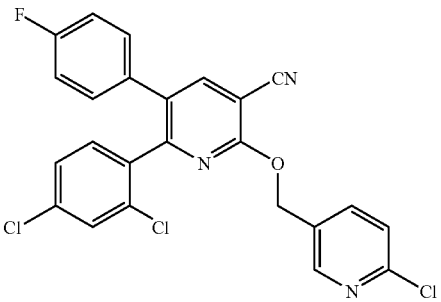

2-[(6-Chloropyridin-3-yl)methoxy]-6-(2,4-dichlorophenyl)-5-(4-fluorophenyl)nicotinonitrile HPLC/MS: 486 (M+3); $R_t$=4.5 min

EXAMPLE 112

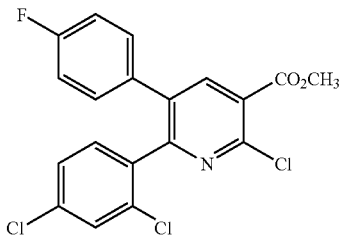

Methyl 2-chloro-6-(2,4-dichlorophenyl)-5-(4-fluorophenyl)nicotinate

To an oven-dried round bottom flask fitted with a condenser was added the product of Step E in Example 104 (0.830 g; 2.12 mmol) and excess phosphorous oxychloride (2.5 mL). The reaction mixture was heated to reflux for 16 hours. The reaction mixture was allowed to cool to room temperature, and the volatiles were removed in vacuo. The reaction mixture was then dissolved in ethyl acetate and washed with saturated $NaHCO_3$ solution (2×), water, brine, dried ($Na_2SO_4$), filtered, and concentrated in vacuo. Purification was done by MPLC (silica gel; 0-10% ethyl acetate:hexane) to afford the desired product: m/e=412 (M+3) $R_t$=4.19 min on LCMS.

EXAMPLE 113

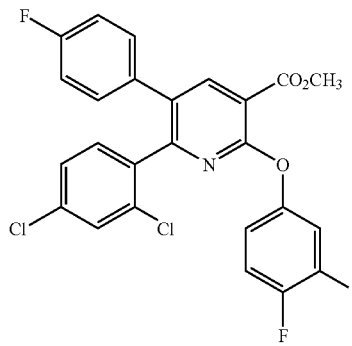

Methyl 6-(2,4-dichlorophenyl)-2-(3,4-difluorophenoxy)-5-(4-fluorophenyl)nicotinate To an oven-dried round bottom flask was added toluene (1 mL), the product of Example 112 (0.050 g; 0.122 mmol), and 3,4-difluorophenol (0.016 g; 0.122 mmol), and cesium carbonate (0.044 g; 0.134 mmol). The reaction mixture was heated at 100° C. and stirred for 4 hours. The reaction mixture was allowed to cool to room temperature, then it was partitioned between ethyl acetate and 2N aq. NaOH solution. The organic portion was separated and washed with more 2N aq. NaOH solution (2×), brine, dried ($Na_2SO_4$), filtered, and concentrated in vacuo. Purification was done by MPLC (silica gel; 0-10% ethyl acetate:hexane) to afford the desired product: m/e=504 (M+1) $R_t$=4.61 min on LCMS.

EXAMPLE 114

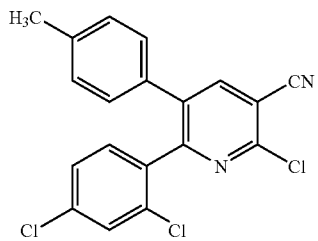

2-Chloro-6-(2,4-dichlorophenyl)-5-(4-methylphenyl)nicotinonitrile

Step A: 1-(2,4-Dichlorophenyl)-2-(4-methylphenyl)ethanone

To an oven-dried three-neck round bottom flask fitted with a condenser and addition funnel charged flushed with nitrogen was added magnesium (2.82 g; 116 mmol) and anhydrous ether (100 mL). A solution of 4-methylbenzyl bromide (12.91 g; 69.7 mmol) in ether (50 mL) was added dropwise via the addition funnel at room temperature. After the addition, the reaction mixture was heated at 40° C. for 2 hours. The reaction mixture was allowed to cool to room temperature and was cannulated to another dried flask charged with a solution of 2,4-dichlorobenzonitrile (10.0 g; 58.0 mmol) in ether (150 mL) under a nitrogen atmosphere. The resulting reaction mixture was stirred at 40° C. for 6 hours. The reaction was cooled to room temperature and quenched slowly with 2N aq. HCl. Partitioned between ethyl acetate and 2N aq. HCl. The organic portion was washed with 2N aq. HCl, water, brine, dried (Na$_2$SO$_4$), filtered, and concentrated in vacuo. The crude product was filtered through a silica gel plug (eluted with 20% ethyl acetate/hexane), and recrystallized from hexane to afford product: m/e=279 (M+1).

Step B: 1-(2,4-Dichlorophenyl)-3-(dimethylamino)-2-(4-methylphenyl)prop-2-en-1-one To a solution of the ketone product from Step A (11.79 g; 42.4 mmol) in DMF (150 mL) in an oven-dried round bottom flask was added N,N-dimethylformamide dimethyl acetal (22.5 mL; 169 mmol) under a nitrogen atmosphere. The reaction was stirred at 75° C. for 16 hours. Most of the volatiles were removed in vacuo to afford the crude product as a oil which was used in the next step without further purification.

Step C: 6-(2,4-Dichlorophenyl)-5-(4-methylphenyl)-2-oxo-1,2-dihydropyridine-3-carbonitrile To a dried round bottom flask was added NaH (3.73 g in 60% disp.; 93.3 mmol), DMF (100 mL), and methanol (3.78 mL; 93.3 mmol) under a nitrogen atmosphere. To this suspension was added a solution of 2-cyanoacetamide (3.92 g; 46.6 mmol) in DMF (30 mL) via syringe. Then a solution of the crude product of Step B (42.4 mmol) in DMF (30 mL) was added via syringe. The resulting reaction mixture was heated to 95° C. and stirred for 3 hours. The reaction was quenched with saturated aq. NaHSO$_4$ solution and extracted with methylene chloride (3×). The combined extracts were dried (Na$_2$SO$_4$), filtered, and concentrated in vacuo. Purification was done by trituration in ethanol. The precipitate was collected and washed with cold ethanol to afford the desired product: m/e=355 (M+1) R$_t$=3.3 min on LCMS.

Step D: 2-Chloro-6-(2,4-dichlorophenyl)-5-(4-methylphenyl)nicotinonitrile

To an oven-dried round bottom flask fitted with a condenser was added the product of Step C (0.350 g; 0.986 mmol) and excess phosphorous oxychloride (1 mL). The reaction mixture was heated to reflux for 16 hours. The reaction mixture was allowed to cool to room temperature, and the volatiles were removed in vacuo. The residue was dissolved in ethyl acetate and washed with saturated NaHCO$_3$ solution (2×), water, brine, dried (Na$_2$SO$_4$), filtered, and concentrated in vacuo. Purification was done by MPLC (silica gel; 0-10% ethyl acetate:hexane) to afford 0.283 g of the desired product: m/e=375 (M+2) R$_t$=4.36 min on LCMS.

EXAMPLE 115

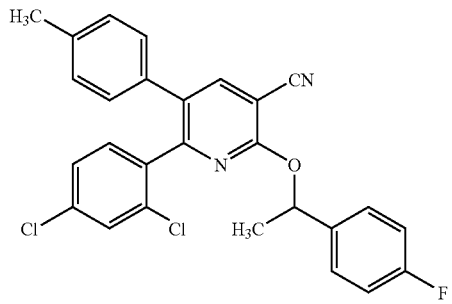

6-(2,4-Dichlorophenyl)-5-(4-methylphenyl)-2-(1-(4-fluorophenyl)ethoxy)nicotinonitrile To an oven-dried round bottom flask was added toluene (1 mL), the product of Step D of Example 114 (0.050 g; 0.134 mmol); 1-(4-flourophenyl)ethanol (0.070 mL; 0.536 mmol), and cesium carbonate (0.218 g; 0.670 mmol). The reaction mixture was heated at 100° C. and stirred for 16 hours. The reaction mixture was allowed to cool to room temperature, then it was partitioned between ethyl acetate and 2N aq. NaOH solution. The organic portion was separated and washed with more 2N aq. NaOH solution (2×), brine, dried (Na$_2$SO$_4$), filtered, and concentrated in vacuo. Purification was done by MPLC (silica gel; 0-10% ethyl acetate:hexane) to afford 0.051 g of the desired product: m/e=355 (M-1-(4-flourophenyl)ethyl group) R$_t$=4.9 min on LCMS.

In the following Examples 116-121 the procedure described in Example 115 was repeated but substituting the appropriate alcohol or phenol in the reaction with 2-chloro-6-(2,4-dichlorophenyl)-5-(4-methylphenyl)nicotinonitrile from Step D in Example 114 to afford the following compounds:

EXAMPLE 116

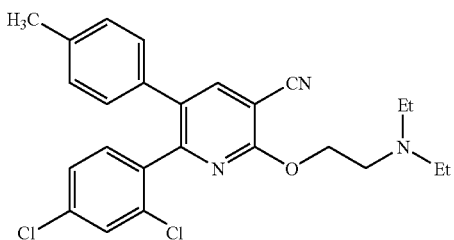

6-(2,4-Dichlorophenyl)-2-[2-(diethylamino)ethoxy]-5-(4-methylphenyl)nicotinonitrile HPLC/MS: 454 (M+1); R$_t$=3.27 min

EXAMPLE 117

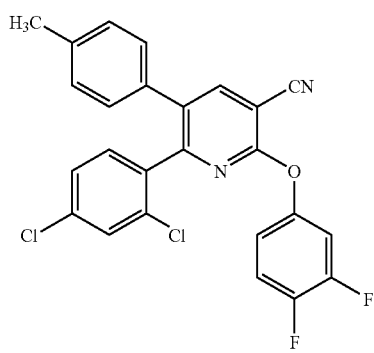

6-(2,4-Dichlorophenyl)-2-(3,4-difluorophenoxy)-5-(4-methylphenyl)nicotinonitrile HPLC/MS: 467 (M+1); $R_t$=4.71 min

EXAMPLE 118

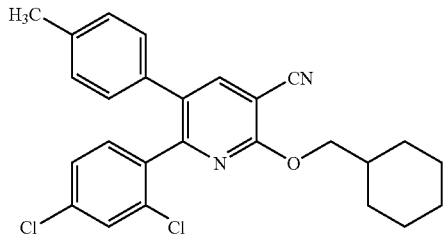

2-(Cyclohexylmethoxy)-6-(2,4-dichlorophenyl)-5-(4-methylphenyl)nicotinonitrile

HPLC/MS: 451 (M+1); $R_t$=5.50 min

EXAMPLE 119

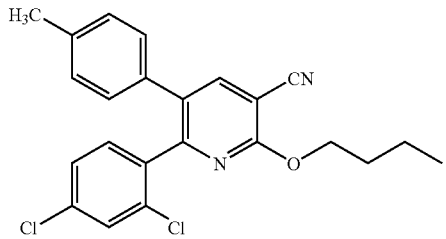

2-Butoxy-6-(2,4-dichlorophenyl)-5-(4-methylphenyl)nicotinonitrile

HPLC/MS: 411 (M+1); $R_t$=5.10 min

EXAMPLE 120

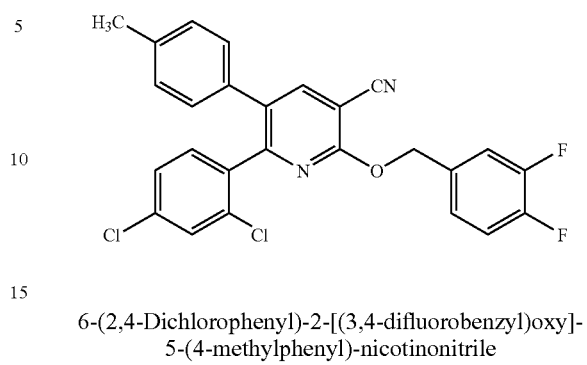

6-(2,4-Dichlorophenyl)-2-[(3,4-difluorobenzyl)oxy]-5-(4-methylphenyl)-nicotinonitrile HPLC/MS: 481 (M+1); $R_t$=4.90 min

EXAMPLE 121

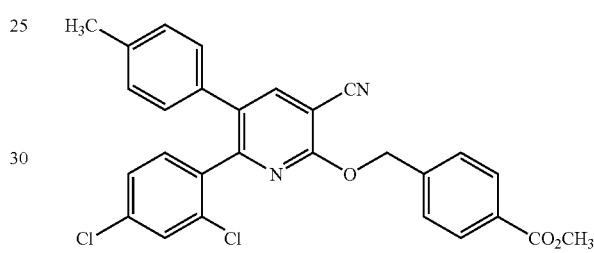

Methyl 4-({[3-cyano-6-(2,4-dichlorolphenyl)-5-(4-methylphenyl)pyridin-2-yl]oxy}methyl)benzoate HPLC/MS: 503 (M+1); $R_t$=4.80 min

EXAMPLE 122

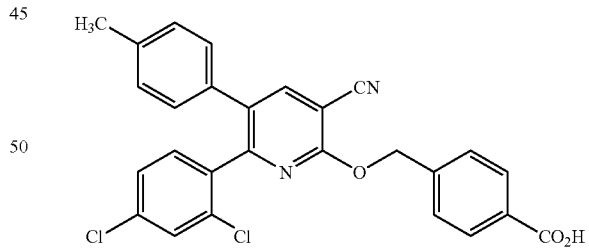

4-({[3-Cyano-6-(2,4-dichlorophenyl)-5-(4-methylphenyl)pyridin-2-yl]oxy}methyl)benzoic acid To a dried round bottom flask was added methanol (2 mL), THF (1 mL), the product of Example 121 (0.100 g; 0.199 mmol), and 3N aq. NaOH (0.2 mL, 0.596 mmol). The reaction mixture was heated at 50° C. and stirred for 2 hours. The reaction mixture was allowed to cool to room temperature, and the methanol was removed in vacuo. The pH was adjusted with 2N aq. HCl solution to pH=5-6. The mixture was extracted with methylene chloride (5×) and the combined extracts were dried (Na₂SO₄), filtered, and concentrated in vacuo. Purification was done by MPLC (silica gel; ethyl acetate:hexane) to afford the desired product: m/e=489 (M+1); R_f=4.3 min on LCMS.

HPLC/MS: 489 (M+1); R_t=4.30 min

EXAMPLE 123

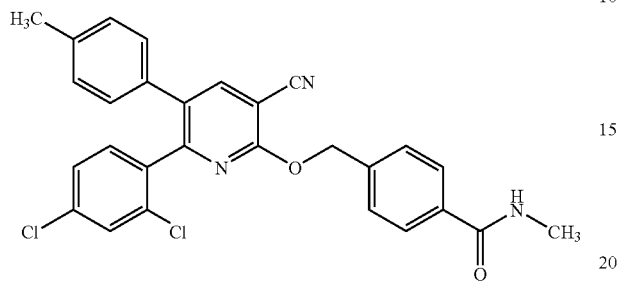

4-({[3-Cyano-6-(2,4-dichlorophenyl)-5-(4-methylphenyl)pyridin-2-yl]oxy}methyl)-N-methylbenzamide To a dried round bottom flask was added the product of Example 122 (0.030 g; 0.0613 mmol), methylamine hydrochloride (0.005 g; 0.0675 mmol), EDC (0.018 g; 0.0919 mmol), DMAP (0.007 g; 0.0613 mmol), N-methylmorpholine (0.028 mL; 0.251 mmol), and methylene chloride (0.5 mL). The reaction mixture was stirred at room temperature overnight. The volatiles were removed, and the residue was taken up in ethyl acetate, washed with saturated NaHCO₃ (2×), water, brine, dried (Na₂SO₄), filtered, and concentrated in vacuo. Purification was done by MPLC (silica gel; 0-50% ethyl acetate:hexane) to afford the desired product: m/e=502 (M+1); R_t=4.2 min on LCMS. HPLC/MS: 502 (M+1); R_t=4.20 min

EXAMPLE 124

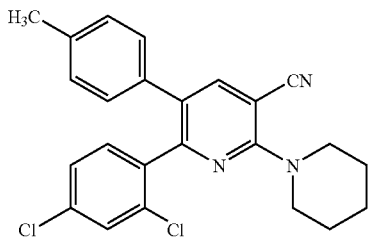

6-(2,4-Dichlorophenyl)-5-(4-methylphenyl)-2-piperidin-1-ylnicotinonitrile

To an oven-dried round bottom flask fitted with a rubber septa was added toluene (1 mL), the product of Step D of Example 114 (0.050 g; 0.134 mmol) and piperidine (0.070 mL; 0.670 mmol). The sealed reaction mixture was heated at 100° C. and stirred for 16 hours. The reaction mixture was allowed to cool to room temperature, then it was partitioned between ethyl acetate and saturated NaHCO₃ solution. The organic portion was separated and washed with more saturated NaHCO₃ solution (2×), brine, dried (Na₂SO₄), filtered, and concentrated in vacuo. Purification was done by MPLC (silica gel; 0-10% ethyl acetate:hexane) to afford the desired product: m/e=422 (M+1) R_t=5.10 min on LCMS.

In the following Examples 125-128 the procedure described in Example 124 was repeated but substituting the appropriate amine in the reaction with 2-chloro-6-(2,4-dichlorophenyl)-5-(4-methylphenyl)nicotinonitrile from Step D of Example 114 to afford the following compounds:

EXAMPLE 125

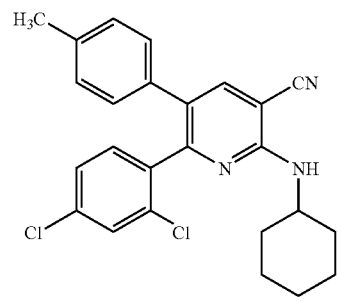

2-(Cyclohexylamino)-6-(2,4-dichlorophenyl)-5-(4-methylphenyl)nicotinonitrile

HPLC-MS: m/e=436 (M+1); R_t=5.10 min.

EXAMPLE 126

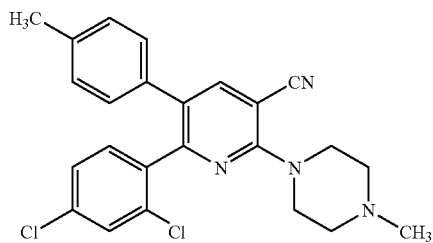

6-(2,4-Dichlorophenyl)-5-(4-methylphenyl)-2-(4-methylpiperazin-1-yl)nicotinonitrile HPLC-MS: m/e=437 (M+1); R_t=3.20 min.

EXAMPLE 127

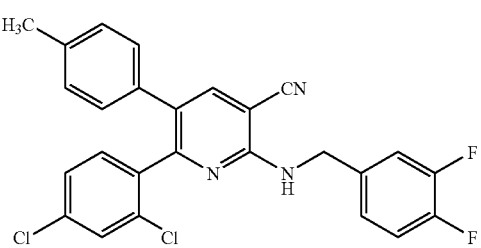

6-(2,4-Dichlorophenyl)-2-[(3,4-difluorobenzyl)amino]-5-(4-methylphenyl)-nicotinonitrile HPLC-MS: m/e=480 (M+1); $R_t$=4.90 min.

EXAMPLE 128

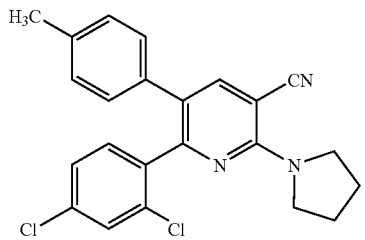

6-(2,4-Dichlorophenyl)-5-(4-methylphenyl)-2-pyrrolidin-1-ylnicotinonitrile

HPLC-MS: m/e=408 (M+1); $R_t$=4.90 min.

EXAMPLE 129

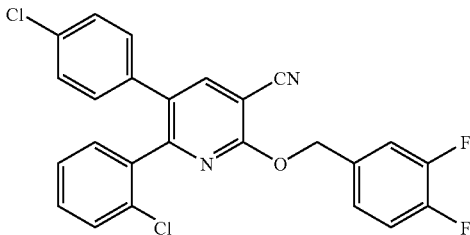

6-(2-Chlorophenyl)-5-(4-chlorophenyl)-2-[(3,4-difluorobenzyl)oxy]nicotinonitrile Step A: 1-(2-Chlorophenyl)-2-(4-chlorophenyl)ethanone To a dried three-neck round bottom flask fitted with a condenser and addition funnel was added magnesium (2.217 g, 91.2 mmol) and anhydrous ether (60 mL). A solution of 4-chlorobenzyl bromide (18.74 g, 91.2 mmol) in ether (100 mL) was added dropwise via the addition funnel at room temperature. After the addition, the reaction mixture was heated at 34° C. for 1 hour. The reaction mixture was allowed to cool to room temperature. One half of the volume of the ether solution was then added to another dried flask charged with a solution of 2-chlorobenzonitrile (5.228 g, 38.0 mmol) in ether (70 mL). The resulting reaction mixture was stirred at 34° C. for 3 hours. The reaction was cooled to room temperature and quenched slowly with 2 M aq. HCl. The solution was diluted with ethyl acetate, and the organic portion was washed with 2N aq. HCl, water, dried (Na$_2$SO$_4$), filtered, and concentrated in vacuo. The crude product was purified by flash chromatography (silica gel) eluting with 7% ethyl acetate/hexane) to afford product.

Step B: 1-(2-Chlorophenyl)-2-(4-chlorophenyl)-3-(dimethylamino)prop-2-en-1-one

To a solution of the ketone product from Step A (5.48 g, 20.67 mmol) in DMF (70 mL) was added N,N-dimethylformamide dimethyl acetal (9.89 g, 82.7 mmol). The reaction was stirred at 75° C. for 16 hours. Most of the volatiles were removed in vacuo to afford the crude product as an oil which was used in the next step (Step C) without further purification.

Step C: 6-(2-Chlorophenyl)-5-(4-chlorophenyl)-2-oxo-1,2-dihydropyridine-3-carbonitrile To the product of step B was added 2-cyanoacetamide (1.912 g, 22.74 mmol), methanol (1.84 mL, 45.5 mmol) and DMF (50 mL). This solution was cannulated into a slurry of NaH (2.067 g, 51.7 mmol, 60% dispersion in mineral oil, washed with hexane) and DMF (24 mL) and then heated to 95° C. for 2.5 hours. The reaction was cooled and then concentrated in vacuo. The residue was diluted with ethyl acetate and then washed with 10% aq. NaHSO$_4$ and water. The organic portion was dried (Na$_2$SO$_4$) and concentrated before suspending the solid in hot ethanol. After cooling, the solid was filtered and washed with ethanol and then hexane. This afforded product. MS (electrospray) m/e 341.1 MH$^+$ ($R_t$=3.1 min LC/MS).

Step D: 6-(2-Chlorophenyl)-5-(4-chlorophenyl)-2-[(3,4-difluorobenzyl)-oxy]nicotinonitrile To the product of Step C (0.500 g, 1.465 mmol) was added Ag$_2$CO$_3$ (0.606 g, 2.198 mmol), DMF (8 mL), and 3,4-difluorobenzyl bromide (0.28 mL, 2.198 mmol). The reaction was heated to 75° C. for 75 min before cooling and filtering through Celite®545 diatomaceous earth. The solution was concentrated and the residue was purified by flash chromatography (silica gel) eluting with a gradient of 15 to 46% ethyl acetate/hexane affording the product. MS (electrospray) m/e 467.0 MH$^+$ ($R_t$=4.7 min LC/MS).

EXAMPLE 130

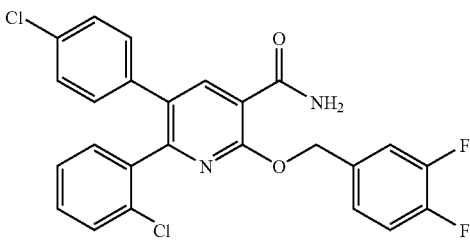

6-(2-Chlorophenyl)-5-(4-chlorophenyl)-2-[(3,4-difluorobenzyl)oxy]nicotinamide

To the product of Step D Example 129 (30.0 mg, 0.0516 mmol, material in the TFA salt form) was added 1,4-dioxane (4 mL), ethanol (0.5 mL), KOH (0.272 mg, 4.92 mmol), H$_2$O (0.6 mL) and H$_2$O$_2$ (0.21 g). The reaction was heated to 95° C. for 22 hours. The solution was concentrated and the residue was dissolved in ethyl acetate before washing with water, drying (Na$_2$SO$_4$) and concentrating. The residue was purified by preparative thin layer chromatography (20 cm×20 cm, 1000 μm, silica gel) eluting with 10.5% ethyl acetate/dichloromethane affording the product. MS (electrospray) m/e 485.2 MH$^+$ ($R_t$=4.2 min LC/MS).

EXAMPLE 131

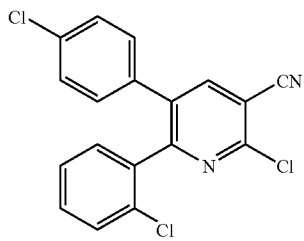

2-Chloro-6-(2-chlorophenyl)-5-(4-chlorophenyl)nicotinonitrile

To the product of Step C of Example 129 (1.50 g, 4.40 mmol) was added POCl$_3$ (5 mL, 53.6 mmol). The mixture was heated to 100° C. for 17 hours before concentrating in vacuo. The residue was dissolved in ethyl acetate and washed with NaHCO$_3$ (saturated, aq.), water, dried (Na$_2$SO$_4$) and concentrated. The residue was purified by flash chromatography (silica gel) eluting with 10% ethyl acetate/hexane affording product. MS (electrospray) m/e 360.9 MH$^+$ (R$_t$=4.1 min LC/MS).

EXAMPLE 132

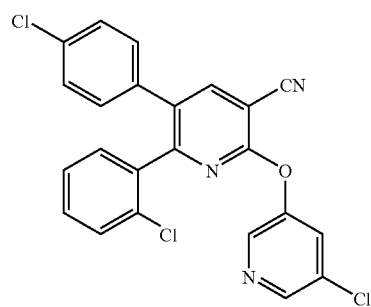

6-(2-Chlorophenyl)-5-(4-chlorophenyl)-2-[(5-chloropyridin-3-yl)oxy]nicotinonitrile To the product of Example 131 (100 mg, 0.2793 mmol) was added 5-chloro-3-pyridinol (181 mg, 1.397 mmol), Cs$_2$CO$_3$ (228 mg, 0.6983 mmol) and toluene (1.5 mL) before heating to 100° C. After stirring 14 hours the reaction solution was filtered and concentrated. The residue was purified by flash chromatography (silica gel) eluting with a gradient of 1 to 3% ethyl acetate/dichloromethane affording the product. MS (electrospray) m/e 453.9 MH$^+$ (R$_t$=4.1 min LC/MS).

EXAMPLE 133

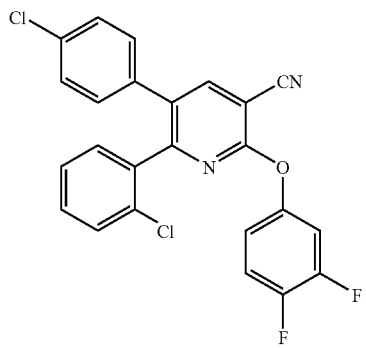

6-(2-Chlorophenyl)-5-(4-chlorophenyl)-2-(3,4-difluorophenoxy)nicotinonitrile

To the product of Example 131 (250 mg, 0.6984 mmol) was added 3,4-difluorophenol (273 mg, 2.095 mmol), Cs$_2$CO$_3$ (683 mg, 2.096 mmol) and toluene (4.5 mL) before heating to 100° C. After stirring 16 hours the reaction solution was filtered and concentrated. The residue was purified by flash chromatography (silica gel) eluting with 10% ethyl acetate/hexane affording the product. MS (electrospray) m/e 453.0 MH$^+$ (R$_t$=4.4 min LC/MS).

EXAMPLE 134

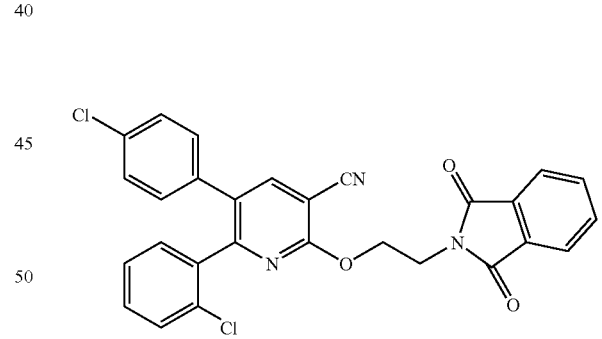

6-(2-Chlorophenyl)-5-(4-chlorophenyl)-2-[2-(1,3-dioxo-1,3-dihydro-2H-isoindol-2-yl)ethoxy]nicotinonitrile Using the procedure described in Example 25, 6-(2-chlorophenyl)-5-(4-chlorophenyl)-2-oxo-1,2-dihydropyridine-3-carbonitrile from Step C of Example 129 was reacted with N-(2-bromoethyl)phthalimide to afford the title compound. MS (electrospray) m/e 513.9 MH$^+$ (R$_t$=4.2 min LC/MS).

EXAMPLE 135

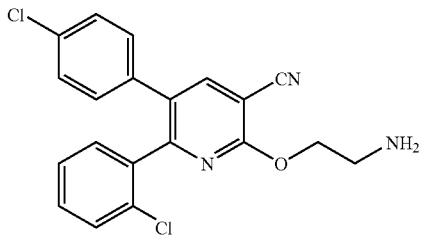

2-(2-Aminoethoxy)-6-(2-chlorophenyl)-5-(4-chlorophenyl)nicotinonitrile

Using the procedure described in Example 26, the product of Example 134 was reacted with hydrazine hydrate to afford the title compound. MS (electrospray) m/e 384.1 MH$^+$ (R$_t$=2.8 min LC/MS).

In the following Examples 136-142, the procedure described in Example 27 was repeated but substituting the appropriate acid chloride, sulfonyl chloride or isocyanate in the reaction with 2-(2-aminoethoxy)-6-(2-chlorophenyl)-5-(4-chlorophenyl)nicotinonitrile from Example 135 to afford the following compounds:

EXAMPLE 136

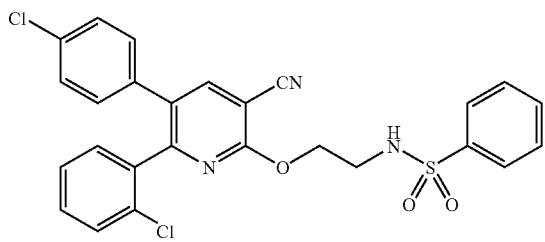

N-(2-{[6-(2-Chlorophenyl)-5-(4-chlorophenyl)-3-cyanopyridin-2-yl]oxy}ethyl)benzenesulfonamide MS (electrospray) m/e 524.0 MH$^+$ (R$_t$=4.1 min LC/MS).

EXAMPLE 137

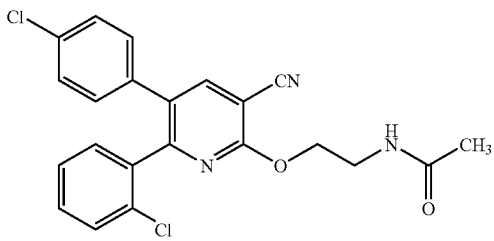

N-(2-{[6-(2-Chlorophenyl)-5-(4-chlorophenyl)-3-cyanopyridin-2-yl]oxy}ethyl)acetamide MS (electrospray) m/e 426.0 MH$^+$ (R$_t$=3.5 min LC/MS).

EXAMPLE 138

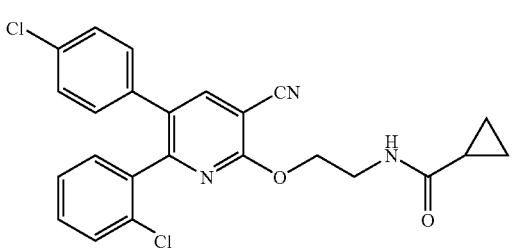

N-(2-{[6-(2-Chlorophenyl)-5-(4-chlorophenyl)-3-cyanopyridin-2-yl]oxy}ethyl)cyclopropanecarboxamide MS (electrospray) m/e 452.0 MH$^+$ (R$_t$=3.8 min LC/MS).

EXAMPLE 139

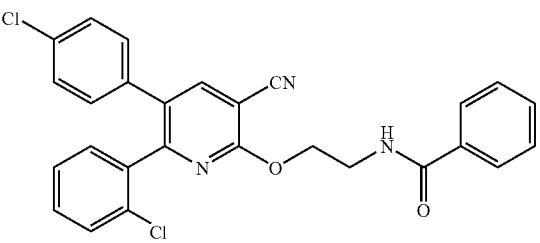

N-(2-{[6-(2-Chlorophenyl)-5-(4-chlorophenyl)-3-cyanopyridin-2-yl]oxy}ethyl)benzamide MS (electrospray) m/e 488.0 MH$^+$ (R$_t$=4.0 min LC/MS).

EXAMPLE 140

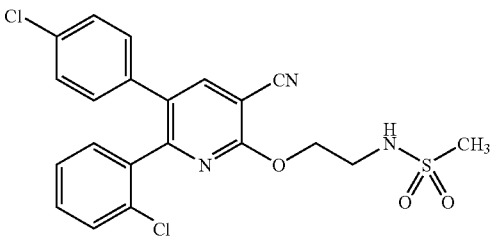

N-(2-{[6-(2-Chlorophenyl)-5-(4-chlorophenyl)-3-cyanopyridin-2-yl]oxy}ethyl)methanesulfonamide MS (electrospray) m/e 462.0 MH$^+$ (R$_t$=3.7 min LC/MS).

EXAMPLE 141

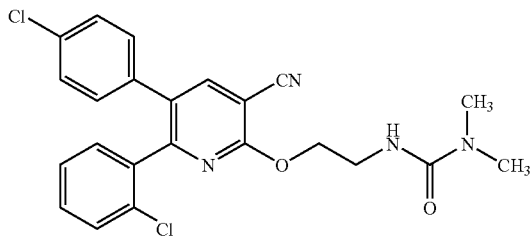

N'-(2-{[6-(2-Chlorophenyl)-5-(4-chlorophenyl)-3-cyanopyridin-2-yl]oxy}ethyl)-N,N-dimethylurea MS (electrospray) m/e 455.0 MH+ ($R_t$=3.6 min LC/MS).

EXAMPLE 142

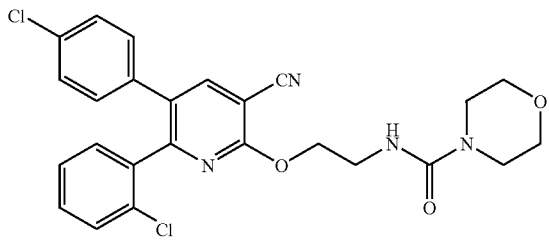

N-(2-{[6-(2-chlorophenyl)-5-(4-chlorophenyl)-3-cyanopyridin-2-yl]oxy}ethyl)morpholine-4-carboxamide MS (electrospray) m/e 497.1 MH+ ($R_t$=3.5 min LC/MS).

EXAMPLE 143

Cannabinoid Receptor-1 (CB1) Binding Assay

Binding affinity determination is based on recombinant human CB1 receptor expressed in Chinese Hamster Ovary (CHO) cells (Felder et al, Mol. Pharmacol. 48: 443-450, 1995). Total assay volume is 250 μL (240 μL CB1 receptor membrane solution plus 5 μL test compound solution plus 5 μL [3H]CP-55940 solution). Final concentration of [3H]CP-55940 is 0.6 nM. Binding buffer contains 50 mM Tris-HCl, pH7.4, 2.5 mM EDTA, 5 mM $MgCl_2$, 0.5 mg/ml fatty acid free bovine serum albumin and protease inhibitors (Cat#P8340, from Sigma). To initiate the binding reaction, 5 μL of radioligand solution is added, the mixture is incubated with gentle shaking on a shaker for 1.5 h at 30° C. The binding is terminated by using 96-well harvester and filtering through GF/C filter presoaked in 0.05% polyethylenimine. The bound radiolabel is quantitated using scintillation counter. Apparent binding affinities for various compounds are calculated from IC50 values (DeBlasi et al., Trends Pharmacol Sci 10: 227-229, 1989).

The binding assay for CB2 receptor is done similarly with recombinant human CB2 receptor expressed in CHO cells.

EXAMPLE 144

Cannabinoid Receptor-1 (CB1) Functional Activity Assay

The functional activation of CB1 receptor is based on recombinant human CB1 receptor expressed in CHO cells (Felder et al, Mol. Pharmacol. 48: 443450, 1995). To determine the agonist activity or inverse agonist activity of any test compound, 50 μL of CB1-CHO cell suspension are mixed with test compound and 70 ul assay buffer containing 0.34 mM 3-isobutyl-1-methylxanthine and 5.1 μM of forskolin in 96-well plates. The assay buffer is comprised of Earle's Balanced Salt Solution supplemented with 5 mM $MgCl_2$, 1 mM glutamine, 10 mM HEPES, and 1 mg/ml bovine serum albumin. The mixture is incubated at room temperature for 30 minutes, and terminated by adding 30 μL/well of 0.5M HCl. The total intracellular cAMP level is quantitated using the New England Nuclear Flashplate and cAMP radioimmunoassay kit.

To determine the antagonist activity of test compound, the reaction mixture also contains 0.5 nM of the agonist CP55940, and the reversal of the CP55940 effect is quantitated. Alternatively, a series of dose response curves for CP55940 is performed with increasing concentration of the test compound in each of the dose response curves.

The functional assay for the CB2 receptor is done similarly with recombinant human CB2 receptor expressed in CHO cells.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of structural formula I:

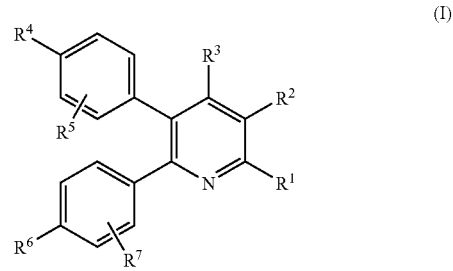

(I)

or a pharmaceutically acceptable salt thereof, wherein;
$R^1$ is selected from:

(1) hydrogen,
(2) halogen,
(3) $C_{1-4}$alkyl,
(4) cycloheteroalkyl,
(5) cycloheteroalkyl-$C_{1-4}$alkyl,
(6) heteroaryl,
(7) aryl-$C_{1-4}$alkyl,
(8) heteroaryl-$C_{1-4}$alkyl;
(9) —$OR^d$,
(10) —$SR^d$,
(11) —O—$(CR^fR^g)_n$—$NR^dR^e$,
(12) —O—$(CR^fR^g)_n$—NH—C(O)—$R^d$,
(13) —O—$(CR^fR^g)_n$—NH—S(O)$_p R^d$,
(14) —O—$(CR^fR^g)_n$—NH—C(O)—$NR^dR^e$,
(15) —O—$(CR^fR^g)_n$—C(O)—$NR^dR^e$,
(16) —$NR^dR^e$,
(17) —C(O)$R^d$,
(18) —$CO_2R^d$,
(19) —CN,
(20) —C(O)$NR^dR^e$,
(21) —$NR^eC(O)R^d$,
(22) —$NR^eC(O)OR^d$,
(23) —$NR^eC(O)NR^dR^e$,
wherein the alkyl groups are optionally substituted with one to four substituents independently selected from $R^a$, and cycloheteroalkyl, aryl and heteroaryl are optionally substituted with one to four substituents independently selected from $R^b$;
$R^2$ is selected from:
(1) hydrogen,
(2) cyano,
(3) —C(O)$OR^d$,
(4) —C(O)$NR^dR^e$,
(5) halogen,
(6) nitro,
(7) trifluoromethyl, and
(8) C(O)NH—$NR^dR^e$;
provided that $R^1$ and $R^2$ are not both hydrogen;
$R^3$ is selected from:
(1) hydrogen,
(2) $C_{1-3}$alkyl,
(3) cycloalkyl, and
(4) trifluoromethyl,
wherein alkyl, and cycloalkyl are optionally substituted with one to four substituents independently selected from $R^a$;
$R^4$, $R^5$, $R^6$ and $R^7$ are each independently selected from:
(1) hydrogen,
(2) halogen,
(3) amino,
(4) carboxy,
(5) $C_{1-4}$alkyl,
(6)
(7) aryl,
(8) aryl $C_{1-4}$alkyl,
(9) trifluoromethyl,
(10) —OC(O)$C_{1-4}$alkyl, and
(11) —OC(O)$NR^dR^e$,
provided that $R^6$ and $R^7$ are not both hydrogen;
each $R^a$ is independently selected from:
(1) —C(O)$R^d$,
(2) —$CO_2R^d$,
(3) —$CO_2(CR^fR^g)_n CONR^dR^e$,
(4) —OC(O)$R^d$,
(5) —CN,
(6) —C(O)$NR^dR^e$,
(7) —$NR^eC(O)R^d$,
(8) —OC(O)$NR^dR^e$,
(9) —$NR^eC(O)OR^d$,
(10) —$NR^eC(O)NR^dR^e$,
(11) —$CR^d$(N—$OR^d$),
(12) —$CF_3$,
(13) —$OCF_3$, and
(14) $C_{3-8}$cycloalkyl;
each $R^b$ is independently selected from:
(1) $R^a$,
(2) $C_{1-4}$ alkyl,
(3) $C_{2-4}$ alkenyl,
(4) $C_{2-4}$ alkynyl,
(5) aryl, and
(6) aryl-$C_{1-4}$ alkyl;
wherein alkyl, alkenyl, alkynyl, and aryl are optionally substituted with one to four substituents selected from a group independently selected from $R^c$;
each $R^c$ is independently selected from:
(1) halogen,
(2) amino,
(3) carboxy,
(4) —$OR^d$,
(5) —$NR^eS(O)_m R^d$,
(6) —$NO_2$,
(7) halogen,
(8) —S(O)$_m R^d$,
(9) —$SR^d$,
(10) —S(O)$_2 OR^d$,
(11) —S(O)$_m NR^dR^e$,
(12) —$NR^dR^e$,
(13) —O$(CR^fR^g)_n NR^dR^e$,
(14) $C_{1-4}$alkyl,
(15) $C_{1-4}$alkoxy,
(16) aryl,
(12) aryl $C_{1-4}$alkyl,
(13) hydroxy,
(14) $CF_3$,
(15) —OC(O)$C_{1-4}$alkyl, and
(16) —OC(O)$NR^dR^e$;
$R^d$ and $R^e$ are independently selected from:
(1) hydrogen,
(2) $C_{1-10}$alkyl, unsubstituted or substituted with one to three substituents selected from $R^h$,
(3) $C_{2-10}$alkenyl;
(4) $C_{2-10}$alkynyl;
(5) cycloalkyl, unsubstituted or substituted with one to three substituents selected from $R^h$;
(6) cycloalkyl-$C_{1-4}$alkyl;
(7) cycloheteroalkyl, unsubstituted or substituted with one to three substituents selected from $R^h$;
(8) cycloheteroalkyl-$C_{1-4}$ alkyl, unsubstituted or substituted with an $R^h$ substituent;
(9) aryl, unsubstituted or substituted with one to three substituents selected from $R^h$;
(10) heteroaryl, unsubstituted or substituted with one to three substituents selected from $R^h$;
(11) aryl-$C_{1-4}$alkyl, unsubstituted or substituted with one to three substituents selected from $R^h$; and
(12) heteroaryl-$C_{1-4}$alkyl, unsubstituted or substituted with one to three substituents selected from $R^h$; or
$R^d$ and $R^e$ together with the atom(s) to which they are attached form a heterocyclic ring of 4 to 7 members containing 0-2 additional heteroatoms independently selected from oxygen, sulfur and N—$R^h$, unsubstituted or substituted with one or two oxo groups;
$R^f$ and $R^g$ are independently selected from
(1) hydrogen, and
(2) $C_{1-4}$alkyl;

each $R^h$ is independently selected from:
(1) halogen,
(2) amino,
(3) hydroxycarbonyl,
(4) $C_{1-4}$alkyl,
(5) $C_{1-4}$alkoxy,
(6) aryl,
(7) aryl $C_{1-4}$alkyl,
(8) hydroxy,
(9) —$CF_3$,
(10) —$OC(O)C_{1-4}$alkyl,
(11) aryloxy,
(12) $C_{1-4}$alkyloxycarbonyl-,
(13) —C(O)—NH—$C_{1-4}$alkyl;
m is selected from 1 and 2;
n is selected from 1, 2, 3 and 4;
p is selected from 0, 1, and 2; and
and pharmaceutically acceptable salts thereof.

2. The compound according to claim 1 or a pharmaceutically acceptable salt thereof, wherein:
$R^1$ is selected from:
(1) hydrogen,
(2) halogen,
(3) $C_{1-4}$alkyl,
(4) cycloheteroalkyl,
(5) cycloheteroalkyl-$C_{1-4}$alkyl,
(6) heteroaryl,
(7) aryl-$C_{1-4}$alkyl,
(8) heteroaryl-$C_{1-4}$alkyl;
(9) —$OR^d$,
(10) —$SR^d$,
(11) —O—$(CR^fR^g)_n$—$NR^dR^e$,
(12) —O—$(CR^fR^g)_n$—NH—C(O)—$R^d$,
(13) —O—$(CR^fR^g)_n$—NH—$S(O)_pR^d$,
(14) —O—$(CR^fR^g)_n$—NH—C(O)—$NR^dR^e$,
(15) —O—$(CR^fR^g)_n$—C(O)—$NR^dR^e$,
(16) —$NR^dR^e$,
(17) —$CO_2H$,
(18) —$C(O)NR^dR^e$,
(19) —$NR^eC(O)R^d$,
(20) —$NR^eC(O)OR^d$,
(21) —$NR^eC(O)NR^dR^e$,
wherein the alkyl groups are optionally substituted with one to four substituents independently selected from $R^a$, and cycloheteroalkyl, aryl and heteroaryl are optionally substituted with one to four substituents independently selected from $R^b$;
$R^2$ is selected from:
(1) hydrogen,
(2) cyano,
(3) —$C(O)OR^d$,
(4) —$C(O)NR^dR^e$,
(5) halogen,
(6) nitro, and
(7) $C(O)NH$—$NR^dR^e$;
provided that $R^1$ and $R^2$ are not both hydrogen;
$R^3$ is selected from:
(1) hydrogen,
(2) $C_{1-3}$alkyl,
(3) cyclopropyl,
(4) trifluoromethyl,
wherein alkyl and cyclopropyl are optionally substituted with a substituent independently selected from $R^a$;
$R^4$, $R^5$, $R^6$ and $R^7$ are each independently selected from:
(1) hydrogen,
(2) halogen,
(3) amino,
(4) carboxy,
(5) $C_{1-4}$alkyl,
(7) aryl,
(8) aryl $C_{1-4}$alkyl,
(9) trifluoromethyl,
(10) —$OC(O)C_{1-4}$alkyl, and
(11) —$OC(O)NR^dR^e$,
provided that $R^6$ and $R^7$ are not both hydrogen;
each $R^a$ is independently selected from:
(1) —$OR^d$,
(2) —$NR^eS(O)_mR^d$,
(3) —$NO_2$,
(4) halogen,
(5) —$S(O)_mR^d$,
(6) —$SR^d$,
(7) —$S(O)_2OR^d$,
(8) —$S(O)_mNR^dR^e$,
(9) —$NR^dR^e$,
(10) —$O(CR^fR^g)_nNR^dR^e$,
(11) —$C(O)R^d$,
(12) —$CO_2R^d$,
(13) —$CO_2(CR^fR^g)_nCONR^dR^e$,
(14) —$OC(O)R^d$,
(15) —CN,
(16) —$C(O)NR^dR^e$,
(17) —$NR^eC(O)R^d$,
(18) —$OC(O)NR^dR^e$,
(19) —$NR^eC(O)OR^d$,
(20) —$NR^eC(O)NR^dR^e$,
(21) —$CR^d(N$—$OR^d)$,
(22) —$CF_3$,
(23) —$OCF_3$, and
(24) $C_{3-8}$cycloalkyl;
each $R^b$ is independently selected from:
(1) $R^a$,
(2) $C_{1-4}$ alkyl,
(3) aryl, and
(4) aryl-$C_{1-4}$ alkyl;
wherein alkyl and aryl are optionally substituted with one to four substituents selected from a group independently selected from $R^c$;
each $R^c$ is independently selected from:
(1) halogen,
(2) amino,
(3) carboxy,
(4) $C_{1-4}$alkyl,
(5) $C_{1-4}$alkoxy,
(6) aryl,
(7) aryl $C_{1-4}$alkyl,
(8) hydroxy,
(9) —$CF_3$,
(10) —$OC(O)C_{1-4}$alkyl, and
(11) —$OC(O)NR^dR^e$;
$R^d$ and $R^e$ are independently selected from:
(1) hydrogen,
(2) $C_{1-10}$alkyl, unsubstituted or substituted with one to three substituents selected from $R^h$,
(3) $C_{2-10}$alkenyl;
(4) $C_{2-10}$alkynyl;
(5) cycloalkyl, unsubstituted or substituted with one to three substituents selected from $R^h$;
(6) cycloalkyl-$C_{1-4}$alkyl-;
(7) cycloheteroalkyl, unsubstituted or substituted with one to three substituents selected from $R^h$;
(8) cycloheteroalkyl-$C_{1-4}$ alkyl- unsubstituted or substituted with an $R^h$ substituent;

(9) aryl, unsubstituted or substituted with one to three substituents selected from $R^h$;
(10) heteroaryl, unsubstituted or substituted with one to three substituents selected from $R^h$;
(11) aryl-$C_{1-4}$alkyl-, unsubstituted or substituted with one to three substituents selected from $R^h$; and
(12) heteroaryl-$C_{1-4}$alkyl-, unsubstituted or substituted with one to three substituents selected from $R^h$; or $R^d$ and $R^e$ together with the atom(s) to which they are attached form a heterocyclic ring of 4 to 7 members containing 0-2 additional heteroatoms independently selected from oxygen, sulfur and N—$R^h$, unsubstituted or substituted with one or two oxo groups;

$R^f$ and $R^g$ are independently selected from
(1) hydrogen, and
(2) $C_{1-4}$alkyl;

each $R^h$ is independently selected from:
(1) halogen,
(2) amino,
(3) hydroxycarbonyl,
(4) $C_{1-4}$alkyl,
(5) $C_{1-4}$alkoxy,
(6) aryl,
(7) aryl $C_{1-4}$alkyl,
(8) hydroxy,
(9) trifluoromethyl,
(10) —OC(O)$C_{1-4}$alkyl,
(11) aryloxy-,
(12) $C_{1-4}$alkyloxycarbonyl-, and
(13) —C(O)—NH—$C_{1-4}$alkyl;

m is selected from 1 and 2;
n is selected from 1, 2, and 3;
p is selected from 0, 1, and 2; and
and pharmaceutically acceptable salts thereof.

3. The compound according to claim 1 or a pharmaceutically acceptable salt thereof, wherein:
$R^1$ is selected from:
(1) hydrogen,
(2) halogen,
(3) $C_{1-4}$alkyl,
(4) cycloheteroalkyl,
(5) heteroaryl,
(6) aryl-$C_{1-4}$alkyl,
(7) heteroaryl-$C_{1-4}$alkyl;
(8) —OR$^d$,
(9) —SR$^d$,
(10) —O—(CH$_2$)$_n$—NR$^d$R$^e$,
(11) —O—(CH$_2$)$_n$—NH—C(O)—R$^d$,
(12) —O—(CH$_2$)$_n$—NH—S(O)$_p$R$^d$,
(13) —O—(CH$_2$)$_n$—NH—C(O)—NR$^d$R$^e$,
(14) —O—(CH$_2$)$_n$—C(O)—NR$^d$R$^e$,
(15) —NR$^d$R$^e$, wherein R$^e$ is hydrogen,
(16) —CO$_2$H,
(17) —C(O)NR$^d$R$^e$,
(18) —NHC(O)R$^d$,
(19) —NHC(O)OR$^d$,
(20) —NHC(O)NR$^d$R$^e$, wherein the alkyl groups are optionally substituted with one to three substituents independently selected from $R^a$, and cycloheteroalkyl, aryl and heteroaryl are optionally substituted with one to three substituents independently selected from $R^b$;

$R^2$ is selected from:
(1) hydrogen,
(2) cyano,
(3) —C(O)OH,
(4) —C(O)OCH$_3$,
(5) —C(O)NR$^d$R$^e$,
(6) halogen,
(7) nitro, and
(8) C(O)NH—NR$^d$R$^e$, wherein R$^e$ is hydrogen;
provided that $R^1$ and $R^2$ are not both hydrogen;
$R^3$ is selected from:
(1) hydrogen, and
(2) methyl;
$R^4$, $R^5$, $R^6$ and $R^7$ are each independently selected from:
(1) hydrogen,
(2) halogen,
(3) amino,
(4) carboxy,
(5) $C_{1-4}$alkyl,
(7) aryl,
(8) aryl $C_{1-4}$alkyl,
(9) trifluoromethyl,
(10) —OC(O)$C_{1-4}$alkyl, and
(11) —OC(O)NR$^d$R$^e$,
provided that $R^6$ and $R^7$ are not both hydrogen;
each $R^a$ is independently selected from:
(1) —OR$^d$,
(2) —NR$^e$S(O)$_m$R$^d$,
(3) —NO$_2$,
(4) halogen,
(5) —S(O)$_m$R$^d$,
(6) —SR$^d$,
(7) —S(O)$_2$OR$^d$,
(8) —S(O)$_m$NR$^d$R$^e$,
(9) —NR$^d$R$^e$,
(10) —O(CR$^f$R$^g$)$_n$—NR$^d$R$^e$,
(11) —O-(CH$_2$)$_n$—NH—C(O)—R$^d$,
(12) —CO$_2$R$^d$,
(13) —CO$_2$(CR$^f$R$^g$)$_n$CONR$^d$R$^e$,
(14) —OC(O)R$^d$,
(15) —CN,
(16) —C(O)NR$^d$R$^e$,
(17) —NR$^e$C(O)R$^d$,
(18) —OC(O)NR$^d$R$^e$,
(19) —NR$^e$C(O)OR$^d$,
(20) —NR$^e$C(O)NR$^d$R$^e$,
(21) —CR$^d$(N—OR$^d$),
(22) —CF$_3$,
(23) —OCF$_3$, and
(24) $C_{3-8}$cycloalkyl;
each $R^b$ is independently selected from:
(1) $R^a$,
(2) $C_{1-4}$ alkyl,
(3) aryl, and
(4) aryl-$C_{1-4}$ alkyl;
wherein alkyl and aryl are optionally substituted with one to three substituents selected from a group independently selected from $R^c$;
each $R^c$ is independently selected from:
(1) halogen,
(2) amino,
(3) carboxy,
(4) $C_{1-4}$alkyl,
(5) $C_{1-4}$alkoxy,
(6) aryl,
(7) aryl $C_{1-4}$alkyl,
(8) hydroxy,
(9) —CF$_3$,
(10) —OC(O)$C_{1-4}$alkyl, and
(11) —OC(O)NR$^d$R$^e$;

$R^d$ is selected from:
(1) hydrogen,
(2) $C_{1-10}$alkyl, unsubstituted or substituted with one to three substituents selected from $R^h$,
(3) $C_{2-4}$ alkenyl;
(4) cycloalkyl, unsubstituted or substituted with one to three substituents selected from $R^h$;
(5) cycloalkyl-$C_{1-4}$alkyl;
(6) cycloheteroalkyl, unsubstituted or substituted with one to three substituents selected from $R^h$;
(7) cycloheteroalkyl-$C_{1-4}$ alkyl, unsubstituted or substituted with an Rh substituent;
(8) aryl, unsubstituted or substituted with one to three substituents selected from $R^h$;
(9) heteroaryl, unsubstituted or substituted with one to three substituents selected from $R^h$;
(10) aryl-$C_{1-4}$alkyl, unsubstituted or substituted with one to three substituents selected from $R^h$; and
(11) heteroaryl-$C_{1-4}$alkyl, unsubstituted or substituted with one to three substituents selected from $R^h$;

$R^e$ is hydrogen, or
$R^d$ and $R^e$ together with the atom(s) to which they are attached form a heterocyclic ring of 4 to 7 members containing 0-2 additional heteroatoms independently selected from oxygen, sulfur and N—$R^h$, unsubstituted or substituted with one or two oxo groups;

$R^f$ and $R^g$ are independently selected from
(1) hydrogen, and
(2) methyl;

each $R^h$ is independently selected from:
(1) halogen,
(2) amino,
(3) hydroxycarbonyl,
(4) $C_{1-4}$alkyl,
(5) $C_{1-4}$alkoxy,
(6) aryl,
(7) aryl $C_{1-4}$alkyl,
(8) hydroxy,
(9) trifluoromethyl,
(10) —OC(O)$C_{1-4}$alkyl,
(11) aryloxy-,
(12) $C_{1-4}$alkyloxycarbonyl-, and
(13) —C(O)—NH—$C_{1-4}$alkyl;

m is selected from 1 and 2;
n is selected from 1, 2, and 3;
p is selected from 0, 1, and 2; and
and pharmaceutically acceptable salts thereof.

4. The compound according to claim 1, selected from:
(1) methyl 2-(benzyloxy)-6-(4-chlorophenyl)-5-(phenyl)pyridine-3-carboxylate;
(2) methyl 2-(allyloxy)-6-(4-chlorophenyl)-5-(phenyl)pyridine-3-carboxylate;
(3) 2-(benzyloxy)-6-(4-chlorophenyl)-5-(phenyl)pyridine-3-nitrile;
(4) 2-(methoxy)-6-(4-chlorophenyl)-5-(phenyl)pyridine-3-nitrile; methyl 2-(methoxy)-6-(4-chlorophenyl)-5-(phenyl)pyridine-3-carboxylate;
(6) methyl 2-(methoxy)-6-(4-chlorophenyl)-5-(phenyl)pyridine-3-carboxylate;
(7) N-(piperidin-1-yl)-2-(methoxy)-6-(4-chlorophenyl)-5-(phenyl)pyridine-3-carboxamide;
(8) 2-(methoxy)-6-(4-chlorophenyl)-5-(phenyl)-3-(piperidin-1-ylcarbonyl)pyridine;
(9) N-(morpholin-4-yl)-2-(methoxy)-6-(4-chlorophenyl)-5-(phenyl)pyridine-3-carboxamide;
(10) N-(t-butyl)-2-(methoxy)-6-(4-chlorophenyl)-5-(phenyl)pyridine-3-carboxamide;
(11) N-(cyclopentyl)-2-(methoxy)-6-(4-chlorophenyl)-5-(phenyl)pyridine-3-carboxamide;
(12) N-(phenyl)-2-(methoxy)-6-(4-chlorophenyl)-5-(phenyl)pyridine-3-carboxamide;
(13) N-(cyclohexyl)-2-(benzyloxy)-6-(4-chlorophenyl)-5-(phenyl)pyridine-3-carboxamide;
(14) N-benzyl-2-(benzyloxy)-6-(4-chlorophenyl)-5-(phenyl)pyridine-3-carboxamide;
(15) N-(n-pentyl)-2-(benzyloxy)-6-(4-chlorophenyl)-5-(phenyl)pyridine-3-carboxamide;
(16) N-(t-butyl)-2-(benzyloxy)-6-(4-chlorophenyl)-5-(phenyl)pyridine-3-carboxamide;
(17) N-(piperidin-1-yl)-2-(benzyloxy)-6-(4-chlorophenyl)-5-(phenyl)pyridine-3-carboxamide;
(18) N,N-dimethyl-2-(benzyloxy)-6-(4-chlorophenyl)-5-(phenyl)pyridine-3-carboxamide;
(19) N-methyl-2-(benzyloxy)-6-(4-chlorophenyl)-5-(phenyl)pyridine-3-carboxamide;
(20) 2-(benzyloxy)-6-(2,4-dichlorophenyl)-5-(4-chlorophenyl)pyridine-3-nitrile;
(21) 2-(4-fluorobenzyloxy)-6-(2,4-dichlorophenyl)-5-(4-chlorophenyl)pyridine-3-nitrile;
(22) 2-(2,4-difluorobenzyloxy)-6-(2,4-dichlorophenyl)-5-(4-chlorophenyl)pyridine-3-nitrile;
(23) 2-(3,4-difluorobenzyloxy)-6-(2,4-dichlorophenyl)-5-(4-chlorophenyl)pyridine-3-nitrile;
(24) 2-(3,5-difluorobenzyloxy)-6-(2,4-dichlorophenyl)-5-(4-chlorophenyl)pyridine-3-nitrile;
(25) 2-(4-trifluoromethylbenzyloxy)-6-(2,4-dichlorophenyl)-5-(4-chlorophenyl)pyridine-3-nitrile;
(26) 5-(4-chlorophenyl)-6-(2,4-dichlorophenyl)-2-[2-(1,3-dioxo-1,3-dihydro-2H-isoindol-2-yl)ethoxy]nicotinonitrile;
(27) 2-(2-aminoethoxy)-5-(4-chlorophenyl)-6-(2,4-dichlorophenyl)nicotinonitrile;
(28) N-(2-{[5-(4-chlorophenyl)-3-cyano-6-(2,4-dichlorophenyl)pyridin-2-yl]oxy}ethyl)benzamide;
(29) N-(2-{[5-(4-chlorophenyl)-3-cyano-6-(2,4-dichlorophenyl)pyridin-2-yl]oxy}ethyl)-4-fluorobenzamide;
(30) N-(2-{[5-(4-chlorophenyl)-3-cyano-6-(2,4-dichlorophenyl)pyridin-2-yl]oxy}ethyl)cyclopentanecarboxamide;
(31) N-(2-{[5-(4-chlorophenyl)-3-cyano-6-(2,4-dichlorophenyl)pyridin-2-yl]oxy}ethyl)cyclobutanecarboxamide;
(32) N-(2-{[5-(4-chlorophenyl)-3-cyano-6-(2,4-dichlorophenyl)pyridin-2-yl]oxy}ethyl)cyclopropanecarboxamide;
(33) 2-chloro-5-(4-chlorophenyl)-6-(2,4-dichlorophenyl)-N-piperidin-1-ylnicotinamide;
(34) N-(n-hexyl)-2-(chloro)-6-(2,4-dichlorophenyl)-5-(4-chlorophenyl)pyridine-3-carboxamide;
(35) N-(n-propyl)-2-(chloro)-6-(2,4-dichlorophenyl)-5-(4-chlorophenyl)pyridine-3-carboxamide;
(36) N-N-(dimethyl)-2-(chloro)-6-(2,4-dichlorophenyl)-5-(4-chlorophenyl)pyridine-3-carboxamide;
(37) 2-chloro-5-(4-chlorophenyl)-6-(2,4-dichlorophenyl) nicotinonitrile;
(38) 2-[(3-chlorobenzyl)oxy]-5-(4-chlorophenyl)-6-(2,4-dichlorophenyl) nicotinonitrile;
(39) 5-(4-chlorophenyl)-2-(cyclohexyloxy)-6-(2,4-dichlorophenyl)nicotinonitrile;
(40) 5-(4-chlorophenyl)-2-[(5-chloropyridin-3-yl)oxy]-6-(2,4-dichlorophenyl)-nicotinonitrile;
(41) 5-(4-chlorophenyl)-2-(3,5-dichlorophenoxy)-6-(2,4-dichlorophenyl) nicotinonitrile;

(42) 5-(4-chlorophenyl)-6-(2,4-dichlorophenyl)-2-(pyridin-3-yloxy)nicotinonitrile;
(43) 5-(4-chlorophenyl)-6-(2,4-dichlorophenyl)-2-(4-methoxyphenoxy)nicotinonitrile;
(44) 2-(3-chlorophenoxy)-5-(4-chlorophenyl)-6-(2,4-dichlorophenyl) nicotinonitrile;
(45) 2-(4-chlorophenoxy)-5-(4-chlorophenyl)-6-(2,4-dichlorophenyl)nicotinonitrile;
(46) 5-(4-chlorophenyl)-6-(2,4-dichlorophenyl)-2-(4-fluorophenoxy)nicotinonitrile;
(47) 5-(4-chlorophenyl)-6-(2,4-dichlorophenyl)-2-(3-fluorophenoxy)nicotinonitrile;
(48) 5-(4-chlorophenyl)-6-(2,4-dichlorophenyl)-2-(3,4-difluorophenoxy) nicotinonitrile;
(49) 5-(4-chlorophenyl)-6-(2,4-dichlorophenyl)-2-[1-(4-fluorophenyl)ethoxy]-nicotinonitrile;
(50) 5-(4-chlorophenyl)-6-(2,4-dichlorophenyl)-2-[(4-fluorophenyl)thio] nicotinonitrile;
(51) 5-(4-chlorophenyl)-6-(2,4-dichlorophenyl)-2-(3,4-difluorobenzyl) nicotinonitrile,
(52) methyl2-(benzyloxy)-6-(2,4-dichlorophenyl)-5-(4-chlorophenyl)pyridine-3-carboxylate;
(53) N-(piperidin-1-yl)-2-(benzyloxy)-6-(2,4-dichlorophenyl)-5-(4-chlorophenyl)pyridine-3-carboxamide;
(54) 2-(benzyloxy)-6-(2,4-dichlorophenyl)-5-(4-chlorophenyl)-3-(piperidinocarbonyl)pyridine;
(55) N-(n-pentyl)-2-(benzyloxy)-6-(2,4-dichlorophenyl)-5-(4-chlorophenyl) pyridine-3-carboxamide;
(56) N-(n-propyl)-2-(benzyloxy)-6-(2,4-dichlorophenyl)-5-(4-chlorophenyl) pyridine-3-carboxamide;
(57) N-(methyl)-2-(benzyloxy)-6-(2,4-dichlorophenyl)-5-(4-chlorophenyl)pyridine-3-carboxamide;
(58) N-N-(dimethyl)-2-(benzyloxy)-6-(2,4-dichlorophenyl)-5-(4-chlorophenyl) pyridine-3-carboxamide;
(59) N-(ethyl)-2-(benzyloxy)-6-(2,4-dichlorophenyl)-5-(4-chlorophenyl)pyridine-3-carboxamide;
(60) N-(n-butyl)-2-(benzyloxy)-6-(2,4-dichlorophenyl)-5-(4-chlorophenyl)pyridine-3-carboxamide;
(61) N-(cyclopentyl)-2-(benzyloxy)-6-(2,4-dichlorophenyl)-5-(4-chlorophenyl) pyridine-3-carboxamide;
(62) 2-(benzyloxy)-6-(2,4-dichlorophenyl)-5-(4-chlorophenyl)pyridine-3-carboxamide;
(63) methyl 6-(2,4-dichlorophenyl)-5-(4-chlorophenyl) pyridine-3-carboxylate;
(64) N-(piperidin-1-yl)-6-(2,4-dichlorophenyl)-5-(4-chlorophenyl)pyridine-3-carboxamide;
(65) 6-(2,4-dichlorophenyl)-5-(4-chlorophenyl)-3-(piperidinocarbonyl)pyridine;
(66) N-(cyclohexyl)-6-(2,4-dichlorophenyl)-5-(4-chlorophenyl)pyridine-3-carboxamide;
(67) N-(n-hexyl)-6-(2,4-dichlorophenyl)-5-(4-chlorophenyl)pyridine-3-carboxamide;
(68) methyl 2-(n-butoxy)-6-(2,4-dichlorophenyl)-5-(4-chlorophenyl)pyridine-3-carboxylate;
(69) methyl 2-(n-pentoxy)-6-(2,4-dichlorophenyl)-5-(4-chlorophenyl)pyridine-3-carboxylate;
(70) methyl2-(cyclopropylmethoxy)-6-(2,4-dichlorophenyl)-5-(4-chlorophenyl)pyridine-3-carboxylate;
(71) methyl 2-(cyclohexylmethoxy)-6-(2,4-dichlorophenyl)-5-(4-chlorophenyl) pyridine-3-carboxylate;
(72) methyl 2-(2-ethoxyethoxy)-6-(2,4-dichlorophenyl)-5-(4-chlorophenyl) pyridine-3-carboxylate;
(73) N-methyl-2-(cyclohexylmethoxy)-6-(2,4-dichlorophenyl)-5-(4-chlorophenyl)pyridine-3-carboxamide;
(74) N-(n-propyl)-2-(cyclohexylmethoxy)-6-(2,4-dichlorophenyl)-5-(4-chlorophenyl)pyridine-3-carboxamide;
(75) 2-(n-butoxy)-6-(2,4-dichlorophenyl)-5-(4-chlorophenyl)pyridine-3-carboxamide;
(76) N-methyl-2-(n-butoxy)-6-(2,4-dichlorophenyl)-5-(4-chlorophenyl)pyridine-3-carboxamide;
(77) N-(n-propyl)-2-(n-butoxy)-6-(2,4-dichlorophenyl)-5-(4-chlorophenyl)pyridine-3-carboxamide;
(78) N-cyclopentyl-2-(n-butoxy)-6-(2,4-dichlorophenyl)-5-(4-chlorophenyl) pyridine-3-carboxamide;
(79) methyl 2-(3,4-difluorobenzyloxy)-6-(2,4-dichlorophenyl)-5-(4-chlorophenyl)pyridine-3-carboxylate;
(80) 5-(4-chlorophenyl)-6-(2,4-dichlorophenyl)-2-[(3,4-difluorobenzyl)oxy] nicotinic acid;
(81) 5-(4-chlorophenyl)-6-(2,4-dichlorophenyl)-2-[(3,4-difluorobenzyl)oxy]-N-methylnicotinamide;
(82) N-(ethyl)-2-(3,4-difluorobenzyloxy)-6-(2,4-dichlorophenyl)-5-(4-chlorophenyl)pyridine-3-carboxamide;
(83) N-(n-propyl)-2-(3,4-difluorobenzyloxy)-6-(2,4-dichlorophenyl)-5-(4-chlorophenyl)pyridine-3-carboxamide;
(84) N-(2-fluoroethyl)-2-(3,4-difluorobenzyloxy)-6-(2,4-dichlorophenyl)-5-(4-chlorophenyl)pyridine-3-carboxamide;
(85) N-(i-propyl)-2-(3,4-difluorobenzyloxy)-6-(2,4-dichlorophenyl)-5-(4-chlorophenyl)pyridine-3-carboxamide;
(86) methyl 2-chloro-5-(4-chlorophenyl)-6-(2,4-dichlorophenyl)nicotinate;
(87) methyl 5-(4-chlorophenyl)-6-(2,4-dichlorophenyl)-2-(3,4-difluorophenoxy)nicotinate;
(88) methyl 5-(4-chlorophenyl)-2-[(5-chloropyridin-3-yl)oxy]-6-(2,4-dichlorophenyl)nicotinate;
(89) 5-(4-chlorophenyl)-6-(2,4-dichlorophenyl)-2-(3,4-difluorophenoxy)nicotinic acid;
(90) 5-(4-chlorophenyl)-6-(2,4-dichlorophenyl)-2-(3,4-difluorophenoxy)-N-ethylnicotinamide;
(91) 5-(4-chlorophenyl)-6-(2,4-dichlorophenyl)-2-(3,4-difluorophenoxy)-N-methylnicotinamide;
(92) 5-(4-chlorophenyl)-6-(2,4-dichlorophenyl)-2-(3,4-difluorophenoxy)-N',N'-dimethylnicotinohydrazide;
(93) 5-(4-chlorophenyl)-6-(2,4-dichlorophenyl)-2-(3,4-difluorophenoxy)-N-pyrrolidin-1-ylnicotinamide;
(94) 5-(4-chlorophenyl)-N-cyclohexyl-6-(2,4-dichlorophenyl)-2-(3,4-difluorophenoxy)nicotinamide;
(95) 5-(4-chlorophenyl)-6-(2,4-dichlorophenyl)-2-(3,4-difluorophenoxy) nicotinamide;
(96) 5-(4-chlorophenyl)-6-(2,4-dichlorophenyl)-2-(3,4-difluorophenoxy)-N-isopropylnicotinamide;
(97) 3-(4-chlorophenyl)-2-(2,4-dichlorophenyl)-6-[(3,4-difluorobenzyl)oxy] pyridine;
(98) methyl 6-(2,4-dichlorophenyl)-5-(4-chlorophenyl) pyridine-2-carboxylate;
(99) N-(cyclohexyl)-6-(2,4-dichlorophenyl)-5-(4-chlorophenyl)pyridine-2-carboxamide;
(100) N-(piperidin-1-yl)-6-(2,4-dichlorophenyl)-5-(4-chlorophenyl)pyridine-2-carboxamide;
(101) 6-(2,4-dichlorophenyl)-5-(4-chlorophenyl)-2-(piperidinyl-1-carbonyl)pyridine;
(102) N-(n-hexyl)-6-(2,4-dichlorophenyl)-5-(4-chlorophenyl)pyridine-2-carboxamide;
(103) N-(cyclopentyl)-6-(2,4-dichlorophenyl)-5-(4-chlorophenyl)pyridine-2-carboxamide;
(104) N-(cycloheptyl)-6-(2,4-dichlorophenyl)-5-(4-chlorophenyl)pyridine-2-carboxamide;
(105) N-(heptyl)-6-(2,4-dichlorophenyl)-5-(4-chlorophenyl)pyridine-2-carboxamide;
(106) N-(benzyl)-6-(2,4-dichlorophenyl)-5-(4-chlorophenyl)pyridine-2-carboxamide;

(107) N-(phenyl)-6-(2,4-dichlorophenyl)-5-(4-chlorophenyl)pyridine-2-carboxamide;
(108) methyl 6-(2,4-dichlorophenyl)-2-[(3,4-difluorobenzyl)oxy]-5-(4-fluorophenyl)nicotinate;
(109) 6-(2,4-dichlorophenyl)-2-[(3,4-difluorobenzyl)oxy]-5-(4-fluorophenyl) nicotinic acid;
(110) 6-(2,4-dichlorophenyl)-2-[(3,4-difluorobenzyl)oxy]-5-(4-fluorophenyl)-N-methylnicotinamide;
(111) 2-[(3-chlorobenzyl)oxy]-6-(2,4-dichlorophenyl)-5-(4-fluorophenyl) nicotinonitrile;
(112) 6-(2,4-dichlorophenyl)-2-[(3,4-difluorobenzyl)oxy]-5-(4-fluorophenyl) nicotinonitrile;
(113) 6-(2,4-dichlorophenyl)-5-(4-fluorophenyl)-2-(pyridin-3-ylmethoxy) nicotinonitrile;
(114) 2-[(4-chlorobenzyl)oxy]-6-(2,4-dichlorophenyl)-5-(4-fluorophenyl) nicotinonitrile;
(115) 2-[(6-chloropyridin-3-yl)methoxy]-6-(2,4-dichlorophenyl)-5-(4-fluorophenyl) nicotinonitrile;
(116) methyl 2-chloro-6-(2,4-dichlorophenyl)-5-(4-fluorophenyl)nicotinate;
(117) methyl 6-(2,4-dichlorophenyl)-2-(3,4-difluorophenoxy)-5-(4-fluorophenyl) nicotinate;
(118) 2-chloro-6-(2,4-dichlorophenyl)-5-(4-methylphenyl)nicotinonitrile;
(119) 6-(2,4-dichlorophenyl)-5-(4-methylphenyl)-2-(1-(4-fluorophenyl)ethoxy)nicotinonitrile;
(120) 6-(2,4-dichlorophenyl)-2-[2-(diethylamino)ethoxy]-5-(4-methylphenyl) nicotinonitrile;
(121) 6-(2,4-dichlorophenyl)-2-(3,4-difluorophenoxy)-5-(4-methylphenyl) nicotinonitrile;
(122) 2-(cyclohexylmethoxy)-6-(2,4-dichlorophenyl)-5-(4-methylphenyl) nicotinonitrile;
(123) 2-butoxy-6-(2,4-dichlorophenyl)-5-(4-methylphenyl)nicotinonitrile;
(124) 6-(2,4-dichlorophenyl)-2-[(3,4-difluorobenzyl)oxy]-5-(4-methylphenyl)-nicotinonitrile;
(125) methyl 4-({[3-cyano-6-(2,4-dichlorophenyl)-5-(4-methylphenyl)pyridin-2-yl]oxy}methyl)benzoate;
(126) 4-({[3-cyano-6-(2,4-dichlorophenyl)-5-(4-methylphenyl)pyridin-2-yl]oxy}methyl)benzoic acid;
(127) 4-({[3-cyano-6-(2,4-dichlorophenyl)-5-(4-methylphenyl)pyridin-2-yl]oxy}methyl)-N-methylbenzamide;
(128) 6-(2,4-dichlorophenyl)-5-(4-methylphenyl)-2-piperidin-1-ylnicotinonitrile;
(129) 2-(cyclohexylamino)-6-(2,4-dichlorophenyl)-5-(4-methylphenyl) nicotinonitrile;
(130) 6-(2,4-dichlorophenyl)-5-(4-methylphenyl)-2-(4-methylpiperazin-1-yl) nicotinonitrile;
(131) 6-(2,4-dichlorophenyl)-2-[(3,4-difluorobenzyl)amino]-5-(4-methylphenyl)-nicotinonitrile;
(132) 6-(2,4-dichlorophenyl)-5-(4-methylphenyl)-2-pyrrolidin-1-ylnicotinonitrile;
(133) 6-(2-chlorophenyl)-5-(4-chlorophenyl)-2-[(3,4-difluorobenzyl)oxy] nicotinonitrile;
(134) 6-(2-chlorophenyl)-5-(4-chlorophenyl)-2-[(3,4-difluorobenzyl)oxy] nicotinamide;
(135) 2-chloro-6-(2-chlorophenyl)-5-(4-chlorophenyl) nicotinonitrile;
(136) 6-(2-chlorophenyl)-5-(4-chlorophenyl)-2-[(5-chloropyridin-3-yl)oxy] nicotinonitrile;
(137) 6-(2-chlorophenyl)-5-(4-chlorophenyl)-2-(3,4-difluorophenoxy)nicotinonitrile;
(138) 6-(2-chlorophenyl)-5-(4-chlorophenyl)-2-[2-(1,3-dioxo-1,3-dihydro-2H-isoindol-2-yl)ethoxy]nicotinonitrile;
(139) 2-(2-aminoethoxy)-6-(2-chlorophenyl)-5-(4-chlorophenyl)nicotinonitrile;
(140) N-(2-{[6-(2-chlorophenyl)-5-(4-chlorophenyl)-3-cyanopyridin-2-yl]oxy}ethyl)benzenesulfonamide;
(141) N-(2-{[6-(2-chlorophenyl)-5-(4-chlorophenyl)-3-cyanopyridin-2-yl]oxy}ethyl)acetamide;
(142) N-(2-{[6-(2-chlorophenyl)-5-(4-chlorophenyl)-3-cyanopyridin-2-yl]oxy}ethyl)cyclopropanecarboxamide;
(143) N-(2-{[6-(2-chlorophenyl)-5-(4-chlorophenyl)-3-cyanopyridin-2-yl]oxy}ethyl)benzamide;
(144) N-(2-{[6-(2-chlorophenyl)-5-(4-chlorophenyl)-3-cyanopyridin-2-yl]oxy}ethyl)methanesulfonamide;
(145) N'-(2-{[6-(2-chlorophenyl)-5-(4-chlorophenyl)-3-cyanopyridin-2-yl]oxy} ethyl)-N,N-dimethylurea;
(146) N-(2-{[6-(2-chlorophenyl)-5-(4-chlorophenyl)-3-cyanopyridin-2-yl]oxy}ethyl)morpholine-4-carboxamide;

and pharmaceutically acceptable salts thereof.

5. The compound according to claim 1 of structural formula II:

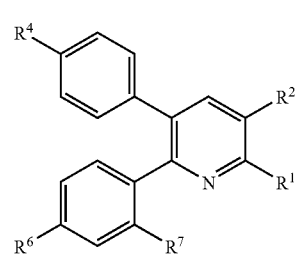

II wherein: $R^1$ is selected from:
(1) hydrogen,
(2) halogen,
(3) $C_{1-4}$alkyl,
(4) cycloheteroalkyl,
(5) cycloheteroalkyl-$C_{1-4}$alkyl,
(6) heteroaryl,
(7) aryl-$C_{1-4}$alkyl,
(8) heteroaryl-$C_{1-4}$alkyl;
(9) —$OR^d$,
(10) —$SR^d$,
(11) —O—$(CR^fR^g)_n$—$NR^dR^e$,
(12) —O—$(CR^fR^g)_n$—NH—C(O)—$R^d$,
(13) —O—$(CR^fR^g)_n$—NH—S(O)$_p$$R^d$,
(14) —O—$(CR^fR^g)_n$—NH—C(O)—$NR^dR^e$,
(15) —O—$(CR^fR^g)_n$—C(O)—$NR^dR^e$,
(16) —$NR^dR^e$,
(17) —$CO_2H$,
(18) —$C(O)NR^dR^e$,
(19) —$NR^eC(O)R^d$,
(20) —$NR^eC(O)OR^d$,
(21) —$NR^eC(O)NR^dR^e$, wherein the alkyl groups are optionally substituted with one to four substituents independently selected from $R^a$, and cycloheteroalkyl, aryl and heteroaryl are optionally substituted with one to four substituents independently selected from $R^b$;

$R^2$ is selected from:
(1) hydrogen,
(2) cyano,
(3) —$C(O)OR^d$,
(4) —$C(O)NR^dR^e$, (5) halogen,
(6) nitro, and
(7) C(O)NH—NR$^d$R$^e$;
provided that R$^1$ and R$^2$ are not both hydrogen;
R$^4$, R$^6$ and R$^7$ are each independently selected from:
  (1) hydrogen,
  (2) halogen,
  (3) amino,
  (4) carboxy,
  (5) C$_{1-4}$alkyl,
  (7) aryl,
  (8) aryl C$_{1-4}$alkyl,
  (9) trifluoromethyl,
  (10) —OC(O)C$_{1-4}$alkyl, and
  (11) —OC(O)NR$^d$R$^e$,
provided that R$^6$ and R$^7$ are not both hydrogen;
each R$^a$ is independently selected from:
  (1) —OR$^d$,
  (2) —NR$^e$S(O)$_m$R$^d$,
  (3) —NO$_2$,
  (4) halogen,
  (5) —S(O)$_m$R$^d$,
  (6) —SR$^d$,
  (7) —S(O)$_2$OR$^d$,
  (8) —S(O)$_m$NR$^d$R$^e$,
  (9) —NR$^d$R$^e$,
  (10) —O(CR$^f$R$^g$)$_n$NR$^d$R$^e$,
  (11) —C(O)R$^d$,
  (12) —CO$_2$R$^d$,
  (13) —CO$_2$(CR$^f$R$^g$)$_n$CONR$^d$R$^e$,
  (14) —OC(O)R$^d$,
  (15) —CN,
  (16) —C(O)NR$^d$R$^e$,
  (17) —NR$^e$C(O)R$^d$,
  (18) —OC(O)NR$^d$R$^e$,
  (19) —NR$^e$C(O)OR$^d$,
  (20) —NR$^e$C(O)NR$^d$R$^e$,
  (21) —CR$^d$(N—OR$^d$),
  (22) —CF$_3$,
  (23) —OCF$_3$, and
  (24) C$_{3-8}$cycloalkyl;
each R$^b$ is independently selected from:
  (1) R$^a$,
  (2) C$_{1-4}$alkyl,
  (3) aryl, and
  (4) aryl-C$_{1-4}$alkyl;
wherein alkyl and aryl are optionally substituted with one to four substituents selected from a group independently selected from R$^c$;
each R$^c$ is independently selected from:
  (1) halogen,
  (2) amino,
  (3) carboxy,
  (4) C$_{1-4}$alkyl,
  (5) C$_{1-4}$alkoxy,
  (6) aryl,
  (7) aryl C$_{1-4}$alkyl,
  (8) hydroxy,
  (9) CF$_3$,
  (10) —OC(O)C$_{1-4}$alkyl, and
  (11) —OC(O)NR$^d$R$^e$;
R$^d$ and R$^e$ are independently selected from:
  (1) hydrogen,
  (2) C$_{1-10}$alkyl, unsubstituted or substituted with one to three substituents selected from R$^h$,
  (3) C$_{2-10}$alkenyl;
  (4) C$_{2-10}$alkynyl;
  (5) cycloalkyl, unsubstituted or substituted with one to three substituents selected from R$^h$;
  (6) cycloalkyl-C$_{1-4}$alkyl-;
  (7) cycloheteroalkyl, unsubstituted or substituted with one to three substituents selected from R$^h$;
  (8) cycloheteroalkyl-C$_{1-4}$alkyl-, unsubtituted or substituted with an Rh substituent;
  (9) aryl, unsubstituted or substituted with one to three substituents selected from R$^h$;
  (10) heteroaryl, unsubstituted or substituted with one to three substituents selected from R$^h$;
  (11) aryl-C$_{1-4}$alkyl-, unsubstituted or substituted with one to three substituents selected from R$^h$; and
  (12) heteroaryl-C$_{1-4}$alkyl-, unsubstituted or substituted with one to three substituents selected from R$^h$; or
R$^d$ and R$^e$ together with the atom(s) to which they are attached form a heterocyclic ring of 4 to 7 members containing 0 to 2 additional heteroatoms independently selected from oxygen, sulfur and N—R$^h$, unsubstituted or substituted with one or two oxo groups;
R$^f$ and R$^g$ are independently selected from
  (1) hydrogen, and
  (2) C$_{1-4}$alkyl;
each R$^h$ is independently selected from:
  (1) halogen,
  (2) amino,
  (3) hydroxycarbonyl,
  (4) C$_{1-4}$alkyl,
  (5) C$_{1-4}$alkoxy,
  (6) aryl,
  (7) aryl C$_{1-4}$alkyl,
  (8) hydroxy,
  (9) trifluoromethyl,
  (10) —OC(O)C$_{1-4}$alkyl,
  (11) aryloxy-,
  (12) C1-4alkyloxycarbonyl-, and
  (13) —C(O)—NH—C$_{1-4}$alkyl;
m is selected from 1 and 2;
n is selected from 1, 2, and 3;
p is selected from 0, 1, and 2; and
and pharmaceutically acceptable salts thereof.

6. The compound according to claim 5, wherein:
R$^1$ is selected from:
  (1) hydrogen,
  (2) halogen,
  (3) C$_{1-4}$alkyl,
  (4) cycloheteroalkyl,
  (5) heteroaryl,
  (6) aryl-C$_{1-4}$alkyl,
  (7) heteroaryl-C$_{1-4}$alkyl;
  (8) —OR$^d$,
  (9) —SR$^d$,
  (10) —O—(CH$_2$)$_n$—NR$^d$R$^e$,
  (11) —O—(CH$_2$)$_n$—NH—C(O)—R$^d$,
  (12) —O—(CH$_2$)$_n$—NH—S(O)$_p$R$^d$,
  (13) —O—(CH$_2$)$_n$—NH—C(O)—NR$^d$R$^e$,
  (14) —O—(CH$_2$)$_n$—C(O)—NR$^d$R$^e$,
  (15) —NR$^d$R$^e$, wherein R$^e$ is hydrogen,
  (16) —CO$_2$H,
  (17) —C(O)NR$^d$R$^e$,
  (18) —NHC(O)R$^d$,
  (19) —NHC(O)OR$^d$,
  (20) —NHC(O)NR$^d$R$^e$,
wherein the alkyl groups are optionally substituted with one to three substituents independently selected from R$^a$, and cycloheteroalkyl, aryl and heteroaryl are optionally substituted with one to three substituents independently selected from $R^b$;

$R^2$ is selected from:
(1) hydrogen,
(2) cyano,
(3) —C(O)OH,
(4) —C(O)OCH$_3$,
(5) —C(O)NR$^d$R$^e$,
(6) halogen,
(7) nitro, and
(8) C(O)NH—NR$^d$R$^e$, wherein $R^e$ is hydrogen;
provided that $R^1$ and $R^2$ are not both hydrogen;

$R^4$, $R^6$ and $R^7$ are each independently selected from:
(1) hydrogen,
(2) halogen,
(3) amino,
(4) carboxy,
(5) C$_{1-4}$alkyl,
(7) aryl,
(8) benzyl,
(9) trifluoromethyl,
(10) —OC(O)C$_{1-4}$alkyl, and
(11) —OC(O)NR$^d$R$^e$,
provided that $R^6$ and $R^7$ are not both hydrogen;

each $R^a$ is independently selected from:
(1) —OR$^d$,
(2) —NR$^e$S(O)$_m$R$^d$,
(3) —NO$_2$,
(4) halogen,
(5) —S(O)$_m$R$^d$,
(6) —SR$^d$,
(7) —S(O)$_2$OR$^d$,
(8) —S(O)$_m$NR$^d$R$^e$,
(9) —NR$^d$R$^e$,
(10) —O(CR$^f$R$^g$)$_n$NR$^d$R$^e$,
(11) —(O)R$^d$,
(12) —CO$_2$R$^d$,
(13) —CO$_2$(CR$^f$R$^g$)$_n$CONR$^d$R$^e$,
(14) —OC(O)R$^d$,
(15) —CN,
(16) —C(O)NR$^d$R$^e$,
(17) —NR$^e$C(O)R$^d$,
(18) —OC(O)NR$^d$R$^e$,
(19) —NR$^e$C(O)OR$^d$,
(20) —NR$^e$C(O)NR$^d$R$^e$,
(21) —CR$^d$(N—OR$^d$),
(22) —CF$_3$,
(23) —OCF$_3$, and
(24) C$_{3-8}$cycloalkyl;

each $R^b$ is independently selected from:
(1) $R^a$,
(2) C$_{1-4}$alkyl,
(3) aryl, and
(4) aryl-C$_{1-4}$alkyl
wherein alkyl and aryl are optionally substituted with one to three substituents selected from a group independently selected from $R^c$;

each $R^c$ is independently selected from:
(1) halogen,
(2) amino,
(3) carboxy,
(4) C$_{1-4}$alkyl,
(5) C$_{1-4}$alkoxy,
(6) aryl,
(7) aryl C$_{1-4}$alkyl,
(8) hydroxy,
(9) CF$_3$,
(10) —OC(O)C$_{1-4}$alkyl, and
(11) —OC(O)NR$^d$R$^e$;

$R^d$ is selected from:
(1) hydrogen,
(2) C$_{1-10}$alkyl, unsubstituted or substituted with one to three substituents selected from $R^h$,
(3) C$_{2-4}$alkenyl;
(4) cycloalkyl, unsubstituted or substituted with one to three substituents selected from $R^h$;
(5) cycloalkyl-C$_{1-4}$alkyl;
(6) cycloheteroalkyl, unsubstituted or substituted with one to three substituents selected from $R^h$;
(7) cycloheteroalkyl-C$_{1-4}$alkyl, unsubstituted or substituted with a $R^h$ substituent;
(8) aryl, unsubstituted or substituted with one to three substituents selected from $R^h$;
(9) heteroaryl, unsubstituted or substituted with one to three substituents selected from $R^h$;
(10) aryl-C$_{1-4}$alkyl, unsubstituted or substituted with one to three substituents selected from $R^h$; and
(11) heteroaryl-C$_{1-4}$alkyl, unsubstituted or substituted with one to three substituents selected from $R^h$;

$R^e$ is hydrogen, or $R^d$ and $R^e$ together with the atom(s) to which they are attached form a heterocyclic ring of 4 to 7 members containing 0 or 1 additional heteroatoms independently selected from oxygen, sulfur and N—$R^h$, unsubstituted or substituted with one or two oxo groups;

$R^f$ and $R^g$ are independently selected from
(1) hydrogen, and
(2) methyl;

each $R^h$ is independently selected from:
(1) halogen,
(2) amino,
(3) hydroxycarbonyl,
(4) C$_{1-4}$alkyl,
(5) C$_{1-4}$alkoxy,
(6) aryl,
(7) aryl C$_{1-4}$alkyl,
(8) hydroxy,
(9) trifluoromethyl,
(10) —OC(O)C$_{1-4}$alkyl,
(11) aryloxy-,
(12) C$_{1-4}$alkyloxycarbonyl-, and
(13) —C(O)—NH—C$_{1-4}$alkyl;

m is selected from 1 and 2;
n is selected from 1, 2, and 3;
p is selected from 0, 1, and 2; and
and pharmaceutically acceptable salts thereof.

7. The compound according to claim 6, wherein:
$R^1$ is selected from:
(1) hydrogen,
(2) chloro,
(3) cycloheteroalkyl, selected from piperidyl, piperazinyl, and perhydroazepine,
(4) heteroaryl, selected from imidazole, triazole, benzimidazole,
(5) benzyl,
(6) —Or$^d$,
(7) —SR$^d$,
(8) —O—(CH$_2$)$_2$—Nr$^d$R$^e$,
(9) —O—(CH$_2$)$_2$—NH—C(O)—R$^d$,
(10) —O—(CH$_2$)$_2$—NH—S(O)$_p$R$^d$,
(12) —O—(CH$_2$)$_n$—C(O)—Nr$^d$R$^e$,
(13) —Nr$^d$R$^e$, wherein $R^e$ is hydrogen,

(14) —CO₂H,
(15) —C(O)Nr$^d$R$^e$,
wherein the cycloheteroalkyl, aryl and heteroaryl are optionally substituted with one to three substituents independently selected from R$^b$;
R² is selected from:
(1) hydrogen,
(2) cyano,
(3) —C(O)OH,
(4) —C(O)OCH₃,
(5) —C(O)Nr$^d$R$^e$,
(6) halogen,
(7) nitro, and
(8) C(O)NH—Nr$^d$R$^e$, wherein R$^e$ is hydrogen;
provided that R¹ and R² are not both hydrogen;
R⁴, R⁶ and R⁷ are each independently selected from:
(1) hydrogen,
(2) halogen,
(3) amino,
(4) carboxy,
(5) methyl,
(6) and
(7) trifluoromethyl;
provided that R⁶ and R⁷ are not both hydrogen;
each R$^b$ is independently selected from:
(1) halogen,
(2) —CF₃,
(3) cyclopropyl, and
(4) methyl;
R$^d$ is selected from:
(1) hydrogen,
(2) C$_{1-10}$alkyl;
(3) C$_{2-4}$alkenyl;
(4) cycloalkyl;
(5) cycloalkyl-C$_{1-4}$alkyl;
(6) cycloheteroalkyl, unsubstituted or substituted with one to three substituents selected from R$^h$;
(7) cycloheteroalkyl-C$_{1-4}$ alkyl, unsubstituted or substitute with a R$^h$ substituent;
(8) aryl, unsubstituted or substituted with one to three substituents selected from R$^h$;
(9) heteroaryl, unsubstituted or substituted with one to three substituents selected from R$^h$;
(10) aryl-C$_{1-4}$alkyl, unsubstituted or substituted with one to two substituents selected from R$^h$; and
(11) heteroaryl-C$_{1-4}$alkyl, unsubstituted or substituted with one to three substituents selected from R$^h$;
R$^e$ is hydrogen, or
R$^d$ and R$^e$ together with the atom(s) to which they are attached form a heterocyclic ring of 4 to 7 members containing 0 or 1 additional heteroatoms independently selected from oxygen, sulfur and N—R$^h$, unsubstituted or substituted with one or two oxo groups;
each R$^h$ is independently selected from:
(1) halogen,
(2) amino,
(3) hydroxycarbonyl,
(4) methyl,
(5) methoxy-,
(6) phenyl,
(7) benzyl,
(8) hydroxy,
(9) trifluoromethyl,
(10) methylcarbonyloxy-,
(11) C$_{1-4}$alkyloxycarbonyl-, and
(12) —C(O)—NH—C$_{1-4}$alkyl;

m is selected from 1 and 2;
n is selected from 1, 2, and 3;
p is selected from 0, 1, and 2; and
and pharmaceutically acceptable salts thereof.

8. The compound according to claim 5, selected from:
(1) 2-(benzyloxy)-5-(4-chlorophenyl)-6-(2,4-dichlorophenyl)nicotinonitrile,
(2) 2-chloro-5-(4-chlorophenyl)-6-(2,4-dichlorophenyl)-N-hexylnicotinamide,
(3) 2-chloro-5-(4-chlorophenyl)-6-(2,4-dichlorophenyl)-N-propylnicotinamide,
(4) 2-(benzyloxy)-5-(4-chlorophenyl)-6-(2,4-dichlorophenyl)-N-methylnicotinamide,
(5) 2-(benzyloxy)-5-(4-chlorophenyl)-6-(2,4-dichlorophenyl)-N,N-dimethylnicotinamide,
(6) 2-(benzyloxy)-5-(4-chlorophenyl)-6-(2,4-dichlorophenyl)-N-propylnicotinamide,
(7) 2-(benzyloxy)-5-(4-chlorophenyl)-6-(2,4-dichlorophenyl)-N-pentylnicotinamide,
(8) 2-(benzyloxy)-5-(4-chlorophenyl)-6-(2,4-dichlorophenyl)-N-piperidin-1-ylnicotinamide,
(9) 2-(benzyloxy)-5-(4-chlorophenyl)-6-(2,4-dichlorophenyl)nicotinamide,
(10) methyl2-(benzyloxy)-5-(4-chlorophenyl)-6-(2,4-dichlorophenyl)nicotinate,
(11) 5-(4-chlorophenyl)-6-(2,4-dichlorophenyl)-N-hexylnicotinamide,
(12) 5-(4-chlorophenyl)-6-(2,4-dichlorophenyl)-2-[(4-fluorobenzyl)oxy]nicotinonitrile,
(13) 5-(4-chlorophenyl)-6-(2,4-dichlorophenyl)-2-[(2,4-difluorobenzyl)oxy]nicotinonitrile,
(14) 5-(4-chlorophenyl)-6-(2,4-dichlorophenyl)-2-[(3,4-difluorobenzyl)oxy]nicotinonitrile,
(15) 5-(4-chlorophenyl)-6-(2,4-dichlorophenyl)-2-{[4-trifluoromethyl)benzyl]oxy}nicotinonitrile,
(16) 5-(4-chlorophenyl)-6-(2,4-dichlorophenyl)-2-[(3,5-difluorobenzyl)oxy]nicotinonitrile,
(17) methyl 5-(4-chlorophenyl)-2-(cyclohexylmethoxy)-6-(2,4-dichlorophenyl)nicotinate,
(18) methyl 5-(4-chlorophenyl)-2-(cyclopropylmethoxy)-6-(2,4-dichlorophenyl)nicotinate,
(19) methyl 5-(4-chlorophenyl)-6-(2,4-dichlorophenyl)-2-(pentyloxy)nicotinate,
(20) 2-(benzyloxy)-5-(4-chlorophenyl)-6-(2,4-dichlorophenyl)-N-ethylnicotinamide,
(21) 2-(benzyloxy)-N-butyl-5-(4-chlorophenyl)-6-(2,4-dichlorophenyl)nicotinamide,
(22) 2-(benzyloxy)-5-(4-chlorophenyl)-N-cyclopentyl-6-(2,4-dichlorophenyl)nicotinamide,
(23) methyl 5-(4-chlorophenyl)-6-(2,4-dichlorophenyl)-2-(2-ethoxyethoxy)nicotinate,
(24) 5-(4-chlorophenyl)-2-(cyclohexylmethoxy)-6-(2,4-dichlorophenyl)-N-methylnicotinamide,
(25) 2-butoxy-5-(4-chlorophenyl)-6-(2,4-dichlorophenyl)nicotinamide,
(26) 2-butoxy-5-(4-chlorophenyl)-6-(2,4-dichlorophenyl)-N-methylnicotinamide,
(27) 2-butoxy-5-(4-chlorophenyl)-6-(2,4-dichlorophenyl)-N-propylnicotinamide,
(28) 2-butoxy-5-(4-chlorophenyl)-N-cyclopentyl-6-(2,4-dichlorophenyl)nicotinamide,
(29) 5-(4-chlorophenyl)-6-(2,4-dichlorophenyl)-2-[(3,4-difluorobenzyl)oxy]-N-ethylnicotinamide,
(30) 5-(4-chlorophenyl)-6-(2,4-dichlorophenyl)-2-[(3,4-difluorobenzyl)oxy]-N-propylnicotinamide,
(31) 5-(4-chlorophenyl)-N-cyclohexyl-6-(2,4-dichlorophenyl)pyridine-2-carboxamide,

(32) 5-(4-chlorophenyl)-6-(2,4-dichlorophenyl)-2-[(3,4-difluorobenzyl)oxy]-N-methylnicotinamide,
(33) 5-(4-chlorophenyl)-6-(2,4-dichlorophenyl)-2-[(3,4-difluorobenzyl)oxy]-N-(2-fluoroethyl)nicotinamide,
(34) 5-(4-chlorophenyl)-6-(2,4-dichlorophenyl)-2-[(3,4-difluorobenzyl)oxy]-N-isopropylnicotinamide,
(35) methyl5-(4-chlorophenyl)-6-(2,4-dichlorophenyl)-2-[(3,4-difluorobenzyl)oxy]nicotinate,
(36) 5-(4-chlorophenyl)-6-(2,4-dichlorophenyl)-N-piperidin-1-ylpyridine-2-carboxamide,
(37) 5-(4-chlorophenyl)-6-(2,4-dichlorophenyl)-N-hexylpyridine-2-carboxamide,
(38) 5-(4-chlorophenyl)-N-cyclopentyl-6-(2,4-dichlorophenyl)pyridine-2-carboxamide,
(39) 5-(4-chlorophenyl)-N-cycloheptyl-6-(2,4-dichlorophenyl)pyridine-2-carboxamide,
(40) 5-(4-chlorophenyl)-6-(2,4-dichlorophenyl)-N-(1-propylbutyl)pyridine-2-carboxamide,
(41) N-benzyl-5-(4-chlorophenyl)-6-(2,4-dichlorophenyl)pyridine-2-carboxamide,
(42) 5,6-bis(2,4-dichlorophenyl)-2-[(3,4-difluorobenzyl)oxy]nicotinonitrile,
(43) 6-(2,4-dichlorophenyl)-5-(3,4-dichlorophenyl)-2-[(3,4-difluorobenzyl)oxy]nicotinonitrile,
(44) 5-(4-chlorophenyl)-6-(2,4-dichlorophenyl)-2-[1-(4-fluorophenyl)ethoxy]nicotinonitrile,
(45) 5-(4-chlorophenyl)-6-(2,4-dichlorophenyl)-2-(3,4-difluorophenoxy)nicotinonitrile,
(46) 2-(1,3-benzodioxol-5-ylmethoxy)-5-(4-chlorophenyl)-6-(2,4-dichlorophenyl)nicotinonitrile,
(47) 5-(4-chlorophenyl)-6-(2,4-dichlorophenyl)-2-(2-methoxyethoxy)nicotinonitrile,
(48) 5-(4-chlorophenyl)-6-(2,4-dichlorophenyl)-2-(3-fluorophenoxy)nicotinonitrile,
(49) 5-(4-chlorophenyl)-2-(cyclohexyloxy)-6-(2,4-dichlorophenyl)nicotinonitrile,
(50) 2-(4-chlorophenoxy)-5-(4-chlorophenyl)-6-(2,4-dichlorophenyl)nicotinonitrile,
(51) 2-(3-chlorophenoxy)-5-(4-chlorophenyl)-6-(2,4-dichlorophenyl)nicotinonitrile,
(52) 5-(4-chlorophenyl)-6-(2,4-dichlorophenyl)-2-(4-methoxyphenoxy)nicotinonitrile,
(53) 5-(4-chlorophenyl)-6-(2,4-dichlorophenyl)-2-(pyridin-3-yloxy)nicotinonitrile,
(54) 2-[(3-chlorobenzyl)oxy]-5-(4-chlorophenyl)-6-(2,4-dichlorophenyl)nicotinonitrile,
(55) 3-(4-chlorophenyl)-2-(2,4-dichlorophenyl)-6-[(3,4-difluorobenzyl)oxy]pyridine,
(56) 5-(4-chlorophenyl)-2-[(5-chloropyridin-3-yl)oxy]-6-(2,4-dichlorophenyl)nicotinonitrile,
(57) methyl5-(4-chlorophenyl)-6-(2,4-dichlorophenyl)-2-(3,4-difluorophenoxy)nicotinate,
(58) 5-(4-chlorophenyl)-6-(2,4-dichlorophenyl)-2-(3,4-difluorophenoxy)-N-methylnicotinamide,
(59) 5-(4-chlorophenyl)-N-cyclohexyl-6-(2,4-dichlorophenyl)-2-(3,4-difluorophenoxy)nicotinamide,
(60) 5-(4-chlorophenyl)-6-(2,4-dichlorophenyl)-2-(3,4-difluorophenoxy)-N-pyrrolidin-1-ylnicotinamide,
(61) 5-(4-chlorophenyl)-6-(2,4-dichlorophenyl)-2-(3,4-difluorophenoxy)-N',N'-dimethylnicotinohydrazide,
(62) 5-(4-chlorophenyl)-6-(2,4-dichlorophenyl)-2-(3,4-difluorophenoxy)-N-ethylnicotinamide,
(63) 5-(4-chlorophenyl)-6-(2,4-dichlorophenyl)-2-(3,4-difluorophenoxy)-N-isopropylnicotinamide,
(64) methyl5-(4-chlorophenyl)-2-[(5-chloropyridin-3-yl)oxy]-6-(2,4-dichlorophenyl)nicotinate,
(65) 5-(4-chlorophenyl)-6-(2,4-dichlorophenyl)-2-(3,4-difluorophenoxy)nicotinamide,
(66) N-(2-{[5-(4-chlorophenyl)-3-cyano-6-(2,4-dichlorophenyl)pyridin-2-yl]oxy}ethyl)cyclopropanecarboxamide,
(67) N-(2-{[5-(4-chlorophenyl)-3-cyano-6-(2,4-dichlorophenyl)pyridin-2-yl]oxy}ethyl)cyclobutanecarboxamide,
(68) N-(2-{[5-(4-chlorophenyl)-3-cyano-6-(2,4-dichlorophenyl)pyridin-2-yl]oxy}ethyl)cyclopentanecarboxamide,
(69) N-(2-{[5-(4-chlorophenyl)-3-cyano-6-(2,4-dichlorophenyl)pyridin-2-yl]oxy}ethyl)benzamide,
(70) N-(2-{[5-(4-chlorophenyl)-3-cyano-6-(2,4-dichlorophenyl)pyridin-2-yl]oxy}ethyl)-4-fluorobenzamide,
(71) 5-(4-chlorophenyl)-6-(2,4-dichlorophenyl)-2-(pyridin-2-yloxy)nicotinonitrile,
(72) 5-(4-chlorophenyl)-3-cyano-N-cyclohexyl-6-(2,4-dichlorophenyl)pyridine-2-carboxamide,
(73) 5-(4-chlorophenyl)-6-(2,4-dichlorophenyl)-2-(3,5-difluorophenoxy)nicotinonitrile,
(74) 5-(4-chlorophenyl)-6-(2,4-dichlorophenyl)-2-(1H-imidazol-1-yl)nicotinonitrile,
(75) [5-(4-chlorophenyl)-6-(2,4-dichlorophenyl)-2-(3,4-difluorophenoxy)pyridin-3-yl]methanol,
(76) 5-(4-chlorophenyl)-6-(2,4-dichlorophenyl)-2-(2-methyl-1H-imidazol-1-yl)nicotinonitrile,
(77) 5-(4-chlorophenyl)-3-cyano-N-cyclopentyl-6-(2,4-dichlorophenyl)pyridine-2-carboxamide,
(78) 5-(4-chlorophenyl)-6-(2,4-dichlorophenyl)-2-(4,4-dimethyl-2-oxo-1,3-oxazolidin-3-yl)nicotinonitrile,
(79) 5-(4-chlorophenyl)-6-(2,4-dichlorophenyl)-2-(tetrahydro-2H-pyran-2-ylmethoxy)nicotinonitrile,
(80) 5-(4-chlorophenyl)-6-(2,4-dichlorophenyl)-2-isopropoxynicotinonitrile,
(81) 5-(4-chlorophenyl)-6-(2,4-dichlorophenyl)-2-ethoxynicotinonitrile,
(82) N-[5-(4-chlorophenyl)-3-cyano-6-(2,4-dichlorophenyl)pyridin-2-yl]benzamide,
(83) N-benzoyl-N-[5-(4-chlorophenyl)-3-cyano-6-(2,4-dichlorophenyl)pyridin-2-yl]benzamide,
(84) 5-(4-chlorophenyl)-6-(2,4-dichlorophenyl)-2-(tetrahydrofuran-3-yloxy)nicotinonitrile,
(85) 5-(4-chlorophenyl)-6-(2,4-dichlorophenyl)-2-(tetrahydrofuran-3-ylmethoxy)nicotinonitrile,
(86) 2-(1H-1,2,3-benzotriazol-1-yl)-5-(4-chlorophenyl)-6-(2,4-dichlorophenyl)nicotinonitrile,
(87) N-[5-(4-chlorophenyl)-3-cyano-6-(2,4-dichlorophenyl)pyridin-2-yl]-3,4-difluorobenzamide,
(88) 5-(4-chlorophenyl)-6-(2,4-dichlorophenyl)-2-(piperidin-1-yloxy)nicotinonitrile,
(89) N-[5-(4-chlorophenyl)-3-cyano-6-(2,4-dichlorophenyl)pyridin-2-yl]-2,2-dimethyipropanamide,
(90) methyl2-(3-chlorophenoxy)-5-(4-chlorophenyl)-6-(2,4-dichlorophenyl)nicotinate,
(91) 2-(3-chlorophenoxy)-5-(4-chlorophenyl)-6-(2,4-dichlorophenyl)-N',N'-dimethylnicotinohydrazide, (92) 5-(4-chlorophenyl)-6-(2,4-dichlorophenyl)-2-(1H-1,2,3-triazol-1-yl)nicotinonitrile, (93) 5-(4-chlorophenyl)-6-(2,4-dichlorophenyl)-2-[(3,4-difluorobenzyl)oxy]-N',N'-dimethylnicotinohydrazide,
(94) methyl2-butoxy-5-(4-chlorophenyl)-6-(2,4-dichlorophenyl)nicotinate,
(95) 5-(4-chlorophenyl)-2-(cyclohexylmethoxy)-6-(2,4-dichlorophenyl)-N-propylnicotinamide,

(96) 5-(4-chlorophenyl)-6-(2,4-dichlorophenyl)-2-(4-fluorophenoxy)nicotinonitrile,
(97) 5-(4-chlorophenyl)-2-(3,5-dichlorophenoxy)-6-(2,4-dichlorophenyl)nicotinonitrile,
(98) 5-(4-chlorophenyl)-6-(2,4-dichlorophenyl)-2-(3,4-difluorobenzyl)nicotinonitrile,
(99) 5-(4-chlorophenyl)-6-(2,4-dichlorophenyl)-2-(3,4-difluorophenoxy)nicotinamide,
(100) 5'-(4-chlorophenyl)-6'-(2,4-dichlorophenyl)-2-oxo-2H-1,2'-bipyridine-3-carbonitrile,
(101) 5-(4-chlorophenyl)-6-(2,4-dichlorophenyl)-2-(isopropylamino)nicotinonitrile, and pharmacuetically acceptable salts thereof.

* * * * *